US012781196B2

(12) United States Patent
Collins et al.

(10) Patent No.: US 12,781,196 B2
(45) Date of Patent: Nov. 3, 2026

(54) LIVE ATTENUATED RESPIRATORY SYNCYTIAL VIRUS

(71) Applicant: The United States of America, as represented by the Secretary, Department of Health and Human Services, Bethesda, MD (US)

(72) Inventors: Peter Collins, Kensington, MD (US); Ursula Buchholz, Silver Spring, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 835 days.

(21) Appl. No.: 18/008,393

(22) PCT Filed: Jun. 4, 2021

(86) PCT No.: PCT/US2021/036030
§ 371 (c)(1),
(2) Date: Dec. 5, 2022

(87) PCT Pub. No.: WO2021/248086
PCT Pub. Date: Dec. 9, 2021

(65) Prior Publication Data

US 2023/0279362 A1 Sep. 7, 2023

Related U.S. Application Data

(60) Provisional application No. 63/035,617, filed on Jun. 5, 2020.

(51) Int. Cl.

| | |
|---|---|
| ***C12N 7/00*** | (2006.01) |
| ***A61K 39/12*** | (2006.01) |
| ***A61K 39/155*** | (2006.01) |
| ***A61P 31/14*** | (2006.01) |
| *A61K 39/00* | (2006.01) |
| *A61K 39/295* | (2006.01) |

(52) U.S. Cl.
CPC ................ *C12N 7/00* (2013.01); *A61K 39/12* (2013.01); *A61K 39/155* (2013.01); *A61P 31/14* (2018.01); *A61K 39/295* (2013.01); *A61K 2039/543* (2013.01); *C12N 2760/18521* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS

| | | | | |
|---|---|---|---|---|
| 7,700,092 | B2 | 4/2010 | Conzelmann | |
| 10,947,512 | B2 | 3/2021 | Peeples et al. | |
| 2005/0100557 | A1 | 5/2005 | Collins et al. | |
| 2017/0189520 | A1* | 7/2017 | Collins | A61K 39/12 |
| 2021/0386842 | A1 | 12/2021 | Holst et al. | |
| 2024/0018193 | A1 | 1/2024 | Kwong et al. | |

FOREIGN PATENT DOCUMENTS

| | | | |
|---|---|---|---|
| CN | 1426462 | A | 6/2003 |
| RU | 2015142981 | A | 4/2017 |
| RU | 2017138373 | A | 2/2019 |
| WO | WO 02/00693 | A2 | 1/2002 |
| WO | WO 2013/154728 | A1 | 10/2013 |
| WO | WO 2014/124238 | A1 | 8/2014 |
| WO | WO 2016/118642 | A1 | 7/2016 |
| WO | WO 2017/100756 | A1 | 6/2017 |
| WO | WO 2017/100759 | A1 | 6/2017 |
| WO | WO 2018/222573 | A1 | 12/2018 |

OTHER PUBLICATIONS

Liang et al., J Virology 2016, https://doi.org/10.1128/jvi.01196-16 (Year: 2016).*

Karron, et al., The Journal of Infectious Diseases, vol. 222, Issue 1, pp. 82-91 (Year: 2019).*

Atreya et al., "The NS1 Protein of Human Respiratory Syncytial Virus is a Potent Inhibitor of Minigenome Transcription and RNA Replication," *J Virol.* 72.2: 1452-1461, Feb. 1998.

Bakre et al., "Human respiratory syncytial virus non-structural protein NS1 modifies miR-24 expression via transforming growth factor-B," *J Gen Virol.* 96: 3179-3191, 2015.

Bitko et al., "Nonstructural Proteins of Respiratory Syncytial Virus Suppress Premature Apoptosis by an NF-KB-Dependent, Interferon-Independent Mechanism and Facilitate Virus Growth," *J Virol.* 81.4: 1786-1795, Feb. 2007.

Boyapalle et al., "Respiratory Syncytial Virus NS1 Protein Colocalizes with Mitochondrial Antiviral Signaling Protein MAVS following Infection," *PLoS One* 7.2: e29386, Feb. 2012 (9 pages).

Bukreyev et al., "Granulocyte-Macrophage Colony-Stimulating Factor Expressed by Recombinant Respiratory Syncytial Virus Attenuates Viral Replication and Increases the Level of Pulmonary Antigen-Presenting Cells," *J Virol.* 75.24: 12128-12140, Dec. 2001.

ClinicalTrials.gov Identifier NCT01459198, "Evaluating the Safety and Immune Response to a Respiratory Syncytial Virus (RSV) Vaccine in Adults, RSV-Seropositive Children, and RSV-Seronegative Infants and Children," First Posted Oct. 25, 2011, downloaded Dec. 5, 2022.

ClinicalTrials.gov Identifier NCT01852266, "Evaluating the Safety and Immune Response to a Single Dose of a Respiratory Syncytial Virus (RSV) Vaccine in RSV-Seronegative Infants and Children," First Posted May 13, 2013, downloaded Dec. 5, 2022.

(Continued)

*Primary Examiner* — Shanon A. Foley
*Assistant Examiner* — Myron G Hill
(74) *Attorney, Agent, or Firm* — Klarquist Sparkman, LLP

(57) ABSTRACT

Reported herein are novel recombinant respiratory syncytial viruses (RSV) having an attenuated phenotype. The recombinant RSV strains described here are suitable for use as live-attenuated RSV vaccines. Also provided are polynucleotide sequences capable of encoding the described viruses, as well as methods for producing and using the viruses.

20 Claims, 32 Drawing Sheets

Specification includes a Sequence Listing.

(56) References Cited

OTHER PUBLICATIONS

ClinicalTrials.gov Identifier NCT01893554, "Evaluating the Safety and Immune Response to a Single Dose of a Respiratory Syncytial Virus (RSV) Vaccine in Infants and Children," First Posted Jul. 9, 2013, downloaded Dec. 5, 2022.
ClinicalTrials.gov Identifier NCT02952339, "Evaluating the Infectivity, Safety, and Immunogenicity of a Recombinant Live-Attenuated Respiratory Syncytial Virus Vaccine in RSV-Seronegative Infants and Children 6 to 24 Months of Age," First Posted Nov. 2, 2016, downloaded Dec. 5, 2022.
ClinicalTrials.gov Identifier NCT03102034, "Evaluating the Infectivity, Safety, and Immunogenicity of a Single Dose of a Recombinant Live-Attenuated Respiratory Syncytial Virus Vaccine (D46/NS2/N/ΔM2-2-HindIII) in RSV-Seronegative Infants 6 to 24 Months of Age," First Posted Apr. 5, 2017, downloaded Dec. 5, 2022.
ClinicalTrials.gov Identifier NCT03227029, "Evaluating the Infectivity, Safety, and Immunogenicity of Recombinant Live-Attenuated RSV Vaccines RSV ΔNS2/Δ1313/I1314L or RSV 276 in RSV-Seronegative Infants 6 to 24 Months of Age," First Posted Jul. 24, 2017, downloaded Dec. 5, 2022.
ClinicalTrials.gov Identifier NCT03387137, "Evaluating the Infectivity, Safety, and Immunogenicity of a Respiratory Syncytial Virus Vaccine (RSV 6120/ΔNS2/1030s) in RSV-Seropositive Children and RSV-Seronegative Infants and Children," First Posted Dec. 29, 2017, downloaded Dec. 5, 2022.
ClinicalTrials.gov Identifier NCT03596801, "Evaluating the Infectivity, Safety and Immunogenicity of Respiratory Syncytial Virus Vaccines, RSV 6120/ΔNS1 and RSV 6120/F1/G2/ΔNS1, in RSV-Seropositive Children and RSV-Seronegative Infants and Children," First Posted Jul. 24, 2018, downloaded Dec. 5, 2022.
ClinicalTrials.gov Identifier NCT03916185, "Safety and Immunogenicity of a Single Dose of the Recombinant Live-Attenuated Respiratory Syncytial Virus (RSV) Vaccines Rsv ΔNS2/Δ1313/I1314L, RSV 6120/ΔNS2/1030s, RSV 276 or Placebo, Delivered as Nose Drops to RSV-Seronegative Children 6 to 24 Months of Age," First Posted Apr. 16, 2019, downloaded Dec. 5, 2022.
Collins et al., "Production of infectious human respiratory syncytial virus from cloned cDNA confirms an essential role for the transcription elongation factor from the 5' proximal open reading frame of the M2 mRNA in gene expression and provides a capability for vaccine development," *Proc Natl Acad Sci USA* 92: 11563-11567, Dec. 1995.
Dhar et al., "2'-5'-Oligoadenylate Synthetase-Like Protein Inhibits Respiratory Syncytial Virus Replication and is Targeted by the Viral Nonstructural Protein 1," *J Virol*. 89.19: 10115-10119, Oct. 2015.
Durbin et al., "Mutations in the C, D, and V Open Reading Frames of Human Parainfluenza Virus Type 3 Attenuate Replication in Rodents and Primates," *Virology* 261: 319-330, 1999.
Graham, "Vaccine development for respiratory syncytial virus," *Curr Opin Virol*. 23: 107-112, Apr. 2017.
International Search Report and Written Opinion issued in International Application No. PCT/US2021/036030, by the European Searching Authority, mailed on Nov. 29, 2021, 21 pages.
Karron et al., "Evaluation of Two Live, Cold-Passaged, Temperature-Sensitive Respiratory Syncytial Virus Vaccines in Chimpanzees and in Human Adults, Infants, and Children," *J Infect Dis*. 176: 1428-1436, 1997.
Karron et al., "Live-Attenuated Respiratory Syncytial Virus Vaccines," *Curr Top Mircobiol Immunol*. 372: 259-284, 2013.
Karron et al., "A gene deletion that up-regulates viral gene expression yields an attenuated RSV vaccine with improved antibody responses in children," *Sci Transl Med*. 7.312: 312ra175, Nov. 2015 (21 pages).
Karron et al., "Safety and Immunogenicity of the Respiratory Syncytial Virus Vaccine RSV/ΔNS2/Δ1313/I1314L in RSV-Seronegative Children," *J Infect Dis*. 222.1: 82-91, Jul. 1, 2020.
Krempl et al., "Recombinant Respiratory Syncytial Virus with the G and F Genes Shifted to the Promoter-Proximal Positions," *J Virol*. 76.23: 11931-11942, Dec. 2002.
Liang et al., "Chimeric Bovine/Human Parainfluenza Virus Type 3 Expressing Respiratory Syncytial Virus (RSV) F Glycoprotein: Effect of Insert Position on Expression, Replication, Immunogenicity, Stability, and Protection against RSV Infection," *J Virol*. 88.8: 4237-4250, Apr. 2014.
Liang et al., "Enhanced Neutralizing Antibody Response Induced by Respiratory Syncytial Virus Prefusion F Protein Expressed by a Vaccine Candidate," *J Virol*. 89.18: 9499-9510, Sep. 2015.
Liang et al., "Packaging and Prefusion Stabilization Separately and Additively Increase the Quantity and Quality of Respiratory Syncytial Virus (RSV)-Neutralizing Antibodies Induced by an RSV Fusion Protein Expressed by a Parainfluenza Virus Vector," *J Virol*. 90.21: 10022-10038, Nov. 2016.
Liang et al., "Improved Prefusion Stability, Optimized Codon Usage, and Augmented Virion Packaging Enhance the Immunogenicity of Respiratory Syncytial Virus Fusion Protein in a Vectored-Vaccine Candidate," *J Virol*. 91.15: e00189-17, Aug. 2017 (23 pages).
Liang et al., "A Parainfluenza Virus Vector Expressing the Respiratory Syncytial Virus (RSV) Prefusion F Protein is More Effective than RSV for Boosting a Primary Immunization with Rsv," *J Virol*. 95.2: e01512-20, 2021 (24 pages).
Lo et al., "Respiratory Syncytial Virus Nonstructural Proteins NS1 and NS2 Mediate Inhibition of Stat2 Expression and Alpha/Beta Interferon Responsiveness," *J Virol*. 79.14: 9315-9319, Jul. 2005.
Luongo et al., "Respiratory Syncytial Virus Modified by Deletions of the NS2 Gene and Amino Acid S1313 of the L Polymerase Protein is a Temperature-Sensitive, Live-Attenuated Vaccine Candidate That is Phenotypically Stable at Physiological Temperature," *J Virol*. 87.4: 1985-1996, Feb. 2013.
Malkin et al., "Safety and Immunogenicity of a Live Attenuated RSV Vaccine in Healthy RSV-Seronegative Children 5 to 24 Months of Age," *PLoS One* 8.10: e77104, Oct. 2013 (10 pages).
Mcfarland et al., "Live Respiratory Syncytial Virus Attenuated by M2-2 Deletion and Stabilized Temperature Sensitivity Mutation 1030s is a Promising Vaccine Candidate in Children," *J Infect Dis*. 221: 534-543, Feb. 2020.
Mclellan et al., "Structure of a Major Antigenic Site on the Respiratory Syncytial Virus Fusion Glycoprotein in Complex with Neutralizing Antibody 101F," *J Virol*. 84.23: 12236-12244, Dec. 2010.
Mclellan et al., "Structure-Based Design of a Fusion Glycoprotein Vaccine for Respiratory Syncytial Virus," *Science* 342.6158: 592-598, Nov. 2013.
Munir et al., "Nonstructural Proteins 1 and 2 of Respiratory Syncytial Virus Suppress Maturation of Human Dendritic Cells," *J Virol*. 82.17: 8780-8796, Sep. 2008.
Munir et al., "Respiratory Syncytial Virus Interferon Antagonist NS1 Protein Suppresses and Skews the Human T Lymphocyte Response," *PLoS One* 7.4: e1001336, Apr. 2011 (17 pages).
Ren et al., "A novel mechanism for the inhibition of interferon regulatory factor-3-dependent gene expression by human respiratory syncytial virus NS1 protein," *J Gen Virol*. 92: 2153-2159, 2011.
Spann et al., "Effects of Nonstructural Proteins NS1 and NS2 of Human Respiratory Syncytial Virus on Interferon Regulatory Factor 3, NF-KB, and Proinflammatory Cytokines," *J Virol*. 79.9: 5353-5362, May 2005.
Straub et al., "Mutation of the elongin C binding domain of human respiratory syncytial virus non-structural protein 1 (NS1) results in degradation of NS1 and attenuation of the virus," *Virology Journal* 8: 252, 2011 (12 pages).
Swanson et al., "Structural basis for immunization with postfusion respiratory syncytial virus fusion F glycoprotein (RSV F) to elicit high neutralizing antibody titers," *Proc Natl Acad Sci USA* 108.23: 9619-9624, Jun. 2011.
Swedan et al., "Respiratory Syncytial Virus Nonstructural Proteins Decrease Levels of Multiple Members of the Cellular Interferon Pathways," *J Virol*. 83.19: 9682-9693, Oct. 2009.
Teng et al., "Recombinant Respiratory Syncytial Virus That Does Not Express the NS1 or M2-2 Protein is Highly Attenuated and Immunogenic in Chimpanzees," *J Virol*. 74.19: 9317-9321, Oct. 2000.

(56) References Cited

OTHER PUBLICATIONS

Whitehead et al., "Recombinant Respiratory Syncytial Virus Bearing a Deletion of either the NS2 or SH Gene is Attenuated in Chimpanzees," J Virol. 73.4: 3438-3442, Apr. 1999.
Wright et al., "Evaluation of a Live, Cold-Passaged, Temperature-Sensitive, Respiratory Syncytial Virus Vaccine Candidate in Infancy," *J Infect Dis*. 182: 1331-1342, 2000.
Wright et al., "The Interferon Antagonist NS2 Protein of Respiratory Syncytial Virus is an Important Virulence Determinant for Humans," J Infect Dis. 193: 573-581, 2006.
Xu et al., "Respiratory Syncytial Virus NS1 Protein Degrades STAT2 by Inducing SOCS1 Expression," *Intervirology* 57: 65-73, 2014.
Yang et al., "Respiratory syncytial virus nonstructural proteins 1 and 2 are crucial pathogenic factors that modulate interferon signaling and Treg cell distribution in mice," *Virology* 485: 223-232, 2015.

* cited by examiner

Deletion of the NS1 gene (ΔNS1)

Deletion of the NS1 and NS2 genes (ΔNS1+2)

LID mutation in the downstream non-translated region of the SH gene of D46

Insertion of the F and G genes into positions 1 and 2 (LID/F1G2)

FIG. 3B. RSV LID/ΔNS1 with F1G2 and F1BBG2 gene shifts

VERO MOI 0.001, Day 4 post-inoculation

FIG. 15E
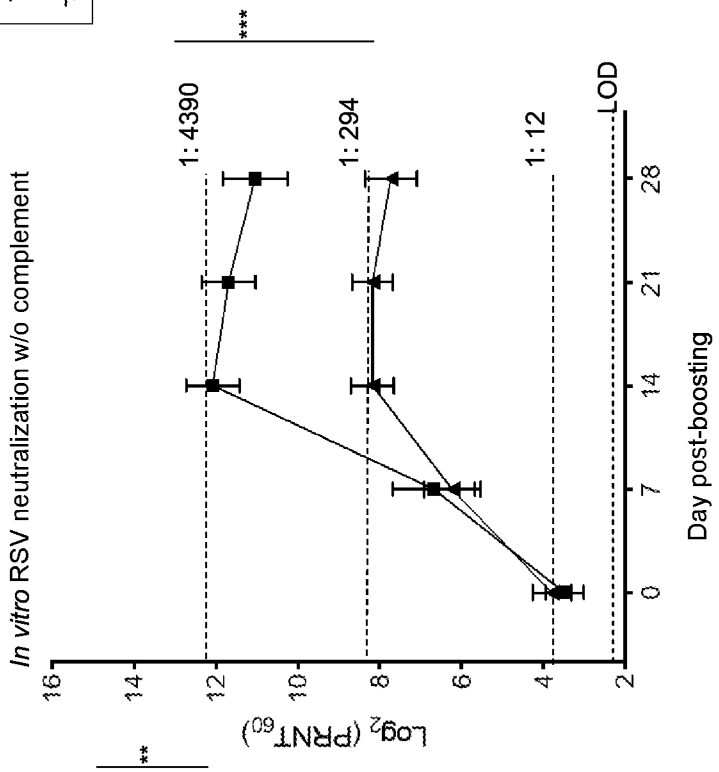
FIG. 15D
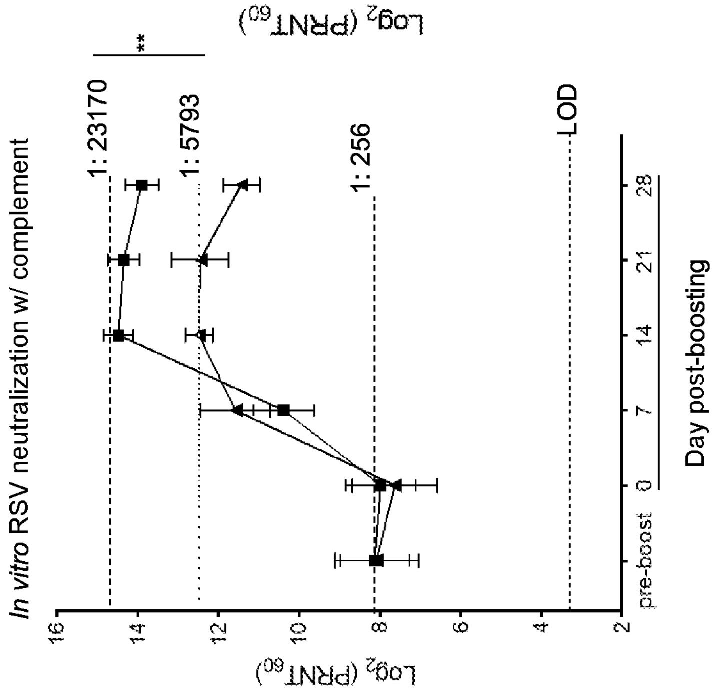

FIG. 21
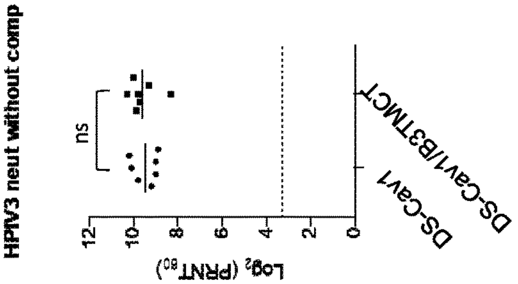
FIG. 20A
FIG. 20B
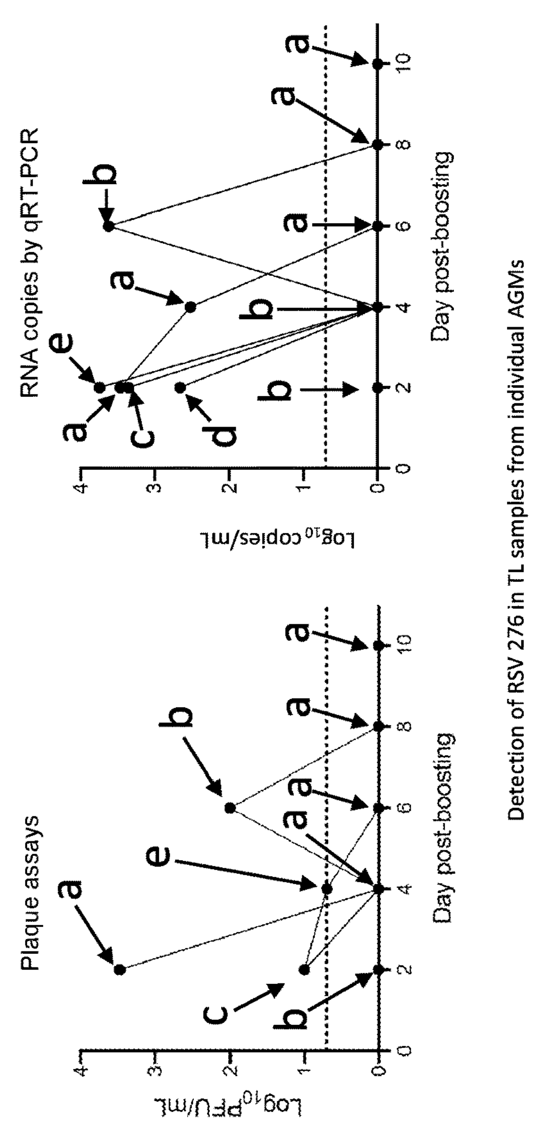

LIVE ATTENUATED RESPIRATORY SYNCYTIAL VIRUS

CROSS REFERENCE TO RELATED APPLICATIONS

This is the U.S. National Stage of International Application No. PCT/US2021/036030, filed Jun. 4, 2021, which was published in English under PCT Article 21(2), which in turn claims the benefit of priority to U.S. Provisional Application No. 63/035,617, filed Jun. 5, 2020. The provisional application is incorporated by reference in its entirety.

PARTIES TO A JOINT RESEARCH AGREEMENT

This invention was made under Public Health Service Cooperative Research and Development Agreement (PHS-CRADA) No. 2013-0810 between the National Institute of Allergy and Infectious Disease at the National Institutes of Health and Sanofi Pasteur, Inc.

FIELD

The subject matter disclosed herein relates to respiratory syncytial virus (RSV) and attenuated, mutant strains thereof suitable for use as vaccines.

BACKGROUND

Human respiratory syncytial virus (RSV) infects nearly everyone worldwide early in life and is responsible for considerable mortality and morbidity. In the United States alone, RSV is responsible for 75,000-125,000 hospitalizations yearly, and conservative estimates indicate that RSV is responsible worldwide for 64 million pediatric infections and 160,000 or more pediatric deaths each year. Another notable feature of RSV is that severe infection in infancy frequently is followed by lingering airway dysfunction, including a predisposition to airway reactivity, that in some individuals lasts for years and can extend into adolescence and beyond. RSV infection exacerbates asthma and may be involved in initiating asthma.

RSV is a member of the Pneumoviridae family and, as such, is an enveloped virus that replicates in the cytoplasm and matures by budding at the host cell plasma membrane. The genome of RSV is a single, negative-sense strand of RNA of 15.2 kilobases that is transcribed by the viral polymerase into 10 mRNAs by a sequential stop-start mechanism that initiates at a single viral promoter at the 3' end of the genome. Each mRNA encodes a single major protein, with the exception of the M2 mRNA that has two overlapping open reading frames (ORFs) encoding two separate proteins M2-1 and M2-2. The 11 RSV proteins are: the RNA-binding nucleoprotein (N), the phosphoprotein (P), the large polymerase protein (L), the attachment glycoprotein (G), the fusion protein (F), the small hydrophobic (SH) surface glycoprotein, the internal matrix protein (M), the two nonstructural proteins NS1 and NS2, and the M2-1 and M2-2 proteins. The RSV gene order is: 3'-NS1-NS2-N-P-M-SH-G-F-M2-L. Each gene is flanked by short conserved transcription signals called the gene-start (GS) signal, present on the upstream end of each gene and involved in initiating transcription of the respective gene, and the gene-end (GE) signal, present at the downstream end of each gene and involved in directing synthesis of a polyA tail followed by release of the mRNA. Transcription initiates at a single promoter at the 3' end and proceeds sequentially.

The development of RSV vaccines has been in progress since the 1960's but has been complicated by a number of factors. For example, immunization of RSV-naïve infants with inactivated RSV has been shown to prime for enhanced disease upon subsequent natural RSV infection, and studies in experimental animals indicate that disease enhancement also is associated with purified RSV subunit vaccines.

Another obstacle to immune protection is that RSV replicates and causes disease in the superficial cells of the respiratory airway lumen, where immune protection has reduced effectiveness. Thus, immune control of RSV infection is inefficient and often incomplete, and it is important for an RSV vaccine to be as immunogenic as possible. Another obstacle to RSV vaccines is that the magnitude of the protective immune response is roughly proportional to the extent of virus replication (and antigen production). Thus, the attenuation of RSV necessary to make a live vaccine typically is accompanied by a reduction in replication and antigen synthesis, and a concomitant reduction in immunogenicity, and therefore it is beneficial to identify a level of replication that is well tolerated yet satisfactorily immunogenic.

Another obstacle is that RSV grows only to moderate titers in cell culture and is often present in long filaments that are difficult to purify. RSV can readily lose infectivity during handling. Another obstacle is the difficulty in identifying and developing attenuating mutations. Appropriate mutations must be attenuating in vivo, but should be minimally restrictive to replication in vitro, since this is preferred for efficient vaccine manufacture. Another obstacle is genetic instability that is characteristic of RNA viruses, whereby attenuating mutations can revert to the wild-type (wt) assignment or to an alternative assignment that confers a non-attenuated phenotype. Instability and de-attenuation are particularly problematic for point mutations.

Taking these factors together, there is a need for live attenuated RSV strains that replicate efficiently in vitro, are maximally immunogenic, are satisfactorily attenuated, and are refractory to de-attenuation.

SUMMARY

Reported herein are embodiments of novel recombinant human RSVs having an attenuated phenotype that are suitable for use as live-attenuated RSV vaccines. The disclosed recombinant RSVs comprise one or more genetic mutations that lead to the attenuated phenotype.

In some embodiments, the recombinant human RSV comprises a genome comprising RSV F, G, NS2, N, P, M, SH, M2, and L genes located at gene positions 1-9, respectively, wherein the F and G genes located at gene positions 1 and 2 are shifted from the native gene positions 8 and 7, respectively, and wherein the genome comprises a deletion of the sequence encoding NS1 protein, and wherein the recombinant RSV is infectious, attenuated, and self-replicating. In several embodiments, the SH gene of the recombinant RSV comprises a deletion of positions 4499-4610 inclusive corresponding to the reference RSV sequence set forth as SEQ ID NO: 1, and C4489T, C4492T, A4495T, A4497G, and G4498A substitutions corresponding to the reference RSV sequence set forth as SEQ ID NO: 1, In some embodiments, the deletion of the sequence encoding NS1 protein comprises a deletion of positions 99-627 inclusive corresponding to the reference RSV sequence set forth as SEQ ID NO: 1. In some embodiments, the L gene encodes an L protein comprising a S1313 residue encoded by an TCA codon and a Y1314K substitution encoded by a AAA codon, wherein the amino acid positions correspond to the reference L protein sequence set forth as SEQ ID NO: 13 (amino acid sequence of the L protein).

In some embodiments, the L gene encodes an L protein comprising a deletion of S1313 and an I1314L substitution, wherein the amino acid positions correspond to the reference L protein sequence set forth as SEQ ID NO: 13.

In some embodiments, the nucleic acid sequence encoding the F protein comprises SEQ ID NO: 14 (F WT) or SEQ ID NO: 15 (FBB). In some embodiments, the genome of the recombinant RSV does not comprise any heterologous genes. In some embodiments, the genome of the recombinant RSV further comprises a deletion of the NS2 gene.

In some embodiments, the RSV genome comprises the modifications as discussed above, and comprises a nucleotide sequence corresponding to a positive-sense sequence at least 99% identical to SEQ ID NO: 3 (LID/F1G2/ΔNS1), SEQ ID NO: 4 (LID/F1BBG2/ΔNS1), SEQ ID NO: 6 (LID/F1G2/ΔNS1/1030s), SEQ ID NO: 7 (LID/F1BBG2/ΔNS1/1030s), SEQ ID NO: 9 (LID/F1G2/ΔNS1/A1313/I1314L), or SEQ ID NO: 10 (LID/F1BBG2/ΔNS1/Δ1313/I1314L). For example, the RSV genome can comprise or consist of a nucleotide sequence corresponding to a positive-sense sequence denoted by SEQ ID NO: 3 (LID/F1G2/ΔNS1), SEQ ID NO: 4 (LID/F1BBG2/ΔNS1), SEQ ID NO: 6 (LID/F1G2/ΔNS1/1030s), SEQ ID NO: 7 (LID/F1BBG2/ΔNS1/1030s), SEQ ID NO: 9 (LID/F1G2/ΔNS1/Δ1313/I1314L), or SEQ ID NO: 10 (LID/F1BBG2/ΔNS1/Δ1313/I1314L).

The embodiments of recombinant RSV disclosed herein can be subtype A RSV or a subtype B RSV.

Also provided herein are methods and compositions related to the expression of the disclosed viruses. For example, isolated polynucleotide molecules that include a nucleic acid sequence encoding the genome or antigenome of the described viruses are provided. Additionally provided are methods of producing a recombinant RSV comprising transfecting a permissive cell culture with a vector comprising a nucleic acid molecule comprising the genome or antigenome of the disclosed recombinant RSV, incubating the cell culture for a sufficient period of time to allow for viral replication; and purifying the replicated recombinant RSV.

Pharmaceutical compositions including the recombinant RSV are also provided. The compositions can further include an adjuvant. Methods of eliciting an immune response in a subject by administering an effective amount of a disclosed recombinant RSV to the subject are also disclosed. In some embodiments, the subject is a human subject, for example, a human subject between 1 and 6 months of age, or between 1 and 12 months of age, or between 1 and 18 months of age, or older.

The foregoing and other features and advantages of this disclosure will become more apparent from the following detailed description of several embodiments which proceeds with reference to the accompanying drawings.

BRIEF DESCRIPTION OF THE DRAWINGS

(FIG. 1A) Details of the ΔNS1 deletion. The 529-nt deletion (nucleotides 99-627 inclusive) begins with and includes nucleotide 99 that is the first nucleotide of the ATG of the NS1 ORF and extends to and includes nucleotide 627 that immediately precedes the ATG (nucleotides 628-630) of the NS2 ORF. This deletion joins the upstream non-translated region of the NS1 gene to the translational start codon of the NS2 ORF. Coded amino acids MDTTHNDN (SEQ ID NO: 21) are shown. (FIG. 1B) Details of the ΔNS1+2 mutation. The 1042-nt deletion (nucleotides 99-1140 inclusive) begins with and includes nucleotide 99 that is the first nucleotide of the ATG of the NS1 ORF and extends to and includes nucleotide 1140 that immediately precedes the ATG (1141-1143) of the N ORF. This joins the upstream non-translated region of the NS1 gene to the translational start codon of the N ORF. Coded amino acids MALSKVKL (SEQ ID NO: 22) are shown. (FIG. 1C) Details of the LID mutation. This consists of the combination of a deletion encompassing most of the downstream non-translated region of the SH gene of D46, together with five translationally-silent substitutions in the last three codons and termination codon of the SH ORF. The 112-nt deletion begins with and includes nucleotide 4499, which immediately follows the TAG termination codon of the SH ORF, and extends to and includes nucleotide 4610, which is 7 nucleotides upstream of the SH gene-end signal. This deletion is combined with synonymous nucleotide substitutions C4489T, C4492T, A4495T, A4497G, and G4498A (bold and underlined). Coded amino acids ARVNT (SEQ ID NO: 23) are shown. Note that RSV LID generally resembles a wild-type RSV and is used in some of the following experiments as a wild-type-like control.

(FIG. 2A). Nucleotides 4630-7551 inclusive were deleted from the RSV antigenomic cDNA to remove the F and G genes. This has the effect of fusing the SH gene-end signal to the F/M2 intergenic region. This mutation is illustrated with an antigenomic D46 cDNA bearing the LID mutation (the LID mutation is indicated with an open triangle above or below the SH gene), although the modifications do not depend on the LID mutation. (FIG. 2B). The G and F ORFs (shaded sequences) were reconstructed into genes in the reverse of their natural order (i.e., F-G instead of G-F). Each ORF was flanked by short non-translated regions and gene-start and gene-end signals, and separated by a short intergenic region consisting of a single nucleotide. Nucleotide adapters with Xho I sites (boxed in FIG. 2B) were added upstream of the F ORF (CTCGAGTTCACC, XhoI site underlined, SEQ ID NO: 28) and downstream of the gene-end-intergenic-gene-start sequence (AGTTAATAAAAAATGGGGCAAATACTCGAG, XhoI site underlined, SEQ ID NO: 29) that follows the G ORF. Four nucleotide substitutions were used to introduce an Xho I site into the noncoding region preceding the NS1 ORF in the LID antigenomic cDNA shown at the bottom, and required mutation of nucleotides 88-91 in the sequence representing the upstream non-translated NS1 gene region, from CTTG (shown in large case) to tcga (shown in small case). Coded amino acids MELLILK (SEQ ID NO: 24), FSN, MSKN (SEQ ID NO: 25), TPRQ (SEQ ID NO: 26), and MDTT (SEQ ID NO: 27) are shown. As shown with the antigenome at the bottom, the F-G gene cassette (cross-hatched rectangles) was inserted into the genomic cDNA using the Xho I sites.

(FIG. 3A) RSV LID plus the ΔNS1 deletion, as is or with the F1G2 or F1BBG2 modifications. (FIG. 3B) RSV LID/ΔNS1 plus the 1030s mutation, as is or with the F1G2 or F1BBG2 modifications. (FIG. 3C) RSV LID/ΔNS1 plus the Δ1313 and I1314L mutations, as is or with the F1G2 or F1BBG2 modifications. (FIG. 3D) RSV LID plus the ΔNS1+2 deletion, as is or with the F1G2 or F1BBG2 modifications.

(FIG. 14A) Study design. Ninety-six hamsters were confirmed to be RSV- and HPIV3-seronegative and were assigned into eight groups of 12 animals each. On day 0, Groups A-D were given a primary IN infection with $10^6$ PFU of RSV D46 in 0.1 ml of L15 medium, and Groups E-H were left uninfected. Six weeks later, sera were collected for determination of pre-boost 60% RSV plaque reduction neutralization titers (RSV-PRNTs). Two days later, primed and unprimed groups in pairs were boosted IN ($10^5$ $TCID_{50}$ for vectors and $10^6$ PFU for RSV) with one of the four viruses: (i) the empty rB/HPIV3 vector (Groups A and E); (ii) DS-Cav1 vector (Groups B and F); (iii) DS-Cav1/B3TMCT vector (Groups C and G); and (iv) RSV D46 (Groups D and H). Five days after boosting, nasal turbinates (NT) and lungs of six hamsters per group were collected for virus titration. From the other six hamsters per group, sera were collected two weeks after boosting to measure RSV- and HPIV3-PRNT, and two days later the animals were challenged IN with $10^6$ PFU RSV D46. Three days following the challenge, NT and lungs were collected for titration of RSV replication. (FIG. 14B, FIG. 14C) Titers of boosting viruses in (FIG. 14B) NT and (FIG. 14C) lung tissue homogenates five days post-boost. Dashed and dotted lines indicate the limit of detection (LOD) for the rB/HPIV3 vectors and RSV D46, respectively. (FIG. 14D) Serum HPIV3-PRNTs two weeks post-boost in primed and unprimed hamsters, assayed without complement. (FIG. 14E, FIG. 14F) Pre-boost and post-boost serum RSV-PRNTs in animals from Groups A-D, that were primed with RSV D46 and boosted with the indicated viruses, assayed with (FIG. 14E) and without (FIG. 14F) added complement. The significance of differences between the indicated comparisons was determined by Student's t-test: ns indicates not significant ($P>0.05$); * indicates $0.01<P<0.05$;  indicates $0.001<P<0.01$; * indicates $0.0001<P<0.001$.

FIGS. 15A-15E. AGM experiment #1: Viral replication and serum RSV-PRNTs in AGMs when the interval between priming and boosting was ~2 months (two months minus nine days). (FIG. 15A) Study design. Twelve AGMs were previously administered a primary infection with one of three RSVs (Table 8) by the combined IN/IT routes. Sera were collected on Day 37 (two weeks before boosting), and RSV-PRNTs were determined in the presence of complement. The AGMs were organized into two groups of six animals each that were balanced with regard to the Day 37 RSV-PRNTs, identity of the priming virus, and sex ratio (Table 8). On day 51 (two months minus nine days) following priming, the groups were boosted with RSV 276 (which is a ΔM2-2 virus; SEQ ID NO: 12) or DS-Cav1/B3TMCT vector by the combined IN/IT routes. Virus shedding was monitored on Days 1-10 post-boost by NP and TL and virus titration. Sera were collected on days 7, 14, 21, and 28 post-boosting. (FIG. 15B, FIG. 15C) Viral titers in the (FIG. 15B) NP and (FIG. 15C) TL, shown as means with brackets indicating SEMs and limits of detection shown as dashed lines (vectors) and dotted lines (RSV). (FIG. 15D) Serum RSV-PRNTs at Day 37 post-priming and Days 0, 7, 14, 21, and 28 post-boosting, assayed in the presence of complement. (FIG. 15E) Serum RSV-PRNT at Days 0, 7, 14, 21, and 28 post-boosting, assayed without complement. D and E are annotated to show the mean serum RSV-PRNT for the combined two groups at the time of boosting (black dashed lines, with mean arithmetic values shown); in addition, dashed colored lines indicate the highest mean serum RSV-PRNT for each group, with the arithmetic values shown. Mean serum RSV-PRNTs are shown with brackets indicating SEMs. Peak mean titers of two groups were compared by Student's t-test:  indicates 0.001<P<0.01; * indicates 0.0001<P<0.001.

(FIG. 16A) Study design. Twenty AGMs were previously administered a primary infection with one of five attenuated RSVs (Table 9) by the combined IN/IT routes. Sera were collected on Days 28 and 154 (the latter being 35 days before boosting), and RSV-PRNTs were determined in the presence of complement. The AGMs were organized into three groups (n=6, 7, and 7) that were balanced with regard to Day-154 serum RSV-PRNTs, identity of the priming virus, and sex ratio (Table 9). On Day 189 (six months plus nine days) post-priming, the groups were boosted with one of three viruses: (i) RSV 276 (n=6), (ii) DS-Cav1 vector (n=7), or (iii) DS-Cav1/B3TMCT vector (n=7). Viral shedding and serum RSV-PRNTs were monitored as described in the legend to FIG. 15. Nasal mucosal lining fluid was collected for IgA analysis using SAM strips on Days 0, 14, 21, 28 post-boosting (see Methods and Materials for details). (FIG. 16B, FIG. 16C) Viral titers in the (FIG. 16B) NP and (FIG. 16C) TL were determined, shown as means with brackets indicating standard error of means (SEMs) and limits of detection shown as dashed lines (vectors) and dotted lines (RSV). (FIG. 16D) Serum RSV-PRNTs at 28, 154, and 189 days post-priming, and 7, 14, 21, and 28 days post-boosting, assayed with complement. (FIG. 16E) RSV-PRNTs at 0, 7, 14, 21, 28 days post-boosting, assayed without complement shown as means with brackets indicating the SEMs. D and E are annotated to show the mean serum RSV-PRNT for the combined three groups at the time of boost (black dashed lines, with mean arithmetic values given); in addition, dashed colored lines indicate the highest mean RSV-PRNT for each group, with arithmetic values given. (FIG. 16F, FIG. 16G) Serum and nasal mucosal IgA responses in AGMs. IgA antibody titers were determined in (FIG. 16F) serum samples collected Days 0, 7, 14, 21, and 28 post-boosting, and (FIG. 16G) nasal mucosal lining fluid collected on Days 0, 14, 21, and 28 post-boosting (note that in the DS-Cav1/BTMCT group, one of the Day 28 SAM specimens did not provide sufficient volume; thus, the Day 28 mean titer of the DS-Cav1/BTMCT vector was calculated for 6 animals only). IgA titers were measured by binding to purified RSV DS-Cav1 F protein in a DELFIA TRF assay. The antibody titers are given as the $\log_2$ dilution of serum or mucosal specimen yielding 400 fluorescence units, shown as means with brackets indicating the SEMs. Mean antibody titers for the combined three groups at the time of boost (Day 0) are indicated by the larger black dotted lines; the titers of all SAM samples on Day 0 were below the detection level (5.3 $\log_2$). The limits of detection (LOD) are indicated by the smaller black dotted line. The dashed colored lines indicate the highest mean antibody titer for each group. Peak mean titers of three groups were compared pairwise by Student's t-test (GraphPad Prism): * indicates 0.01<P<0.05;  indicates 0.001<P<0.01; * indicates 0.0001<P<0.001; ns indicates P>0.05, not significant.

(FIG. 17A) Study design. Four AGMs were previously administered a primary infection with the live-attenuated vaccine candidate RSV 276 (Table 10). Sera were collected on Day 429 (two weeks before boosting) and RSV-PRNTs were determined with complement. The AGMs were distributed into two groups of two animals each, such that the groups had similar individual and mean RSV-PRNTs based on the Day 429 sera (Table 10). On Day 443 (15 months minus seven days) post-priming, sera were collected and the two groups were boosted with DS-Cav1/B3TMCT vector (n=2) or RSV 276 (n=2) administered IN and IT at dose of $10^6$ $TCID_{50}$ (DS-Cav1/B3TMCT vector) or PFU (RSV 276) per site. Viral replication and serological responses were monitored as described in the legends to FIGS. 15 and 16. (FIG. 17B, FIG. 17C) Viral titers in the (FIG. 17B) NP and (FIG. 17C) TL, shown as means with limits of detection shown as dashed lines. Symbols indicate titers for individual animals, and the lines indicates mean values. (FIG. 17D) Serum RSV-PRNTs at Day 429 post-priming and Days 0, 7, 14, 21, and 28 post-boosting, assayed with complement. (FIG. 17E) Serum RSV-PRNTs at Days 0, 7, 14, 21, 28 post-boosting, assayed without complement. D is annotated to show the mean serum RSV-PRNT for the combined two groups at the time of boosting (black dashed line in D, with the mean arithmetic value 1:26 shown); in addition, D and E are annotated with dashed colored lines that indicate the highest mean serum RSV-PRNT for each group, with the arithmetic values shown.

FIGS. 20A-20B. Replication of boosting RSV 276 in the tracheal lavage (TL) from AGMs primed with attenuated RSV ~6 months earlier. From the experiment in FIG. 16, the titers of RSV 276 in TL on Days 2, 4, 6, 8 and 10 post-boosting were quantified by immunoplaque assay (FIG. 20A) and RT-qPCR specific for both positive- and negative-sense RSV M gene sequence (FIG. 20B). Each color represents an individual monkey. The limit of detection is indicated with a dotted line.

FIG. 21. Serum HPIV3-PRNTs induced by DS-Cav1 and DS-Cav1/B3TMCT vectors in AGMs primed with live-attenuated RSV 6 months earlier. From the experiment in FIG. 16, sera collected 2 weeks after boosting by DS-Cav1 and DS-Cav1/B3TMCT vectors were analyzed by HPIV3 PRNT assays without complement. The dots indicate individual animals; group means are indicated with short horizontal lines. The dotted line indicates the limit of detection. Mean serum HPIV3-PRNTs of two groups were compared by Student's t-test: ns indicates P>0.05, not significant.

SEQUENCE LISTING

Figure 1A:
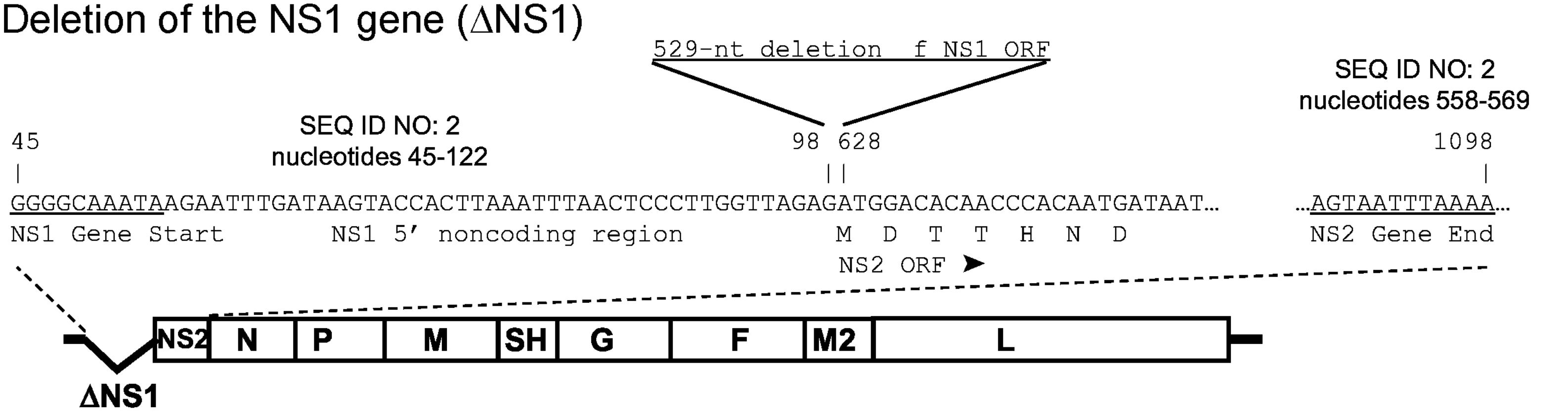
FIGS. 1A-1C. Deletion of NS1 (ΔNS1), deletion of NS1 and NS2 together (ΔNS1+2), and deletion and modification of part of the SH gene of D46 (LID mutation).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~356 kb), which was created on Nov. 15, 2022 which is incorporated by reference herein. In the accompanying sequence listing:

SEQ ID NO: 1 is the antigenomic nucleic acid sequence of RSV D46.

SEQ ID NO: 2 is the antigenomic nucleic acid sequence of RSV LID/ΔNS1.

SEQ ID NO: 3 is the antigenomic nucleic acid sequence of RSV LID/F1G2/ΔNS1.

SEQ ID NO: 4 is the antigenomic nucleic acid sequence of RSV LID/F1BBG2/ΔNS1.

SEQ ID NO: 5 is the antigenomic nucleic acid sequence of RSV LID/ΔNS1/1030s.

SEQ ID NO: 6 is the antigenomic nucleic acid sequence of RSV LID/F1G2/ΔNS1/1030s.

SEQ ID NO: 7 is the antigenomic nucleic acid sequence of RSV LID/F1BBG2/ΔNS1/1030s.

SEQ ID NO: 8 is the antigenomic nucleic acid sequence of RSV LID/ΔNS1/Δ1313/I1314L.

SEQ ID NO: 9 is the antigenomic nucleic acid sequence of RSV LID/F1G2/ΔNS1/Δ1313/I1314L.

SEQ ID NO: 10 is the antigenomic nucleic acid sequence of RSV LID/F1BBG2/ΔNS1/Δ1313/I1314L.

SEQ ID NO: 11 is the antigenomic nucleic acid sequence of RSV D46/NS2/N/ΔM2-2-HindIII.

SEQ ID NO: 12 is the antigenomic nucleic acid sequence of RSV 276 genome.

SEQ ID NO: 13 is the amin acid sequence of the L protein from D46.

SEQ ID NO: 14 is the amino acid sequence of the RSV F protein from D46.

SEQ ID NO: 15 is the amino acid sequence of RSV FBB protein.

SEQ ID NO: 16 is the antigenomic sequence of B/HPIV3 DS-Cav1.

SEQ ID NO: 17 is the antigenomic sequence of B/HPIV3 DS-Cav1/B3TMCT.

SEQ ID NO: 18 is the antigenomic sequence of RSV LID/ΔNS2/1030s.

SEQ ID NO: 19 is the antigenomic sequence of RSV LID/ΔNS2/Δ1313/I1314L.

SEQ ID NOs: 20-29 are fragments of DNA and protein sequences.

DETAILED DESCRIPTION

Major challenges to developing pediatric vaccines against RSV include the immaturity of the immune system during infancy, immune-suppression by maternal antibodies, inefficient immune protection at the superficial epithelium of the respiratory tract, viral suppression of host responses such as the suppression of host interferon and apoptosis responses by NS1 and NS2, and vaccine-induced enhanced disease that has been observed in studies with inactivated or subunit RSV vaccines in virus-naïve recipients (Kim et al., *Amer. J. Epidemiol.* 89:422-434, 1969; Ottolini et al., *Viral Immunol.* 13:231-236, 2000; Schneider-Ohrum et al., *J. Virol.* 91:e02180-16, 2017). Thus, despite substantial effort, a need remains for an effective immunogen that induces a protective immune response to RSV.

The present disclosure provides recombinant RSV that is attenuated, infectious, and self-replicating and that meets the above-discussed need.

I. SUMMARY OF TERMS

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the term "comprises" means "includes." Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

About: Plus or minus 5% from a reference amount. For example, "about 5" refers to 4.75 to 5.25. A ratio of "about 5:1" refers to a ratio of from 4.75:1 to 5.25:1.

Adjuvant: A vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. Adjuvants are described, for example, in Singh (ed.) Vaccine Adjuvants and Delivery Systems. Wiley-Interscience, 2007.

Administration: The introduction of a composition into a subject by a chosen route. Administration can be local or systemic. For example, if the chosen route is intranasal, the composition (such as a composition including a disclosed attenuated RSV) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in a polypeptide with a different amino acid.

Attenuated: A virus that is "attenuated" or has an "attenuated phenotype" refers to a virus that has decreased virulence compared to a reference virus under similar conditions of infection. Attenuation usually is associated with decreased virus replication as compared to replication of a reference wild-type virus under similar conditions of infection, and thus "attenuation" and "restricted replication" often are used synonymously. In some hosts (typically non-natural hosts, including experimental animals), disease is not evident during infection with a reference virus in question, and restriction of virus replication can be used as a surrogate marker for attenuation. In some embodiments, a disclosed attenuated RSV exhibits at least about 10-fold or greater decrease, such as at least about 100-fold or greater decrease in virus titer in the upper or lower respiratory tract of a mammal compared to non-attenuated, wild type virus titer in the upper or lower respiratory tract, respectively, of a mammal of the same species under the same conditions of infection. Examples of mammals include, but are not limited to, humans, mice, rabbits, rats, hamsters, such as for example *Mesocricetus auratus*, and non-human primates, such as for example *Ceropithiecus aethiops*. An attenuated RSV may display different phenotypes including without limitation altered growth, temperature sensitive growth, host range restricted growth, or plaque size alteration.

Control: A reference standard. In some embodiments, the control is a negative control sample obtained from a healthy patient. In other embodiments, the control is a positive control sample obtained from a patient diagnosed with RSV infection. In still other embodiments, the control is a historical control or standard reference value or range of values (such as a previously tested control sample, such as a group of RSV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Effective amount: An amount of agent that is sufficient to elicit a desired response, such as an immune response in a subject. It is understood that to obtain a protective immune response against a virus of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to elicit a protective immune response.

In one example, a desired response is to inhibit or reduce or prevent RSV infection. The RSV infection does not need to be completely eliminated or reduced or prevented for the method to be effective. For example, administration of an effective amount of the agent can decrease the RSV infection (for example, as measured by infection of cells, or by number or percentage of subjects infected by RSV) by a desired amount, for example by at least 50%, at least 60%, at least 70%, at least 80%, at least 90%, at least 95%, at least 98%, or even at least 100% (elimination or prevention of detectable RSV infection), as compared to a suitable control.

Gene: A nucleic acid sequence that comprises control and coding sequences necessary for the transcription of an RNA, whether an mRNA or otherwise. For instance, a gene may comprise a promoter, one or more enhancers or silencers, a nucleic acid sequence that encodes a RNA and/or a polypeptide, downstream regulatory sequences and, possibly, other nucleic acid sequences involved in regulation of the expression of an mRNA.

A "gene" of a recombinant RSV as described herein refers to a portion of the recombinant RSV encoding an mRNA and typically begins at the upstream (3') end with a gene-start (GS) signal and ends at the downstream (5') end with the gene-end (GE) signal. In this context, the term gene also embraces what is referred to as a "translational open reading frame", or ORF, particularly in the case where a protein is expressed from an additional ORF rather than from a unique mRNA. To construct a disclosed recombinant RSV, one or more genes or genome segments may be deleted, inserted or substituted in whole or in part.

Heterologous: Originating from a different genetic source. A heterologous gene included in a recombinant genome is a gene that does not originate from that genome.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Infectious and Self-Replicating Virus: A virus that is capable of entering and replicating in a cultured cell or cell of an animal or human host to produce progeny virus capable of the same activity.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic composition: A preparation of immunogenic material capable of stimulating an immune response, which in some examples can be administered for the prevention, amelioration, or treatment of infectious or other types of disease. The immunogenic material may include attenuated or killed microorganisms (such as bacteria or viruses), or antigenic proteins, peptides or DNA derived from them. Immunogenic compositions comprise an antigen (such as a virus) that induces a measurable T cell response against the antigen, or induces a measurable B cell response (such as production of antibodies) against the antigen. In one example, an immunogenic composition comprises a disclosed recombinant RSV that induces a measurable CTL response and/or a measurable B cell response (such as production of antibodies) against RSV when administered to a subject. For in vivo use, the immunogenic composition will typically include a recombinant virus in a pharmaceutically acceptable carrier and may also include other agents, such as an adjuvant.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% pure, such as at least 75%, 80%, 90%, 95%, 98%, 99%, or even 99.9% pure.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "polynucleotide." A nucleic acid molecule is usually at least 10 bases in length, unless otherwise specified. The term includes single- and double-stranded forms of DNA. A nucleic acid molecule may include either or both naturally occurring and modified nucleotides linked together by naturally occurring and/or non-naturally occurring nucleotide linkages.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, PA, 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost immunization: An immunization protocol including administration of a first immunogenic composition (the prime immunization) followed by administration of a second immunogenic composition (the boost immunization) to a subject to induce a desired immune response. A suitable time interval between administration of the prime and the boost, and examples of such timeframes are disclosed herein. In some embodiments, the prime, the boost, or both the prime and the boost additionally include an adjuvant.

Recombinant: A recombinant nucleic acid molecule or protein or virus is one that has been produced by recombinant DNA methods, typically from cloned cDNA(s). The cDNA sequence(s) may be identical to that of a biologically-derived molecule(s), or may contain a sequence(s) that is not naturally-occurring: for example, includes one or more nucleic acid substitutions, deletions or insertions, and/or has a sequence that is made by an artificial combination of two otherwise separated segments of sequence. This artificial combination can be accomplished, for example, by chemical synthesis, targeted mutation of a naturally occurring nucleic acid molecule or protein, or, artificial manipulation of isolated segments of nucleic acids, for example, by genetic engineering techniques.

Respiratory Syncytial Virus (RSV): An enveloped non-segmented negative-sense single-stranded RNA virus of the family Pneumoviridae, genus *Orthopneumovirus*. The RSV genome is ~15,000 nucleotides in length (15,223 for KT 992094) and includes 10 genes encoding 11 proteins, including the glycoproteins SH, G and F. The F protein mediates fusion, allowing entry of the virus into the cell cytoplasm and also promoting the formation of syncytia. Two antigenic subgroups of human RSV strains have been described, the A and B subgroups, based primarily on differences in the antigenicity of the G glycoprotein. RSV strains for other species are also known, including bovine RSV. Several animal models of infection by human RSV and closely-related animal counterparts are available, including model organisms infected with human RSV, as well as model organisms infected with species-specific RSV, such as use of bRSV infection in cattle (see, e.g., Bern et al., *Am J, Physiol. Lung Cell Mol. Physiol.,* 301: L148-L156, 2011; and Nam and Kun (Eds.). Respiratory Syncytial Virus: Prevention, Diagnosis and Treatment. Nova Biomedical Nova Science Publisher, 2011; and Cane (Ed.) Respiratory Syncytial Virus. Elsevier Science, 2007.)

Unless context indicates otherwise, the positioning of RSV nucleic acid residues is according to the reference RSV antigenomic sequence provided herein as SEQ ID NO: 1, which is an RSV strain A2 antigenomic sequence, also provided as Genbank accession number KT 992094.1 (incorporated by reference herein), and is described in Collins, et al., Proc Natl Acad Sci USA, 92:11563-11567 1995. This sequence is also known as the "D46" antigenomic RSV sequence.

Sequence identity: The percentage of nucleotide or amino acid sequence assignments that are identical between two or more compared nucleotide or amino acid sequences, with gaps permitted to maximize the percent identity. The higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Subject: Living multi-cellular vertebrate organisms, a category that includes human and non-human mammals. In an example, a subject is a human. In a particular example, the subject is a newborn infant. In an additional example, a subject is selected that is in need of inhibiting an RSV infection. For example, the subject is either uninfected and at risk of RSV infection or is infected in need of treatment.

Under conditions sufficient for: A phrase that is used to describe any environment that permits a desired activity.

II. RECOMBINANT RSV

Disclosed herein are mutations that are useful in producing recombinant strains of human RSV exhibiting a range of attenuation phenotypes and are suitable for use as attenuated, live vaccines in humans. As reported herein, particular combinations of mutations to wt RSV result in a live, attenuated virus that elicits a superior immune response.

Further disclosed herein are methods and compositions related to the expression of the disclosed viruses. For example, isolated polynucleotide molecules that include a nucleic acid sequence encoding the genome or antigenome of the described viruses are disclosed.

The recombinant RSV provided herein comprises a genome or antigenome containing modifications or mutations as described in detail herein relative to wild-type RSV that attenuate the recombinant RSV. The wild-type RSV genome or antigenome encodes the following 11 proteins: the RNA-binding nucleoprotein (N), the phosphoprotein (P), the large polymerase protein (L), the attachment surface glycoprotein (G), the fusion surface glycoprotein (F), the small hydrophobic surface glycoprotein (SH), the internal matrix protein (M), the two nonstructural proteins NS1 and NS2, and the M2-1 and M2-2 proteins. The genome of RSV is a single strand of negative sense RNA of about 15.2 kb comprising 10 genes encoding 10 mRNAs. Each mRNA encodes a single protein, except for the M2 mRNA which encodes two separate proteins M2-1 and M2-2. The RSV gene order is: 3'-NS1-NS2-N-P-M-SH-G-F-M2-L with a single viral promoter located at the 3'end. Thus, in the native RSV genome NS1 is at position 1, NS2 at position 2, N at position 3, P at position 4, M at position 5, SH at position 6, G at position 7, F at position 8, M2 at position 9 and L at position 10. This organization is shown schematically in FIG. 1C.

In several embodiments, the recombinant RSV provided herein comprises a genome with RSV F, G, NS2, N, P, M, SH, M2, and L genes located at gene positions 1-9, respectively, wherein the F and G genes located at gene positions 1 and 2 are shifted from the native gene positions 8 and 7, respectively. The genome of the recombinant RSV further comprises a modification that deletes the sequence encoding the NS1 protein. In some embodiments, the deletion comprises a deletion of positions 99-626 corresponding to the reference RSV sequence set forth as SEQ ID NO: 1 (wt recombinant RSV strain A2, Genbank KT 992094). In several embodiments, the genome of the recombinant RSV provided herein further comprises a deletion of 112 nucleotides corresponding to positions 4499-4610 inclusive corresponding to the reference RSV sequence set forth as SEQ ID NO: 1, and C4489T, C4492T, A4495T, A4497G, and G4498A of SEQ ID NO: 1. This deletion and the five nucleotide substitution are collectively called the "LID" mutation or modification. As discussed in the examples below, the novel combination of these modifications to the native RSV genome results in a recombinant RSV that elicits a superior immune response.

As used herein, and unless contect indicates otherwise, virus names are descriptive rather than limiting. The full set of modifications or mutations in each virus is not necessarily listed fully in the name. Additionally, unless context indicates otherwise, the order of appearance of modifications/mutations and forward slashes in a virus name can vary: for example, "LID/F1G2/ΔNS1" is the same as "LID/ΔNS1/F1G1."

In several embodiments, the recombinant RSV provided herein comprises a genome comprising a deletion of the sequence encoding NS1 protein, wherein the deletion is a deletion of of positions 99-627 corresponding to the reference RSV sequence set forth as SEQ ID NO: 1, and wherein the recombinant RSV is infectious, attenuated, and self-replicating. In several such embodiments, the genome of the recombinant RSV provided herein further comprises a deletion of 112 nucleotides corresponding to positions 4499-4610 inclusive corresponding to the reference RSV sequence set forth as SEQ ID NO: 1, and C4489T, C4492T, A4495T, A4497G, and G4498A of SEQ ID NO: 1. As discussed in the examples below, the novel combination of these modifications to the native RSV genome results in a recombinant RSV that elicits a superior immune response.

In some embodiments, the recombinant RSV further comprises an L protein comprising a S1313 residue encoded by a TCA codon and a Y1314K substitution encoded by a AAA codon, wherein the amino acid positions correspond to the reference L protein sequence set forth as SEQ ID NO: 13 (amino acid sequence of the L protein). This pair of mutations is called "1030s" and was developed and optimized by reverse genetics to be highly refractory to de-attenuation (Luongo, et al. 2012. J Virol 86:10792-10804).

In some embodiments, the recombinant RSV further comprises an L protein comprising a deletion of S1313 and an I1314L substitution, wherein the amino acid positions correspond to the reference L protein sequence set forth as SEQ ID NO: 13. This pair of mutations is called "Δ1313/I1314L" and was developed and optimized by reverse genetics to be highly refractory to de-attenuation (Luongo, et al. 2013. J Virol 87:1985-1996).

In some embodiments, the F protein of the recombinant RSV is encoded by a wild-type sequence, such as SEQ ID NO: 14. In other embodiments, the recombinant RSV may comprise one or more changes in the F protein sequence. For example, in some embodiments, a native or naturally occurring nucleotide sequence encoding a protein of the RSV may be replaced with a codon optimized sequence designed for increased expression in a selected host, in particular the human. For example, in some embodiments, the F protein of the recombinant RSV is encoded by the codon optimized sequence FBB ("FBB") (SEQ ID NO: 15). Different versions of codon optimization can be obtained.

In several embodiments, the genome of the recombinant RSV does not comprise any heterologous genes.

In some embodiments, the genome of the recombinant RSV comprises the one or more mutations as discussed above, and a nucleic acid sequence complementary to an antigenomic sequence at least 90% (such as at least 95%, at least 96%, at least 97%, at least 98%, or at least 99%) identical to SEQ ID NO: 1 (D46 sequence). In some embodiments, the genome of the recombinant RSV is a D46 genome modified with the one or more mutations as discussed above. In several embodiments, the genome of the recombinant RSV comprises the one or more mutations as discussed herein, and any remaining sequence difference of the genome of the recombinant RSV compared to the genomic sequence of D46 RSV (SEQ ID NO: 1) is biologically insignificant (for example, the remaining sequence differences do not include changes to the wild-type genomic sequence that modify a known cis-acting signal or change amino acid coding, or measurably affect in vitro replication or plaque size of the virus).

The embodiments of recombinant RSV disclosed herein can be subtype A RSV or a subtype B RSV. The embodiments of recombinant RSV disclosed herein are infectious, attenuated, and self-replicating.

In some embodiments, the recombinant RSV comprises a RSV genome comprising RSV NS2, N, P, M, SH, G, F M2, and L genes located at gene positions 1-9, respectively, wherein the genome comprises a deletion of the sequence encoding NS1 protein. In several such embodiments, the SH gene of the recombinant RSV comprises a deletion of positions 4499-4610 corresponding to the reference RSV sequence set forth as SEQ ID NO: 1, and C4489T, C4492T, A4495T, A4497G, and G4498A substitutions corresponding to the reference RSV sequence set forth as SEQ ID NO: 1. In some such embodiments, the genome of the recombinant RSV comprises a nucleic acid sequence complementary to a positive-sense anitgenomic sequence at least 90%, at least 95%, at least 98%, and/or at least 99% identical to SEQ ID NO: 2 (RSV LID/ΔNS1). In some such embodiments, the genome of the recombinant RSV comprises a nucleic acid sequence complementary to the positive-sense anitgenomic sequence set forth as SEQ ID NO: 2 (RSV LID/ΔNS1).

In some embodiments, the recombinant RSV comprises a RSV genome comprising RSV F, G, NS2, N, P, M, SH, M2, and L genes located at gene positions 1-9, respectively, wherein the F and G genes located at gene positions 1 and 2 are shifted from the native gene positions 8 and 7, respectively, and the genome comprises a deletion of the sequence encoding NS1 protein. In several such embodiments, the SH gene of the recombinant RSV comprises a deletion of positions 4499-4610 corresponding to the reference RSV sequence set forth as SEQ ID NO: 1, and C4489T, C4492T, A4495T, A4497G, and G4498A substitutions corresponding to the reference RSV sequence set forth as SEQ ID NO: 1. In some such embodiments, the genome of the recombinant RSV comprises a nucleic acid sequence complementary to a positive-sense anitgenomic sequence at least 90%, at least 95%, at least 98%, and/or at least 99% identical to SEQ ID NO: 3 (RSV LID/F1G2/ΔNS1). In some such embodiments, the genome of the recombinant RSV comprises a nucleic acid sequence complementary to the positive-sense anitgenomic sequence set forth as SEQ ID NO: 3 (RSV LID/F1G2/ΔNS1).

In some embodiments, the recombinant RSV comprises a RSV genome comprising RSV F, G, NS2, N, P, M, SH, M2, and L genes located at gene positions 1-9, respectively, wherein the F and G genes located at gene positions 1 and 2 are shifted from the native gene positions 8 and 7, respectively, and the L gene encodes an L protein comprising a S1313 residue encoded by an TCA codon and a Y1314K substitution encoded by a AAA codon, wherein the amino acid positions correspond to the reference L protein sequence set forth as SEQ ID NO: 13. In several such embodiments, the SH gene of the recombinant RSV comprises a deletion of positions 4499-4610 corresponding to the reference RSV sequence set forth as SEQ ID NO: 1, and C4489T, C4492T, A4495T, A4497G, and G4498A substitutions corresponding to the reference RSV sequence set forth as SEQ ID NO: 1. In some such embodiments, the genome of the recombinant RSV comprises a nucleic acid sequence complementary to a positive-sense anitgenomic sequence at least 90%, at least 95%, at least 98%, and/or at least 99% identical to SEQ ID NO: 6 (RSV LID/F1G2/ΔNS1/1030s). In some such embodiments, the genome of the recombinant RSV comprises a nucleic acid sequence complementary to the positive-sense anitgenomic sequence set forth as SEQ ID NO: 6 (RSV LID/F1G2/ΔNS1/1030s).

In some embodiments, the recombinant RSV comprises a RSV genome comprising RSV F, G, NS2, N, P, M, SH, M2, and L genes located at gene positions 1-9, respectively, wherein the F and G genes located at gene positions 1 and 2 are shifted from the native gene positions 8 and 7, respectively, the genome comprises a deletion of the sequence encoding NS1 protein, and the L gene encodes an L protein comprising a deletion of S1313 and an I1314L substitution, wherein the amino acid positions correspond to the reference L protein sequence set forth as SEQ ID NO: 13.

In several such embodiments, the SH gene of the recombinant RSV comprises a deletion of positions 4499-4610 corresponding to the reference RSV sequence set forth as SEQ ID NO: 1, and C4489T, C4492T, A4495T, A4497G, and G4498A substitutions corresponding to the reference RSV sequence set forth as SEQ ID NO: 1. In some such embodiments, the genome of the recombinant RSV comprises a nucleic acid sequence complementary to a positive-sense anitgenomic sequence at least 90%, at least 95%, at least 98%, and/or at least 99% identical to SEQ ID NO: 9 (RSV LID/F1G2/ΔNS1/Δ1313/I1314L). In some such embodiments, the genome of the recombinant RSV comprises a nucleic acid sequence complementary to the positive-sense anitgenomic sequence set forth as SEQ ID NO: 9 (RSV LID/F1G2/ΔNS1/Δ1313/I1314L).

In some embodiments, the recombinant RSV comprises a RSV genome comprising RSV F, G, NS2, N, P, M, SH, M2, and L genes located at gene positions 1-9, respectively, wherein the F and G genes located at gene positions 1 and 2 are shifted from the native gene positions 8 and 7, respectively, the F protein is encoded by the sequence set forth as SEQ ID NO: 15 (FBB), and the genome comprises a deletion of the sequence encoding NS1 protein. In several such embodiments, the SH gene of the recombinant RSV comprises a deletion of positions 4499-4610 corresponding to the reference RSV sequence set forth as SEQ ID NO: 1, and C4489T, C4492T, A4495T, A4497G, and G4498A substitutions corresponding to the reference RSV sequence set forth as SEQ ID NO: 1. In some such embodiments, the genome of the recombinant RSV comprises a nucleic acid sequence complementary to a positive-sense anitgenomic sequence at least 90%, at least 95%, at least 98%, and/or at least 99% identical to SEQ ID NO: 4 (RSV LID/F1BBG2/ΔNS1). In some such embodiments, the genome of the recombinant RSV comprises a nucleic acid sequence complementary to the positive-sense anitgenomic sequence set forth as SEQ ID NO: 4 (RSV LID/F1BBG2/ΔNS1).

In some embodiments, the recombinant RSV comprises a RSV genome comprising RSV F, G, NS2, N, P, M, SH, M2, and L genes located at gene positions 1-9, respectively, wherein the F and G genes located at gene positions 1 and 2 are shifted from the native gene positions 8 and 7, respectively, the F protein is encoded by the sequence set forth as SEQ ID NO: 15 (FBB), the genome comprises a deletion of the sequence encoding NS1 protein, and the L gene encodes an L protein comprising a S1313 residue encoded by an TCA codon and a Y1314K substitution encoded by a AAA codon, wherein the amino acid positions correspond to the reference L protein sequence set forth as SEQ ID NO: 13. In several such embodiments, the SH gene of the recombinant RSV comprises a deletion of positions 4499-4610 corresponding to the reference RSV sequence set forth as SEQ ID NO: 1, and C4489T, C4492T, A4495T, A4497G, and G4498A substitutions corresponding to the reference RSV sequence set forth as SEQ ID NO: 1. In some such embodiments, the genome of the recombinant RSV comprises a nucleic acid sequence complementary to a positive-sense anitgenomic sequence at least 90%, at least 95%, at least 98%, and/or at least 99% identical to SEQ ID NO: 7 (RSV LID/F1BBG2/ΔNS1/1030s). In some such embodiments, the genome of the recombinant RSV comprises a nucleic acid sequence complementary to the positive-sense anitgenomic sequence set forth as SEQ ID NO: 7 (RSV LID/F1BBG2/ΔNS1/1030s).

In some embodiments, the recombinant RSV comprises a RSV genome comprising RSV F, G, NS2, N, P, M, SH, M2, and L genes located at gene positions 1-9, respectively, wherein the F and G genes located at gene positions 1 and 2 are shifted from the native gene positions 8 and 7, respectively, and wherein the genome comprises a deletion of the sequence encoding NS1 protein, and wherein the L gene encodes an L protein comprising a deletion of S1313 and an I1314L substitution, wherein the amino acid positions correspond to the reference L protein sequence set forth as SEQ ID NO: 13. In several such embodiments, the SH gene of the recombinant RSV comprises a deletion of positions 4499-4610 corresponding to the reference RSV sequence set forth as SEQ ID NO: 1, and C4489T, C4492T, A4495T, A4497G, and G4498A substitutions corresponding to the reference RSV sequence set forth as SEQ ID NO: 1. In some such embodiments, the genome of the recombinant RSV comprises a nucleic acid sequence complementary to a positive-sense anitgenomic sequence at least 90%, at least 95%, at least 98%, and/or at least 99% identical to SEQ ID NO: 10 (RSV LID/F1BBG2/ΔNS1/Δ1313/I1314L). In some such embodiments, the genome of the recombinant RSV comprises a nucleic acid sequence complementary to the positive-sense anitgenomic sequence set forth as SEQ ID NO: 10 (RSV LID/F1BBG2/ΔNS1/Δ1313/I1314L).

In some embodiments, the recombinant RSV comprises a deletion of the non-translated sequences in genes, in the intergenic regions, and in the trailer region, in addition to the modifications noted above.

Viruses are named herein by listing the combination of mutations present in them and are descriptive rather than limiting. The use of the symbol "/" in a virus name (as in RSV LID/ΔNS1/1030s which denotes RSV D46 comprising the mutations ΔNS1, LID, and 1030s) has no significance apart from being present to make the name easier to read, particularly when present in text. Hence, RSV LID/ΔNS1/1030s is the same as RSV LID/ΔNS1/1030s and RSV LID/ΔNS1/1030s. RSV is not always used in a name. The names of antigenomic cDNAs and their encoded RSVs typically are interchangeable.

Unless context indicates otherwise, the numbering used in this disclosure is based on the sequence of the RSV A2 strain D46, provided herein as SEQ ID NO: 1 and viral genomic sequences described are in positive-sense. With regard to sequence numbering of nucleotide and amino acid sequence positions for the described viruses, a convention was used whereby each nucleotide or amino acid residue in a given viral sequence retained the sequence position number that it has in the RSV D46 strain provided as SEQ ID NO: 1, irrespective of any modifications. Thus, although a number of genomes contain deletions and/or insertions that cause changes in nucleotide length, and in some cases amino acid length, the numbering of all of the other residues (nucleotide or amino acid) in the genome and encoded proteins remains unchanged. It also is recognized that, even without the expedient of this convention, one skilled in the art can readily identify corresponding sequence positions between viral genomes or proteins that might differ in length, guided by sequence alignments as well as the positions of open reading frames, well-known RNA features such as gene-start and gene-end signals, and amino acid sequence features.

The Examples utilize RSV strain A2 of antigenic subgroup A, which is the most widely used experimental strain and also is the parent of numerous live attenuated RSV vaccine candidates that have been evaluated in clinical studies. Given that a variety of additional RSV strains exist (e.g., RSV B1, RSV Long, RSV Line 19), those skilled in the art will appreciate that certain strains of RSV may have nucleotide or amino acid insertions or deletions that alter the position of a given residue. For example, if a protein of another RSV strain had, in comparison with strain A2, two additional amino acids in the upstream end of the protein, this would cause the amino acid numbering of downstream residues relative to strain A2 to increase by an increment of two. However, because these strains share a large degree of sequence identity, those skilled in the art would be able to determine the location of corresponding sequences by simply aligning the nucleotide or amino acid sequence of the A2 reference strain with that of the strain in question. Therefore, it should be understood that the amino acid and nucleotide positions described herein, though specifically enumerated in the context of this disclosure, can correspond to other positions when a sequence shift has occurred or due to sequence variation between virus strains. In the comparison of a protein, or protein segment, or gene, or genome, or genome segment between two or more related viruses, a "corresponding" amino acid or nucleotide residue is one that is thought to be exactly or approximately equivalent in function in the different species.

In addition to the above described modifications to recombinant RSV, different or additional modifications in RSV clones can be made to facilitate manipulations, such as the insertion of unique restriction sites in various intergenic regions or elsewhere. Nontranslated gene sequences can be removed to increase capacity for inserting foreign sequences.

Introduction of the foregoing, defined mutations into an infectious RSV clone can be achieved by a variety of well-known methods. By "infectious clone" is meant cDNA or its product, synthetic or otherwise, which can be transcribed into genomic or antigenomic RNA capable of producing an infectious virus. The term "infectious" refers to a virus or viral structure that is capable of replicating in a cultured cell or animal or human host to produce progeny virus or viral structures capable of the same activity. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA is well-known by those of ordinary skill in the art and has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. A mutated subfragment can then be assembled into the complete antigenome or genome cDNA. Mutations can vary from single nucleotide changes to replacement of large cDNA pieces containing one or more genes or genome regions.

In some embodiments, the disclosed recombinant RSV can be produced using a recombinant DNA-based technique called reverse genetics (Collins, et al. 1995. Proc Natl Acad Sci USA 92:11563-11567). This system allows de novo recovery of infectious virus entirely from cDNA in a qualified cell substrate under defined conditions. Reverse genetics provides a means to introduce predetermined mutations into the RSV genome via the cDNA intermediate. Specific attenuating mutations were characterized in preclinical studies and combined to achieve the desired level of attenuation. Derivation of vaccine viruses from cDNA minimizes the risk of contamination with adventitious agents and helps to keep the passage history brief and well documented. Once recovered, the engineered virus strains propagate in the same manner as a biologically derived virus. As a result of passage and amplification, the vaccine viruses do not contain recombinant DNA from the original recovery.

Recombinant RSV may be produced by the intracellular coexpression of a cDNA that encodes the RSV genomic RNA, together with those viral proteins necessary to generate a transcribing, replicating nucleocapsid. Plasmids encoding other RSV proteins may also be included with these essential proteins. Alternatively, RNA may be synthesized in in vitro transcription reactions and transfected into cultured cells.

To propagate a RSV virus for vaccine use and other purposes, a number of cell lines which allow for RSV growth may be used. RSV grows in a variety of human and animal cells. Preferred cell lines for propagating attenuated RS virus for vaccine use include DBSFRhL-2, MRC-5, and Vero cells. Highest virus yields are usually achieved with epithelial cell lines such as Vero cells. Cells are typically inoculated with virus at a multiplicity of infection ranging from about 0.001 to 1.0, or more, and are cultivated under conditions permissive for replication of the virus, e.g., at about 30-37° C. and for about 3-10 days, or as long as necessary for virus to reach an adequate titer. Temperature-sensitive viruses often are grown using 32° C. as the "permissive temperature." Virus is removed from cell culture and separated from cellular components, typically by well-known clarification procedures, e.g., centrifugation, and may be further purified as desired using procedures well known to those skilled in the art.

RSV which has been attenuated as described herein can be tested in various well known and generally accepted in vitro and in vivo models to confirm adequate attenuation, resistance to phenotypic reversion, and immunogenicity for vaccine use. In in vitro assays, the modified virus, which can be a multiply attenuated, biologically derived or recombinant RSV, is tested for temperature sensitivity of virus replication or "ts phenotype," and for the small plaque phenotype. Modified virus also may be evaluated in an in vitro human airway epithelium (HAE) model, which appears to provide a means of ranking viruses in the order of their relative attenuation in non-human primates and humans (Zhang et al 2002 J Virol 76:5654-5666; Schaap-Nutt et al 2010 Vaccine 28:2788-2798; Ilyushina et al 2012 J Virol 86:11725-11734). Modified viruses are further tested in animal models of RSV infection. A variety of animal models (e.g., murine, cotton rat, and primate) have been described and are known to those skilled in the art.

Recombinant viruses may be evaluated in cell culture, rodents and non-human primates for infectivity, replication kinetics, yield, efficiency of protein expression, and genetic stability. While these semi-permissive systems may not reliably detect every difference in replication, substantial differences in particular may be detected. Also recombinant strains may be evaluated successively in adults, seropositive children, and seronegative children. In some cases, where a previous similar strain has already been shown to be well-tolerated in seronegative children, a new strain may be evaluated directly in seronegative children. Evaluation may be done, for example, in groups of 10 vaccine recipients and 5 placebo recipients, which is a small number that allows simultaneous evaluation of multiple candidates. Candidates may be evaluated in the period immediately post-immunization for vaccine virus infectivity, replication kinetics, shedding, tolerability, immunogenicity, and genetic stability, and the vaccinees may be subjected to surveillance during the following RSV season for safety, RSV disease, and changes in RSV-specific serum antibodies, as described in Karron, et al. 2015, Science Transl Med 2015 7(312): 312ra175, which is incorporated herein in its entirety. Thus, analysis of selected representative viruses may provide for relatively rapid triage to narrow down candidates to identify the most optimal.

Also provided herein are isolated polynucleotides that encode the described mutated viruses, make up the described genomes or antigenomes, express the described genomes or antigenomes, or encode various proteins useful for making recombinant RSV in vitro. The nucleic acid sequences of a number of exemplary polynucleotides are also provided. Included within the embodiments provided herein are polynucleotides comprising sequences that consist or consist essentially of any of the aforementioned nucleic acid sequences. Further included are polynucleotides that possess at least 90, 91, 92, 93, 94, 95, 96, 97, 98, 99 percent or more identity, or any number in between, to any of the aforementioned sequences or SEQ ID NOs provided herein, as well as polynucleotides that hybridize to, or are the complements of the aforementioned molecules.

These polynucleotides can be included within or expressed by vectors in order to produce a recombinant RSV. Accordingly, cells transfected with the isolated polynucleotides or vectors are also included.

In additional embodiments, compositions (e.g., isolated polynucleotides and vectors incorporating an RSV-encoding cDNA) and methods are provided for producing a recombinant RSV. Also provided are novel, isolated polynucleotide molecules and vectors incorporating such molecules that comprise a RSV genome or antigenome which is modified as described herein. Also provided is the same or different expression vector comprising one or more isolated polynucleotide molecules encoding the RSV proteins. These proteins also can be expressed directly from the genome or antigenome cDNA. The vector(s) are preferably expressed or coexpressed in a cell or cell-free lysate, thereby producing an infectious mutant RSV particle or subviral particle.

Also provided is a method for producing one or more purified RSV protein(s) which involves infecting a host cell permissive of RSV infection with a recombinant RSV strain under conditions that allow for RSV propagation in the infected cell. After a period of replication in culture, the cells are lysed and recombinant RSV is isolated therefrom. One or more desired RSV protein(s) is purified after isolation of the virus, yielding one or more RSV protein(s) for vaccine, diagnostic and other uses.

The above methods and compositions yield infectious viral or subviral particles, or derivatives thereof. An infectious virus is comparable to the authentic RSV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, L and M2-1 proteins is an example of a subviral particle which can initiate an infection if introduced into the cytoplasm of cells. Subviral particles include viral particles which lack one or more protein(s), protein segment(s), or other viral component(s) not essential for infectivity.

In other embodiments the invention provides a cell or cell free lysate containing an expression vector which comprises an isolated polynucleotide molecule encoding mutant RSV genome or antigenome as described above, and an expression vector (the same or different vector) which comprises one or more isolated polynucleotide molecules encoding the N, P, L and RNA polymerase elongation factor proteins of RSV. One or more of these proteins also can be expressed from the genome or antigenome cDNA. Upon expression the genome or antigenome and N, P, L, and RNA polymerase elongation factor proteins combine to produce an infectious RSV viral or sub-viral particle.

III. IMMUNOGENIC COMPOSITIONS

Immunogenic compositions comprising a disclosed recombinant RSV and a pharmaceutically acceptable carrier are also provided. Such compositions can be administered to a subject by a variety of modes, for example, by an intranasal route. Standard methods for preparing administrable immunogenic compositions are described, for example, in such publications as *Remingtons Pharmaceutical Sciences,* $19^{th}$ Ed., Mack Publishing Company, Easton, Pennsylvania, 1995.

Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

The immunogenic composition can contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic composition can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance the immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the recombinant virus, and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, MA), among many other suitable adjuvants well known in the art, may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some instances it may be desirable to combine the immunogenic composition including the recombinant RSV, with other pharmaceutical products (e.g., vaccines) which induce protective responses to other viral agents, particularly those causing other childhood illnesses. For example, a composition including a recombinant RSV as described herein can also include other vaccines recommended by the Advisory Committee on Immunization Practices (ACIP; cdc.gov/vaccines/acip/index.html) for the targeted age group (e.g., infants from approximately one to six months of age). These additional vaccines include, but are not limited to, IN-administered vaccines. As such, a recombinant RSV as described herein may be administered simultaneously with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

In some embodiments, the immunogenic composition can be provided in unit dosage form for use to induce an immune response in a subject, for example, to prevent RSV infection in the subject. A unit dosage form contains a suitable single preselected dosage for administration to a subject, or suitable marked or measured multiples of two or more preselected unit dosages, and/or a metering mechanism for administering the unit dose or multiples thereof.

IV. METHODS OF ELICITING AN IMMUNE RESPONSE

Provided herein are methods of eliciting an immune response in a subject by administering an immunogenic composition containing a disclosed recombinant RSV to the subject. Upon immunization, the subject responds by producing antibodies specific for RSV. In addition, innate and cell-mediated immune responses are induced, which can provide antiviral effectors as well as regulating the immune response. As a result of the immunization the host becomes at least partially or completely immune to RSV infection, or resistant to developing moderate or severe RSV disease, particularly of the lower respiratory tract.

In additional embodiments, a method of eliciting an immune response in a subject by administering to the subject an immunogenic composition containing a recombinant RSV comprising a genome comprising a deletion of the sequence encoding NS1 protein (such as a deletion of of positions 99-627 corresponding to the reference RSV sequence set forth as SEQ ID NO: 1), and wherein the recombinant RSV is infectious, attenuated, and self-replicating. In some such embodiments, the genome of the recombinant RSV comprises a SH gene comprising a deletion of positions 4499-4610 corresponding to the reference RSV sequence set forth as SEQ ID NO: 1, and C4489T, C4492T, A4495T, A4497G, and G4498A substitutions corresponding to the reference RSV sequence set forth as SEQ ID NO: 1. In some such embodiments, the genome of the recombinant RSV comprises a nucleic acid seuqnece complementary to an antigenomic sequence set forth as SEQ ID NO: 2 (LID/ΔNS1), or at least 99% identical thereto. Upon immunization, the subject responds by producing antibodies specific for RSV. In addition, innate and cell-mediated immune responses are induced, which can provide antiviral effectors as well as regulating the immune response. As a result of the immunization the host becomes at least partially or completely immune to RSV infection, or resistant to developing moderate or severe RSV disease, particularly of the lower respiratory tract.

Because nearly all humans are infected with RSV by the age of 5, the entire birth cohort is included as a relevant population for immunization. This could be done, for example, by beginning an immunization regimen anytime from birth to 6 months of age, from 6 months of age to 5 years of age, in pregnant women (or women of child-bearing age) to protect their infants by passive transfer of antibody, family members of newborn infants or those still in utero, and subjects greater than 50 years of age. The scope of this disclosure is meant to include maternal immunization. In several embodiments, the subject is a human subject that is seronegative for RSV specific antibodies. In additional embodiments, the subject is no more than one year old, such as no more than 6 months old, no more than 3 months, or no more than 1 month old.

Subjects at greatest risk of RSV infection with severe symptoms (e.g. requiring hospitalization) include children with prematurity, bronchopulmonary dysplasia, and congenital heart disease are most susceptible to severe disease. During childhood and adulthood, disease is milder but can be associated with lower airway disease and is commonly complicated by sinusitis. Disease severity increases in the institutionalized elderly (e.g., humans over 65 years old). Severe disease also occurs in persons with severe combined immunodeficiency disease or following bone marrow or lung transplantation. In some embodiments, these subjects can be selected for administration of a disclosed recombinant RSV.

The immunogenic compositions containing the recombinant RSV are administered to a subject susceptible to or otherwise at risk of RSV infection in an "effective amount" which is sufficient to induce or enhance the individual's immune response capabilities against RSV. The immunogenic composition may be administered by any suitable method, including but not limited to, via injection, aerosol delivery, nasal spray, nasal droplets, oral inoculation, or topical application. In some embodiments, the vaccine may be administered intranasally or subcutaneously or intramuscularly. In some embodiments, it may be administered to the upper respiratory tract. This may be performed by any suitable method, including but not limited to, by spray, droplet or aerosol delivery. Often, the composition will be administered to an individual seronegative for antibodies to RSV or possessing transplacentally acquired maternal antibodies to RSV.

Upon immunization with an effective amount of a disclosed recombinant RSV, the subject responds by producing antibodies specific for RSV virus proteins, e.g., F and G glycoproteins. In addition, innate and cell-mediated immune responses are induced, which can provide antiviral effectors as well as regulating the immune response. As a result of the immunization the host becomes at least partially or completely immune to RSV infection, or resistant to developing moderate or severe RSV disease, particularly of the lower respiratory tract.

In a preferred embodiment, the attenuated virus is administered according to established human intranasal administration protocols (e.g., as discussed in Karron et al. JID 191:1093-104, 2005). Briefly, adults or children are inoculated intranasally via droplet with an effective amount of the recombinant RSV, typically in a volume of 0.5 ml of a physiologically acceptable diluent or carrier. This has the advantage of simplicity and safety compared to parenteral immunization with a non-replicating virus. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has not been observed with a live virus.

The precise amount of immunogen administered and the timing and repetition of administration will be determined by various factors, including the patient's state of health and weight, the mode of administration, the nature of the formulation, etc. Dosages will generally range from about 3.0

$\log_{10}$ to about 6.0 $\log_{10}$ plaque forming units ("PFU") or more of virus per patient, more commonly from about 4.0 $\log_{10}$ to 5.0 $\log_{10}$ PFU virus per patient. In one embodiment, about 5.0 $\log_{10}$ to 6.0 $\log_{10}$ PFU per patient may be administered during infancy, such as between 1 and 6 months of age, and one or more additional booster doses could be given 2-6 months or more later. In another embodiment, young infants could be given a dose of about 5.0 $\log_{10}$ to 6.0 $\log_{10}$ PFU per patient at approximately 2, 4, and 6 months of age, which is the recommended time of administration of a number of other childhood vaccines. In yet another embodiment, an additional booster dose could be administered at approximately 10-15 months of age.

The embodiments of recombinant RSV described herein, and immunogenic compositions thereof, are administered to a subject in an amount effective to induce or enhance an immune response against the RSV antigens in the recombinant RSV in the subject. An effective amount will allow some growth and proliferation of the virus, in order to produce the desired immune response, but will not produce viral-associated symptoms or illnesses. Based on the guidance provided herein and knowledge in the art, the proper amount of recombinant RSV to use for immunization cane determined.

The resulting immune response can be characterized by a variety of methods. These include taking samples of nasal washes or sera for analysis of RSV-specific antibodies, which can be detected by tests including, but not limited to, complement fixation, plaque neutralization, enzyme-linked immunosorbent assay, luciferase-immunoprecipitation assay, and flow cytometry. In addition, immune responses can be detected by assay of cytokines in nasal washes or sera, ELISPOT of immune cells from either source, quantitative RT-PCR or microarray analysis of nasal wash or serum samples, and restimulation of immune cells from nasal washes or serum by re-exposure to viral antigen in vitro and analysis for the production or display of cytokines, surface markers, or other immune correlates measures by flow cytometry or for cytotoxic activity against indicator target cells displaying RSV antigens. In this regard, individuals are also monitored for signs and symptoms of upper respiratory illness.

A desired immune response is to inhibit subsequent infection with RSV. The RSV infection does not need to be completely inhibited for the method to be effective. For example, administration of an effective amount of a disclosed recombinant RSV can decrease subsequent RSV infection (for example, as measured by infection of cells, or by number or percentage of subjects infected by RSV) by a desired amount, for example by at least 10%, at least 20%, at least 50%, at least 60%, at least 70%, at least 80%, at least 90%, at least 95%, at least 98%, or even at least 100% (prevention of detectable RSV infection), as compared to a suitable control.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, hamster, cotton rat, bovine, ovine, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a effective amount of the composition (for example, amounts that are effective to elicit a desired immune response or alleviate one or more symptoms of a targeted disease).

Administration of the recombinant RSV to a subject can elicit the production of an immune response that is protective against serious lower respiratory tract disease, such as pneumonia and bronchiolitis, or croup, when the subject is subsequently infected or re-infected with a wild-type RSV. While the naturally circulating virus is still capable of causing infection, particularly in the upper respiratory tract, there is a reduced possibility of rhinitis as a result of the immunization and a possible boosting of resistance by subsequent infection by wild-type virus. Following immunization, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

An immunogenic composition including one or more of the disclosed recombinant RSV viruses can be used in coordinate (or prime-boost) immunization protocols or combinatorial formulations. It is contemplated that there can be several boosts, and that each boost can be a different disclosed immunogen. It is also contemplated in some examples that the boost may be the same immunogen as another boost, or the prime. In certain embodiments, novel combinatorial immunogenic compositions and coordinate immunization protocols employ separate immunogens or formulations, each directed toward eliciting an anti-viral immune response, such as an immune response to RSV proteins. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

In some embodiments, a disclosed recombinant RSV (such as any one of RSV LID/ΔNS1 (SEQ ID NO: 2), RSV LID/F1G2/ΔNS1 (SEQ ID NO: 3), RSV LID/F1BBG2/ΔNS1 (SEQ ID NO: 4), RSV LID/F1G2/ΔNS1/1030s (SEQ ID NO: 6), RSV LID/F1BBG2/ΔNS1/1030s (SEQ ID NO: 7), RSV LID/F1G2/ΔNS1/Δ1313/I1314L (SEQ ID NO: 9), or RSV LID/F1BBG2/ΔNS1/Δ1313/I1314L (SEQ ID NO: 10)) is used for the prime immunization and the boost comprises immunization with a RSV 276 virus (SEQ ID NO: 12), a B/HPIV3 DS-Cav1 virus (SEQ ID NO: 16), or a B/HPIV3 DS-Cav1/B3TMCT virus (SEQ ID NO: 17).

In some embodiments, the prime comprises administration of a RSV LID/ΔNS2/Δ1313/I1314Lvirus (SEQ ID NO: 19), a RSV LID/F1BBG2/ΔNS1 virus (SEQ ID NO: 4), a RSV LID/ΔNS virus (SEQ ID NO: 2), a RSV LID/ΔNS2/1030s virus (SEQ ID NO: 18), or a RSV D46/NS2/N/ΔM2-2-HindIII virus (SEQ ID NO: 11), and the boost comprises administration of a RSV 276 virus (SEQ ID NO: 12).

In some embodiments, the prime comprises administration of a RSV LID/ΔNS2/Δ1313/I1314Lvirus (SEQ ID NO: 19), a RSV LID/F1BBG2/ΔNS1 virus (SEQ ID NO: 4), a RSV LID/ΔNS virus (SEQ ID NO: 2), a RSV LID/ΔNS2/1030s virus (SEQ ID NO: 18), a RSV D46/NS2/N/ΔM2-2-HindIII virus (SEQ ID NO: 11), or a RSV 276 virus (SEQ ID NO: 12), and the boost comprises administration of a B/HPIV3 DS-Cav1/B3TMCT virus (SEQ ID NO: 17).

In some embodiments, the prime comprises administration of a RSV LID/ΔNS2/Δ1313/I1314Lvirus (SEQ ID NO:

19), a RSV LID/F1BBG2/ΔNS1 virus (SEQ ID NO: 4), a RSV LID/ΔNS virus (SEQ ID NO: 2), a RSV LID/ΔNS2/1030s virus (SEQ ID NO: 18), a RSV D46/NS2/N/ΔM2-2-HindIII virus (SEQ ID NO: 11), or a RSV 276 virus (SEQ ID NO: 12), and the boost comprises administration of a B/HPIV3 DS-Cav1 virus (SEQ ID NO: 16).

In some embodiments, the prime comprises administration of a RSV LID/ΔNS2/Δ1313/I1314L virus (SEQ ID NO: 19) and the boost comprises administration of a B/HPIV3 DS-Cav1 virus (SEQ ID NO: 16). In some embodiments, the prime comprises administration of a RSV LID/ΔNS2/Δ1313/I1314Lvirus (SEQ ID NO: 19) and the boost comprises administration of a B/HPIV3 DS-Cav1/B3TMCT virus (SEQ ID NO: 17). In some embodiments, the prime comprises administration of a RSV LID/ΔNS2/Δ1313/I1314Lvirus (SEQ ID NO: 19) and the boost comprises administration of a RSV 276 virus (SEQ ID NO: 12).

In some embodiments, the prime comprises administration of a RSV LID/ΔNS2/1030s virus (SEQ ID NO: 18) and the boost comprises administration of a B/HPIV3 DS-Cav1 virus (SEQ ID NO: 16). In some embodiments, the prime comprises administration of a RSV LID/ΔNS2/1030s virus (SEQ ID NO: 18) and the boost comprises administration of a B/HPIV3 DS-Cav1/B3TMCT virus (SEQ ID NO: 17). In some embodiments, the prime comprises administration of a RSV LID/ΔNS2/1030s virus (SEQ ID NO: 18) and the boost comprises administration of a RSV 276 virus (SEQ ID NO: 12).

In some embodiments, the prime comprises administration of a RSV 276 virus (SEQ ID NO: 12) and the boost comprises administration of a B/HPIV3 DS-Cav1 virus (SEQ ID NO: 16). In some embodiments, the prime comprises administration of a RSV 276 virus (SEQ ID NO: 12) and the boost comprises administration of a B/HPIV3 DS-Cav1/B3TMCT virus (SEQ ID NO: 17).

In some embodiments, the prime comprises administration of a RSV LID/F1BBG2/ΔNS1 virus (SEQ ID NO: 4) and the boost comprises administration of a B/HPIV3 DS-Cav1 virus (SEQ ID NO: 16). In some embodiments, the prime comprises administration of a RSV LID/F1BBG2/ΔNS1 virus (SEQ ID NO: 4) and the boost comprises administration of a B/HPIV3 DS-Cav1/B3TMCT virus (SEQ ID NO: 17). In some embodiments, the prime comprises administration of a RSV LID/F1BBG2/ΔNS1 virus (SEQ ID NO: 4) and the boost comprises administration of a RSV 276 virus (SEQ ID NO: 12).

In some embodiments, the prime comprises administration of a RSV LID/ΔNS1 virus (SEQ ID NO: 2) and the boost comprises administration of a B/HPIV3 DS-Cav1 virus (SEQ ID NO: 16). In some embodiments, the prime comprises administration of a RSV LID/ΔNS1 virus (SEQ ID NO: 2) and the boost comprises administration of a B/HPIV3 DS-Cav1/B3TMCT virus (SEQ ID NO: 17). In some embodiments, the prime comprises administration of a RSV LID/ΔNS1 virus (SEQ ID NO: 2) and the boost comprises administration of a RSV 276 virus (SEQ ID NO: 12).

In some embodiments, the prime comprises administration of a RSV D46/NS2/N/ΔM2-2-HindIII virus (SEQ ID NO: 11) and the boost comprises administration of a B/HPIV3 DS-Cav1 virus (SEQ ID NO: 16). In some embodiments, the prime comprises administration of a RSV D46/NS2/N/ΔM2-2-HindIII virus (SEQ ID NO: 11) and the boost comprises administration of a B/HPIV3 DS-Cav1/B3TMCT virus (SEQ ID NO: 17). In some embodiments, the prime comprises administration of a RSV D46/NS2/N/ΔM2-2-HindIII virus (SEQ ID NO: 11) and the boost comprises administration of a RSV 276 virus (SEQ ID NO: 12).

In any of the prime-boost immunization methods provided herein, the prime and boost may be administered intranasally to the subject at a dose of about 5.0 $\log_{10}$ PFU to about 6.0 $\log_{10}$ PFU. In any of the prime-boost immunization methods provided herein, a suitable subject may be selected for immunization, such as a human subject of five years old or younger. In the prime-boost immunization methods provided herein, the virus is administered to the subject by a suitable method, such as intranasal administration.

In some embodiments, the recombinant RSV as disclosed herein is administered intranasally to human subject 5 years of age or younger (such as about 2 years of age or younger) at a dose of 3.0 $\log_{10}$ to 7.0 $\log_{10}$ PFU, for example, a dose of about 5.0 $\log_{10}$ to about 6.0 $\log_{10}$ PFU (such as a dose of about 6.0 $\log_{10}$ PFU).

In some embodiments, the recombinant RSV as disclosed herein is administered intranasally to a RSV-seropositive human subject 5 years of age or younger (such as about 2 years of age or younger) at a dose of 3.0 $\log_{10}$ to 7.0 $\log_{10}$ PFU (such as a dose of about 6.0 $\log_{10}$ PFU), and wherein a titer of the recombinant RSV in nasal wash taken during the first 2 weeks post administration is 3.0 $\log_{10}$ PFU/ml of nasal wash or less, and the recombinant RSV administered to the subject is attenuated such that within the first month following intranasal administration to a subject, the subject exhibits no or mild (Grade 1) respiratory/febrile illness that is comparable in kind and severity to that of comparable subjects who did not receive the virus.

In some embodiments, the recombinant RSV as disclosed herein is administered intranasally to a RSV-seropositive human subject 5 years of age or younger (such as about 2 years of age or younger) at a dose of 3.0 $\log_{10}$ to 7.0 $\log_{10}$ PFU (such as a dose of about 6.0 $\log_{10}$ PFU), and wherein a titer of the recombinant RSV in nasal wash taken during the first 2 weeks post administration is 3.0 $\log_{10}$ PFU/ml of nasal wash or less.

In some embodiments, the recombinant RSV as disclosed herein is administered intranasally to a RSV-seropositive human subject 5 years of age or younger (such as about 2 years of age or younger) at a dose of 3.0 $\log_{10}$ to 7.0 $\log_{10}$ PFU (such as a dose of about 6.0 $\log_{10}$ PFU), and wherein administration of the recombinant RSV elicits an increase in serum RSV-specific antibodies in ≥75% of recipients.

The resulting immune response can be characterized by a variety of methods. These include taking samples of nasal washes or sera for analysis of RSV-specific antibodies, which can be detected by tests including, but not limited to, complement fixation, plaque neutralization, enzyme-linked immunosorbent assay, luciferase-immunoprecipitation assay, and flow cytometry. In addition, immune responses can be detected by assay of cytokines in nasal washes or sera, ELISPOT of immune cells from either source, quantitative RT-PCR or microarray analysis of nasal wash or serum samples, and restimulation of immune cells from nasal washes or serum by re-exposure to viral antigen in vitro and analysis for the production or display of cytokines, surface markers, or other immune correlates measures by flow cytometry or for cytotoxic activity against indicator target cells displaying RSV antigens. In this regard, individuals are also monitored for signs and symptoms of upper respiratory illness.

EXAMPLES

The materials, information, and methods described in this disclosure provide an array of attenuated strains with graded attenuation phenotypes, and provide guidance in selecting suitable vaccine candidate strains based on clinical benchmarks. The following examples are provided to illustrate particular features of certain embodiments, but the scope of the claims should not be limited to those features exemplified.

Example 1

Recombinant Respiratory Syncytial Virus Bearing NS1 Deletion and F and G Gene Shifts This example describes recombinant attenuated RSV including a deletion of the NS1 gene in combination with one or more additional mutations.

The NS1 and NS2 proteins independently—and to some extent cooperatively—mediate strong suppression of host innate immune responses and apoptosis, and also have been found to suppress and alter adaptive immune responses. NS1 appears to play the greater role in many of these activities. The mechanisms by which NS1 and NS2 suppress and alter host responses are numerous and are incompletely identified and incompletely characterized. Both proteins, and especially NS1, inhibit the induction of type I and type III interferons (IFNs) as well as pro-inflammatory cytokines. This inhibition involves multiple mechanisms. For example, NS1 and NS2 inhibit intracellular signaling pathways, such as by binding to RIG-I and MAVS to block their interaction, and by promoting the degradation of RIG-I, TRAF3, TBK1, and IKKε (Boyapalle, et al. 2012. PLoS One 7:e29386; Sweden, et al. 2009. J Virol 83:9682-9693). NS1 can block IRF3 activation, its nuclear translocation, and its interaction with transcription co-activators on the IFN-β promoter (Spann, et al. 2005. J Virol 79:5353-5362; Ren, et al. 2011. J Gen Virol 92:2153-2159). Both proteins have been reported to inhibit signaling from the type I IFN receptor (IFNAR), which otherwise amplifies the INF response and induces dozens of proteins that contribute to an antiviral state. For example, both proteins, and especially NS2, have been described to promote degradation of STAT2 (Lo, et al. 2005, J Virol 79:9315-9319; Xu, et al. 2014. Intervirology 57:65-73). NS1 also has been shown to directly interfere with a component of the IFN-induced antiviral state, namely the 2'-5'-Oligoadenylate Synthetase-Like (OASL) protein that otherwise inhibits RSV replication (Dhar, et al. 2015. J Virol 89:10115-10119). Both proteins, and especially NS1, suppress the induction of the cellular apoptosis in response to RSV infection, with the effect of prolonging the survival of the infected cells and increasing the production of progeny RSV (Bitko, et al. 2007. J Virol 81:1786-1795). Both proteins, and especially NS1, suppress the development of adaptive immunity by suppressing the maturation of dendritic cells (DC), by skewing the activation of T cell subsets—partially through antagonizing the IFN response, and by altering the response of regulatory T cells (Munir, et al. 2008. J Virol 82:8780-8796; Munir, et al. 2011. PLoS Pathogen 7:e1001336; Yang, et al. 2015. Virology 485:223-232). The NS1 protein also has been shown to facilitate RSV infection by modifying the expression of specific miRNAs (Bakre, et al. 2015. J Gen Virol 96:3179-3191; Zhang, et al. 2016. Biochem Biophys Res Comm 478:1436-1441). The NS1 protein, and to a lesser extent the NS2 protein, also have been shown to downregulate RNA synthesis in a mini-genome system, suggesting that they have a direct effect on viral gene expression and/or genome replication that remains to be defined (Atreya, et al. 1998. J Virol 72:1452-1461). This list of activities and mechanisms attributed to NS1 and NS2 is by no means complete or fully characterized.

Deletion or silencing of either or both genes attenuates RSV replication in vivo, with deletion of NS1 having a greater attenuating effect than NS2 in seronegative chimpanzees (Whitehead, et al. 1999. J Virol 73:3438-3442; Teng, et al. 2000. J Virol 74:9317-9321), which are considered the most predictive surrogate for RSV-naïve humans. It is presumed that the increased IFN and apoptosis responses in the absence of the NS1 and/or NS2 proteins are major factors in this attenuation. However, the significance and impact of the many NS1-mediated and NS2-mediated activities on RSV replication in its native human host, and on the attenuation and the immunogenicity of live-attenuated RSV vaccine candidates in humans, remain under investigation and are incompletely understood. Several experimental vaccines bearing the deletion of NS2 in combination with various point mutations have been evaluated in humans. One of these vaccine viruses, rA2cpΔNS2, which combined a ΔNS2 deletion with five point mutations in the N, F, and L proteins from a cold-passaged (cp) RSV strain, was under-attenuated in seropositive children (Wright, et al. 2006. J Infect Dis 193:573-581). Two other vaccine viruses, rA2cp248/404ΔNS2 and rA2cp530/1009ΔNS2, which each had the further addition of a different pair of attenuating temperature-sensitivity (ts) mutations (248/404 or 530/1009), were over-attenuated in seronegative children (Wright, et al. 2006. J Infect Dis 193:573-581). These studies confirmed that deletion of NS2 was attenuating in the human host, but none of the viruses was considered suitably attenuated for further evaluation as a pediatric vaccine. Previously, no RSV bearing the deletion of the NS1 gene had been evaluated in humans; in the present disclosure, we present data from a Phase I clinical trial in RSV-seropositive children 12-59 months of age and RSV-seronegative children 6-24 months of age.

Design of Recombinant RSV with ΔNS1 and Additional Mutations

The RSV antigenome that was used for constructing the recombinant RSV was the wild-type RSV strain A2 antigenomic cDNA called D46. This antigenomic cDNA also is sometimes referred to in the literature as D53. D46 is the basis for the present reverse genetics system (Collins, et al. 1995. Proc Natl Acad Sci USA 92:11563-11567), and its complete sequence is shown in U.S. Pat. No. 6,790,449 and in GenBank KT992094, and provided herein as SEQ ID NO: 1.

FIG. 1A illustrates the deletion of the NS1 gene. The 529-nt deletion (nucleotides 99-627 inclusive) begins with and includes nucleotide 99 that is the first nucleotide of the ATG of the NS1 ORF and extends to and includes nucleotide 627 that immediately precedes the ATG (nucleotides 628-630) of the NS2 ORF. This deletion joins the upstream non-translated region of the NS1 gene to the translational start codon of the NS2 ORF.

Figure 1B:
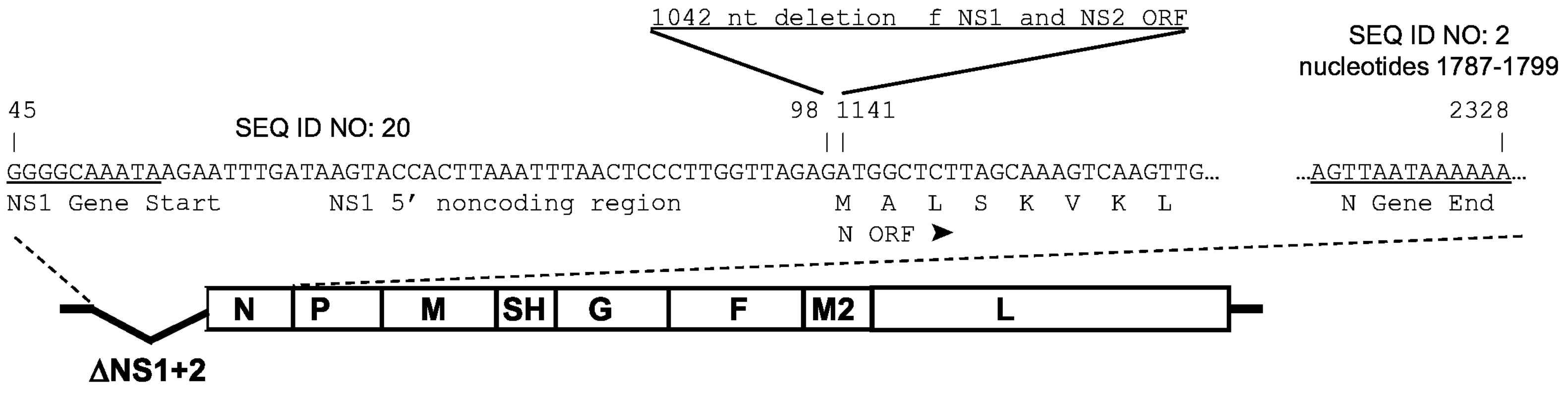

FIG. 1B illustrates the deletion of the NS1 and NS2 ORFs along with most of their flanking gene sequences from their native positions 1 and 2 in the genome. The 1042-nt deletion (nucleotides 99-1140 inclusive) begins with and includes nucleotide 99 that is the first nucleotide of the ATG of the NS1 ORF and extends to and includes nucleotide 1140, which immediately precedes the ATG (1141-1143) of the N ORF. This joins the upstream non-translated region of the NS1 gene to the translational start codon of the N ORF.

Figure 1C:
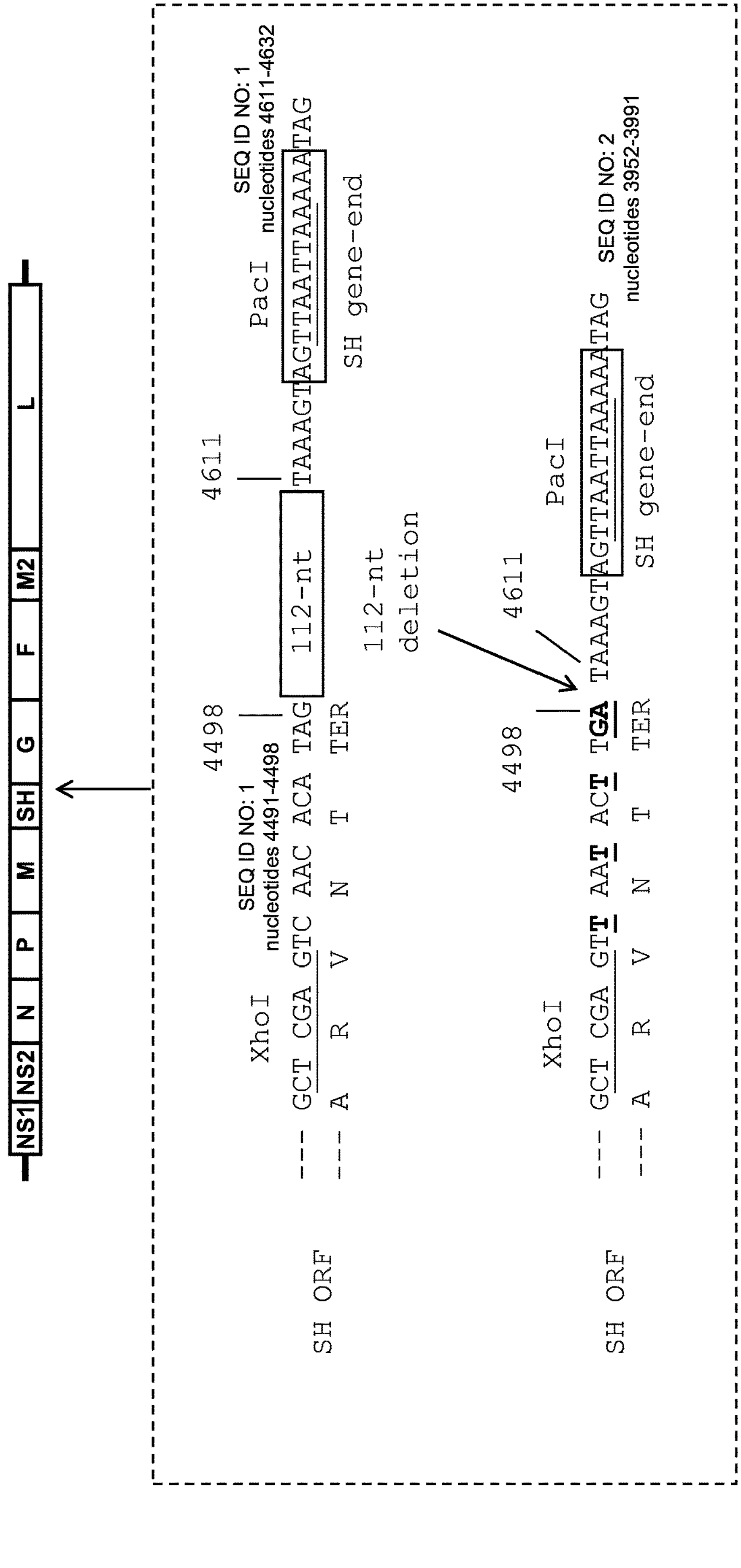

FIG. 1C illustrates the "LID" mutation, which includes a 112-nucleotide deletion of the downstream non-translated region of the SH gene of D46 together with 5 nucleotide substitutions (C4489T, C4492T, A4495T, A4497G, and G4498A) that involve the last three codons and stop codon of the SH ORF and do not change amino acid coding (Bukreyev, et al. 2001. J Virol 75:12128-12140). Note that RSV bearing the LID mutation generally appeared to have a wild-type-like phenotype in pre-clinical studies (Bukreyev, et al. 2001. J Virol 75:12128-12140), although this does not preclude possible subtle differences such as modestly increased replication in cell culture.

Figure 2A:
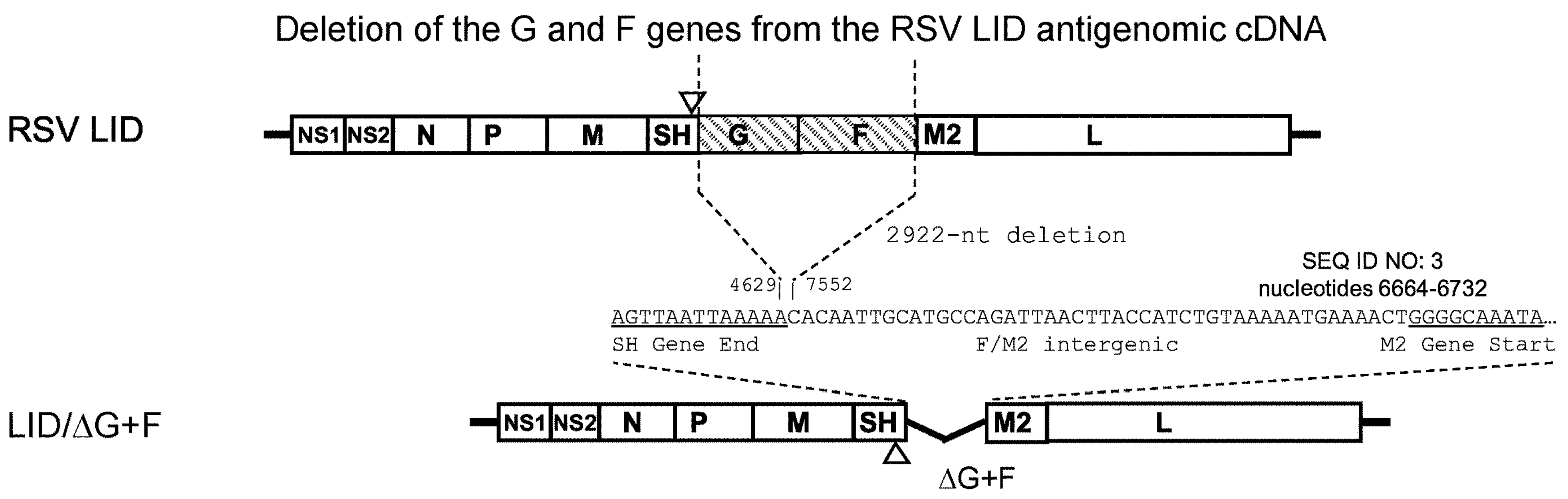
FIGS. 2A and 2B. Shift of the G and F genes from their natural genome positions (gene positions 7 and 8, respectively) to be promoter proximal and to have F preceding G (rather than the natural order of G preceding F) in gene positions 1 and 2 for F and G, respectively.
Figure 2B:
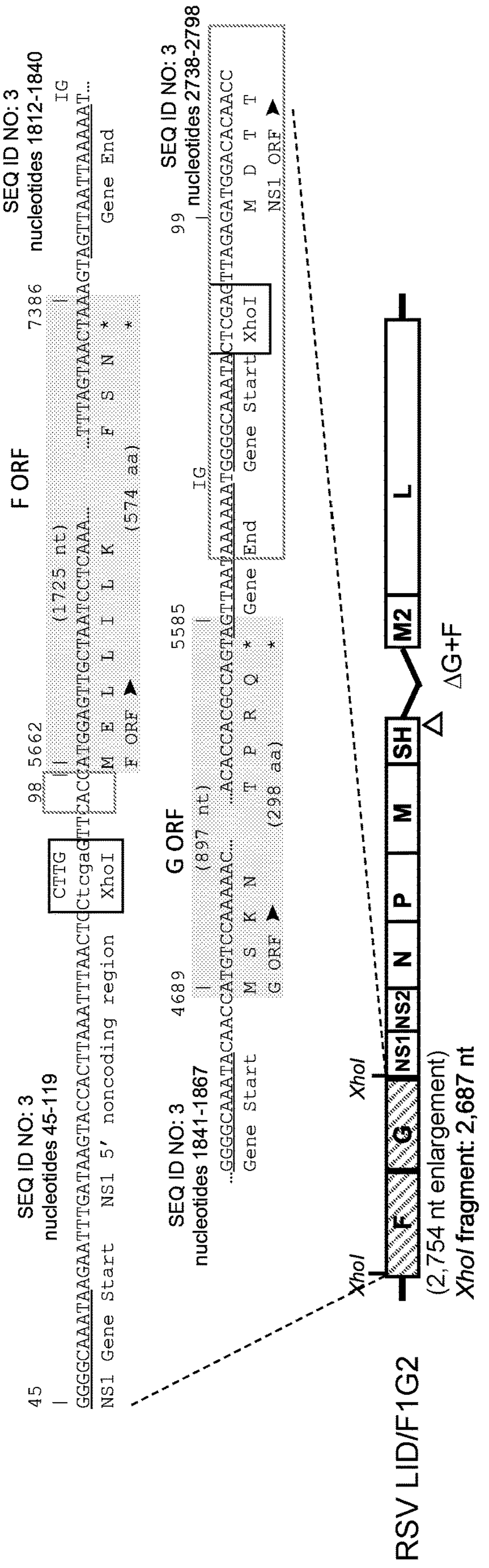

FIG. 2 illustrates the shift of the G and F genes from their natural genome positions to be promoter proximal and to have F preceding G (rather than the natural order of G preceding F). FIG. 2A illustrates deletion of the F and G genes from RSV LID. Nucleotides 4630-7551 inclusive were deleted from the RSV antigenomic cDNA to remove the F and G genes. This has the effect of fusing the SH gene-end signal to the F/M2 intergenic region. This mutation is illustrated with an antigenomic cDNA bearing the LID mutation (indicated with an open triangle above or below the SH gene), although the modifications do not depend on the LID mutation. FIG. 2B illustrates insertion of the F and G genes in gene positions 1 and 2, respectively, of the recombinant RSV antigenome. The G and F ORFs (shaded sequences) were reconstructed into genes in the reverse of their natural order (i.e., F-G instead of G-F). Each ORF was designed so that in the final construct (the antigenomic cDNA) it would be flanked by short non-translated regions and gene-start and gene-end signals, with the F and G genes separated by a short intergenic region consisting of a single nucleotide. Nucleotide adapters with Xho I sites were added upstream and downstream of the F and G ORFs: creation of the upstream Xho I site required mutation of nucleotides 88-91, in the sequence representing the upstream non-translated NS1 gene region, from CTTG (shown in large case) to tcga (shown in small case) in the LID antigenomic cDNA. As shown with the antigenome at the bottom, the F-G gene cassette (cross-hatched rectangles) was inserted into the genomic cDNA using the Xho I sites.

FIG. 3 provides genome maps of RSV strains bearing various combinations of mutations including the LID mutation (the LID mutation is indicated with an open triangle above the SH gene); deletion of G and F from their natural positions (ΔG+F) and their shift to the $2^{nd}$ and $1^{st}$ gene positions, respectively (F1G2, with F and G in the reverse of their natural order G-F); F1G2 in which the F ORF has been codon optimized (F1BBG2); deletion of the NS1 gene (ΔNS1); addition of the 1030s mutation, consisting of the L assignments 1321K(AAA) and 1313S(TCA); addition of the Δ1313 and I1314L(CTG) mutations in L; and deletion of both the NS1 and NS2 genes (ΔNS1+2). The LID/F1BBG2/ΔNS1, LID/F1BBG2/ΔNS1/1030s, LID/F1BBG2/ΔNS1/Δ1313/I1314L, and LID/ΔNS1+2/F1BBG2 constructs shown contain the codon optimized F1BB2 ORF: parallel constructs called LID/F1G2/ΔNS1, LID/F1G2/ΔNS1/1030s, LID/F1G2/ΔNS1/Δ1313/I1314L, and LID/F1G2/ΔNS1+2 contained the non-optimized wild-type version (not shown).

The recombinant RSVs were recovered by reverse genetics (see Collins et al. 1995. Proc Natl Acad Sci USA 92:11563-7). RSVs were grown at 32° C. in Vero cells. The complete genome sequences of all viruses were confirmed by automated Sanger sequencing analysis of un-cloned RT-PCR products to be free of adventitious mutations detectable above background.

Assessment of the Recombinant RSVs In Vitro

Figure 4:
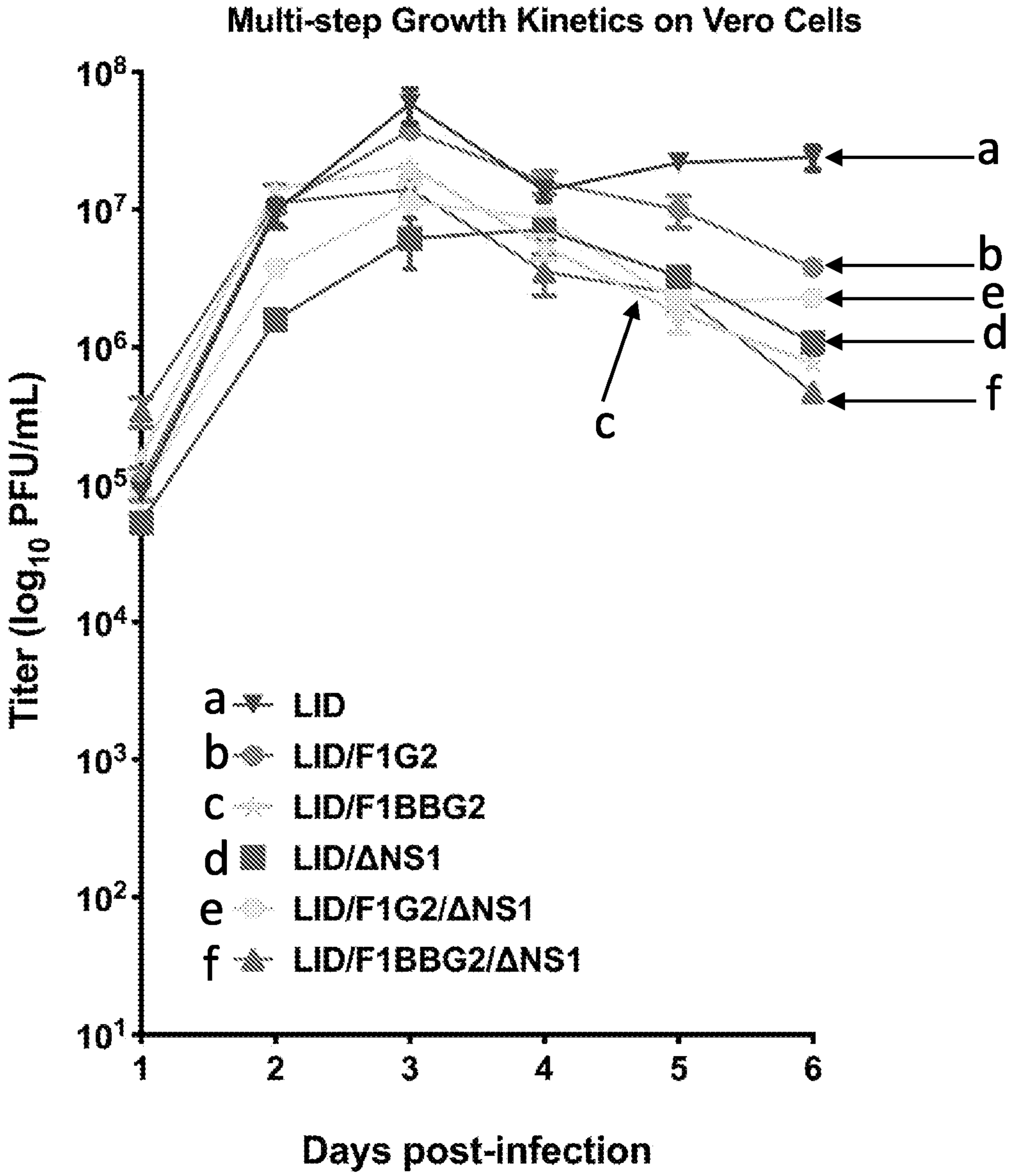
FIG. 4. Multi-cycle growth kinetics of the indicated recombinant RSVs in Vero cells. This shows that viruses bearing the LID, ΔNS1, F1G2, and F1BBG2 mutations in various combinations replicate to reasonable titers in Vero cells, the cell substrate for vaccine manufacture.

The kinetics and yield of multi-cycle replication of various recombinant RSV was assessed in African green monkey Vero cells (FIG. 4), which are unable to produce type I interferons in response to virus infection. This shows that viruses bearing the LID, ΔNS1, F1G2, and F1BBG2 mutations in various combinations replicate to reasonable titers in Vero cells, the cell substrate for vaccine manufacture. Note that the RSV LID virus is a wild-type-like virus and thus serves as a wild-type-like control in this and subsequent experiments.

Figure 5:
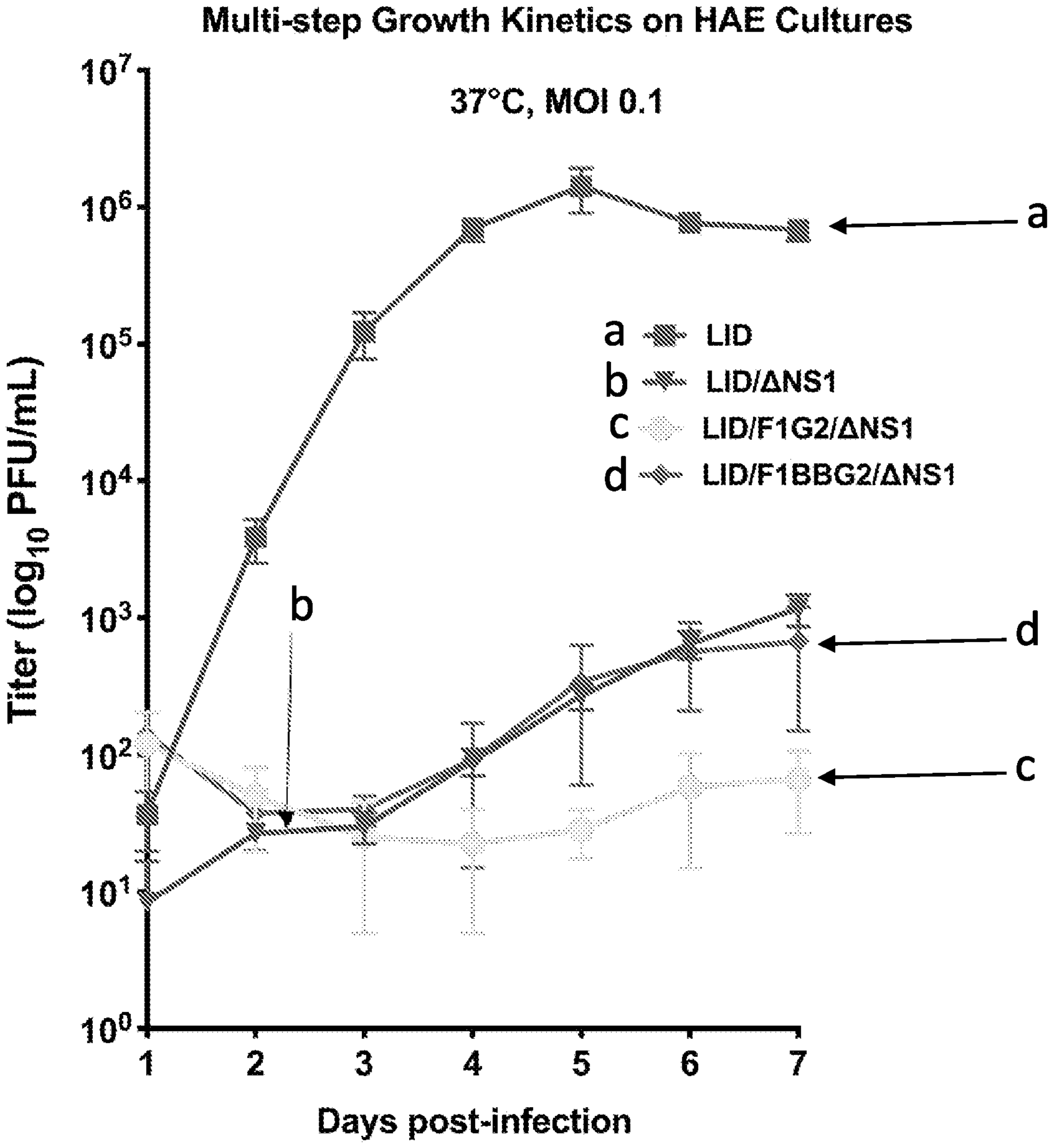
FIG. 5. Multi-cycle growth kinetics of the indicated recombinant RSVs in human airway epithelial (HAE) cell cultures. HAE cultures form a differentiated, polarized, pseudostratified, mucocilliary tissue that closely resembles authentic airway epithelium. Attenuated replication in these cultures is predictive of attenuated replication in non-human primates and humans. These data show that viruses bearing the ΔNS1, F1G2, and F1BBG2 modifications are strongly attenuated.

The multicycle growth kinetics of the various recombinant RSV were also assessed in human airway epithelial (HAE) cell cultures (FIG. 5). HAE cultures form a differentiated, polarized, pseudostratified, mucocilliary tissue that closely resembles authentic airway epithelium. Attenuated replication in these cultures is predictive of attenuated replication in non-human primates and humans. These data show that viruses bearing the ΔNS1 modification, alone or combined with the F1G2 and F1BBG2 modifications, was strongly attenuated compared to the RSV LID parent.

Figure 6:
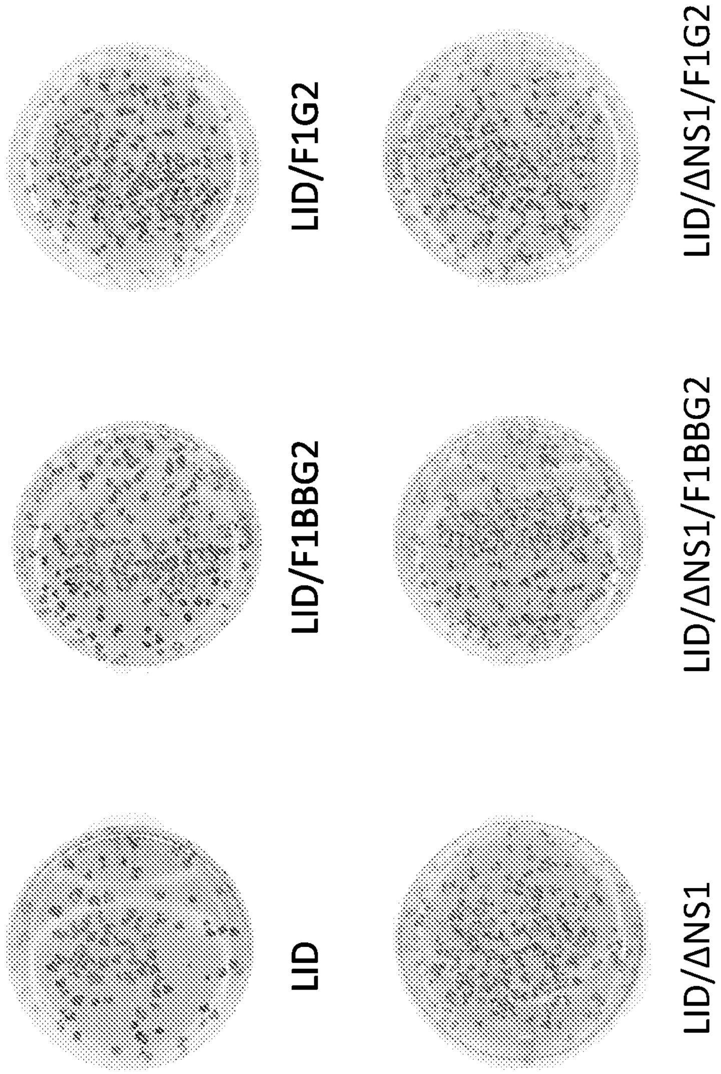
FIG. 6. Recombinant RSVs bearing the LID, F1BBG2, F1G2, and ΔNS1 mutations in various combinations readily form plaques on Vero cells.
Figure 7:
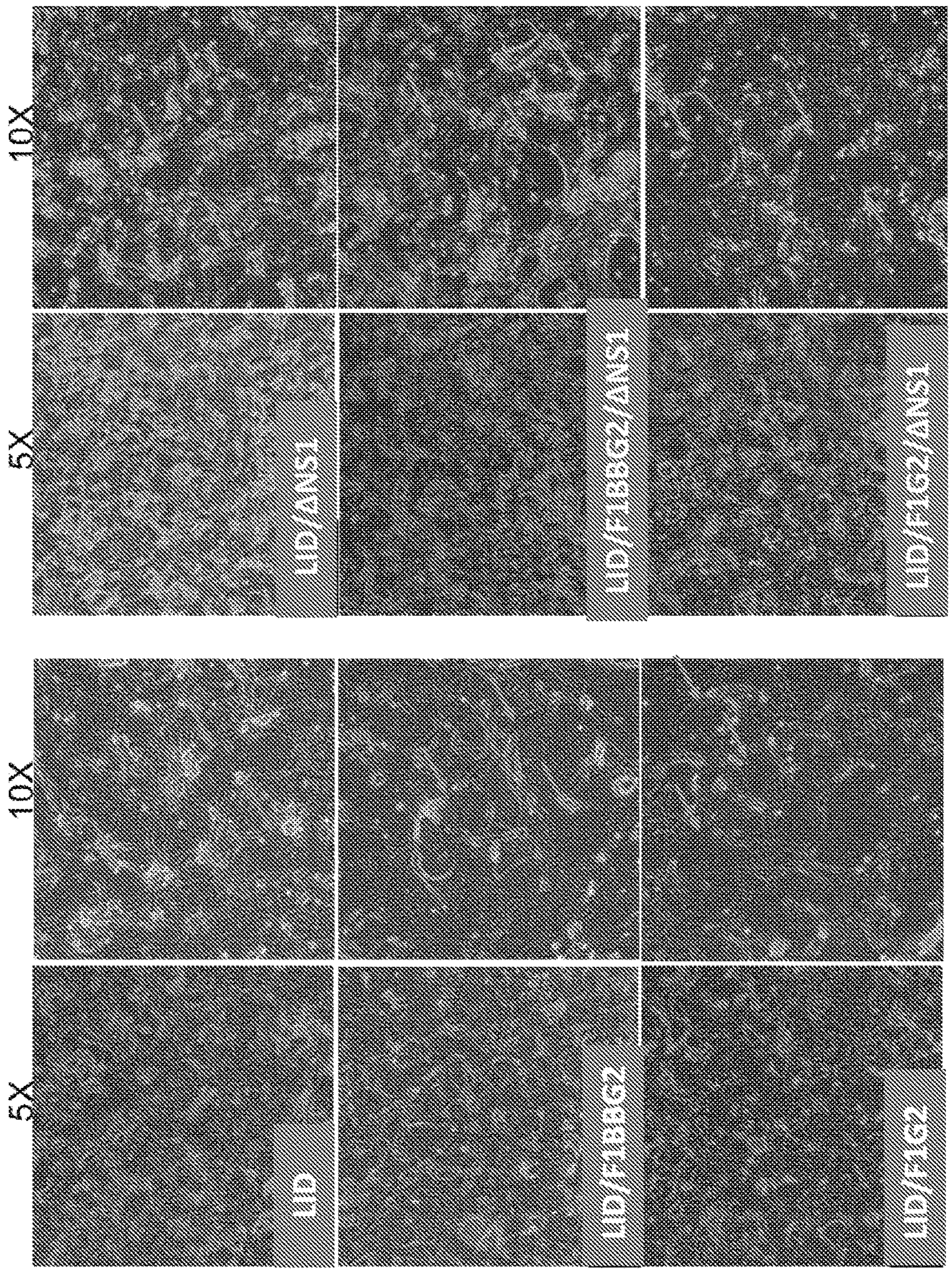
FIG. 7. Recombinant RSVs bearing the F1G2 and F1BBG2 gene shifts direct the formation of large syncytia in Vero cells during multi-cycle replication, consistent with increased expression of the F protein. Examples of syncytia are indicated with arrows.

The plaque- and syncytia forming properties of the recombinant RSVs were assessed on Vero cells (FIGS. 6 and 7). Recombinant RSVs bearing the LID, F1BBG2, F1G2, and ΔNS1 mutations in various combinations readily form plaques on Vero cells, and recombinant RSVs bearing the F1G2 and F1BBG2 gene shifts direct the formation of large syncytia in Vero cells during multi-cycle replication, consistent with increased expression of the F protein.

Figure 8:
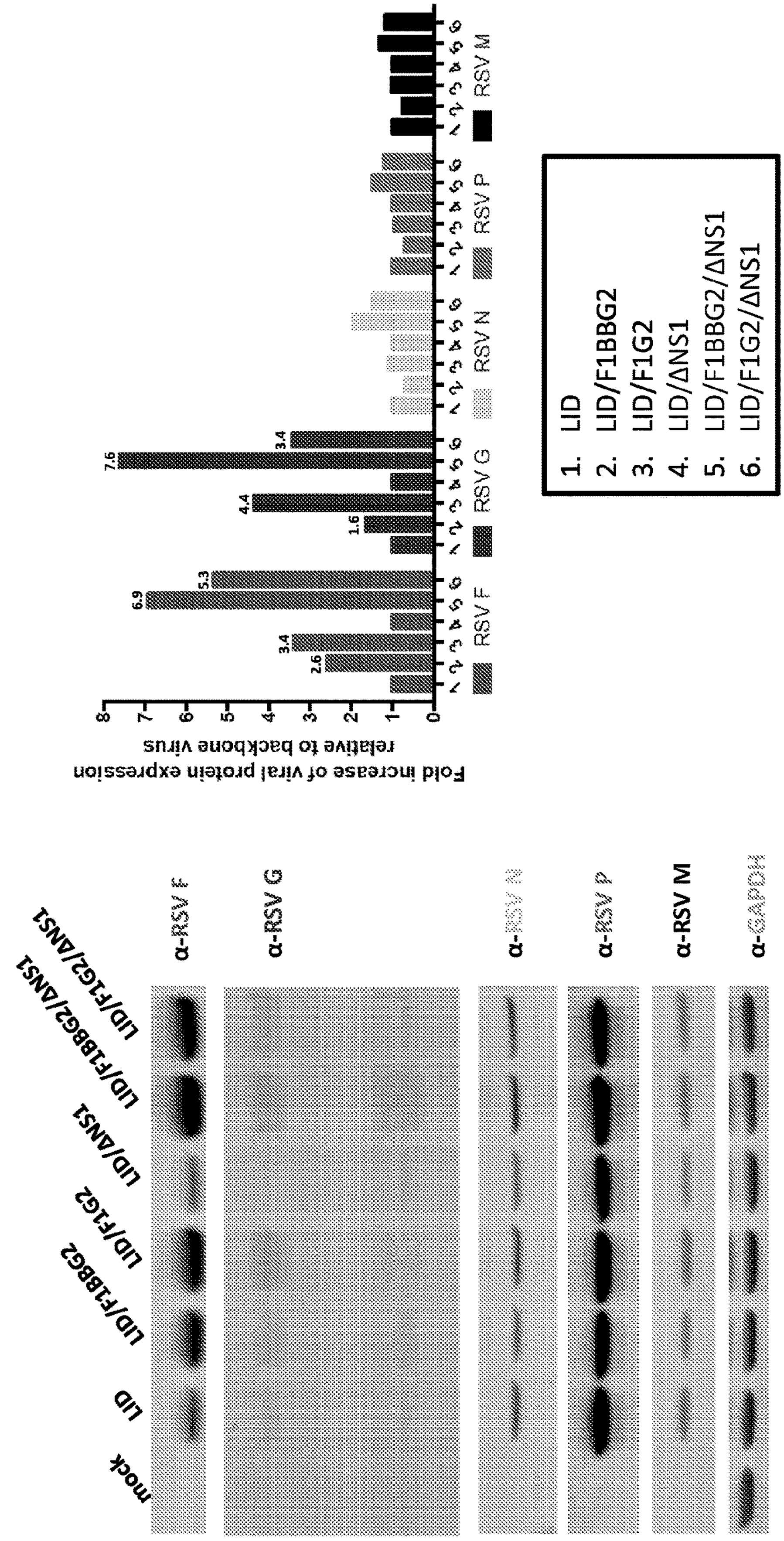
FIG. 8. Increased expression of the RSV F and G proteins in Vero cells infected with recombinant RSVs bearing the F1G2 and F1BBG2 modifications. Vero cells were infected at an MOI of 3 PFU/cell, and cells were harvested 24 h post-infection and analyzed by gel electrophoresis under denaturing and reducing conditions and Western blot analysis using antibodies of the indicated specificities. The levels of expression of the RSV F, G, N, P, and M proteins relative to RSV LID as 1.0 are shown at the right. This shows that the gene shifts of RSV G and F increase their expression with little effect on the other genes.

Additionally, Vero cells infected with recombinant RSVs bearing the F1G2 and F1BBG2 modifications showed increased expression of the RSV F and G proteins in Vero cells (FIG. 8), as determined by gel electrophoresis under denaturing and reducing conditions and Western blot analysis using antibodies of the indicated specificities, with the levels of RSV F, G, N, P, and M protein expression shown to the right relative to RSV LID as 1.0.

Figure 9:
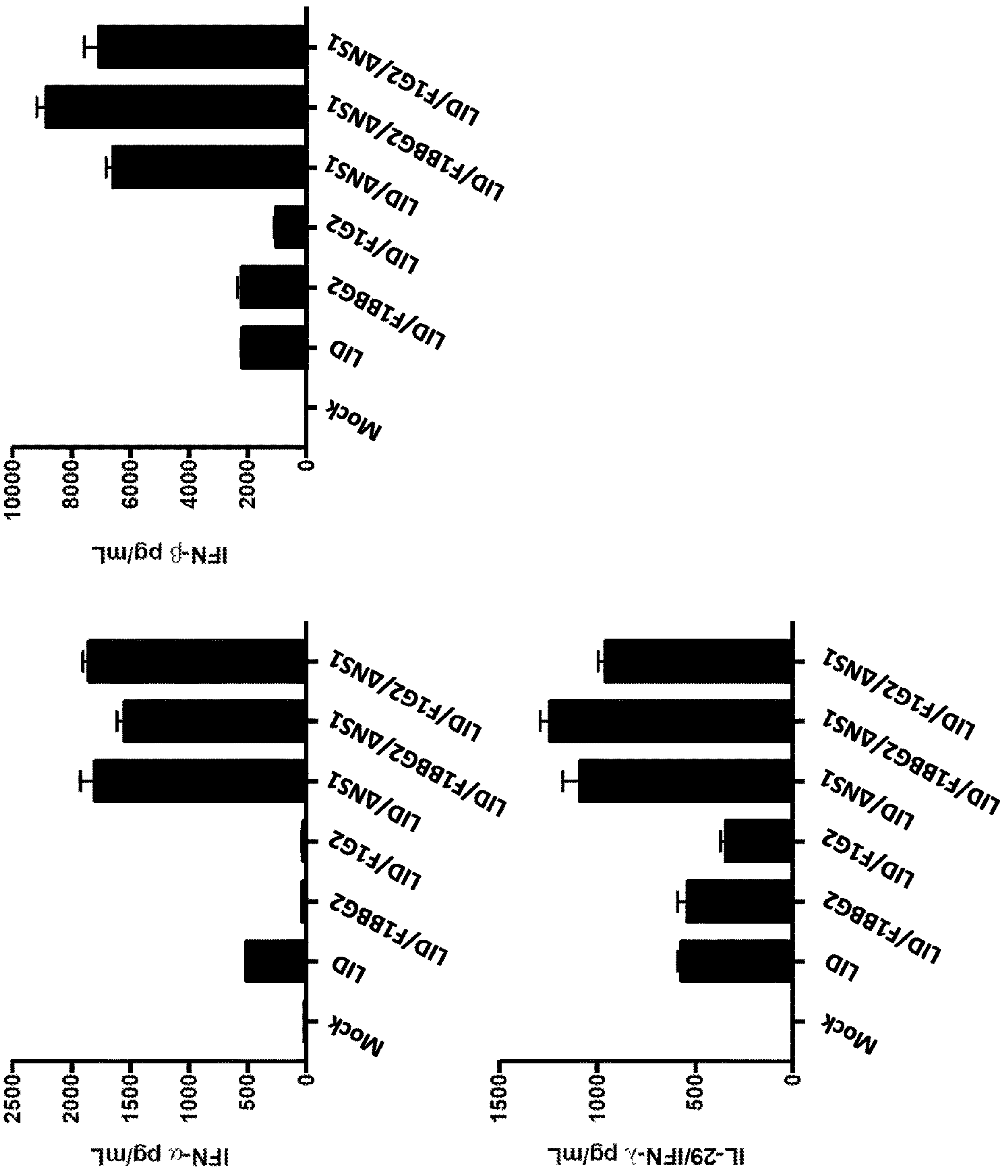
FIG. 9. Increased expression of type 1 (α, β) and type III (λ) interferons in human airway A549 cells infected with recombinant RSVs lacking the NS1 gene. A549 cells were infected with an MOI of 3 PFU/cell and tissue culture medium supernatants were collected 24 h post-infection. IFN concentrations were determined by ELISA. This shows that deletion of the RSV NS1 gene results in a substantial increase in the expression of host cell interferons.

The recombinant RSV were also assessed in human airway A549 cells, which are competent for interferon responses to viral infection. Cells infected with recombinant RSVs lacking the NS1 gene showed increased expression of type 1 (α, β) and type III (λ) interferons (FIG. 9). The A549 cells were infected with an MOI of 3 PFU/cell and tissue culture medium supernatants were collected 24 h post-infection. IFN concentrations in the medium supernatants were determined by ELISA. This showed that deletion of the NS1 gene resulted in a substantial increase in the expression of type I and type III interferons, which may stimulate immune responses and attenuate virus replication.

Assessment of the Recombinant RSVs in Experimental Animals

Figure 10A:
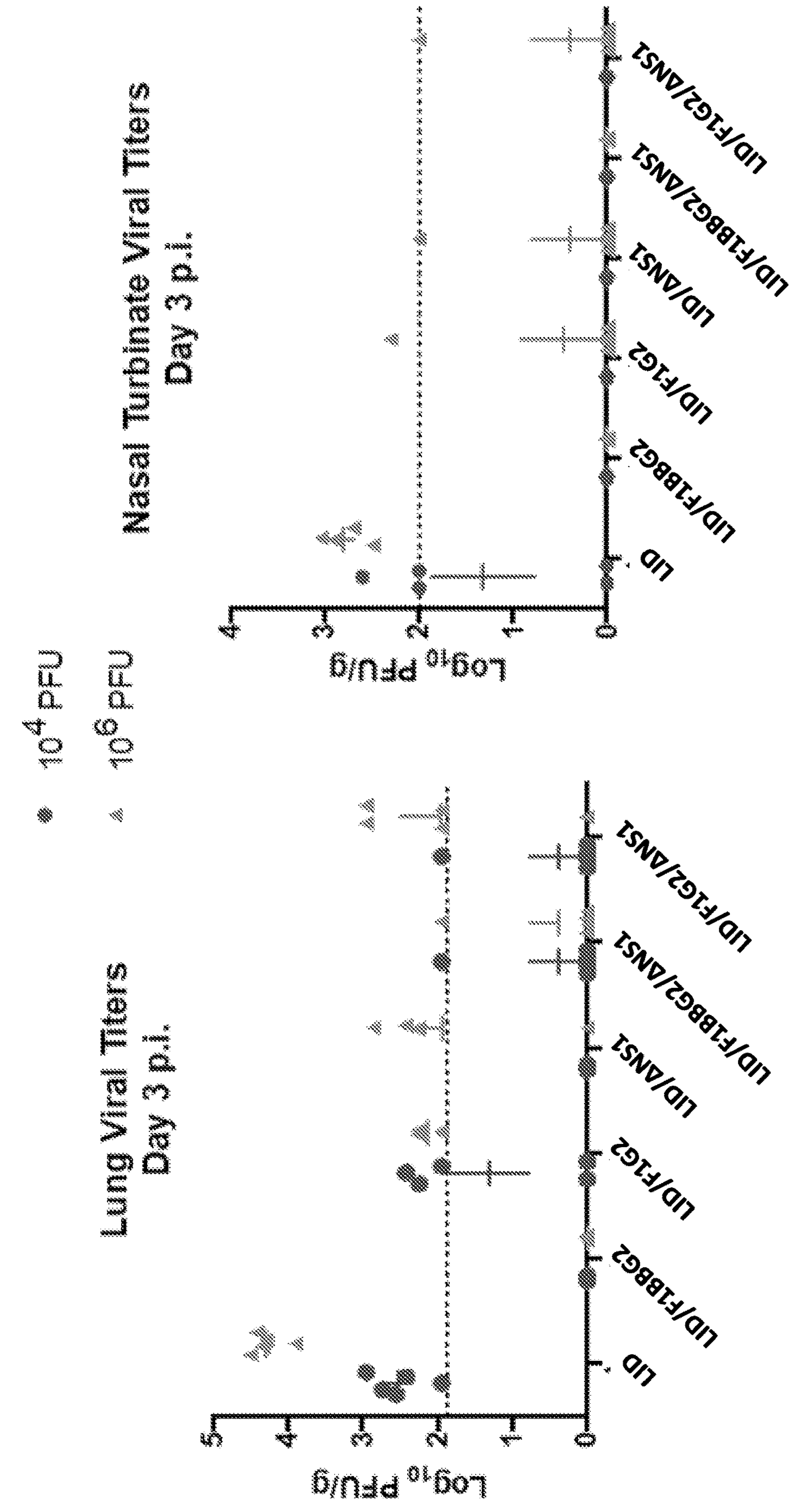
FIGS. 10A and 10B. The presence of the F1G2 or F1BBG2 or ΔNS1 modifications results in reduced RSV replication in the respiratory tract of mice. Six-week-old BALB/c mice were infected with a dose of $10^4$ or $10^6$ PFU per animal of each indicated RSV. Five animals per virus and dose were sacrificed at 3 (FIG. 10A) and 5 (FIG. 10B) days post-infection, and nasal turbinates and lungs were harvested, homogenized, and viral titers determined by plaque assay.
Figure 10B:
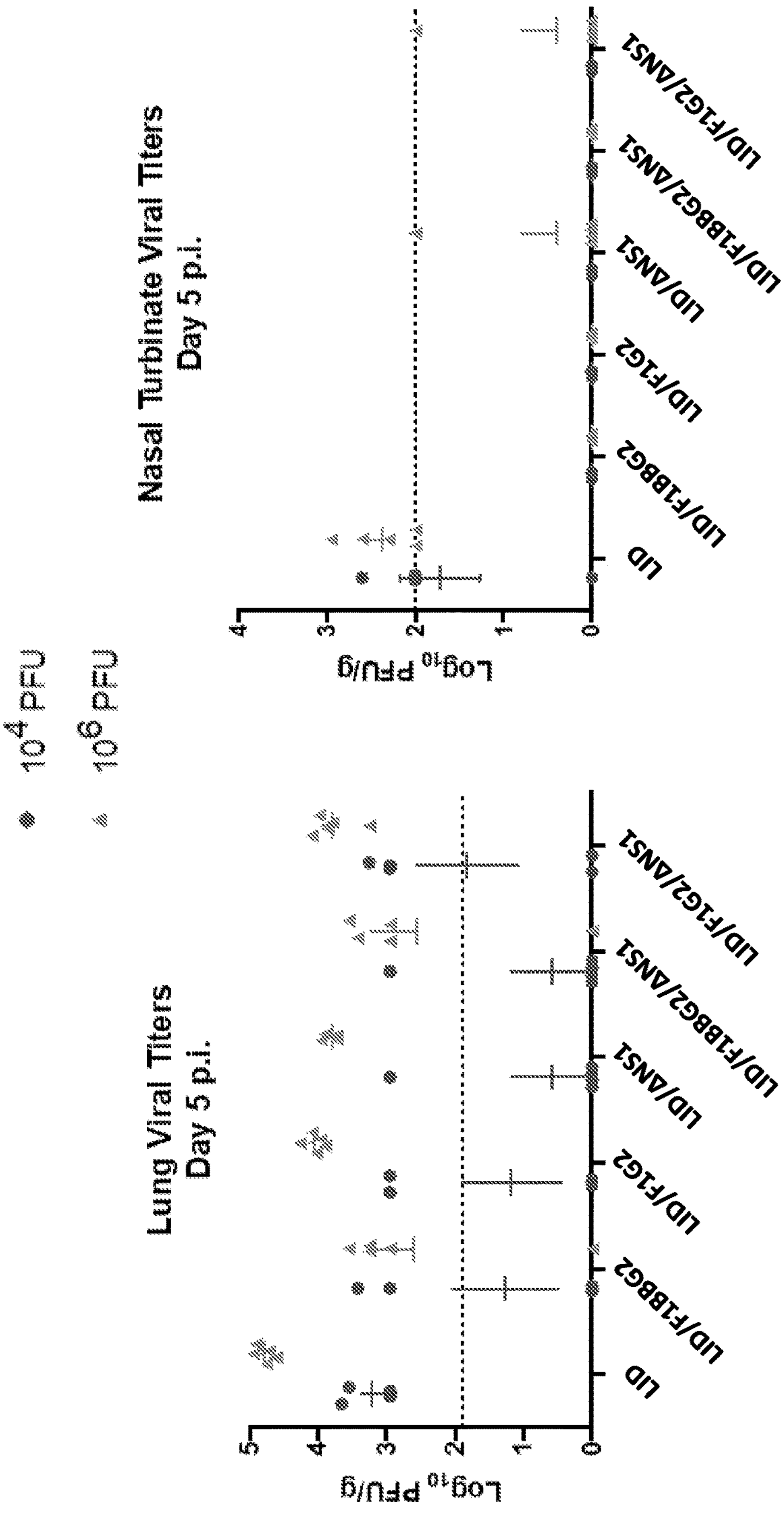

The recombinant RSVs were assessed in mice (FIG. 10). The presence of the F1G2 or F1BBG2 modifications with or without deletion of NS1 and the LID mutations led to reduced RSV replication in the upper and lower respiratory tract of mice compared to the RSV LID virus, which is a wild-type-like virus. For these assays, six-week-old BALB/c mice were infected with a dose of $10^4$ or $10^6$ PFU per animal of each indicated RSV. Five animals per virus and dose were sacrificed at 3 and 5 days post-infection, and nasal turbinates and lungs were harvested, homogenized, and viral titers determined by plaque assay.

Figure 11:
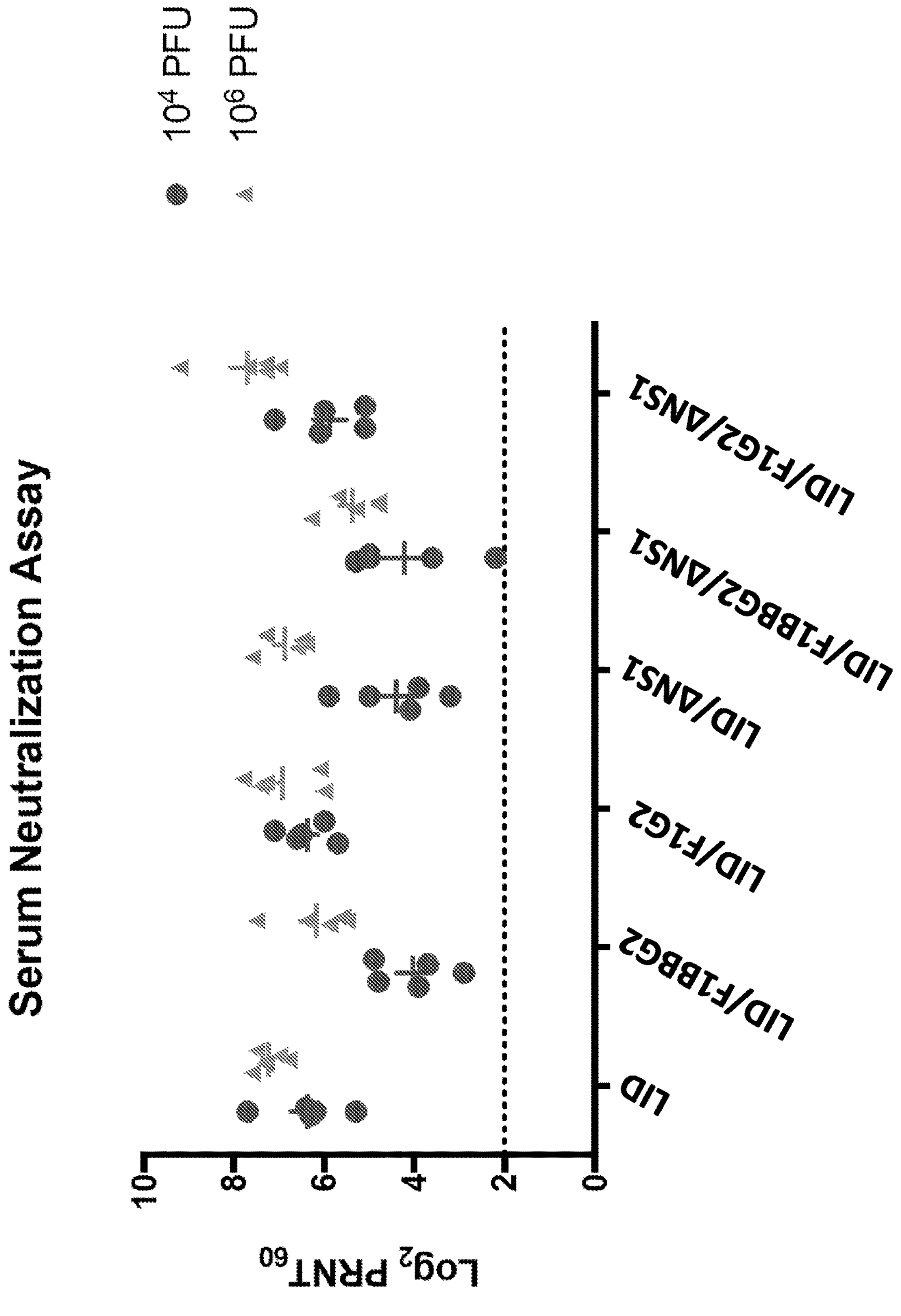
FIG. 11. Despite their restricted replication, recombinant RSVs bearing the indicated combinations of the ΔNS1, F1G2, and F1BBG2 modifications induced titers of RSV-neutralizing serum antibodies that compared well with the LID virus. Animals were infected as described in FIG. 10, and serum samples were collected 28 days post-infection.

Despite their restricted replication in the upper and lower respiratory tract, the recombinant RSVs bearing the indicated combinations of the LID, ΔNS1, F1G2, and F1BBG2 modifications induced titers of RSV-neutralizing serum antibodies that compared well with the LID virus, which is a wild-type-like virus (FIG. 11). For these assays, six-week-old BALB/c mice were infected with a dose of $10^4$ or $10^6$ PFU per animal of each indicated RSV, and serum samples were collected 28 days post-infection.

Figure 12:
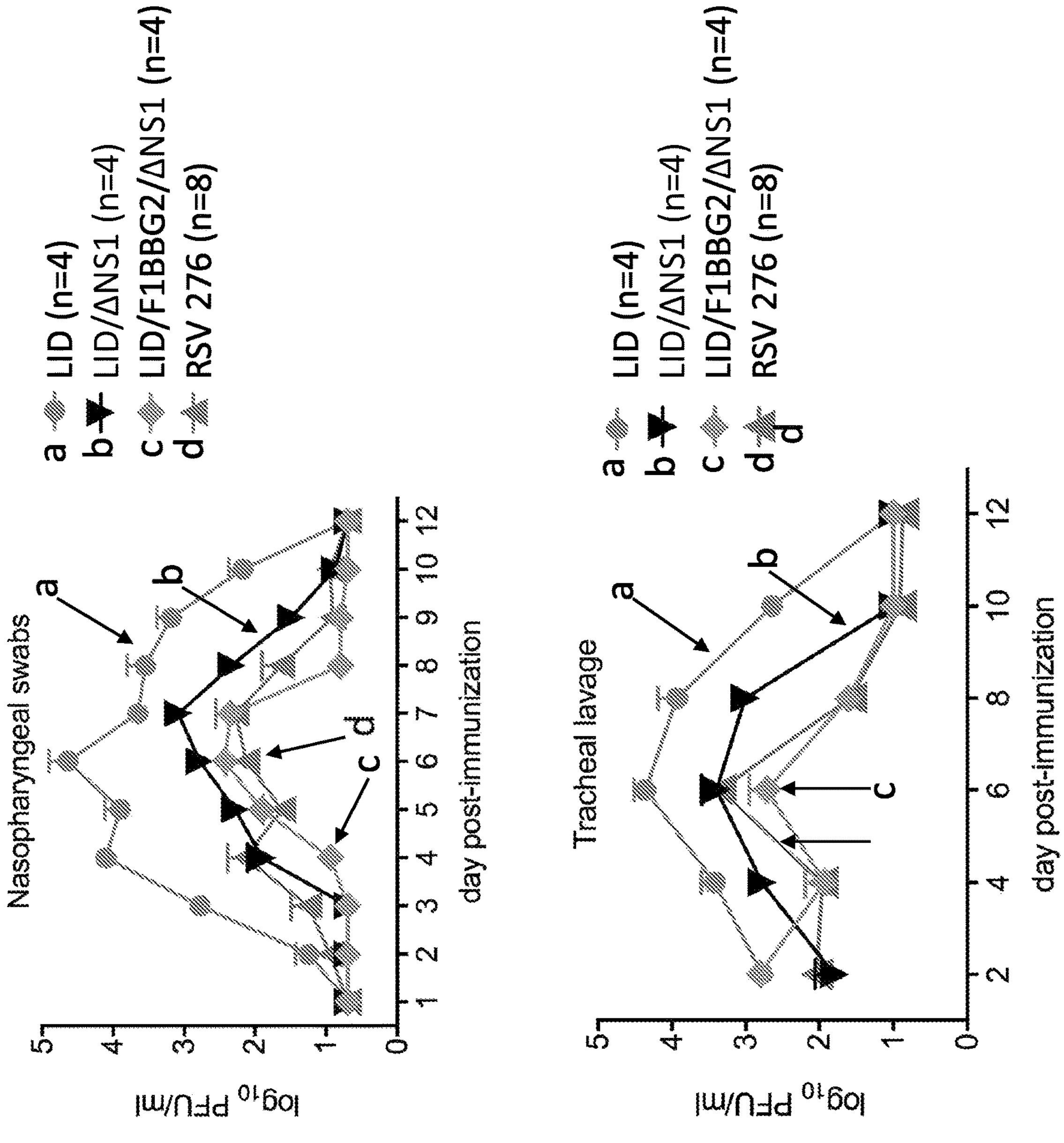
FIG. 12. AGM data from Tables 1 and 2.
Figure 13:
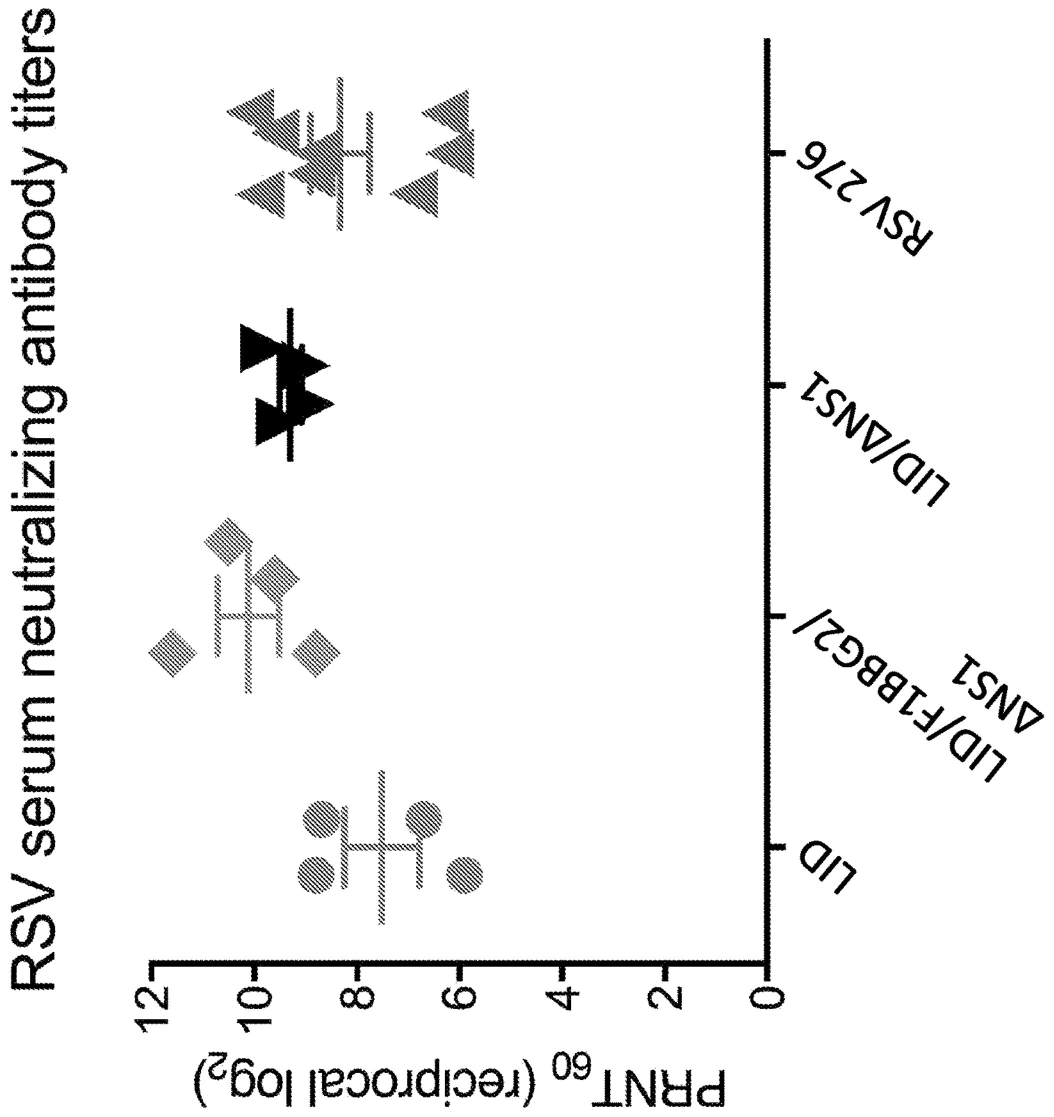
FIG. 13. AGM data from Table 3.

African green monkeys (AGMs) were used to assess RSV LID/ΔNS1 and LID/F1BBG2/ΔNS1, in comparison with the ΔNS2-bearing RSV ΔNS2/Δ1313/I1314L, the ΔM2-2-bearing RSV 276, and wild type virus. Four animals were infected for each virus, and virus titers were determined from nasopharyngeal and tracheal lavage samples from each animal (Tables 1 and 2; FIG. 12). Serum samples were also obtained from each animal, and serum $PRNT_{60}$ titers determined (Table 3; FIG. 13). The results show that LID/F1BBG2/ΔNS1 has a promising attenuation phenotype and elicits a superior immune response.

TABLE 1

Viral Titers of Nasopharyngeal Swab Samples from AGMs Inoculated with RSV ΔNS1 Mutants, Compared with ΔNS2 and ΔM2-2 Mutants and Recombinant wt RSV rA2.

| Virus Test Article[a] | AGM ID | NP virus titer ($log_{10}$ PFU/mL) on indicated days[b] 1 | 2 | 3 | 4 | 5 | 6 | 7 | 8 | 9 | 10 | 12/14 | Peak virus titer | Sum of daily titers[c] |
|---|---|---|---|---|---|---|---|---|---|---|---|---|---|---|
| Wt RSV A2 | 7209 | — | — | 3.1 | 4.4 | 4.4 | 5.2 | 3.6 | 4.1 | 3.4 | 2.0 | — | 5.2 | 31.3 |
| | 7467 | — | 0.7 | 2.8 | 3.8 | 2.1 | 3.9 | 3.4 | 3.2 | 1.9 | 2.0 | — | 3.9 | 24.5 |
| | 7468 | — | 1.7 | 2.6 | 4.0 | 3.9 | 3.7 | 3.6 | 2.7 | 3.6 | 2.6 | — | 4.0 | 29.1 |
| | 7492 | 0.7 | 1.2 | 2.3 | 3.9 | 2.9 | 3.9 | 3.9 | 2.4 | 1.7 | 1.0 | — | 3.9 | 24.3 |
| | Mean | | | | | | | | | | | | **4.2** | **27.2** |
| LID/ΔNS1 | 8960 | — | 0.7 | — | 1.7 | 2.2 | 2.7 | 2.8 | 1.8 | — | — | — | 2.8 | 13.7 |
| | 8992 | — | 0.7 | — | 0.7 | 2.6 | 2.7 | 2.9 | 2.6 | 1.9 | 0.7 | — | 2.9 | 15.8 |
| | 8904 | — | — | — | 1.7 | 1.2 | 2.4 | 2.8 | 1.3 | — | 1.2 | — | 2.8 | 12.3 |
| | 8951 | — | — | — | 2.3 | 2.3 | 3.1 | 3.5 | 2.6 | 1.5 | — | — | 3.5 | 17.0 |
| | Mean | | | | | | | | | | | | **3.0** | **14.7** |
| LID/ΔNS1/ | 8922 | — | 0.7 | — | — | 2.3 | 2.6 | 2.7 | — | — | — | — | 2.7 | 10.7 |
| F1BBG2 | 8974 | — | — | — | 1.3 | 1.8 | 2.7 | 2.5 | 0.7 | — | — | — | 2.7 | 11.1 |
| | 8966 | — | — | 0.7 | — | 1.8 | 2.2 | 1.7 | — | — | — | — | 2.2 | 8.9 |
| | 8994 | — | — | — | — | 1.0 | 1.0 | 1.5 | 1.0 | 1.0 | — | — | 1.5 | 7.6 |
| | Mean | | | | | | | | | | | | **2.2** | **9.2** |
| RSV ΔNS2/ | 7648 | — | — | 1.7 | 1.2 | 1.8 | 2.9 | 2.2 | 4.0 | 3.7 | 3.4 | — | 4.0 | 22.0 |
| Δ1313/I1314L | 7692 | — | — | — | — | 1.9 | — | — | 3.3 | 1.0 | 1.5 | — | 3.3 | 10.2 |
| | 7714 | — | — | 0.7 | — | 1.3 | — | — | 1.4 | 2.4 | 2.8 | — | 2.8 | 10.7 |
| | 7764 | — | — | — | 0.7 | 0.7 | 1.0 | — | 2.3 | 1.2 | 2.9 | — | 2.9 | 10.5 |
| | Mean | | | | | | | | | | | | **3.2** | **13.3** |
| RSV 276[d] | 8918 | — | — | — | — | — | — | — | — | — | — | — | — | 3.9 |
| | 8902 | — | 1.5 | 2.0 | 2.9 | 2.5 | 3.0 | 3.1 | 2.5 | 1.4 | 1.3 | — | 3.1 | 21.0 |
| | 8913 | — | — | — | — | — | 0.7 | 1.4 | 1.0 | — | — | — | 1.4 | 6.0 |
| | 8952 | — | — | — | — | 0.7 | 0.7 | 1.5 | — | — | 1.2 | — | 1.5 | 6.5 |
| | Mean | | | | | | | | | | | | **1.6** | **9.3** |

[a]Monkeys were inoculated i.n. and i.t. with $10^6$ PFU of the indicated virus in a 1 mL inoculum per site (total dose = $2 \times 10^6$ PFU/AGM).
[b]Virus titrations were performed on Vero cells. The lower limit of detection was 1.0 $log_{10}$ PFU/mL. Samples with no detectable virus are represented as "—".
Peak titers for each animal are underlined. Mean peak titers of [c]The sum of daily titers is used as an estimate for the magnitude of shedding (area under the curve). A value of 0.35 was used for samples with no detectable virus.
[d]A ΔM2-2 virus.

TABLE 2

Viral Titers of Tracheal Lavage Samples from AGMs Inoculated with RSV ΔNS1 Mutants, Compared with ΔNS2 and ΔM2-2 Mutants and Recombinant wt RSV rA2.

| Virus Test Article[a] | AGM ID | TL virus titer ($log_{10}$ PFU/mL) on indicated day[b] 2 | 4 | 6 | 8 | 10 | 12/14 | Peak virus titer | Sum of daily titers [c] |
|---|---|---|---|---|---|---|---|---|---|
| Wt RSV A2 | 7209 | 3.0 | 3.8 | 4.3 | 4.5 | 2.6 | — | 4.5 | 18.9 |
| | 7467 | 3.0 | 3.0 | 4.3 | 3.4 | 2.8 | — | 4.3 | 17.2 |
| | 7468 | 2.5 | 1.7 | 2.9 | 3.0 | 2.9 | — | 3.0 | 13.7 |
| | 7492 | 1.9 | 3.5 | 4.7 | 3.3 | — | — | 4.7 | 14.8 |
| | Mean: | | | | | | | **4.1** | **16.2** |
| LID/ΔNS1 | 8960 | — | — | 1.5 | 2.7 | — | — | 2.7 | 7.0 |
| | 8992 | — | 2.9 | 3.6 | 2.7 | 1.0 | — | 3.6 | 11.6 |
| | 8904 | 2.3 | 2.7 | 3.8 | 3.1 | — | — | 3.8 | 13.3 |
| | 8951 | — | 3.0 | 1.5 | 3.3 | — | — | 3.3 | 9.9 |
| | Mean: | | | | | | | **3.3** | **10.5** |
| LID/ΔNS1/ | 8922 | 3.0 | 2.5 | 1.3 | 1.3 | — | — | 3.0 | 9.5 |
| F1BBG2 | 8974 | 2.3 | 1.3 | 2.4 | 1.7 | — | — | 2.4 | 9.1 |
| | 8966 | 3.1 | — | 3.2 | — | — | — | 3.2 | 10.4 |
| | 8994 | 1.0 | — | 2.0 | — | — | — | 2.0 | 5.8 |
| | Mean: | | | | | | | **2.7** | **8.7** |
| RSV ΔNS2/ | 7648 | — | — | — | 1.5 | — | — | 1.5 | 5.0 |
| Δ1313/I1314L | 7692 | — | — | — | 1.0 | 1.7 | — | 1.7 | 5.5 |
| | 7714 | — | — | — | — | — | — | — | 4.2 |

TABLE 2-continued

Viral Titers of Tracheal Lavage Samples from AGMs Inoculated with RSV ΔNS1 Mutants, Compared with ΔNS2 and ΔM2-2 Mutants and Recombinant wt RSV rA2.

| Virus Test Article[a] | AGM ID | TL virus titer ($log_{10}$ PFU/mL) on indicated day[b] 2 | 4 | 6 | 8 | 10 | 12/14 | Peak virus titer | Sum of daily titers [c] |
|---|---|---|---|---|---|---|---|---|---|
| | 7764 | — | — | — | 1.3 | — | — | 1.3 | 4.8 |
| | Mean: | | | | | | | **1.4** | **4.9** |
| RSV 276[d] | 8918 | — | 1.7 | 2.3 | 1.6 | 1.0 | — | 2.3 | 8.0 |
| | 8902 | 2.2 | 1.6 | 2.9 | 2.1 | — | — | 2.9 | 10.3 |
| | 8913 | — | — | 3.2 | 1.3 | — | — | 3.2 | 7.3 |
| | 8952 | 1.8 | 2.1 | 1.6 | 1.8 | — | — | 2.1 | 8.8 |
| | Mean: | | | | | | | **2.6** | **8.6** |

[a]Monkeys were inoculated i.n. and i.t. with $10^6$ PFU of the indicated virus in a 1 mL inoculum per site (total dose = $2 \times 10^6$ PFU/AGM).
[b]Virus titrations were performed on Vero cells. The lower limit of detection was 1.0 $log_{10}$ PFU/mL. Samples with no detectable virus are represented as "—". Underlined value indicates maximum titer for each animal.
[c] The sum of daily titers is used as an estimate for the magnitude of shedding (area under the curve). Values of 0.7 are used for samples with no detectable virus.
[d]A ΔM2-2 virus.

TABLE 3

Serum $PRNT_{60}$ Titers in AGMs Inoculated with RSV ΔNS1 Mutants, Compared with ΔNS2 and ΔM2-2 Mutants and Recombinant wt RSV rA2.

| Virus Test Article | AGM ID | RSV Neutralization Titer (Log2 of reciprocal) on days 0 | 21 | 28 |
|---|---|---|---|---|
| Wt RSV rA2 | 7209 | <3.3 [a] | 7.1 | 6.7 |
| | 7467 | <3.3 | 8.1 | 8.7 |
| | 7468 | <3.3 | 5.9 | 5.9 |
| | 7492 | <3.3 | 7.7 | 8.8 |
| | Mean: | | 7.2 | 7.5 |
| LID/ΔNS1 | 8960 | <3.3 | 8.4 | 8.9 |
| | 8992 | <3.3 | 9.5 | 9.5 |
| | 8904 | <3.3 | 8.9 | 9.8 |
| | 8951 | <3.3 | 9.4 | 9.0 |
| | Mean: | | 9.1 | 9.3 |
| LID/F1BBG2/ΔNS1 | 8922 | <3.3 | 10.9 | 11.6 |
| | 8974 | <3.3 | 9.2 | 9.6 |
| | 8966 | <3.3 | 10.3 | 10.5 |
| | 8994 | <3.3 | 8.2 | 8.8 |
| | Mean: | | 9.7 | 10.1 |
| RSV ΔNS2/ Δ1313/I1314L | 7648 | <3.3 | 6.4 | 6.8 |
| | 7692 | <3.3 | 6.6 | 6.4 |
| | 7714 | <3.3 | 4.4 | 6.1 |
| | 7764 | <3.3 | 5.5 | 6.0 |
| | Mean: | | 5.8 | 6.3 |
| RSV 276 [b] | 8918 | <3.3 | 6.1 | 6.2 |
| | 8902 | <3.3 | 8.4 | 8.8 |
| | 8913 | <3.3 | 8.8 | 8.9 |
| | 8952 | <3.3 | 9.7 | 9.9 |
| | Mean: | | 8.4 | 8.5 |

[a] The lower limit of detection of the 60% Plaque Reduction assay is 3.3 ($Log_2$ of the dilution reciprocal). Samples below the lower limit of detection are recorded as "—".
[b] A ΔM2-2 virus.

Example 2

Assessment of Recombinant RSVs in Human Subjects

Information from studies in experimental animals often is not fully accurate for the prediction of the magnitude of attenuation, tolerability, and immunogenicity in humans, and in particular in infants and young children who are most at risk for RSV infection and are the primary targets of vaccine development. Further, experimental animals typically are adult animals with mature immune systems, compared to the immature and less-effective immune systems of infants and young children. Relevant to a respiratory virus, the size, structure, and composition of the upper and lower respiratory tracts of experimental animals can have differences compared to humans. In addition, the effects of deleting RSV accessory proteins—such as the NS1 and NS2 proteins described in the present disclosure—cannot be assumed to be identical in experimental animals and humans, since these viral proteins have evolved to interact with human host cell proteins and may not have the same interactions and effects with corresponding proteins in experimental animals. Thus, clinical trials in infants and young children are important for evaluation of candidate pediatric RSV vaccines.

Notably, most live-attenuated RSV strains that appeared to be promising as pediatric vaccine candidates based on pre-clinical studies including in experimental animals, and that were advanced to Phase I clinical studies, were found to be insufficiently promising to be advanced to further clinical studies. Karron et al recently reviewed clinical studies of 19 live-attenuated RSV strains as pediatric vaccine candidates evaluated over more than 25 years (Karron et al 2013 In Challenges and Opportunities for Respiratory Syncytial Virus Vaccines, Current Topics in Microbiology and Immunology 372, pp 259-284). Of ten biologically-derived live-attenuated RSV strains in that review, none had been found suitable for further study. Of nine additional recombinantly-derived live-attenuated candidates in that review, only one, RSV Medi/ΔM2-2 (Karron et al Sci Transl Med 312:ra175; ClinicalTrials.gov Identifier: NCT01459198), appeared possibly suitable for further clinical study but was not advanced. Subsequently, five additional recombinantly-derived live-attenuated RSV strains have been evaluated in Phase I clinical studies for which sufficient data were obtained to determine their suitability for further clinical evaluation. These additional strains are (i) RSV LID/ΔM2-2 (McFarland et al. 2018. Live-attenuated respiratory syncytial virus vaccine candidate with deletion of RSV synthesis regulatory protein M2-2 is immunogenic in children. J. Infect. Dis. 217:1347-55; ClinicalTrials.gov Identifier: NCT02040831 and NCT02237209); (ii) RSV D46/cp/M2-2 (ClinicalTrials-.gov Identifier NCT02601612); (iii) RSV LID/cp/ΔM2-2 (Cunningham et al. 2019. Live-attenuated respiratory syncytial virus vaccine with deletion of RNA synthesis regulatory protein M2-2 and cold-passage mutations is over-attenuated. Open Forum Infect Dis. 2019 May 6; 6(6): ofz212. doi: 10.1093/ofid/ofz212. eCollection 2019 June; ClinicalTrials.gov Identifier: NCT02890381 and NCT02948127); (iv) RSV LID/ΔM2-2/1030s (McFarland et al. 2020. Live respiratory syncytial attenuated by M2-2 deletion and stabilized temperature sensitivity mutation 1030s is a promising vaccine candidate in children. J. Infect. Dis. 221:534-43; ClinicalTrials.gov Identifier: NCT02952339 and NCT02794870), and (v) RSV D46/NS2/N/ΔM2-2-HindIII (McFarland et al. 2020. Live-attenuated respiratory syncytial virus vaccine with M2-2 deletion and with SH non-coding region is highly immunogenic in children. J. Infect. Dis. 2020 Feb. 1. pii: jiaa049. doi: 10.1093/infdis/jiaa049. [Epub ahead of print]; ClinicalTrials.gov Identifier: NCT03102034). Of these five additional viruses, only RSV LID/ΔM2-2/1030s appears suitable to advance to further clinical study. Therefore, out of a total of 24 live-attenuated RSV strains evaluated over more than 25 years that looked promising in pre-clinical studies and were advanced to pediatric clinical studies, only two (Medi/ΔM2-2 and LID/ΔM2-2/1030s) were considered candidates for further clnical study. Thus, clinical evaluation of live-attenuated RSV vaccine candidates in infants and young children is unpredictable and historically has not had a high success rate.

Figure 3A:
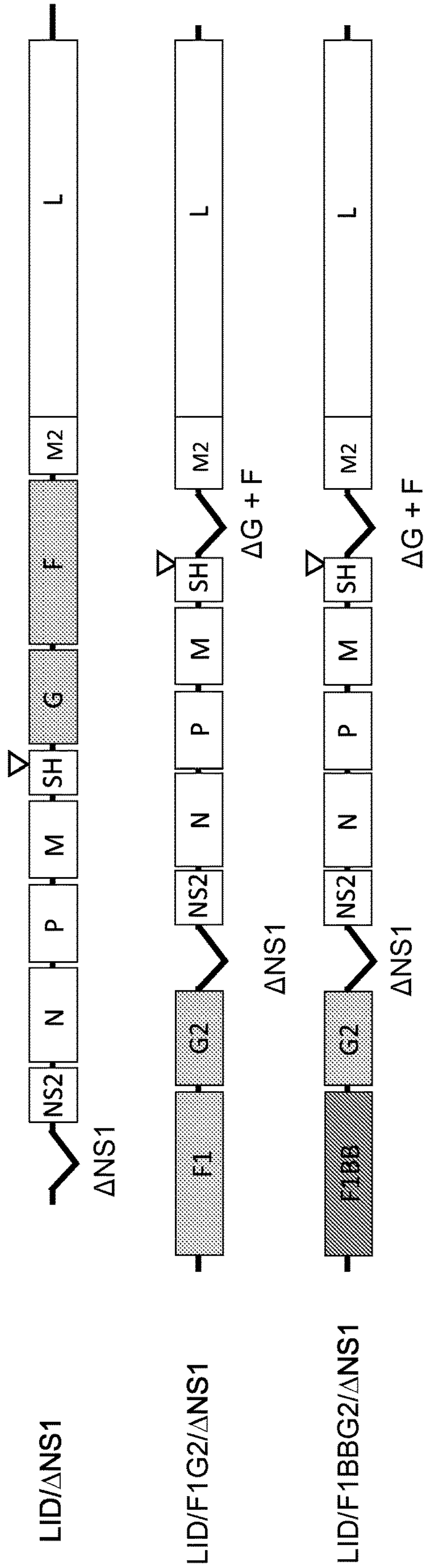
FIGS. 3A-3D. Genome maps of RSV strains bearing various combinations of mutations including the LID mutation (the LID mutation is indicated with an open triangle over the SH gene); deletion of G and F from their natural positions (ΔG+F) and shift to the $2^{nd}$ and $1^{st}$ gene positions, respectively (F1G2, with F and G in the reverse of their natural order G-F); F1G2 in which the F ORF has been codon optimized (F1BBG2); deletion of the NS1 gene (ΔNS1); addition of the "stabilized" 1030s mutation (i.e., refractory to de-attenuation), consisting of the L assignments 1321K(AAA) and 1313S(TCA); addition of the "stabilized" Δ1313 and I1314L(CTG) mutations (i.e., refractory to de-attenuation) in L; and deletion of both the NS1 and NS2 genes (ΔNS1+2).
Figure 3B:
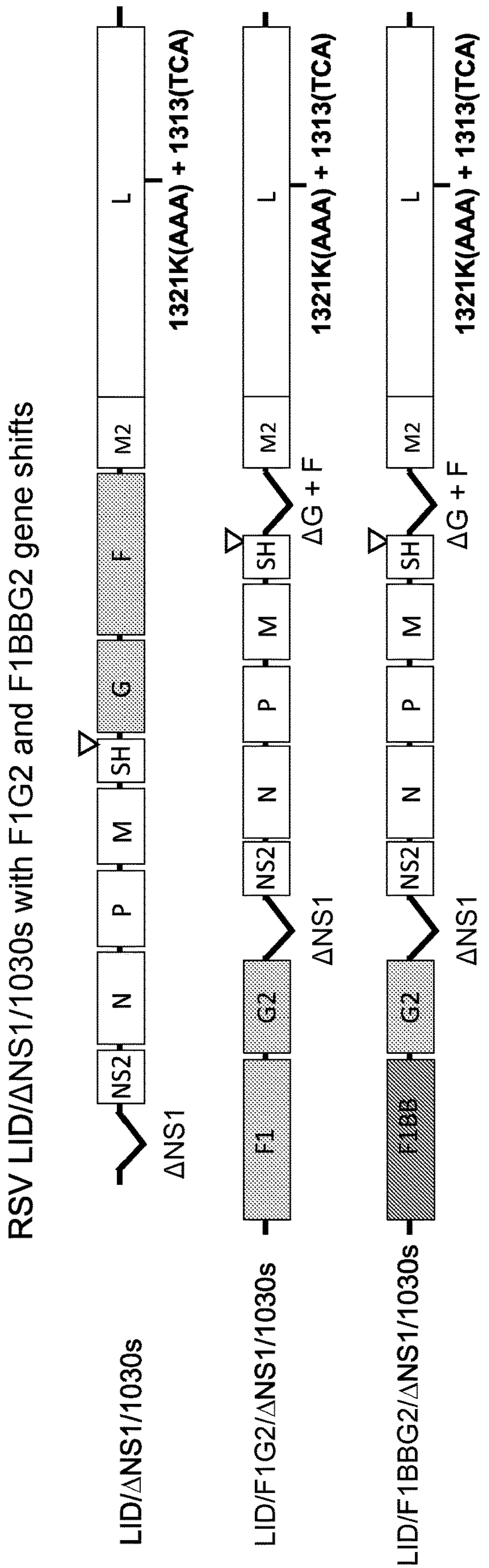
Figure 3C:
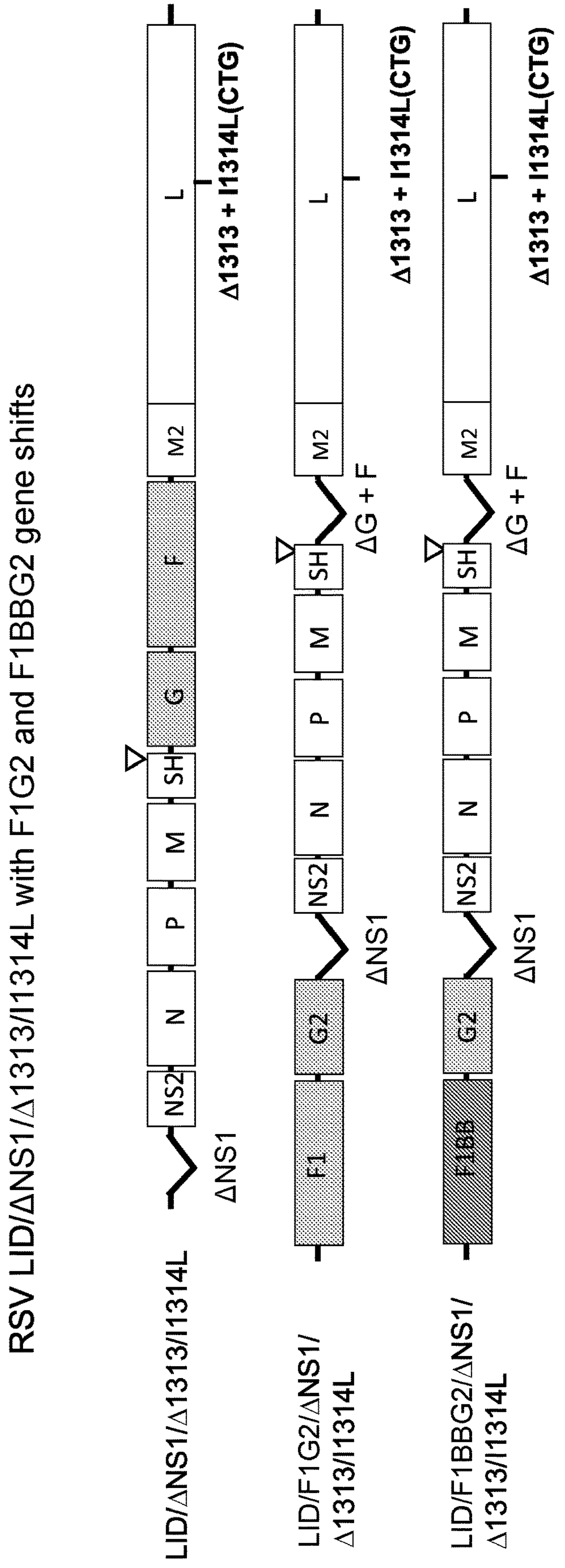
Figure 3D:
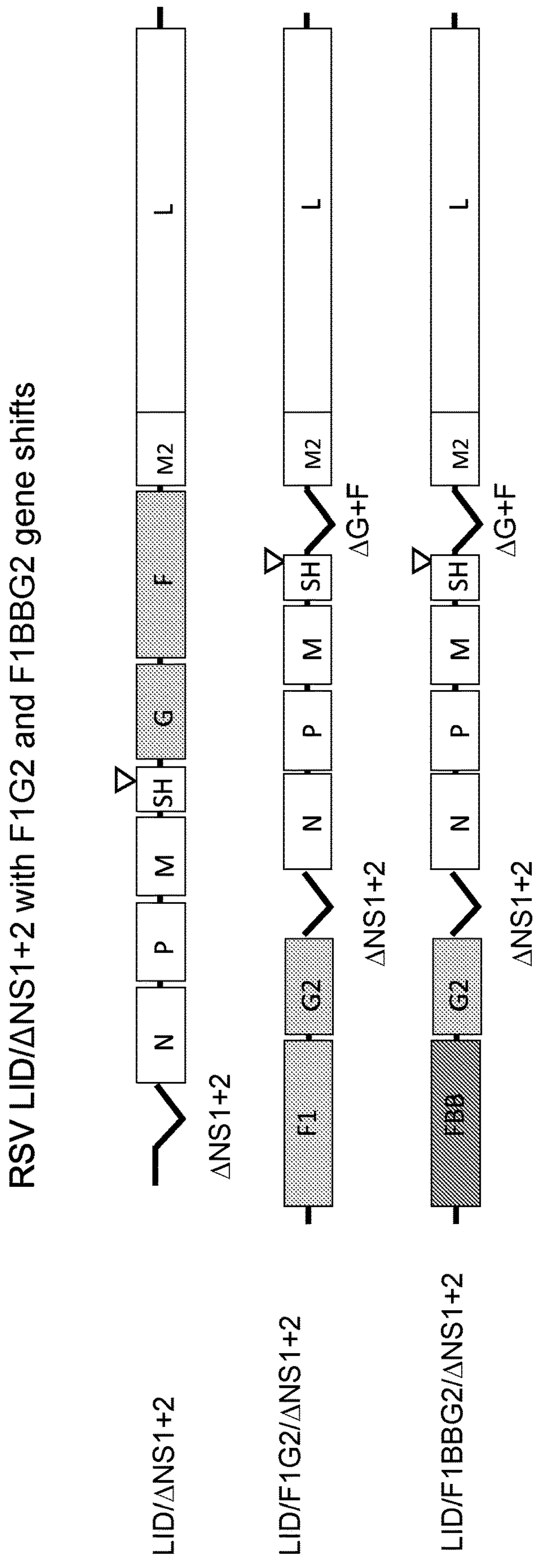

Two viruses in this disclosure were advanced to a Phase I clinical study in children as candidate live-attenuated pediatric RSV vaccines, namely RSV LID/ΔNS1 and RSV LID/F1G2/ΔNS1 (see FIG. 3A for genome maps). This study provides the first clinical evaluation of two independent modifications/mutations in a live RSV strain: (i) deletion of the NS1 gene and (ii) shifting the F and G genes from their usual positions 8 and 7, respectively, to positions 1 and 2, respectively. To prepare CTM acceptable for human use, seed virus for each mutant was generated de novo by reverse genetics from cDNAs electroporated into cGMP-qualified Vero cells that had been generated from World Health Organization Vero cells. cGMP-qualified CTM for each mutant was prepared from seed virus in the same cell substrate at Charles River Laboratories. Full-genome sequence analysis using RT-PCR amplification confirmed that the two preparations of seed virus and the two preparations of CTM were free of detectable adventitious mutations. Pre-clinical safety testing confirmed that the two preparations of CTM were suitable for human administration.

Single doses of LID/ΔNS1 and LID/FlG2/ΔNS1 were evaluated side-by-side with placebo recipients in sequential, randomized, double-blind, placebo-controlled studies in RSV-seropositive children aged 12-59 months at a dose of 6.0 $\log_{10}$ PFU (LID/ΔNS1) or 5.8 $\log_{10}$ PFU (LID/F1G2/ΔNS1) and in RSV-seronegative children aged 6-24 months at a dose of 5.0 $\log_{10}$ PFU. Children were randomized 2:2:1 to receive LID/ΔNS1, LID/F1G2/ΔNS1, or placebo, respectively, administered as nose drops (0.5 ml per subject, given as approximately 0.25 ml per nostril). The clinical protocol, consent forms, and Investigator's Brochure were developed by CIR and NIAID investigators; Investigational New Drug application, FDA revew, informed consent, Institutional Review Board review, randomization, blinding, unblinding, study conduct, and review by the NIAID Data Safety Monitoring Board were performed essentially as described previously (Karron et al. 2015. A gene deletion that up-regulates viral gene expression yields an attenuated RSV vaccine with improved antibody responses in children. Sci Transl Med7:312ra175.).

Children were enrolled between April 1 and October 31 each year, outside of RSV season. Clinical assessments were performed and nasal wash (NW) samples were obtained on the following days following vaccine administration: RSV-seropositive children, study days 0, 3-7 and 10; RSV-seronegative children, study days 0, 3, 5, 7, 10, 12, 14, 17, 28±1 day at each time point. Adverse events were collected through day 28 for RSV-seropositive and RSV-seronegative children; serious adverse events and LRIs were collected through day 56 for RSV-seronegative children, with additional physical examinations performed and NW samples obtained in the event of LRI. Fever, upper respiratory illness (URI; including rhinorrhea, pharyngitis, and hoarseness), cough, LRI, and otitis media were defined as described elsewhere (Karron et al. 1997. Evaluation of two live, cold-passaged, temperature-sensitive respiratory syncytial virus vaccines in chimpanzees and in adult humans. J Infect Dis 176:1428-36). When illnesses occurred, NW samples were tested for other viruses and *mycoplasma* by means of real-time reverse-transcription polymerase chain reaction (RT-PCR) (Respiratory Pathogens 21 kit; Fast Track Diagnostics, Luxembourg). Vaccine virus in NW fluid was quantified by immunoplaque assay using a mixture of 3 monoclonal antibodies (mAbs) to RSV F (mAbs 1129, 1243, and 1269 and by quantitative RT-PCR (RT-qPCR) (Karron 2015 ibid). Serum samples were obtained before inoculation and approximately 1 month after inoculation of RSV-seropositive participants and 2 months after inoculation of RSV-seronegative participants. Serum samples were tested for RSV-neutralizing antibodies using a complement-enhanced 60% RSV plaque-reduction neutralization assay, and for immunoglobulin G (IgG) antibodies to the RSV F glycoprotein using an enzyme-linked immunosorbent assay (Karron et al. 2015, ibid). The plaque reduction neutralization titer (PRNT) and RSV F IgG titer are expressed as reciprocal $\log_2$ values. Antibody responses were defined as ≥4-fold increases in titer compared to pre-vaccination titer. Infection with vaccine was defined as detection of vaccine virus by culture or RT-qPCR and/or a ≥4-fold rise in serum RSV PRNT or in RSV F IgG. The mean peak titer of vaccine virus shedding (in $\log_{10}$ PFU/mL) was calculated for infected vaccinees only. PRNT and RSV F IgG titers were transformed to $\log_2$ values for calculation of means, and the Student t test was used to compare means between groups. Serum antibody titers were calculated for all subjects: those with titers below the limit of detection were assigned values of 2.3 $\log_2$ (PRNT) and 4.6 $\log_2$ (ELISA). Rates of illness and antibody responses were compared using the 2-tailed Fisher exact test.

The RSV LID/ΔNS1 and LID/F1G2/ΔNS1 vaccine candidates were evaluated first in RSV-seropositive children 12-59 months of age in order to confirm that they were sufficiently attenuated to evaluate in RSV-seronegative children (Tables 4 and 5). The RSV-seropositive children were enrolled in years 2018 and 2019. Each vaccine was administered to 10 subjects each, and the placebo (consisting of L-15 tissue culture medium) was administered to 5 subjects. Mild respiratory or febrile illness occurring between study days 0 and 28 was observed in 30%, 50%, and 40% of participants who received RSV LID/ΔNS1, LID/F1G2/ΔNS1, and placebo, respectively (Table 4). No instances of lower respiratory tract illness (LRI) were observed during this period. In the vaccine recipients, each of these incidents of mild respiratory/febrile illness was contemporaneous with detection of adventitious respiratory pathogens (data not shown). None of the subjects in any group shed detectable vaccine virus, indicative of attenuation (Table 4). A single vaccine recipient (LID/F1G2/ΔNS1 group) had a ≥4-fold rise in serum RSV-neutralizing and RSV-F-binding antibodies, but without detected vaccine virus shedding or adventitious RSV (Tables 4 and 5). This low level of immunogenicity also was indicative of attenuation. Thus, both of these new vaccine candidates were sufficiently attenuated to be advanced to evaluation in RSV-seronegative, younger children.

Therefore, the RSV LID/ΔNS1 and LID/F1G2/ΔNS1 vaccine candidates were evaluated in RSV-seronegative children 6-24 months of age, the age group that likely will be the major target for a pediatric RSV vaccine (Tables 5 and 6). Enrollment initiated in 2019 and is still in progress. Data are available for 4 subjects in each vaccine group and 2 placebo recipients (complete enrollment will be 14-20 subjects per vaccine group and 7-10 for the placebo recipients, for a total of 35-50 subjects). Mild respiratory or febrile illness between study days 0 and 28 was observed in 50%, 75%, and 50% of participants who received RSV LID/ΔNS1, LID/F1G2/ΔNS1, and placebo, respectively (Table 6). None of these incidents appeared to be linked to vaccine virus shedding (data not shown). There were no incidents of LRI. Two of the vaccine recipients in the LID/ΔNS1 group shed vaccine virus, with mean peak titers of 2.1 $\log_{10}$ PFU (culture) and 5.4 $\log_{10}$ copy number (RT-PCR). In the LID/F1G2/ΔNS1 group, all four of the vaccine recipients shed vaccine virus detectable by culture and/or RT-PCR, with mean peak titers of 1.3 $\log_{10}$ PFU (culture) and 3.9 $\log_{10}$ copy number (RT-PCR) (Table 6). A ≥4-fold rise in serum RSV-neutralizing and/or RSV-F-binding antibodies was not observed for any recipients of the RSV LID/ΔNS1 virus, but was detected for 75% of the recipients of the RSV LID/F1G2/ΔNS1 virus, with mean titers of 5.5 $\log_2$ (PRNT) and 10.8 $\log_2$ (ELISA)(Table 7).

Based on these initial data, the two new viruses (LID/ΔNS1 and LID/F1G2/ΔNS1) appeared to be highly attenuated and well-tolerated (attenuated). In both RSV-seropositive and RSV-seronegative subjects, the frequency of mild respiratory/febrile disease was approximately the same as for placebo recipients, and usually appeared to be contemporaneous with adventitious agents.

Both viruses appeared to be highly restricted. In RSV-seropositive subjects, there was no observed shedding of either virus, whether assayed by culture or RT-PCR, and only one vaccine recipient had a serum RSV-specific antibody response. In RSV-seronegative subjects, 50% of recipients of LID/ΔNS1 shed virus detected by culture and RT-PCR, but only at low titers. In RSV-seronegative subjects, 50% and 100% of recipients of LID/F1G2/ΔNS1 shed virus detected by culture and RT-PCR, respectively, and only at low titers.

In RSV-seronegative recipients, the LID/ΔNS1 virus did not induce ≥4-fold increases in serum RSV-PRNT and ELISA antibody responses, whereas the LID/F1G2/ΔNS1 virus induced ≥4-fold increases in serum RSV-PRNT and ELISA antibodiesin 75% of recipients.

In summary, this study provided the first evaluation in humans of two modifications to a live-attenuated RSV vaccine candidate: (i) deletion of the NS1 gene, and (ii) shifting the positions of the F and G genes from 8 and 7 to 1 and 2, respectively. Deletion of the NS1 gene resulted in viruses that were highly attenuated, well-tolerated highly-restricted and, in the case of LID/F1G2/ΔNS1, moderately immunogenic. The F1G2 gene shift appeared to increase immunogenicity, increasing the percentage of recipients with a ≥4-fold serum antibody response from 0% (LID/ΔNS1) to 75% (LID/F1G2/ΔNS1). This study remains in progress and will enroll additional RSV-seronegative subjects 6-24 months of age.

The available data raised the possibility that these viruses may be over-attenuated at the dose of 5.0 $\log_{10}$ PFU, since we generally consider it preferable to have a frequency of infectivity detected by culture of approximately 85% or greater, and to have mean peak titers of shed virus detected by culture of 3.0 to 4.0 $\log_{10}$ PFU/ml in order to have sufficient antigenic load. Of course, further data from the ongoing clinical study should have clarify the properties of these viruses. If either or both viruses are deemed to be over-attenuated, this likely can be compensated for by increasing the dose from 5.0 $\log_{10}$ PFU to 6.0 $\log_{10}$ PFU, as was done previously with another live-attenuated RSV candidate described below.

We previously evaluated, in RSV-seropositive and RSV-seronegative children, a virus called RSV ΔNS2/Δ1313/I1314L (with deletion of the NS2 gene and the presence of the Δ1313 codon deletion in L and stabilizing I1314L mutation in L) (Karron 2019. Safety and Immunogenicity of the Respiratory Syncytial Virus Vaccine RSV/ΔNS2/Δ1313/I1314L in RSV-Seronegative Children. J Infect Dis. pii: jiz408. doi: 10.1093/infdis/jiz408. [Epub ahead of print]; ClinicalTrials.gov Identifier: NCT01893554). When administed to RSV-seronegative children at a dose of 5.0 $\log_{10}$ PFU, the RSV ΔNS2/Δ1313/I1314L virus was well-tolerated. Shedding was detectable in 1 of 15 recipients by culture (peak titer 1.4 $\log_{10}$ PFU/ml) and in 11 of 15 recipients by RT-PCR (mean peak titer 3.0 $\log_{10}$ copies/ml). When administered at the 10-fold higher dose of 6.0 $\log_{10}$ PFU, infectivity was substantially improved, with shedding detected in 16 of 20 recipients by culture (mean peak titer of 1.8 $\log_{10}$ PFU/ml) and 18 of 20 recipients by RT-PCR (mean peak titer of 3.5 $\log_{10}$ copies/ml). Importantly, the percentage of recipients with a ≥4-fold rise in serum PRNT increased from 53% to 80%. The increase in dose had no effect on tolerability: the incidence of mild respiratory/febrile illness at the 5.0 and 6.0 $\log_{10}$ doses was 73% and 55%, respectively, compared to 14% and 70% for each respective placebo recipient group.

In conclusion, a Phase I clinical study in RSV-seronegative children 6-24 months of age showed that, at a dose of 5.0 $\log_{10}$ PFU, RSV LID/ΔNS1 and LID/F1G2/ΔNS1 are highly-attenuated, highly restricted, well tolerated, and that LID/F1G2/ΔNS1 is moderately immunogenic. Shifting the F and G genes to positions 1 and 2 was associated with increased immunogenicity.

TABLE 4

Clinical and virologic responses of RSV-seropositive children 12 to 59 months of age to $10^6$ PFU of recombinant live-attenuated respiratory syncytial virus vaccine, RSV LID/ΔNS1, or $10^{5.8}$ PFU of RSV LID/F1G2/ΔNS1, or placebo.

| | | Viral Detection (Immunoplaque assay) | | | Viral Detection (PCR) | | | | | |
|---|---|---|---|---|---|---|---|---|---|---|
| Group, Subject number | Age at Inoculation (months) | Duration | Days | Peak Titer (log10) | Duration | Days | Peak Copy Number (log10) | Respiratory or Febrile Illness | Any Antibody Response | Infected |
| RSV LID/ΔNS1 | | | | | | | | | | |
| 1 | 59 | 0 | 0 | 0.5 | 0 | 0 | 1.7 | 0 | 0 | 0 |
| 2 | 59 | 0 | 0 | 0.5 | 0 | 0 | 1.7 | 1 | 0 | 0 |
| 3 | 38 | 0 | 0 | 0.5 | 0 | 0 | 1.7 | 0 | 0 | 0 |
| 4 | 22 | 0 | 0 | 0.5 | 0 | 0 | 1.7 | 1 | 0 | 0 |
| 5 | 25 | 0 | 0 | 0.5 | 0 | 0 | 1.7 | 0 | 0 | 0 |
| 6 | 24 | 0 | 0 | 0.5 | 0 | 0 | 1.7 | 1 | 0 | 0 |
| 7 | 38 | 0 | 0 | 0.5 | 0 | 0 | 1.7 | 0 | 0 | 0 |
| 8 | 39 | 0 | 0 | 0.5 | 0 | 0 | 1.7 | 0 | 0 | 0 |
| 9 | 29 | 0 | 0 | 0.5 | 0 | 0 | 1.7 | 0 | 0 | 0 |
| 10 | 51 | 0 | 0 | 0.5 | 0 | 0 | 1.7 | 0 | 0 | 0 |
| Mean | 38.4 | 0 | 0 | 0.5 | 0 | 0 | 1.7 | 3/10 | 0/10 | 0/10 |
| SD | 14.0 | 0 | 0 | 0.0 | 0 | 0 | 0.0 | | | |
| RSV LID/F1G2/ΔNS1 | | | | | | | | | | |
| 11 | 59 | 0 | 0 | 0.5 | 0 | 0 | 1.7 | 1 | 0 | 0 |
| 12 | 54 | 0 | 0 | 0.5 | 0 | 0 | 1.7 | 1 | 0 | 0 |
| 13 | 37 | 0 | 0 | 0.5 | 0 | 0 | 1.7 | 0 | 0 | 0 |
| 14 | 53 | 0 | 0 | 0.5 | 0 | 0 | 1.7 | 1 | 0 | 0 |
| 15 | 25 | 0 | 0 | 0.5 | 0 | 0 | 1.7 | 1 | 0 | 0 |
| 16 | 26 | 0 | 0 | 0.5 | 0 | 0 | 1.7 | 0 | 0 | 0 |
| 17 | 44 | 0 | 0 | 0.5 | 0 | 0 | 1.7 | 0 | 1 | 1 |
| 18 | 33 | 0 | 0 | 0.5 | 0 | 0 | 1.7 | 1 | 0 | 0 |
| 19 | 17 | 0 | 0 | 0.5 | 0 | 0 | 1.7 | 0 | 0 | 0 |
| 20 | 51 | 0 | 0 | 0.5 | 0 | 0 | 1.7 | 0 | 0 | 0 |
| Mean | 39.9 | 0 | 0 | 0.5 | 0 | 0 | 1.7 | 5/10 | 1/10 | 1/10 |
| SD | 14.4 | 0 | 0 | 0.0 | 0 | 0 | 0.0 | | | |
| Placebo | | | | | | | | | | |
| 21 | 28 | 0 | 0 | 0.5 | 0 | 0 | 1.7 | 1 | 0 | 0 |
| 22 | 34 | 0 | 0 | 0.5 | 0 | 0 | 1.7 | 0 | 0 | 0 |
| 23 | 49 | 0 | 0 | 0.5 | 0 | 0 | 1.7 | 0 | 0 | 0 |
| 24 | 36 | 0 | 0 | 0.5 | 0 | 0 | 1.7 | 1 | 0 | 0 |
| 25 | 18 | 0 | 0 | 0.5 | 0 | 0 | 1.7 | 0 | 0 | 0 |
| Mean | 33 | 0 | 0 | 0.5 | 0 | 0 | 1.7 | 2/5 | 0/5 | 0/5 |
| SD | 11.4 | 0 | 0 | 0.0 | 0 | 0 | 0.0 | | | |

TABLE 5

Immunologic responses of RSV-seropositive children 12 to 59 months of age to $10^6$ PFU of recombinant live-attenuated respiratory syncytial virus vaccine, RSV LID/ΔNS1, or $10^{5.8}$ PFU of RSV LID/F1G2/ΔNS1, or placebo.

| | | Serum RSV neutralizing antibody (reciprocal log2) | | | Serum IgG ELISA RSV F antibody (reciprocal log2) | | |
|---|---|---|---|---|---|---|---|
| Group, Subject number | Age at Inoculation (months) | Pre-inoculation | Post-inoculation | ≥4 fold rise | Pre-inoculation | Post-inoculation | ≥4 fold rise |
| RSV LID/ΔNS1 | | | | | | | |
| 1 | 59 | 7.8 | 7.3 | 0 | 13.4 | 13.1 | 0 |
| 2 | 59 | 10.5 | 10.1 | 0 | 17.2 | 15.8 | 0 |
| 3 | 38 | 6.9 | 7.2 | 0 | 14.2 | 14.1 | 0 |
| 4 | 22 | 10.9 | 9.1 | 0 | 16.7 | 16.4 | 0 |
| 5 | 25 | 12.5 | 10.7 | 0 | 17.7 | 17.6 | 0 |
| 6 | 24 | 6.7 | 5.6 | 0 | 12.8 | 11.8 | 0 |
| 7 | 38 | 6.5 | 5.5 | 0 | 14.2 | 13.9 | 0 |
| 8 | 39 | 6.2 | 5.8 | 0 | 14.2 | 14.2 | 0 |
| 9 | 29 | 7.1 | 6.1 | 0 | 14.4 | 14.0 | 0 |
| 10 | 51 | 9.7 | 9.4 | 0 | 14.6 | 14.7 | 0 |
| Mean | 38.4 | 8.5 | 7.7 | 0/10 | 14.9 | 14.6 | 0/10 |

TABLE 5-continued

Immunologic responses of RSV-seropositive children 12 to 59 months of age to $10^6$ PFU of recombinant live-attenuated respiratory syncytial virus vaccine, RSV LID/ΔNS1, or $10^{5.8}$ PFU of RSV LID/F1G2/ΔNS1, or placebo.

| | | Serum RSV neutralizing antibody (reciprocal log2) | | | Serum IgG ELISA RSV F antibody (reciprocal log2) | | |
|---|---|---|---|---|---|---|---|
| Group, Subject number | Age at Inoculation (months) | Pre-inoculation | Post-inoculation | ≥4 fold rise | Pre-inoculation | Post-inoculation | ≥4 fold rise |
| SD | 14.0 | 2.2 | 2.0 | | 1.7 | 1.7 | |
| RSV LID/F1G2/ΔNS1 | | | | | | | |
| 11 | 59 | 8.0 | 7.4 | 0 | 14.3 | 14.2 | 0 |
| 12 | 54 | 7.6 | 7.6 | 0 | 14.2 | 13.9 | 0 |
| 13 | 37 | 7.1 | 7.0 | 0 | 14.9 | 14.7 | 0 |
| 14 | 53 | 8.0 | 8.0 | 0 | 14.8 | 14.4 | 0 |
| 15 | 25 | 8.2 | 7.5 | 0 | 15.4 | 15.3 | 0 |
| 16 | 26 | 6.8 | 6.1 | 0 | 12.4 | 12.9 | 0 |
| 17 | 44 | 6.3 | 9.1 | 1 | 13.3 | 16.3 | 1 |
| 18 | 33 | 5.1 | 4.9 | 0 | 12.0 | 12.1 | 0 |
| 19 | 17 | 5.6 | 6.5 | 0 | 12.7 | 13.3 | 0 |
| 20 | 51 | 5.6 | 6.6 | 0 | 12.2 | 12.2 | 0 |
| Mean | 39.9 | 6.8 | 7.1 | 1/10 | 13.6 | 13.9 | 1/10 |
| SD | 14.4 | 1.1 | 1.1 | | 1.3 | 1.3 | |
| Placebo | | | | | | | |
| 21 | 28 | 8.5 | 7.2 | 0 | 15.3 | 14.7 | 0 |
| 22 | 34 | 7.5 | 7.1 | 0 | 13.9 | 14.1 | 0 |
| 23 | 49 | 6.7 | 6.7 | 0 | 13.7 | 13.5 | 0 |
| 24 | 36 | 9.8 | 8.9 | 0 | 15.1 | 15.2 | 0 |
| 25 | 18 | 5.9 | 5.4 | 0 | 12.3 | 13.1 | 0 |
| Mean | 33 | 7.7 | 7.1 | 0/5 | 14.1 | 14.1 | 0/5 |
| SD | 11.4 | 1.5 | 1.3 | | 1.2 | 0.9 | |

TABLE 6

Clinical and virologic responses of RSV-seronegative children 6 to 24 months of age to $10^5$ PFU of recombinant live-attenuated respiratory syncytial virus vaccine, RSV LID/ΔNS1, or RSV LID/F1G2/ΔNS1, or placebo.

| | | Viral Detection (Immunoplaque assay) | | | Viral Detection (PCR) | | | | | |
|---|---|---|---|---|---|---|---|---|---|---|
| Group, Subject number | Age at Inoculation (months) | Duration | Days | Peak Titer (log10) | Duration | Days | Peak Copy Number (log10) | Respiratory or Febrile Illness | Any Antibody Response | Infected |
| RSV LID/ΔNS1 | | | | | | | | | | |
| 1 | 11 | 0 | 0 | 0.5 | 0 | 0 | 1.7 | 0 | 0 | 0 |
| 2 | 7 | 7 | 5, 7 | 2.7 | 10 | 5, 7, 10 | 5.6 | 0 | 0 | 1 |
| 3 | 8 | 14 | 9, 12, 14 | 1.5 | 16 | 5, 7, 9, 12, 14, 16 | 5.1 | 1 | 0 | 1 |
| 4 | 14 | 0 | 0 | 0.5 | 0 | 0 | 1.7 | 1 | 0 | 0 |
| Mean | 10.0 | 10.5 | | 2.1 | 13.0 | | 5.4 | 2/4 | 0/4 | 2/4 |
| SD | 3.2 | 4.9 | | 0.8 | 4.2 | | 0.4 | | | |
| RSV LID/F1G2/ΔANS1 | | | | | | | | | | |
| 5 | 15 | 0 | 0 | 0.5 | 14 | 5, 9, 12, 14 | 3.7 | 1 | 1 | 1 |
| 6 | 8 | 0 | 0 | 0.5 | 12 | 7, 12 | 3.6 | 1 | 0 | 1 |
| 7 | 22 | 7 | 7 | 1.3 | 14 | 7, 10, 12, 14 | 4.0 | 1 | 1 | 1 |
| 8 | 16 | 11 | 9, 11 | 1.2 | 16 | 9, 11, 14, 16 | 4.3 | 0 | 1 | 1 |
| Mean | 15.3 | 9.0 | | 1.3 | 14.0 | | 3.9 | 3/4 | 3/4 | 4/4 |
| SD | 5.7 | 2.8 | | 0.1 | 1.6 | | 0.3 | | | |
| Placebo | | | | | | | | | | |
| 9 | 14 | 0 | 0 | 0.5 | 0 | 0 | 1.7 | 1 | 0 | 0 |
| 10 | 16 | 0 | 0 | 0.5 | 0 | 0 | 1.7 | 0 | 0 | 0 |
| Mean | 15 | 0.0 | | 0.5 | 0.0 | | 1.7 | 1/2 | 0/2 | 0/2 |
| SD | 1.4 | 0.0 | | 0.0 | 0.0 | | 0.0 | | | |

TABLE 7

Immunologic responses of of RSV-seronegative children 6 to 24 months of age to $10^5$ PFU of recombinant live-attenuated respiratory syncytial virus vaccine, RSV LID/ΔNS1, or RSV LID/F1G2/ΔNS1, or placebo.

| | | Serum RSV neutralizing antibody (reciprocal log2) | | | Serum IgG ELISA RSV F antibody (reciprocal log2) | | |
|---|---|---|---|---|---|---|---|
| Group, Subject number | Age at Inoculation (months) | Pre-inoculation | Post-inoculation | ≥4 fold rise | Pre-inoculation | Post-inoculation | ≥4 fold rise |
| RSV LID/ΔNS1 | | | | | | | |
| 1 | 11 | 2.3 | 3.6 | 0 | 7.2 | 7.7 | 0 |
| 2 | 7 | 2.3 | 4.2 | 0 | 8.1 | 9.9 | 0 |
| 3 | 8 | 2.3 | 2.3 | 0 | 7.1 | 6.1 | 0 |
| 4 | 14 | 3.6 | 2.3 | 0 | 11.2 | 11.3 | 0 |
| Mean | 10.0 | 2.6 | 3.1 | 0/4 | 8.4 | 8.8 | 0/4 |
| SD | 3.2 | 0.6 | 0.9 | | 1.9 | 2.3 | |
| RSV LID/F1G2/ΔNS1 | | | | | | | |
| 5 | 15 | 2.3 | 4.6 | 1 | 4.6 | 10.5 | 1 |
| 6 | 8 | 2.3 | 3.5 | 0 | 7.6 | 7.8 | 0 |
| 7 | 22 | 2.3 | 5.8 | 1 | 4.6 | 11.9 | 1 |
| 8 | 16 | 2.3 | 8.2 | 1 | 4.6 | 12.8 | 1 |
| Mean | 15.3 | 2.3 | 5.5 | 3/4 | 5.4 | 10.8 | 3/4 |
| SD | 5.7 | 0.0 | 2.0 | | 1.5 | 2.2 | |
| Placebo | | | | | | | |
| 9 | 14 | 2.3 | 2.3 | 0 | 4.6 | 4.6 | 0 |
| 10 | 16 | 2.3 | 2.3 | 0 | 4.6 | 4.6 | 0 |
| Mean | 15 | 2.3 | 2.3 | 0/2 | 4.6 | 4.6 | 0/2 |
| SD | 1.4 | 0.0 | 0.0 | | 0.0 | 0.0 | |

Example 3

Prime-Boost Immunization with Live-Attenuated RSV Vaccines

In the present study, the boosting effect of rB/HPIV3 vectors expressing DS-Cav1-stabilized RSV pre-F protein, with or without the B3TMCT mutation, were evaluated in comparison with RSV. Boosting was evaluated in hamsters and African Green monkeys (AGMs) that previously had a primary RSV infection. In addition, the effect of different time intervals (~2, ~6, and ~15 months) between the prime and boost was evaluated in AGMs. The results show that, in either experiment animal and for any of the time intervals, a boost by a rB/HPIV3 vector expressing RSV F engineered for enhanced immunogenicity induced significantly higher titers of serum RSV-neutralizing antibodies compared to a boost by RSV, particularly antibodies that are capable of neutralizing RSV in vitro without added complement and thus are particularly potent.

The RSV F and G proteins are the two RSV neutralization antigens and the major protective antigens. F is generally considered to be a more potent neutralization and protective antigen than G, and its amino acid sequence is much more conserved among RSV strains. RSV F is produced in a pre-fusion (pre-F) conformation that is metastable and can readily be triggered to undergo a major irreversible conformational rearrangement that drives membrane fusion and leaves F in a highly stable post-fusion (post-F) conformation (See McLellan et al. 2010. Structure of a major antigenic site on the respiratory syncytial virus fusion glycoprotein in complex with neutralizing antibody 101F. J Virol 84:12236-44; Swanson et al. 2011. Structural basis for immunization with postfusion respiratory syncytial virus fusion F glycoprotein (RSV F) to elicit high neutralizing antibody titers. Proc Natl Acad Sci USA 108:9619-24; McLellan et al. 2013. Structure of RSV fusion glycoprotein trimer bound to a prefusion-specific neutralizing antibody. Science 340:1113-7). Pre-F and post-F share some neutralizing epitopes, but most of the neutralizing activity in convalescent human sera recognizes epitopes specific to pre-F (Graham. 2017. Vaccine development for respiratory syncytial virus. Curr Opin Virol 23:107-112). RSV F can be substantially stabilized in the pre-F conformation by structure-based engineering, such as by the introduction of a disulfide bond called "DS" and two hydrophobic cavity-filling amino acid substitutions called "Cav1" (McLellan et al. 2013. Structure-based design of a fusion glycoprotein vaccine for respiratory syncytial virus. Science 342:592-8). DS-Cav-stabilized pre-F is substantially more immunogenic in rodents and non-human primates than post-F either as a subunit vaccine or expressed by a parainfluenza virus (PIV) vector (Liang et al. 2015. Enhanced Neutralizing Antibody Response Induced by Respiratory Syncytial Virus Prefusion F Protein Expressed by a Vaccine Candidate. J Virol 89:9499-510).

A number of attenuated derivatives of RSV strain A2 have been developed as candidate live-attenuated IN RSV vaccines (See Karron et al. 2013. Live-attenuated respiratory syncytial virus vaccines. Curr Top Microbiol Immunol 372:259-84). Some of these attenuated viruses have been shown to be well-tolerated and immunogenic in phase I studies in infants and young children.

Additionally, a PIV vector strategy to express RSV antigen, principally the F protein, from an added gene has been pursued. HPIV serotypes 1, 2, and 3 are important pediatric respiratory viruses, and HPIV3 is second only to RSV as a major cause of severe pediatric respiratory infection. The PIVs are enveloped non-segmented negative-sense RNA viruses that are related to RSV and belong to the family Paramyxoviridae of the order Mononegavirales. rB/HPIV3 consists of the bovine PIV3 (BPIV3) genome (which confers attenuation in humans and non-human primates by host range restriction) in which the BPIV3 F and hemagglutinin-neuraminidase (HN) glycoprotein genes (encoding the two PIV3 neutralization and major protective antigens) were replaced by their counterparts from human PIV3 (HPIV3).

Results

Figure 14A:
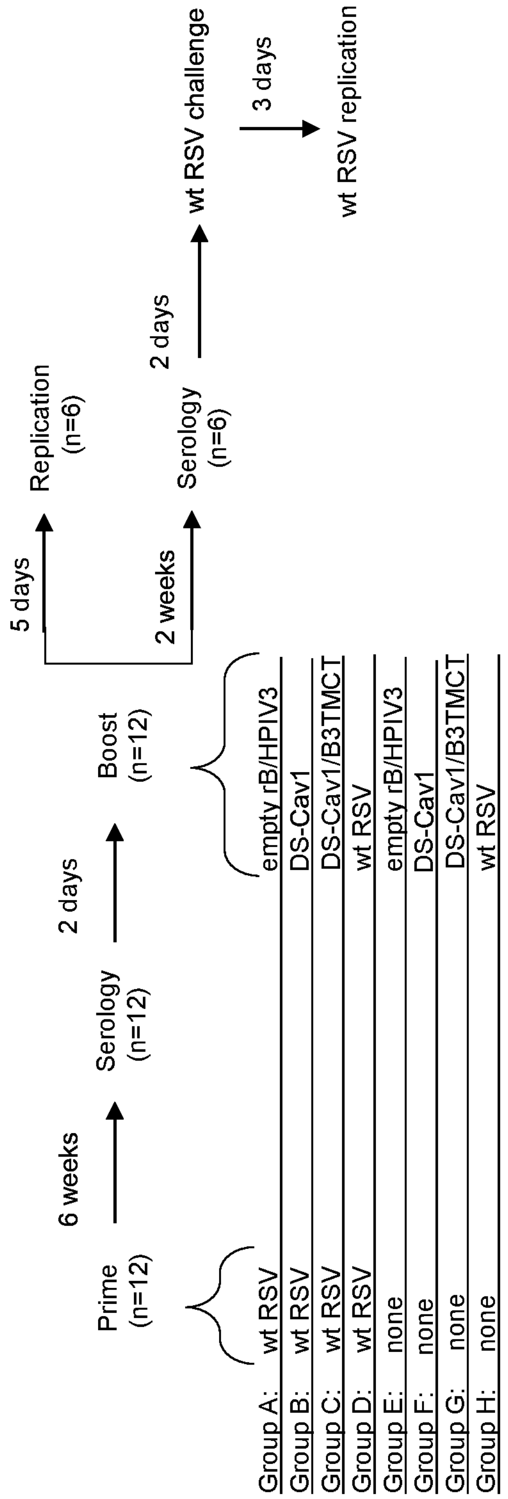
FIGS. 14A-14F. Evaluation of a prime-boost regimen of selected immunogens in hamsters.

Comparison of booster immunization with RSV versus rB/HPIV3-RSV-pre-F vectors in hamsters previously infected with RSV. Two rB/HPIV3 vectors were previously described (Liang et al. 2017. Improved Prefusion Stability, Optimized Codon Usage, and Augmented Virion Packaging Enhance the Immunogenicity of Respiratory Syncytial Virus Fusion Protein in a Vectored-Vaccine Candidate. J Virol 91): rB/HPIV3/DS-Cav1 (abbreviated DS-Cav1 vector) that expresses RSV F with greatly increased stability in the pre-F conformation by the DS-Cav1 mutations; and rB/HPIV3/DS-Cav1/B3TMCT (abbreviated DS-Cav1/B3TMCT vector) that expresses RSV F with the same DS-Cav1 mutations plus replacement of its TMCT domains with those of the BPIV3 F protein to achieve efficient incorporation into the vector virion. These two vectors were compared to RSV D46 for the ability to infect and induce a secondary or booster response of serum RSV-neutralizing antibodies in hamsters that previously had received a single primary IN infection with RSV D46 (FIG. 14A). RSV D46 was used for the infections because attenuated RSV strains are poorly infectious in hamsters due to a strong host range restriction.

Forty-eight hamsters were confirmed to be seronegative for RSV and HPIV3, placed into four groups (Groups A-D, n=12 each), and primed by IN inoculation with $10^6$ PFU RSV D46 per animal (FIG. 14A). Forty-eight additional RSV- and HPIV3-seronegative hamsters in four groups (Groups E-H, n=12 each) were left unprimed for comparison. Six weeks post-priming, sera were collected to measure RSV- and HPIV3-PRNTs. Two days later, pairs of primed and unprimed groups were boosted IN with: (i) empty rB/HPIV3 vector (Groups A and E); (ii) DS-Cav1 vector (Groups B and F); (iii) DS-Cav1/B3TMCT vector (Groups C and G); or (iv) RSV D46 (Groups D and H). The vectors were given at a dose of $10^5$ $TCID_{50}$ per animal, and RSV D46 at a dose of $10^6$ PFU. Five days after boosting, six hamsters per group were sacrificed and nasal turbinates (NT) and lungs were harvested and assayed by immunoplaque assay (RSV) or limiting dilution assay (rB/HPIV3 vectors) to measure infectious virus titers. For the other six hamsters per group, sera were collected two weeks post-boost to measure RSV- and HPIV3-PRNT. Two days later, the animals were challenged IN with RSV D46 as described below.

Analysis of virus titers in unprimed animals five days following the boost showed that the DS-Cav1 and DS-Cav1/B3TMCT vectors replicated to lower titers than the empty vector in the NT and lungs (FIGS. 14B and 14C, lanes 3 and 5 versus 1, respectively), indicating attenuation due to the presence of the RSV F insert. The DS-Cav1/B3TMCT vector was somewhat more attenuated than the DS-Cav1 vector and consistent with the idea that incorporation of RSV F into the vector envelope might interfere with vector replication.

Figure 14D:
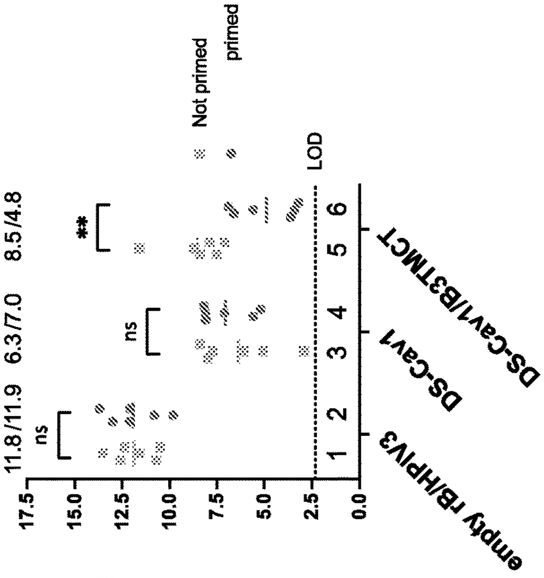
Figure 14C:
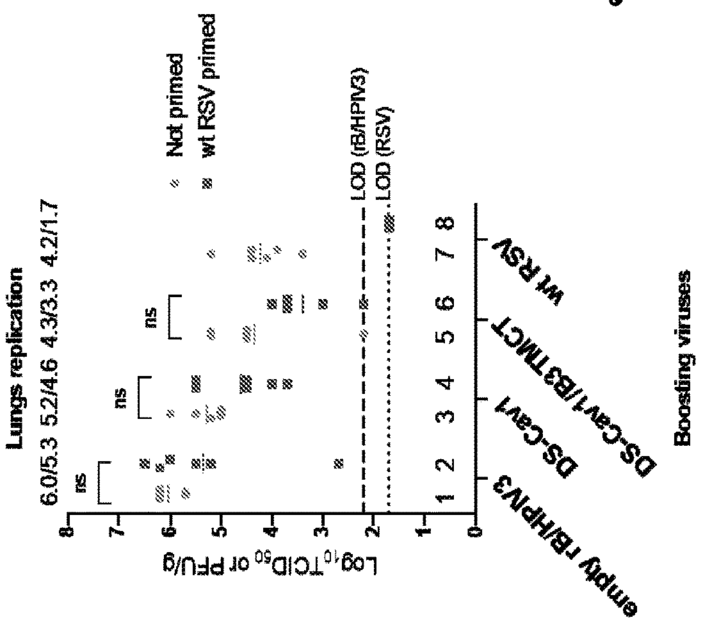
Figure 14B:
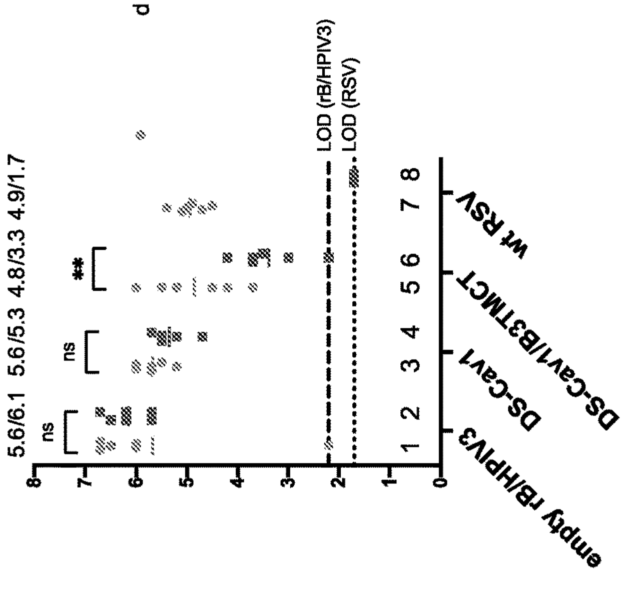

Comparison of RSV-primed versus unprimed animals (FIGS. 14B and 14C: even lanes versus odd lanes) showed that the priming immunization completely restricted the replication of the RSV D46 boost (FIGS. 14B, 14C, lane 8 versus 7) but had no effect on replication of the empty rB/HPIV3 vector (lane 2 versus 1), consistent with the expectation that RSV-specific immunity would restrict the replication of RSV but not rB/HPIV3. Priming with RSV resulted in a modest restriction (2-fold in the NT, 4-fold in the lungs) of the replication the DS-Cav1 vector (FIGS. 14B, 14C, lane 4 versus 3), and a somewhat greater restriction of the DS-Cav1/B3TMCT vector (32-fold in the NT, 10-fold in the lungs; FIGS. 14B and 14C, lane 6 versus 5), although the difference between primed and unprimed groups was statistically significant only for the DS-Cav1/B3TMCT vector in the NT (FIG. 14B, lane 6 versus 5). These observations suggested that the expression of RSV F by rB/HPIV3 conferred a low level of sensitivity to restriction by RSV-specific immunity that was increased somewhat when RSV F was packaged into the vector virion.

Analysis of the titers of HPIV3-neutralizing antibodies in sera collected from unprimed animals two weeks following the boost showed that the presence of either RSV insert in the rB/HPIV3 vector was associated in a decrease in HPIV3-neutralizing antibodies compared to the empty vector (FIG. 14D, lanes 3 and 5 versus 1), consistent with the decreased replication associated with the insert as noted above. The presence of the DS-Cav1 insert did not detectably reduce HPIV3 immunogenicity in primed versus unprimed animals (FIG. 14D, lane 4 versus 3), but the DS-Cav1/B3TMCT insert resulted in a significant decrease in HPIV3 immunogenicity in primed versus unprimed animals (FIG. 14D, lane 6 versus 5), consistent with its restriction as noted above.

Figure 14F:
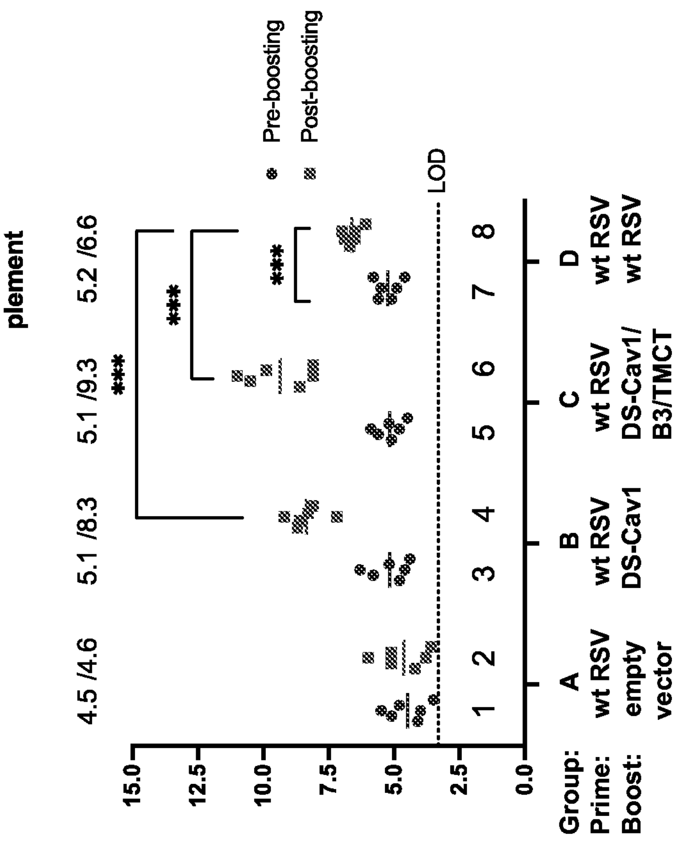
Figure 14E:
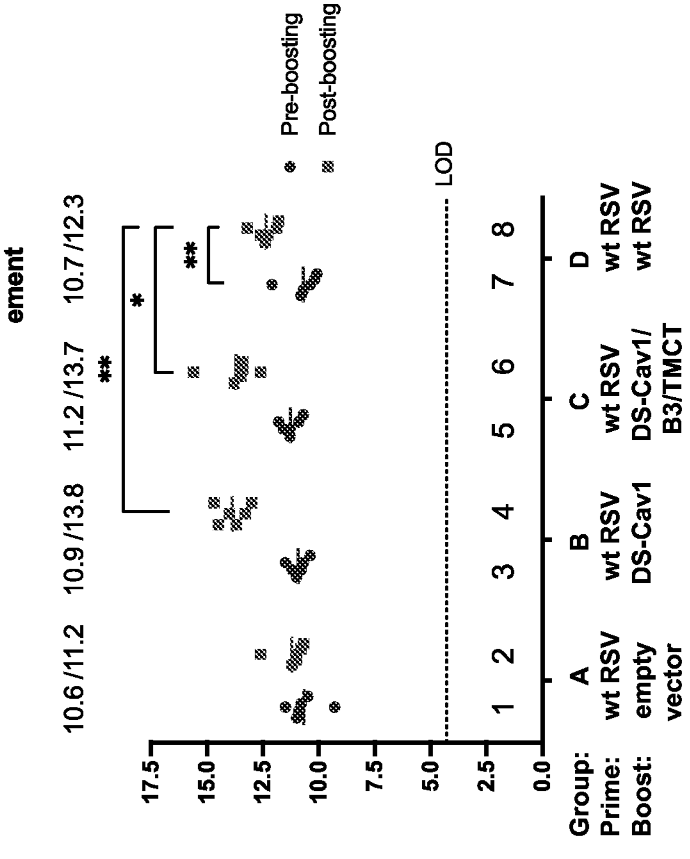

Serum RSV-PRNTs induced by priming and boosting were determined by assays with or without added guinea pig complement (FIGS. 14E and 14F). The addition of complement can confer steric hindrance and viral lysis activity to antibodies, resulting in enhanced detection of RSV-specific antibodies that might otherwise have poor neutralizing activity. The neutralization assay in the absence of added complement is a more stringent assay for "high-quality" antibodies that directly neutralize RSV (see Liang et al. 2016. Packaging and Prefusion Stabilization Separately and Additively Increase the Quantity and Quality of Respiratory Syncytial Virus (RSV)-Neutralizing Antibodies Induced by an RSV Fusion Protein Expressed by a Parainfluenza Virus Vector. J Virol 90:10022-10038; Liang et al. 2017. Improved Prefusion Stability, Optimized Codon Usage, and Augmented Virion Packaging Enhance the Immunogenicity of Respiratory Syncytial Virus Fusion Protein in a Vectored-Vaccine Candidate. J Virol 91).

The initial priming infection with RSV D46 induced high serum RSV-PRNTs measured in the presence of complement, and lower RSV-PRNTs measured in the absence of complement. Specifically, the sera collected from Groups A-D six weeks following priming had mean serum RSV-PRNTs within the range 10.6 $\log_2$ (1:1,552) to 11.2 $\log_2$ (1:2,353) determined with complement (FIG. 14E), and 4.5 $\log_2$ (1:23) to 5.2 $\log_2$ (1:37) determined without complement (FIG. 14F).

Boosting with RSV D46 increased the mean serum RSV-PRNT measured with complement (FIG. 14E, lane 7 versus 8) by 3-fold, to a post-boost mean titer of 12.3 $\log_2$ (1:5,043), and increased the mean serum RSV-PRNT measured without complement (FIG. 14F, lane 7 versus 8) also by 3-fold, to a post-boost mean titer of 6.6 $\log_2$ PRNT (1:97).

Boosting with the DS-Cav1 and DS-Cav1/B3TMCT vectors increased the mean serum RSV-PRNT measured with complement by 8- and 6-fold, respectively, to remarkably high post-boost mean titers of 13.8 $\log_2$ (1:14,263) and 13.7 $\log_2$ (1:13,308) (FIG. 14E, lane 3 versus 4 for DS-Cav1, and lane 5 versus 6 for DS-Cav1/B3TMCT). Pre- and post-boost mean serum RSV-PRNTs measured without complement increased by 9- and 18-fold, respectively, to post-boost mean titers of 8.3 $\log_2$ (1:315) and 9.3 log 2 (1:630) (FIG. 14F, lanes 3 versus 4 for DS-Cav1 vector and 5 versus 6 for DS-Cav1/B3TMCT vector).

The six animals per group used for post-boost serology also were challenged two days following serum collection by IN infection with $10^6$ PFU of RSV D46 per animal, and NT and lungs were collected 3 days post-challenge and challenge RSV titers were determined by immunoplaque assay. Animals that were not primed with RSV and were boosted with empty rB/HPIV3 vector, and thus had no RSV-specific immunity, had approximately 5.0 $\log_{10}$ PFU/g tissue of challenge RSV in the NT and lungs. All of the hamsters in the other groups, which had been primed and/or boosted with RSV D46 and/or rB/HPIV3 expressing RSV F, had no detectable infectious challenge RSV in the NT and lungs (data not shown). Thus, all of the combinations of priming and/or boosting were highly protective in this semi-permissive model for RSV replication and could not be distinguished based on protective efficacy.

In summary, when rB/HPIV3 vectors were used for the booster immunization, there was substantial vector replication and robust increases in serum RSV-PRNT, resulting in very high titers. In contrast, when RSV D46 was used as a boost, its replication was highly restricted and the increase in RSV-PRNT was significantly lower. Furthermore, the fold-increase in serum RSV-PRNT induced by the rB/HPIV3 vectors was greater for the high-quality RSV neutralizing serum antibodies measured without complement.

Comparison of booster immunizations in AGMs. Booster immunizations also were evaluated in AGMs that had previously been primed by a single RSV infection by the combined IN/IT routes ($10^6$ PFU per site). The viruses used in these primary immunizations were various attenuated derivatives of RSV strain A2, or the wt strain rRSV A/Maryland/001/11 (which, like strain A2, is from subgroup A). The priming RSVs are listed in Tables 8-10 and described below. Note that we treated all of these viruses as being equivalent with respect to priming, although we did distribute the animals that received the various viruses evenly between boosting groups. In three separate experiments (AGM experiments #1-#3), the previously-primed AGMs were given a single booster infection by the combined IN/IT routes with an attenuated RSV ($10^6$ PFU per site) or DS-Cav1/B3TMCT vector ($10^6$ $TCID_{50}$ per site). In experiment #2, additional RSV-primed AGMs received DS-Cav1 vector ($10^6$ $TCID_{50}$ per site). In all cases, the booster RSV was a live-attenuated vaccine candidate called RSV 276, which is a version of RSV strain A2 attenuated by deletion of most of the M2-2 ORF.

For 12 animals (AGM experiment #1, FIG. 15 and Table 8), the time interval between prime and boost was ~2 months (specifically 51 days, which equal two months minus nine days). For 20 other animals (AGM experiment #2, FIG. 16 and Table 9), the time interval between prime and boost was ~6 months (specifically 189 days, which equal six months plus nine days). For the remaining four animals (AGM experiment #3, FIG. 17 and Table 10), the time interval was ~15 months (specifically 443 days, which equal 15 months minus seven days).

To monitor virus shedding following the boost, NP and TL were collected daily and every other day, respectively, for ten consecutive days, and virus titers were determined by immunoplaque assay (RSV) or limiting dilution (B/HPIV3 vectors). Sera were collected on one or more days prior to the day of the boost, on the day of the boost, and every seven days thereafter for four consecutive weeks, and PRNTs were determined.

AGM experiment #1: Booster immunization of AGMs ~2 months (two months minus nine days) following priming with RSV. Twelve AGMs were available that had previously received a single priming immunization with one of three different RSVs (Table 8): (i) RSV LID/ΔNS1, an NS1 gene-deletion mutant; (ii) RSV LID/F1G2/ΔNS1, a derivative of the preceding virus in which the RSV F and G genes were moved to the $1^{st}$ and $2^{nd}$ genome position in order to increase their expression; and (iii) the subgroup A wt strain rRSV A/Maryland/001/11. On Day 37 post-priming (two weeks before boosting) sera were collected and analyzed to determine RSV-PRNT in the presence of complement, and to confirm HPIV3-seronegativity. The 12 AGMs were redistributed into two groups of six animals each organized so that the two groups had similar numbers of animals with high, medium, or low Day 37 serum RSV-PRNTs, had essentially identical group mean RSV-PRNTs, and were balanced with regard to the identities of the priming viruses and sex ratio (Table 8).

TABLE 8

Group assignments of AGMs that were boosted ~2 months following priming (experiment #1).

| Animal ID | Sex | Priming RSV | Boosting virus | Pre-boosting serum RSV-neutralizing titer ($Log_2$ PRNT) [a] | Mean pre-boosting RSV serum-neutralizing titer ($Log_2$ PRNT) | Post-boosting RSV serum RSV-neutralizing titer ($Log_2$ PRNT) [b] |
|---|---|---|---|---|---|---|
| 9131 | M | LID/F1G2/ΔNS1 | RSV 276 | 4 | 8.1 | 12.8 |
| 9128 | F | LID/F1G2/ΔNS1 | (n = 6) | 8.1 | | 13.6 |
| 9147 | M | LID/ΔNS1 | | 6.5 | | 11.2 |
| 9136 | F | LID/ΔNS1 | | 8.8 | | 13 |
| 9143 | F | A/Maryland/001/11 | | 10.3 | | 12.4 |
| 9141 | M | A/Maryland/001/11 | | 10.8 | | 11.9 |
| 9084 | M | LID/F1G2/ΔNS1 | DS-Cav1/ | 6.9 | 8.1 | 15.5 |
| 9135 | F | LID/F1G2/ΔNS1 | B3TMCT | 5.5 | | 15.3 |
| 9140 | M | LID/ΔNS1 | (n = 6) | 7.8 | | 13.1 |
| 9116 | F | LID/ΔNS1 | | 7.4 | | 13.8 |
| 9161 | M | A/Maryland/001/11 | | 10.2 | | 14.6 |
| 9173 | F | A/Maryland/001/11 | | 11 | | 14.6 |

[a] Sera were collected two weeks before boosting and were analyzed with RSV PRN assay with added complement. Values are for individual animals.
[b] Sera were collected two weeks after boosting and were analyzed with RSV PRN assay with added complement. Values are for individual animals.

Figure 19:
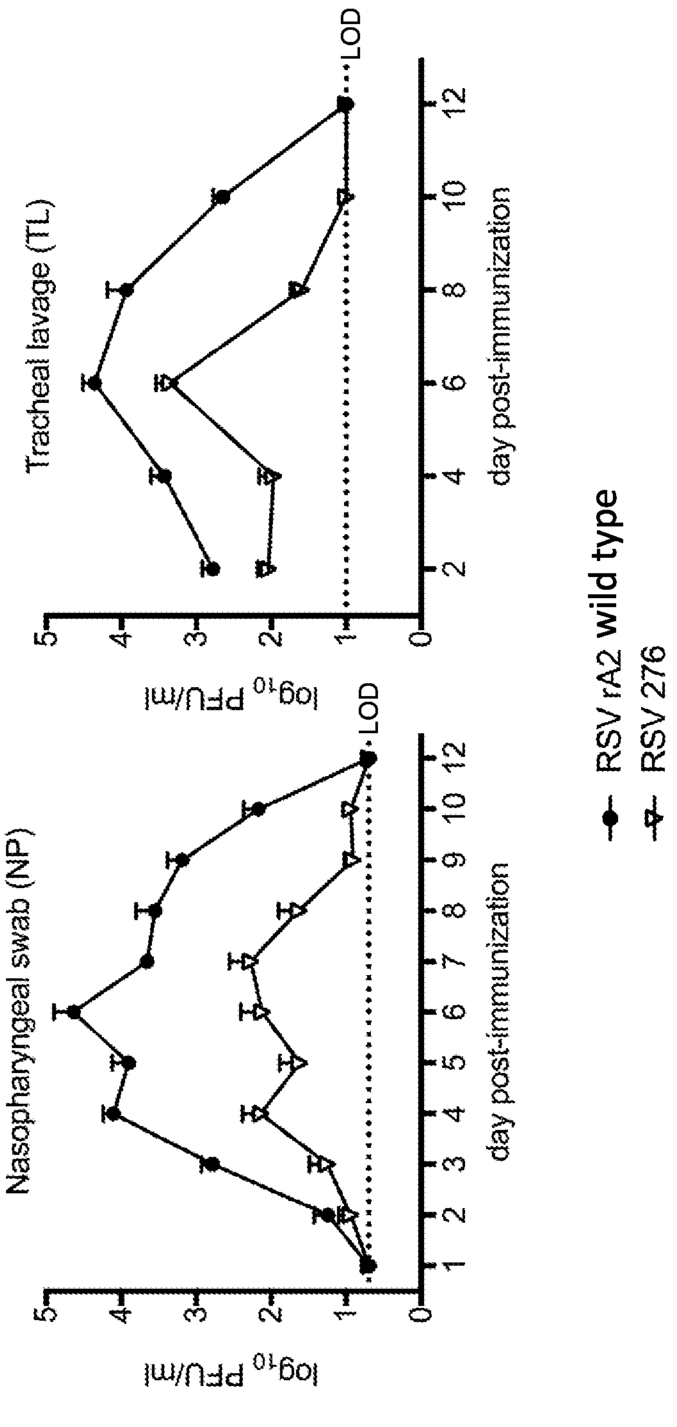
FIG. 19. Replication of RSV 276 and wt rRSV in RSV-seronegative AGMs. RSV-seronegative AGMs were infected by the combined IN/IT routes with $10^6$ PFU of RSV 276 (n=8) or wt rRSV (n=4) in a 1-mL inoculum per site. NP and TL were collected daily and every second day, respectively, for 10 days plus on Day 12. Viral titers were determined by immunoplaque assay and are shown as group means for each time point. Brackets indicate the SEM, and the limits of detection shown as dotted lines. The eight animals infected with RSV 276 here are ones shown in Tables 8 and 10 that subsequently were boosted in AGM experiments #1 and #3.

On Day 51, one group was boosted with RSV 276 and the other with DS-Cav1/B3TMCT vector. NP, TL, and serum specimens were collected to evaluate virus shedding and immunogenicity (FIGS. 15B-15E). Shedding of RSV 276 was detected only in trace amounts on a single day in the NP and was not detected in the TL. It was evident that the very low shedding of RSV 276 was due to restriction by RSV-specific immunity in the RSV-primed animals because, in a previous experiment, infection of four RSV-seronegative AGMs with RSV 276 resulted in substantial viral shedding over a period of 10 days, with the highest peak mean titers approaching 3.0 $\log_{10}$ PFU/ml in NP and TL (FIG. 19). In contrast, shedding of DS-Cav1/B3TMCT vector was substantial over 10 days in both the NP and TL, with peak mean titers of approximately 5.0 $\log_{10}$ $TCID_{50}$/ml in the NP and 3.4 $\log_{10}$ $TCID_{50}$/ml in the TL (FIGS. 15B and 15C).

Figure 15A:
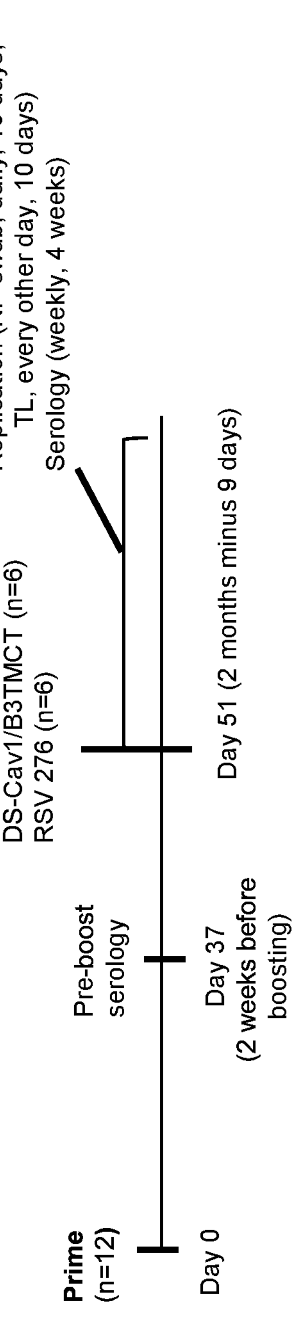
Figure 15B:
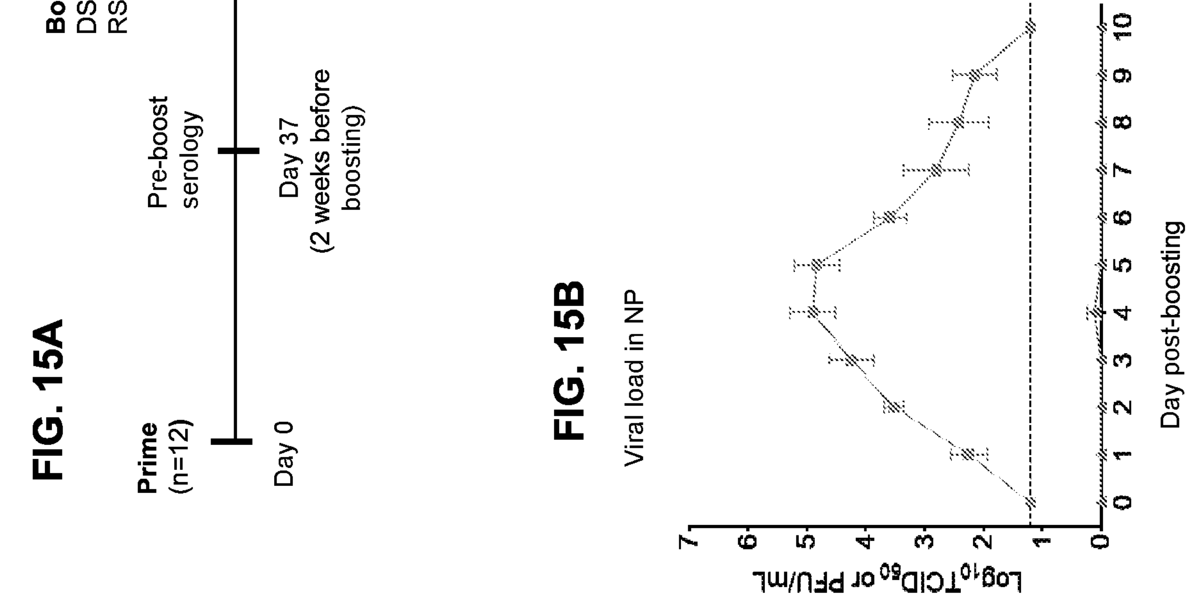
Figure 15C:
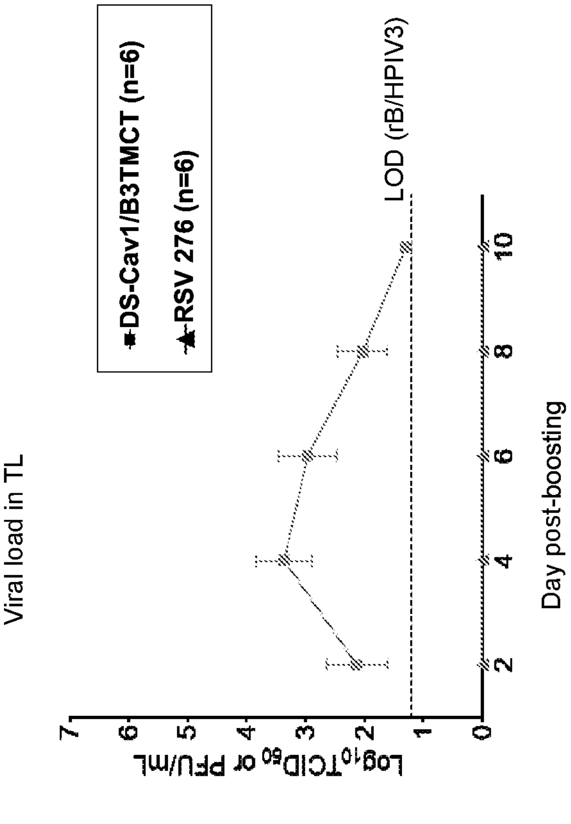

The mean pre-boost serum RSV-PRNT for all 12 animals measured with complement was 1:256 (FIG. 15D). Boosting with RSV 276 and the DS-Cav1/B3TMCT vector increased the serum RSV-PRNTs measured with complement by 22-fold and 91-fold over the pre-boost titer to peak mean titers of 1:5,793 and 1:23,170, respectively (occurring on day 14 post-boost), which were significantly different (FIG. 15D). The peak mean post-boost serum RSV-PRNT for the vector was 4-fold greater than for RSV 276.

Measured in the absence of complement, the mean pre-boost serum RSV-PRNT for all 12 animals was 1:12 (FIG. 15E). Boosting with RSV 276 and the DS-Cav1/B3TMCT vector increased the titer by 25-fold and 366-fold, respectively, to peak mean titers of 1:294 and 1:4,390, respectively (occurring on day 14 post-boost; FIG. 15E), which were significantly different. The peak mean post-boost serum RSV-PRNT for the vector was 15-fold greater than for RSV 276. Thus, the vector had a stronger boosting effect than RSV 276, particularly for "high-quality" neutralizing antibodies detected without complement.

AGM experiment #2: Booster immunization of AGMs ~6 months (6 months plus nine days) following priming with RSV. Twenty other AGMs were available that had previously received a single priming immunization with one of five different RSVs (Table 9): (i) RSV D46/NS2/N/ΔM2-2-HindIII, a M2-2 deletion mutant; (ii) RSV LID/ΔNS2/1030s, a NS2 deletion mutant with a genetically stabilized temperature sensitivity (ts) mutation in the L polymerase; (iii) RSV LID/ΔNS1, an NS1 deletion mutant that also was one of the priming viruses in experiment #1, but in different AGMs; (iv) RSV LID/F1BBG2/ΔNS1/, a version of the preceding LID/ΔNS1 mutant in which the F gene was codon-optimized for increased translation and the F and G genes were moved to the $1^{st}$ and $2^{nd}$ genome positions, respectively, for increased expression; and (v) RSV 276 (described above), which also is the attenuated ΔM2-2 RSV used in the boosts, as already noted.

TABLE 9

Group assignments of AGMs that were boosted ~6 months following priming (experiment #2).

| Animal ID | Sex | Priming RSV | Boosting virus | Pre-boosting serum RSV-neutralizing titer ($Log_2$ PRNT)[a] | Mean pre-boosting RSV serum-neutralizing titer ($Log_2$ PRNT) | Post-boosting RSV serum RSV-neutralizing titer ($Log_2$ PRNT) [b] |
|---|---|---|---|---|---|---|
| 8926 | M | D46/NS2/N/ΔM2-2-HindIII | RSV 276 | 7.1 | 6.0 | 11.4 |
| 8983 | M | LID/ΔNS2/1030s | (n = 6) | 8 | | 11.4 |
| 8974 | F | LID/F1BBG2/ΔNS1 | | 6.9 | | 13.3 |
| 8951 | M | LID/ΔNS1 | | 3.3 | | 12 |
| 8960 | F | LID/ΔNS1 | | 5.2 | | 13.3 |
| 8918 | F | RSV 276 | | 5.7 | | 12.3 |
| 8938 | F | D46/NS2/N/ΔM2-2-HindIII | DS-Cav1 | 6.7 | 6.0 | 14.8 |
| 8911 | M | D46/NS2/N/ΔM2-2-HindIII | (n = 7) | 4.3 | | 16.2 |
| 8928 | F | LID/ΔNS2/1030s | | 7.5 | | 13.4 |
| 8994 | M | LID/F1BBG2/ΔNS1 | | 4.5 | | 14.3 |
| 8966 | M | LID/F1BBG2/ΔNS1 | | 5.1 | | 16.1 |
| 8992 | F | LID/ΔNS1 | | 6.6 | | 14.5 |
| 8913 | M | RSV 276 | | 7.3 | | 13.6 |
| 9041 | F | D46/NS2/N/ΔM2-2-HindIII | DS-Cav1/ | 7.1 | 6.1 | 14.9 |
| 9045 | M | LID/ΔNS2/1030s | B3TMCT | 8.5 | | 14.1 |
| 8940 | F | LID/ΔNS2/1030s | (n = 7) | 6.7 | | 12.9 |
| 8922 | F | LID/F1BBG2/ΔNS1 | | 5.1 | | 22.3 |
| 8904 | M | LID/ΔNS1 | | 7.1 | | 15.2 |
| 8902 | M | RSV 276 | | 3.7 | | 14.4 |
| 8952 | M | RSV 276 | | 4.7 | | 15.5 |

[a]Sera collected 35 days before boosting were analyzed with RSV PRN assay with added complement. Values are for individual animals.
[b] Sera collected two weeks after boosting were analyzed with RSV PRN assay with added complement. Values are for individual animals.

Following the primary immunization, sera were collected on Days 28 and 154 and analyzed to measure RSV-PRNTs in the presence of complement as well as to confirm HPIV3-seronegativity (one animal, #AG 8960 [Table 9], was found to be HPIV3-seropositive and therefore was assigned to be boosted by RSV rather than a rB/HPIV3 vector). The 20 AGMs were re-distributed into three groups (n=6, 7, and 7) organized to balance the Day-154 serum RSV-PRNTs, the identities of the priming viruses, and sex ratio (Table 9). On Day 189 (6 months plus nine days) post-priming, the three groups were boosted with RSV 276, DS-Cav1 vector, or DS-Cav1/B3TMCT vector. NP, TL, and serum specimens were collected to evaluate virus shedding and immunogenicity (FIG. 16).

Figures 16A, 16B, 16C:
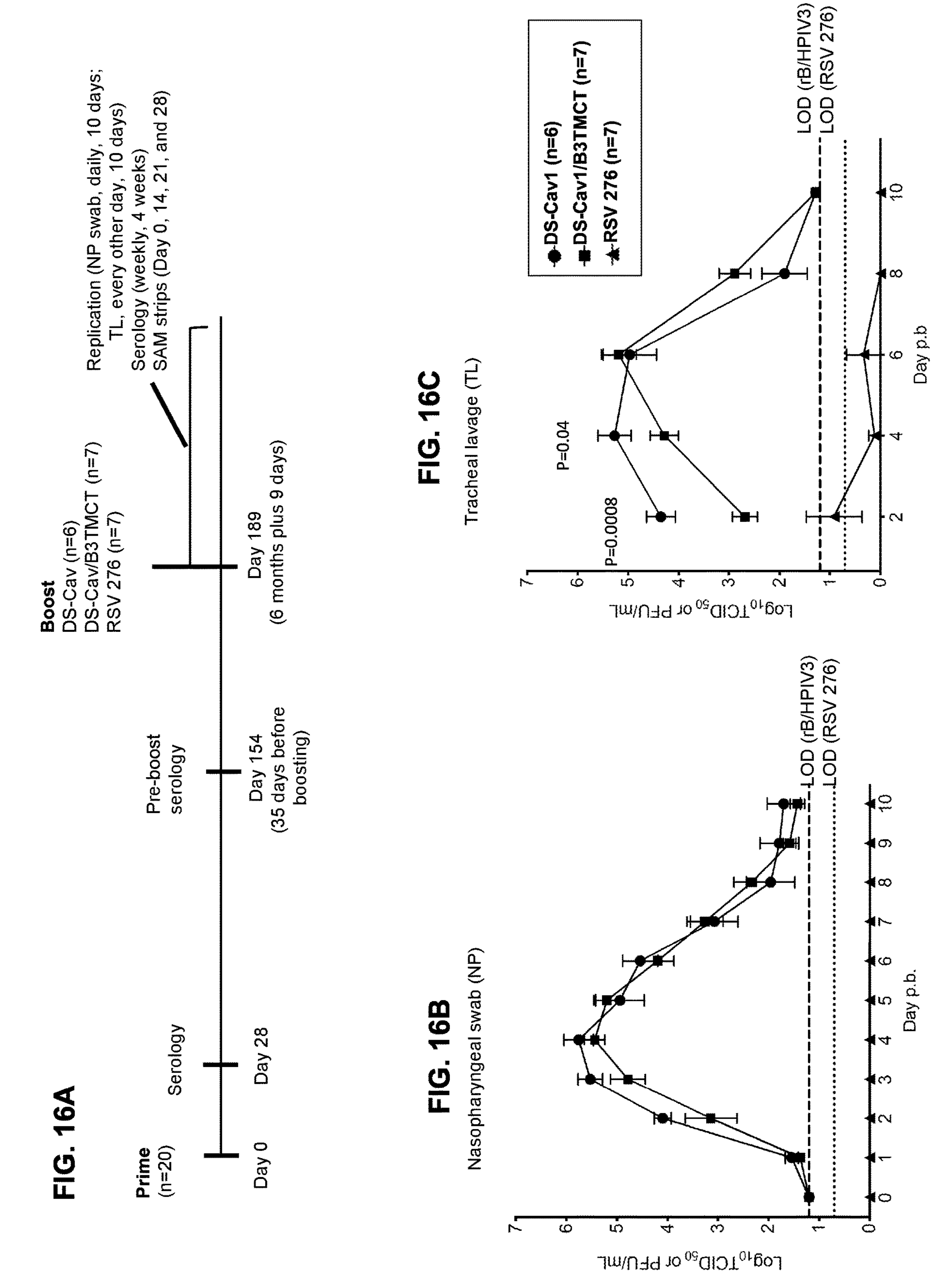
FIGS. 16A-16G. AGM experiment #2: Viral replication and serum RSV-PRNTs in AGMs when the interval between priming and boosting was ~6 months (six months plus nine days).

Shedding of RSV 276 was undetectable in the NP by immunoplaque assay (FIG. 16B), whereas there was low, sporadic detection of RSV 276 in the TL (FIG. 16C). Evaluation of TL specimens for a number of animals by RT-qPCR (that detected both positive- and negative-sense RSV M RNA) was more sensitive, yielding a greater number of samples positive for RSV RNA, with titers up to 450-5,500 RNA molecules/ml (FIG. 20). In contrast, shedding of the DS-Cav1 and DS-Cav1/B3TMCT vectors was detected abundantly by limiting dilution assay in the NP and TL over a period of 8 to 10 days, with similar peak mean titers of approximately 5.5 $\log_{10}$ $TCID_{50}$/ml in the NP and 5.0 $\log_{10}$ $TCID_{50}$/ml in the TL. The DS-Cav1/B3TMCT vector appeared to replicate slightly slower than the DS-Cav1 vector, but this difference was significant only on Days 2 and 4 in the TL (FIG. 16C). The two vectors eventually reached similar peak NP and TL titers (FIGS. 16B and 16C).

Figure 16D:
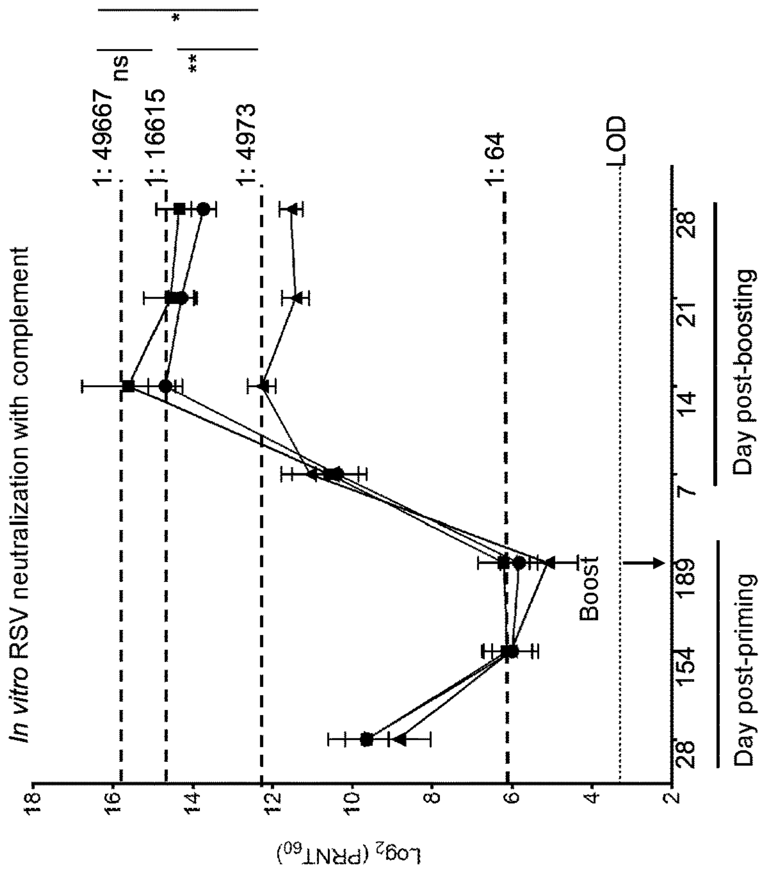

When measured by neutralization assays with complement (FIG. 16D), the mean serum RSV-PRNT in the 20 AGMs induced by the primary immunization with the attenuated RSVs approached 10 $Log_2$ (1:1,024) at Day 28 (FIG. 16D), and then decreased to 1:64 on Day 189 when the boost was given. Boosting with RSV 276, DS-Cav1 vector, and DS-Cav1/B3TMCT vector increased the peak mean serum RSV-PRNTs measured with complement by 78-fold, 260-fold, and 776-fold, respectively, to peak mean titers of 1:4,973, 1:16,615, and 1:49,667 (occurring 14 days post-boost; FIG. 16D), which were significantly different for each vector versus RSV 276. The peak mean post-boost serum RSV-PRNTs for the DS-Cav1 and DS-Cav1/B3TMCT vectors were 3-fold and 10-fold higher, respectively, than for RSV 276. The DS-Cav1/B3TMCT vector appeared to be slightly more immunogenic than the DS-Cav1 despite its slightly slower replication noted above, which might be due to the B3TMCT modification, but the difference was not statistically significant (FIG. 16D).

When measured by PRN assay without complement (FIG. 16E), the mean pre-boost serum RSV-PRNT in the 20 AGMs was 1:8. Boosting with RSV 276, DS-Cav1 vector, and DS-Cav1/B3TMCT vector increased the peak mean serum RSV-PRNT by 37-fold, 315-fold, and 446-fold, respectively, to titers of 1:294, 1:2,521, and 1:3,565 (occurring 14 days post-boost), which were significantly different for each vector versus RSV 276. The peak mean post-boost serum RSV-PRNTs for the DS-Cav1 and DS-Cav1/B3TMCT vectors were 9-fold and 12-fold higher than for RSV 276.

The ability of boosts with the DS-Cav1 and DS-Cav1/B3TMCT vectors to induce serum HPIV3-neutralizing antibodies was compared using HPIV3 neutralization assays without added complement (FIG. 21). Note that the animals were seronegative for HPIV3 before the boosts, and thus these inoculations were primary immunizations with respect to HPIV3. The two vectors induced very similar peak mean serum HPIV3-PRNTs (1:724 and 1:776, respectively, occurring on day 14 post-innoculation), indicating they were essentially equally immunogenic for HPIV3. This is in agreement with the observation that the two vectors replicated to similar peak titers in AGMs (FIGS. 16B and 16C).

Figure 16E:
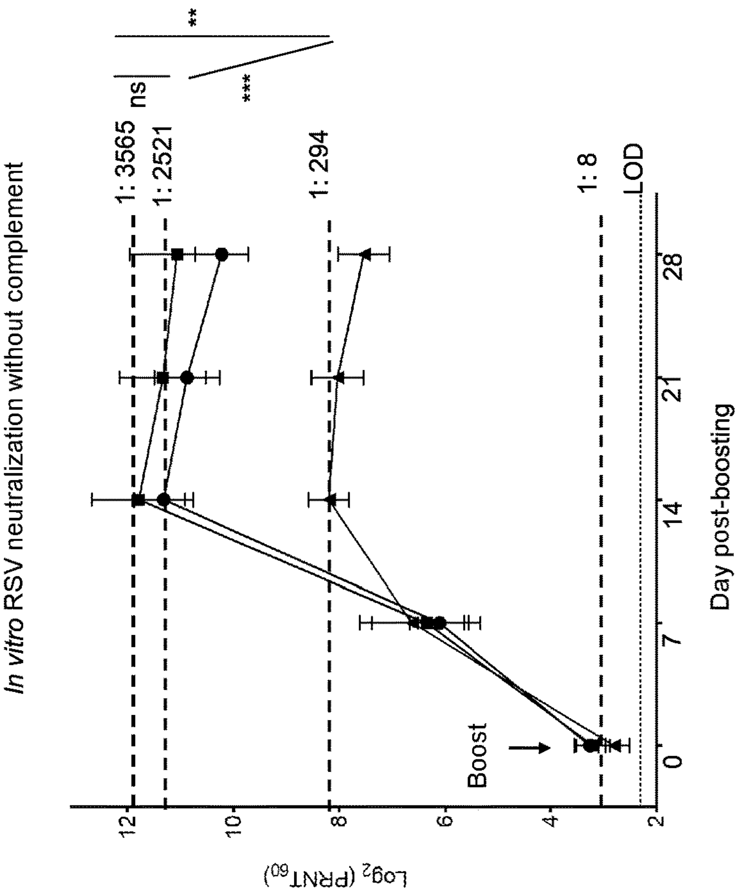
Figure 16G:
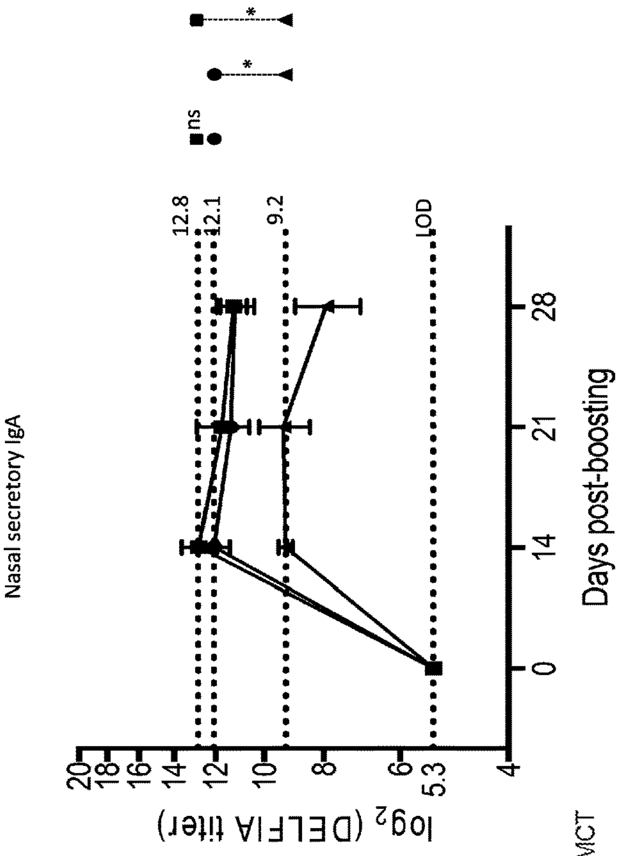
Figure 16F:
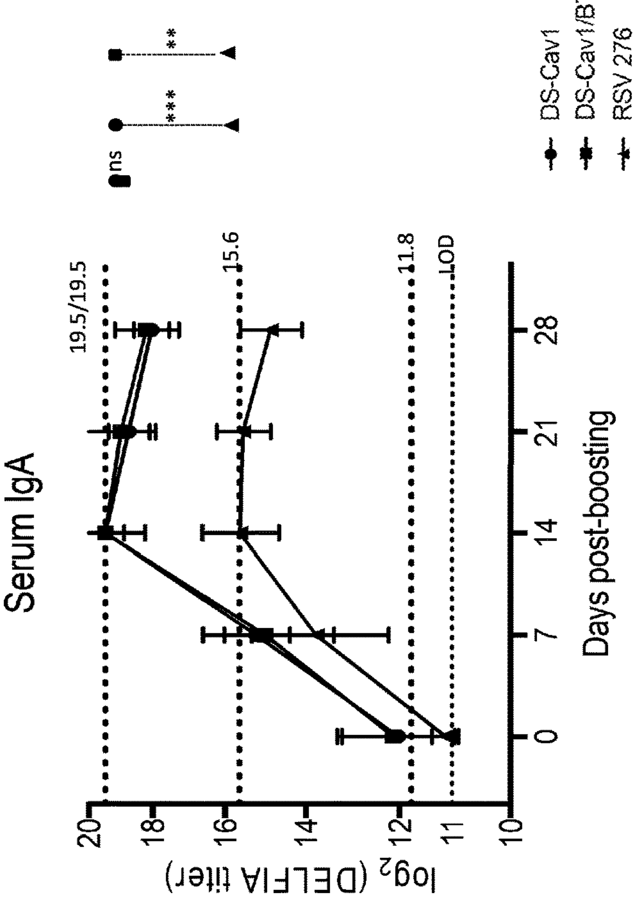

The ability of the boosts with the DS-Cav1 and DS-Cav1/B3TMCT vectors versus RSV 276 to induce serum and mucosal IgA antibodies that bind RSV DS-Cav1 F protein was also assessed (FIGS. 16F and 16G). A highly sensitive DELFIA TRF immunoassay was used to detect monkey IgA binding to purified recombinant RSV DS-Cav1 F protein as antigen. The IgA titers are expressed as the $\log_2$ dilution yielding 400 fluorescence units in the DELFIA TRF assay. Boosting with the two vectors induced strong serum IgA responses: peak mean titers following boosts with the two vectors were identical (19.5 $\log_2$) and were about 16-fold higher than those induced by boosting with RSV 276 (15.6 $\log_2$). The peak serum IgA response was detected at 14 days post-boost, coinciding with the peak serum RSV-neutralizing antibody response. Since the respiratory mucosal antibody response is considered to be particularly effective in limiting RSV infection, we also evaluated the nasal mucosal IgA response to the boosts. Nasal mucosal lining fluid was collected using absorptive membranes (SAM strips). This method provides relatively concentrated mucosal samples, suitable to detect IgA (FIG. 16G). In all groups, the peaks of the mucosal IgA responses were at day 14 following the boosts (FIG. 16G), coinciding with the peaks of the serum IgA (FIG. 16F) and the serum RSV-neutralizing antibodies (FIGS. 16D and 16E). Again, the DS-Cav1 and DS-Cav1/B3TMCT vectors induced similarly strong responses (peak mean titers of 12.1 and 12.8 $\log_2$, respectively), whereas the response to RSV 276 was about 8-fold lower (peak mean titer of 9.2 $\log_2$). Thus, the DS-Cav1 and DS-Cav1/B3TMCT vectors significantly exceeded RSV 276 in their ability to boost the serum and mucosal IgA antibody responses to the RSV pre-F protein.

AGM experiment #3: Booster immunization of AGMs ~15 months (15 months minus seven days) following priming with RSV. Four other AGMs were available that had previously received a single primary immunization with RSV 276 (Table 10). On Day 429 following the primary infection (and two weeks before boosting), sera were collected and analyzed to determine RSV-PRNT in the presence of complement, and to confirm HPIV3-seronegativity. The AGMs were distributed into two groups (n=2 each) that were balanced with regard to serum RSV-PRNTs and sex ratios (Table 10). On Day 443 (15 months minus seven days) following the primary infection, the two groups were boosted with RSV 276 or DS-Cav1/B3TMCT vector and viral replication and serological responses were monitored as described above.

TABLE 10

Group assignments of AGMs that were boosted ~15 months following priming (experiment #3).

| Animal ID | Sex | Priming RSV | Boosting virus | Pre-boosting serum RSV-neutralizing titer ($Log_2$ PRNT) [a] | Mean pre-boosting RSV serum-neutralizing titer ($Log_2$ PRNT) | Post-boosting RSV serum RSV-neutralizing titer ($Log_2$ PRNT) [b] |
|---|---|---|---|---|---|---|
| 8903 | M | RSV 276 | RSV 276 | 6.2 | 5.4 | 14 |
| 8986 | F | RSV 276 | (n = 6) | 4.6 | | 11.6 |
| 8900 | M | RSV 276 | DS-Cav1/B3TMCT | 5.2 | 4.7 | 15.9 |
| 9025 | F | RSV 276 | (n = 6) | 4.2 | | 13.9 |

[a] Sera were collected two weeks before boosting and were analyzed with RSV PRN assay with added complement. Values are for individual animals.
[b] Sera were collected two weeks after boosting and were analyzed with RSV PRN assay with added complement. Values are for individual animals.

Figure 17A:
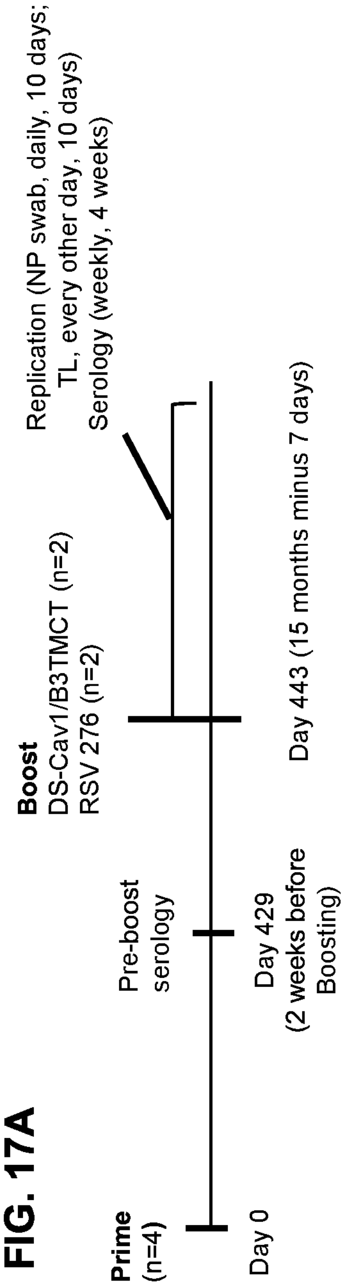
FIGS. 17A-17E. AGM experiment #3: Viral replication and serum RSV-PRNTs in AGMs when the interval between priming and boosting was ~15 months (15 months minus seven days).
Figure 17B:
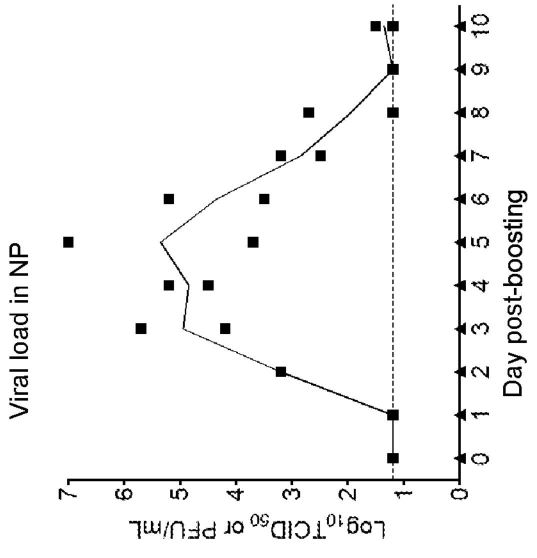
Figure 17C:
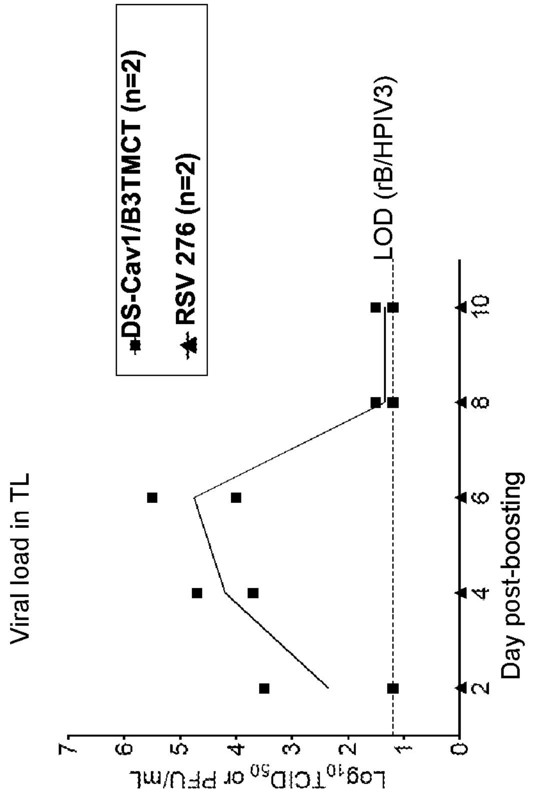
Figure 17E:
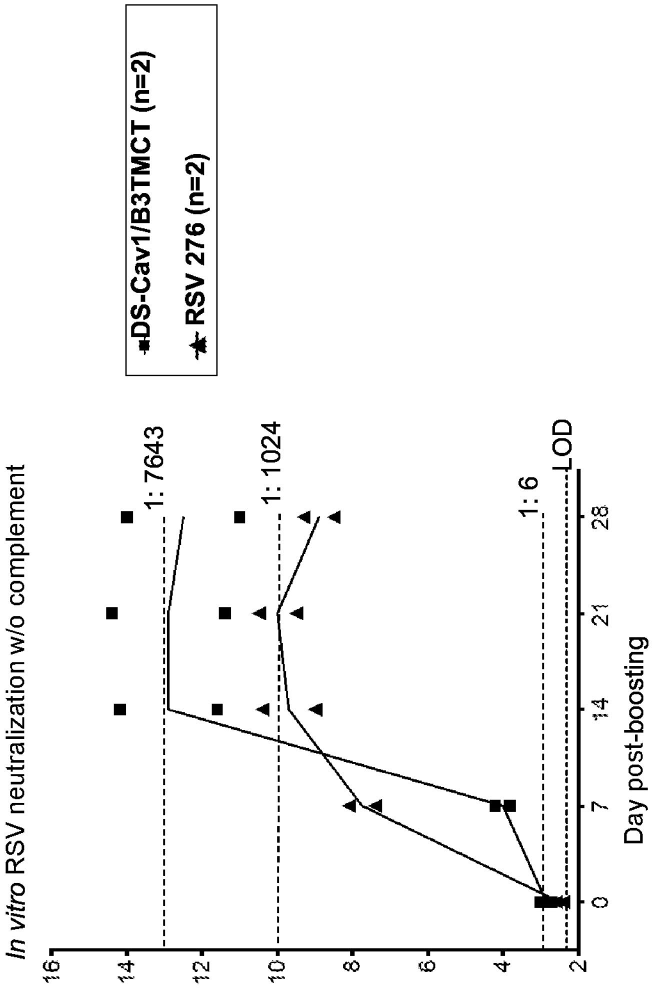

Replication of RSV 276 following the ~15-month interval was highly restricted, with no virus detected by immunoplaque assay of the NP and TL, whereas replication of the DS-Cav1/B3TMCT vector was robust (FIGS. 17B and 17C).

Figure 17D:
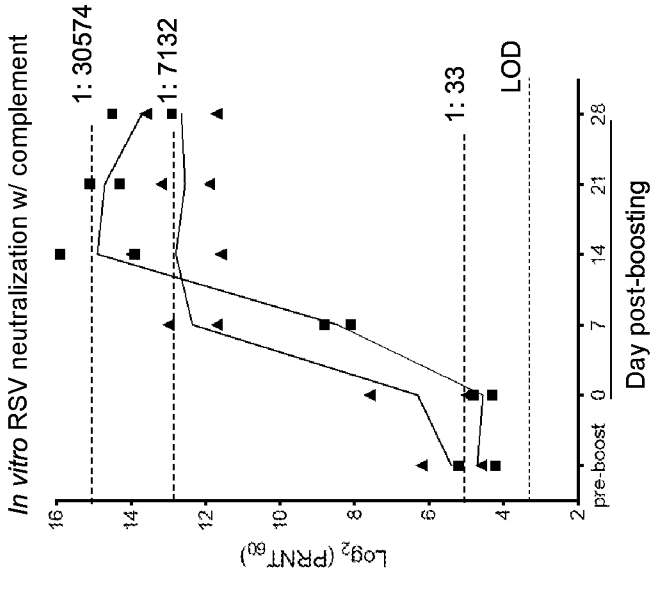

The mean pre-boost serum RSV-PRNT for the four animals measured with complement was 1:33 (FIG. 17D). Boosting with RSV 276 and DS-Cav1/B3TMCT vector increased the peak mean serum RSV-PRNT measured in the presence of complement by 216-fold and 926-fold, respectively, to titers of 1:7,132 and 1:30,574 (occurring on day 14, FIG. 17D). The peak mean post-boost serum RSV-PRNT for the vector was 4-fold higher than for RSV 276.

The mean pre-boost serum RSV-PRNT for the four animals measured without complement was 1:6 (FIG. 17D). Boosting with RSV 276 and the DS-Cav1/B3TMCT vector increased the peak mean serum RSV-PRNTs by 171-fold and 1,274-fold, respectively, to titers of 1:1,024 and 1:7,643 (occurring on day 14, FIG. 17E). The peak mean post-boost serum RSV-PRNT for the vector was 7-fold higher than for RSV 276.

RSV serum antibodies suppressed DS-Cav1/B3TMCT vector replication in vitro. Because the replication of the DS-Cav1/B3TMCT vector in hamsters was significantly reduced in the NT by RSV-specific immunity from the primary infection (FIGS. 14B-14D), whether replication of this vector in vitro could be inhibited by RSV-neutralizing antibodies was investigated. LLC-MK2 cells were infected with the empty rB/HPIV3 vector or with the DS-Cav1 or DS-Cav1/B3TMCT vector at an MOI of 0.01, and then incubated with medium containing 10% heat-inactivated (56° C. for 30 min) serum from uninfected hamsters or from hamsters infected with RSV D46 or rB/HPIV3 (from the experiment in FIG. 14), in the absence of added complement (FIG. 18). Replication of the vectors in the presence of added hamster sera was monitored by taking a small aliquot of culture medium supernatant daily for three consecutive days for virus titration.

Figures 18A, 18B, 18C:
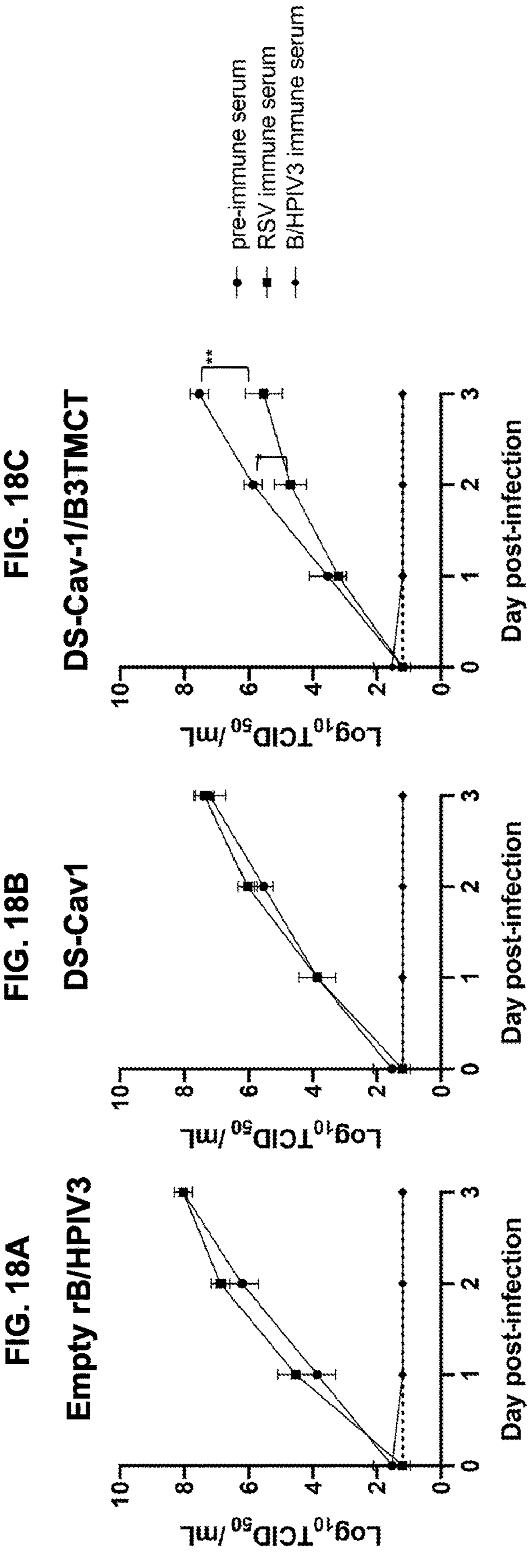
FIGS. 18A-18C. Multicycle replication of rB/HPIV3 vectors in vitro in the presence or absence of RSV-neutralizing antibodies. LLC-MK2 cells were infected by empty rB/HPIV3 vector (FIG. 18A), DS-Cav1 vector (FIG. 18B), or DS-Cav1/B3TMCT vector (FIG. 18C) at an MOI of 0.01 $TCID_{50}$ per cell. After adsorption for one h, cells were washed three times with cell culture medium and then incubated with culture medium containing 10% of one of the following sera (which had been previously heated at 56° C. for 30 min): pre-immune hamster serum, or pooled sera from hamsters infected with RSV D46 or with empty rB/HPIV3 vector, in the absence of added complement. The hamster sera were from the experiment in FIG. 14. The different treatments were performed in triplicate. An aliquot of medium was taken daily for three consecutive days after infection, flash-frozen, and viral titers were determined. The significance of difference between the replication in the presence of the pre-immune serum and RSV immune serum were determined by student-t tests: *, P<0.05; **, P<0.01.

As expected, rB/HPIV3-immune serum completely inhibited the replication of all three vector constructs (FIGS. 18A-18C, black curve) while the pre-immune serum, collected prior to the primary immunization, did not affect the replication of any construct (FIGS. 18A-18C). RSV-immune serum had no effect on the replication of empty rB/HPIV3 vector (FIG. 18A) or DS-Cav1 vector (FIG. 18B), but it significantly reduced the replication of the DS-Cav1/B3TMCT vector by Days 2 and 3, the latter by 100-fold (FIG. 18C). These results indicated that RSV-specific serum antibodies inhibited replication of the DS-Cav1/B3TMCT vector, but not the DS-Cav1 vector.

DISCUSSION

Non-limiting approaches to developing a pediatric RSV vaccine include (i) attenuated derivatives of RSV, and (ii) rB/HPIV3 expressing the RSV F protein from an added gene. Both approaches have provided promising candidates presently under evaluation for primary immunization, but their usefulness for booster immunization was less clear. In previous pediatric clinical studies, live-attenuated RSVs as vaccine candidates were inefficient (at least with regard to inducing increases in RSV-specific serum antibodies) in booster immunizations administered in successive doses over several months. For example, when the live-attenuated RSV called MEDI-559 was given to infants and young children in three successive doses at 2-month intervals, the second and third doses generally were poorly infectious and inefficient in boosting serum antibody responses in those subjects who had a "take" with a previous dose (See Malkin et al. 2013. Safety and immunogenicity of a live attenuated RSV vaccine in healthy RSV-seronegative children 5 to 24 months of age. PLoS One 8:e77104). Similar findings were made when the live-attenuated RSV cpts248/404 was given to infants and young children in two successive doses at an interval of 4-6 weeks (See Wright et al. 2000. Evaluation of a live, cold-passaged, temperature-sensitive, respiratory syncytial virus vaccine candidate in infancy. J Infect Dis 182:1331-42). Similar findings also have been made with attenuated versions of PIV3 given in successive doses at intervals of up to 6 months. Thus, in a "homologous" prime-boost (i.e., successive doses of the same vaccine virus), an attenuated RSV (or PIV3) usually is infectious and substantially immunogenic for serum virus-neutralizing antibodies only for the first "take", at least within a time interval of 6 months or less. Incidentally, the situation is different when the secondary infection is with RSV D46 rather than an attenuated RSV. Specifically, in vaccine trials in which subjects received an attenuated RSV during the summer and had natural exposure to community RSV D46 during the following winter, there were 20- to 40-fold boosts in serum RSV-PRNT (See Karron et al. 2015. A gene deletion that up-regulates viral gene expression yields an attenuated RSV vaccine with improved antibody responses in children. Sci Transl Med 7:312ra175). Thus, the poor immunogenicity of repeat doses of attenuated RSVs appears largely due to their attenuation.

The present study investigated a "heterologous" prime-boost strategy. In this strategy, a primary immunization with RSV was boosted by a secondary immunization with rB/HPIV3 expressing RSV F protein from an added gene. The RSV F protein was substantially stabilized in the pre-F conformation by the DS-Cav1 mutations and, in the case of the DS-Cav1/B3TMCT vector used in each experiment, contained the B3TMCT modification that mediates efficient packaging of RSV F into the vector virion. While the rB/HPIV3 vector itself is antigenically distinct from RSV, it does express an RSV antigen, in this case the F protein. This might be targeted by RSV-specific immunity including RSV-specific serum antibodies, as measured in the present study, as well as other effectors that historically have been less well characterized, including RSV-specific mucosal antibodies and cellular immunity. With regard to RSV-specific antibodies, binding to RSV F expressed by the vector probably would not directly block vector infection and spread because the RSV F in this study was largely non-functional for fusion due to the DS-Cav1 mutations and therefore presumably would have minimal or no contribution to vector replication and spread. However, the expression of RSV F in vector-infected cells might target those cells for destruction by cytotoxic T cells or antibody-dependent cell-mediated cytotoxicity. In addition, as noted, the DS-Cav1/B3TMCT vector used in all of experiments in the present study expressed the B3TMCT version of RSV F protein that was efficiently packaged in the vector virion, and this might target the vector virion for destruction such as by opsonization. Binding of antibodies to packaged RSV F might also create steric hindrance that interferes with the vector HN and F proteins during attachment and entry. It also was possible that antibody responses to RSV F might be suppressed by pre-existing F-specific antibodies.

Homologous and heterologous boosting was assessed in hamsters. When hamsters were given a primary infection with RSV D46 and a homologous booster infection with RSV D46 ~6 weeks later, there was no detectable infectious RSV in harvested NT and lung tissue, consistent with the expectation that RSV-specific immunity would severely restrict replication of an RSV boost. However, there was a significant, ~3-fold increase in serum RSV-PRNT measured with or without added complement, suggesting that some infection and antigen expression had occurred. In hamsters boosted with the empty rB/HPIV3 vector, there was no difference in virus titers in the NT and lungs between RSV-primed versus unprimed animals, showing that RSV-specific immunity indeed did not restrict the rB/HPIV3 backbone. In contrast, the replication of the DS-Cav1 and DS-Cav1/B3TMCT vectors exhibited a modest amount of restriction in RSV-primed versus unprimed animals, although the difference was significant only in the case of the DS-Cav1/B3TMCT vector in the NT. This suggests that expression of the unpackaged version of the RSV F protein resulted in a marginal restriction of the vectors by RSV-specific immunity, and expression of the packaged version of RSV F protein resulted in a somewhat greater restriction. This was associated with a significant decrease in the induction of serum HPIV3-neutralizing antibodies by the DS-Cav1/B3TMCT vector (but not the DS-Cav1 vector) in RSV-primed versus unprimed hamsters, providing another indication of reduced DS-Cav1/B3TMCT vector replication. In the RSV-primed hamsters, the DS-Cav1 and DS-Cav1/B3TMCT vectors induced increases in serum RSV-PRNT assayed with complement of 8- and 6-fold versus 3-fold for RSV D46; when assayed without complement, the increases were 9-and 18-fold versus 3-fold, respectively. The resulting peak mean post-boost serum RSV-PRNTs assayed with and without complement were significantly greater for the vectors than for RSV D46. Thus, these results in hamsters showed that (i) homologous boosts with RSV D46 were highly restricted and modestly immunogenic; (ii) the empty rB/HPIV3 vector was unrestricted by RSV-specific immunity; (iii) expression of RSV F by rB/HPIV3 conferred a low level of sensitivity to restriction by RSV-specific immunity that became significant when RSV F was packaged into the vector virion, and (iv) boosts with the vectors were significantly more immunogenic than with RSV D46.

Boosting also was evaluated in AGMs that previously had a primary RSV infection. Three different time intervals between the primary RSV infection and the boost were evaluated: ~2, ~6, and ~15 months. It was anticipated that pre-boost host immunity might diminish with increasing interval of time, which might affect the efficiency of the boost. Indeed, the mean pre-boost serum RSV-PRNTs diminished progressively in the ~2-, ~6-, and ~15-month groups, with respective titers of 1:256, 1:64, and 1:33 measured with complement, and 1:12, 1:8, and 1:6 measured without complement. It's reasonable to suppose that other immune effectors induced by the primary RSV infection, such as mucosal antibodies and cellular immunity, also diminished with time.

The replication of the RSV 276 boost was highly and nearly-equally restricted following each time interval, with only sporadic traces of shed infectious virus. Thus, there was no difference between the time intervals in the ability to strongly restrict this attenuated RSV. Although shedding of infectious RSV was highly restricted, there presumably was some viral infection and antigen expression leading to the observed secondary immune response. This is supported by the RT-qPCR performed in experiment #2 that detected shedding of viral nucleic acid, which may have included progeny virus that was neutralized by secretory antibodies and not detected by an infectivity assay.

In contrast to RSV, the DS-Cav1/B3TMCT vector replicated robustly. The peak mean titers of vector in the NP and TLs were very similar for experiments #2 and #3, ranging from 4.8 to 5.4 $\log_{10}$ $TCID_{50}$/ml. This level of shedding of DS-Cav1/B3TMCT vector was similar to that observed previously in RSV- and HPIV3-seronegative rhesus macaques (See Liang et al. 2017. Improved Prefusion Stability, Optimized Codon Usage, and Augmented Virion Packaging Enhance the Immunogenicity of Respiratory Syncytial Virus Fusion Protein in a Vectored-Vaccine Candidate. J Virol 91), suggesting that there was little or no restriction of the vector by pre-existing immunity to RSV following the ~6-month and ~15-month time intervals. In contrast, for experiment #1 (~2-month time interval), the titers of shed DS-Cav1/B3TMCT vector were lower by approximately 0.5 $\log_{10}$ $TCID_{50}$/ml in the NP and by 1.4 to 1.8 $\log_{10}$ $TCID_{50}$/ml in the TL (Table 11). This might indicate that expression of RSV F by this vector, and the packaging of RSV F into the vector virion, conferred a moderate amount of sensitivity to restriction by RSV-specific immunity following the shortest interval, similar to the restriction of the DS-Cav1/B3TMCT vector in RSV-primed versus unprimed hamsters. Since cellular immunity induced by a primary infection may persist only for several months, as noted above for the hamster model, this may have contributed to the restriction of the DS-Cav1/B3TMCT vector observed at ~2 months but not at ~6 and ~15 months. In any event, however, the restriction following the ~2-month interval was small and not statistically significant.

TABLE 11

Pre-boost serum RSV-neutralizing titers in AGMs boosted with DS-Cav1/B3TMCT and peak mean titers of post-boosting replication and RSV-neutralizing antibodies in 2-month, 6-month, and 15-month study cohorts

| Study cohort | Pre-boosting serum RSV-neutralizing titer (with complement)[a] | Peak mean titer in NP[b] | Peak mean titer in TL[b] | Post-boosting serum RSV-neutralizing titer (with complement)[c] | Post-boosting serkum RSV-neutralizing titer (without complement)[c] |
|---|---|---|---|---|---|
| ~2-month | 8.1 ± 2.1 | 4.9 ± 1.0 | 3.4 ± 1.2 | 14.5 | 12.9 |
| ~6-month | 6.1 ± 1.7 | 5.4 ± 0.5 | 5.2 ± 0.9 | 15.6 | 11.8 |
| ~15-month | 4.7 ± 0.7 | 5.4 ± 2.3 | 4.8 ± 1.1 | 14.9 | 12.1 |

[a]Sera were collected two weeks (~2-month and ~15-month studies) or 35 days (~6-month study) before boosting and were analyzed by RSV PRN assay with added complement and expressed as mean $\log_2$, PRNT.

[b]NP and TL were collected daily and every second day, respectively, for 10 days post-boost and titrated by limiting dilution. Titers are in $TCID_{50}$ per ml. Means were calculated for each day, and the peak mean titer for each virus is shown.

[c]Sera were collected two weeks following boosting and analyzed by RSV PRN assay with or without complement, as weeks following boosting and analyzed by RSV PRN assay with or without complement, as indicated, with titers expressed as mean $\log_2$PRNT.

To investigate possible restriction in AGMs associated with packaging of RSV F protein into the vector virion, the post-boost replication of the DS-Cav1/B3TMCT vector (which efficiently packages RSV F) was compared to that of the DS-Cav1 vector (which is very inefficient for packaging) in AGM experiment #2 (~6-month interval following priming). The replication of the DS-Cav1/B3TMCT vector hypothetically might have been reduced compared to the DS-Cav1 vector by (i) interference in vector replication due to packaging the RSV F protein into the vector virion, and/or (ii) restriction due to RSV-specific immunity targeted to the packaged RSV F protein, as already noted. The kinetics of replication of the DS-Cav1/B3TMCT vector were slightly slower than for the DS-Cav1 vector, but the difference was modest and was significant only for Days 2 and 4 in the TL, and the peak titers for the two vectors were similar. We did find that RSV-specific hamster antiserum inhibited the replication of the DS-Cav1/B3TMCT vector, and not the DS-Cav1 or empty vector, in cell culture (in the absence of complement). In this in vitro setting, the inhibition presumably was due to the binding of antibodies to RSV F packaged in the vector virions, and may not fully recapitulate the mechanism(s) that might operate in vivo.

Boosting with RSV 276 following intervals of ~2, ~6, and ~15 months resulted in increases in peak mean serum RSV-PRNT measured with complement of, respectively, 22-fold, 78-fold, and 216-fold, resulting in peak mean titers of 1:5,793, 1:4,973, and 1:7,132. When measured without complement, the respective increases in peak mean serum RSV-PRNT were 25-fold, 37-fold, and 171-fold, and resulted in peak mean titers of 1:294, 1:294, and 1:1,024. Thus, the post-boost serum RSV-PRNTs were generally similar among the different time intervals except that the titers following the ~15-month interval were slightly higher (1-fold with complement and 3.5-fold without complement) compared to the other intervals.

For the DS-Cav1/B3TMCT vector, boosting following intervals of ~2, ~6, and ~15 months resulted in increases in peak mean serum RSV-PRNT measured with complement of, respectively, 91-fold, 776-fold, and 926-fold, resulting in peak mean post-boost serum RSV-PRNTs of 1:23,170, 1:49,667, and 1:30,574. When measured without complement, the respective increases were 366-fold, 446-fold, and 1,274-fold, resulting in peak mean post-boost serum RSV-PRNTs of 1:4,390, 1:3,565, and 1:7,643. Thus, the post-boost titers were generally similar among the different time intervals, with differences that were no greater than 2-fold and were not consistent for any interval.

When compared in AGM experiment #2, boosting with the DS-Cav1/B3TMCT vector versus the DS-Cav1 vector induced a 3-fold greater serum RSV-PRNT measured with complement, and a 1.4-fold greater titer measured without complement. In the hamster study, boosting with the DS-Cav1/B3TMCT vector versus the DS-Cav1 vector was greater only for serum RSV-PRNT measured without complement, and only 2-fold.

In the AGM experiments, the peak mean post-boost serum RSV-PRNTs for the vectors were exceptionally high: up to 1:49,667 and 1:7,643 assayed with and without complement, respectively. This raises the possibility that some of the greater instances of boosting with the vectors might have been blunted due to limitations on the magnitude of the immune response. The titers for the vectors were higher than for RSV 276 when assayed with complement (3- to 10-fold), and the difference was even greater when assayed without complement (7-to 15-fold). Both vectors also induced significantly greater responses of serum and mucosal IgA compared to RSV 276, with little difference between the two vectors. The greater immunogenicity of the boosts by the vectors compared to RSV likely reflects both their higher level of replication (and resulting greater antigen expression) and the DS-Cav1 and B3TMCT modifications to the RSV F protein.

Because immune responses to RSV are reduced during infancy, it could be important to boost RSV-specific immunity following primary immunization with a pediatric RSV vaccine. In this study, boosting with an attenuated PIV vector expressing RSV F with DS-Cav1 and B3TMCT modifications was substantially more immunogenic than boosting with an attenuated RSV, particularly for "high quality" RSV-neutralizing antibodies that neutralize in vitro without added complement. The results were similar whether the interval between priming and boosting was ~2, ~6, or ~15 months. This suggests that a PIV vector could be effective in boosting during the same vaccination season or, alternatively, during the following year. In addition, a PIV-vectored RSV vaccine may be well-suited for primary immunization of young infants who have passive serum RSV-neutralizing antibodies from maternal transfer, including following maternal immunization, or from passive antibody immunoprophylaxis, including the use of antibody engineered for increased half-life. These passive antibodies might restrict an attenuated RSV, but not a PIV-vectored RSV vaccine. The use of an attenuated PIV3 vector also provides immunization against HPIV3, which is second only to RSV as an agent of severe acute pediatric respiratory disease.

Materials and Methods

Viruses. The RSVs in this example were recombinant (r) wild type (wt) or attenuated versions of the subgroup A strain A2 (Genbank KT992094) prepared using reverse genetics (Collins et al. 1995. Production of infectious human respiratory syncytial virus from cloned cDNA confirms an essential role for the transcription elongation factor from the 5' proximal open reading frame of the M2 mRNA in gene expression and provides a capability for vaccine development. Proc Natl Acad Sci USA 92:11563-7). The attenuated RSVs are described in the Results. One additional RSV was rRSV A/Maryland/001/11, which is a recombinant version of the wt subgroup A strain RSV A/Maryland/001/11 that was isolated from a nasal wash collected in 2011 from an adult with acute respiratory illness. The F and G proteins of the Maryland/001/11 strain have 97% and 86% amino acid sequence identity with strain A2. The rB/HPIV3 constructs were previously described (Liang et al. 2017. Improved Prefusion Stability, Optimized Codon Usage, and Augmented Virion Packaging Enhance the Immunogenicity of Respiratory Syncytial Virus Fusion Protein in a Vectored-Vaccine Candidate. J Virol 91) and express modified versions of the F protein of RSV strain A2 (Genbank KT992094) from an added gene in the second gene position. The vector constructs were: (i) rB/HPIV3, which is the empty vector; (ii) rB/HPIV3/DS-Cav1 (abbreviated as DS-Cav1 vector), which expresses RSV F protein with increased stability in the pre-F conformation due to the DS and Cav1 mutations (McLellan et al. 2013. Structure-based design of a fusion glycoprotein vaccine for respiratory syncytial virus. Science 342:592-8); and (iii) rB/HPIV3/DS-Cav1/B3TMCT (abbreviated as DS-Cav1/B3TMCT vector), which expresses RSV F with the DS-Cav1 mutations and with its TM and CT domains replaced by those of BPIV3 F. In addition, as previously described, the RSV F ORF used in the vector constructs had been modified by codon optimization (GenScript, Piscataway, NJ) and had been further modified by two amino acid substitutions called HEK (K66E and Q101P) that make F identical at the amino acid level to an early passage of RSV strain A2.

RSVs and rB/HPIV3 vectors were grown at 32° C. in Vero and LLC-MK2 cells, respectively. The complete genome sequences of all viruses were confirmed by automated Sanger sequencing analysis of un-cloned RT-PCR products to be free of adventitious mutations detectable above background (except for ~30 and ~120 nucleotides at the 3' and 5' ends, respectively, which include the primer binding sites and were not sequenced).

Titration of infectious virus and serum antibodies. Titers of RSV preparations were determined by plaque assay in Vero cells with immunostaining using a mixture of three F-specific monoclonal antibodies, as described previously (Luongo et al. 2013. Respiratory syncytial virus modified by deletions of the NS2 gene and amino acid S1313 of the L polymerase protein is a temperature-sensitive, live-attenuated vaccine candidate that is phenotypically stable at physiological temperature. J Virol 87:1985-96); titers are reported as $\log_{10}$ plaque forming units (PFU) per ml or g. Titers of rB/HPIV3 vectors were determined by limiting dilution in LLC-MK2 cells, with virus-positive wells detected by hemadsorption with guinea pig erythrocytes, as described previously (Durbin et al. 1999. Mutations in the C, D, and V open reading frames of human parainfluenza virus type 3 attenuate replication in rodents and primates. Virology 261: 319-30); titers are reported as $\log_{10}$ 50% tissue culture infectious doses ($TCID_{50}$) per ml or g.

Serum RSV- or HPIV3-neutralizing antibody titers were determined by 60% plaque reduction neutralization (PRN) assays on Vero cells using RSV or HPIV3 expressing green fluorescent protein (GFP) (Liang et al. 2014. Chimeric bovine/human parainfluenza virus type 3 expressing respiratory syncytial virus (RSV) F glycoprotein: effect of insert position on expression, replication, immunogenicity, stability, and protection against RSV infection. J Virol 88:4237-50). The assays were performed in the presence (RSV) or absence (RSV, HPIV3) of 5% added guinea pig complement (Cedarlane, Burlington, NC) as noted. The 60% plaque reduction neutralization titers (PRNTs) are reported in $\log_2$ and/or arithmetic values. Prior to primary infection, animals were confirmed to be RSV- or HPIV3-seronegative by, respectively, a PRN assay with complement or a hemagglutination-inhibition assay using guinea pig erythrocytes (Coates et al. 1966. An antigenic analysis of respiratory syncytial virus isolates by a plaque reduction neutralization test. Am J Epidemiol 83:299-313; van Wyke Coelingh et al. 1988. Attenuation of bovine parainfluenza virus type 3 in nonhuman primates and its ability to confer immunity to human parainfluenza virus type 3 challenge. J Infect Dis 157:655-62).

Animal studies. Animal studies were carried out in accordance with the Guide for Care and Use of Laboratory Animals of the National Institutes of Health and were approved by the NIAID Animal Care and Use Committee.

A single prime-boost experiment was performed in Syrian Golden hamsters as described in the legend to FIG. 14 and the accompanying Results section.

Three prime-boost experiments were performed in African green monkeys (AGM Experiments #1-#3, Tables 8-10, and FIGS. 15-17, respectively). The primary AGM infections with RSV were performed using a number of different RSVs that mostly were attenuated derivatives of RSV strain A2 and are described in the Results and Tables 8-10. In those studies, RSV was administered by the combined IN/intratracheal (IT) routes at a dose per site of $10^6$ PFU in 1 ml of L-15 medium. Booster infections with RSV or the DS-Cav/B3TMCT or DS-Cav1 vectors in AGMs in the present study were administered in the same way, by the combined IN/IT routes at a dose per site of $10^6$ PFU (RSV) or $10^6$ $TCID_{50}$ (vectors) in 1 ml of L-15 medium. Following inoculation, nasopharyngeal swabs (NP) and tracheal lavages (TL) were collected daily and every other day, respectively, for 10 days, and were flash-frozen on dry ice and stored at −80° C. until titration. Sera were collected prior to inoculation on the day of the boost and every seven days thereafter for four consecutive weeks.

In AGM Experiment #2, nasal mucosal lining fluid was sampled on the day of boosting and on days 14, 21, and 28 post-boosting using synthetic adsorptive matrix (SAM) strips (Nasosorption FXi, Hunt Developments, UK). SAM strips were gently placed on the nasal mucosa of the lower turbinate of one nostril, held in place for 30 seconds, and placed into a microtube pre-filled with 300 μl of phosphate buffered saline buffer (PBS) containing 3% bovine serum albumin (BSA) and 0.1% Tween 20. Samples were flash frozen on dry ice and kept at −80° C. until use. Mucosal and serum IgA titers were determined by dissociation-enhanced lanthanide fluorescence immunoassay (DELFIA) as described below.

RSV RNA copy numbers in AGM TL samples were quantified by reverse transcription-quantitative PCR assay (RT-qPCR) that was specific for both positive- and negative-sense RSV M gene sequence. Frozen AGM TL samples were briefly thawed in a 37° C. water bath and immediately kept on ice. After clarification by centrifugation at 800 g for 5 min at 4° C., the total RNA in TL samples was extracted using QIAamp Viral RNA Mini Kit (Qiagen). cDNA was generated by reverse transcription using Applied Biosystem RT kit (ThermoFisher Scientific) with random hexamer primers, and analyzed by the M-specific qPCR. For comparison, a standard curve was generated using a DNA plasmid encoding the full-length genome of wt RSV A2 strain (LID) analyzed by the same qPCR assay. The copy number of reverse-transcribed RSV RNA in TL samples was interpolated from the standard curve. Statistical analyses were performed using GraphPad Prism version 8, GraphPad Software, San Diego, California USA.

Detection of IgA antibodies using a dissociation-enhanced lanthanide fluorescence immunoassay (DELFIA). Serum and mucosal IgA were detected by DELFIA immunoassay. Briefly, recombinant RSV DS-Cav1 F protein was expressed in HEK293 cells and purified as described previously (McLellan et al. 2013. Structure-based design of a fusion glycoprotein vaccine for respiratory syncytial virus. Science 342:592-8). Ninety-six-well DELFIA yellow plates (Perkin Elmer, Waltham MA) were coated with 100 ng/well of purified RSV DS-Cav1 F protein diluted in 100 μl of carbonate-bicarbonate buffer (Millipore Sigma, St. Louis MO) and incubated at 4° C. overnight. All washes in the assay were performed once with 200 μl/well of wash buffer (1×DELFIA wash concentrate, Perkin Elmer, Waltham MA). After overnight antigen coating, plates were washed and incubated with 100 μl/well of blocking solution (PBS containing 0.1% Tween-20 and 3% BSA) at 37° C. for 1 h. Plates were washed and 100 μl of serum samples in 4-fold dilution series in blocking solution were added and incubated at 4° C. overnight. Following a wash, 100 μl/well of anti-monkey IgA biotin conjugate (Alpha Diagnostic, San Antonio, TX) diluted 1:5000 in blocking solution was added and incubated at 37° C. for 1 h. Plates were washed and 100 μl/well of Europium (Eu)-conjugated streptavidin diluted 1:2000 in DELFIA assay buffer (Perkin Elmer, Waltham, MA), was added. After incubation at 37° C. for 1 h, plates were washed and incubated with 100 μl/well of DELFIA enhancement solution (Perkin Elmer) at room temperature with gentle shaking for 20 minutes. Fluorescence was measured using a Eu-specific time-resolved fluorescence (TRF) program (340 nm excitation, 615 nm emission) in a Synergy Neo 2 plate reader (BioTek, Winooski, VT). The blocking solution was used to generate blank values, and an average of 24 blank values plus 3 standard deviations was used as a cut-off (corresponding to 400 fluorescence units). Test sample dilutions corresponding to 400 fluorescence units were interpolated from sigmoidal standard curves using GraphPad Prism version 8 (GraphPad Software, San Diego, California USA) and were expressed as $log_2$ values.

It will be apparent that the precise details of the methods or compositions described may be varied or modified without departing from the spirit of the described embodiments. We claim all such modifications and variations that fall within the scope and spirit of the claims below.

It is claimed:

1. A method of eliciting an immune response to RSV in a subject, comprising administering an effective amount of an immunogen to the subject, wherein administering the effective amount comprises a prime-boost administration, and wherein:

(i) the prime comprises administration of a RSV ΔNS2/Δ1313/I1314L virus, a RSV LID/F1BBG2/ΔNS1 virus, a RSV LID/ΔNS1 virus, a RSV LID/ΔNS2/1030s virus, a RSV D46/NS2/N/ΔM2-2-HindIII virus, or a RSV 276 virus; and the boost comprises administration of a B/HPIV3 DS-Cav1 virus, or a B/HPIV3 DS-Cav1/B3TMCT virus; or (ii) the prime comprises administration of a RSV ΔNS2/Δ1313/I1314L virus, a RSV LID/F1BBG2/ΔNS1 virus, a RSV LID/ΔNS1 virus, a RSV LID/ΔNS2/1030s virus, or a RSV D46/NS2/N/ΔM2-2-HindIII virus; and the boost comprises administration of a RSV 276 virus.

2. The method of claim 1, wherein:

the prime comprises intranasal administration of RSV ΔNS2/Δ1313/I1314L virus, a RSV LID/ΔNS2/1030s virus, or a RSV 276 virus; and the boost comprises intranasal administration of a B/HPIV3 DS-Cav1/B3TMCT virus or a B/HPIV3 DS-Cav1 virus.

3. The method of claim 1, wherein:

the RSV 276 virus comprises an antigenomic sequence set forth as SEQ ID NO: 12, the B/HPIV3 DS-Cav1/B3TMCT virus comprises an antigenomic sequence set forth as SEQ ID NO: 17, the B/HPIV3 DS-Cav1 virus comprises an antigenomic sequence set forth as SEQ ID NO: 16, the RSV LID/F1BBG2/ΔNS1 virus comprises an antigenomic sequence set forth as SEQ ID NO: 4, the RSV LID/ΔNS1 virus comprises an antigenomic sequence set forth as SEQ ID NO: 2, the RSV LID/ΔNS2/1030s virus comprises an antigenomic sequence set forth as SEQ ID NO: 18;

the RSV LID/ΔNS2/Δ1313/I1314L virus comprises an antigenomic sequence set forth as SEQ ID NO: 19, and the RSV D46/ΔNS2/N/ΔM2-2-HindIII virus comprises an antigenomic sequence set forth as SEQ ID NO: 11.

4. The method of claim 1, wherein the subject is a human.

5. The method of claim 1, wherein the RSV virus is administered intranasally.

6. The method of claim 5, wherein the RSV virus is administered via injection, aerosol delivery, nasal spray or nasal droplets.

7. The method of claim 4, wherein the subject is 5 years of age or younger.

8. The method of claim 7, wherein the subject is 2 years of age or younger.

9. The method of claim 8, wherein the subject is between 1 and 6 months of age.

10. The method of claim 1, wherein the subject is seronegative for RSV.

11. The method of claim 1, wherein the subject is seropositive for RSV.

12. The method of claim 1, wherein the RSV virus is administered intranasally to the subject at a dose of from 3.0 $\log_{10}$ PFU to 7.0 $\log_{10}$ PFU.

13. The method of claim 12, wherein the RSV virus is administered at a dose of from about 5.0 $\log_{10}$ PFU to about 6.0 $\log_{10}$ PFU.

14. The method of claim 13, wherein the RSV virus is administered at a dose of about 6.0 $\log_{10}$ PFU.

15. The method of claim 12, wherein the subject is a RSV-seropositive human subject 5 years of age or younger.

16. The method of claim 15, wherein the subject is 2 years of age or younger.

17. The method of claim 1, wherein the immune response is a protective immune response.

18. The method of claim 1, wherein within the first month following administration, the subject exhibits no or mild (Grade 1) respiratory/febrile illness that is comparable in kind and severity to that of comparable subjects who did not receive the virus.

19. The method of claim 1, wherein a titer of the RSV virus in nasal wash taken during the first 2 weeks post administration is 3.0 $\log_{10}$ PFU/ml of nasal wash or less.

20. The method of claim 1, wherein the prime-boost administration elicits an increase in serum RSV-specific antibodies in ≥75% of recipients.

* * * * *

SEQUENCE LISTING

```
<160> NUMBER OF SEQ ID NOS: 29

<210> SEQ ID NO 1
<211> LENGTH: 15223
<212> TYPE: DNA
<213> ORGANISM: Respiratory Syncytial Virus

<400> SEQUENCE: 1

acgggaaaaa atgcgtacaa caaacttgca taaaccaaaa aaatggggca aataagaatt     60

tgataagtac cacttaaatt taactccctt ggttagagat gggcagcaat tcattgagta    120

tgataaaagt tagattacaa aatttgtttg acaatgatga agtagcattg ttaaaaataa    180

catgctatac tgataaatta atacatttaa ctaatgcttt ggctaaggca gtgatacata    240

caatcaaatt gaatggcatt gtgtttgtgc atgttattac aagtagtgat atttgcccta    300

ataataatat tgtagtaaaa tccaatttca caacaatgcc agtactacaa aatggaggtt    360

atatatggga aatgatggaa ttaacacatt gctctcaacc taatggtcta ctagatgaca    420

attgtgaaat taaattctcc aaaaaactaa gtgattcaac aatgaccaat tatatgaatc    480

aattatctga attacttgga tttgatctta atccataaat tataattaat atcaactagc    540

aaatcaatgt cactaacacc attagttaat ataaaactta acagaagaca aaaatggggc    600

aaataaatca attcagccaa cccaaccatg gacacaaccc acaatgataa tacaccacaa    660

agactgatga tcacagacat gagaccgttg tcacttgaga ccataataac atcactaacc    720

agagacatca taacacacaa atttatatac ttgataaatc atgaatgcat agtgagaaaa    780

cttgatgaaa gacaggccac atttacattc ctggtcaact atgaaatgaa actattacac    840

aaagtaggaa gcactaaata taaaaaatat actgaataca acacaaaata tggcactttc    900

cctatgccaa tattcatcaa tcatgatggg ttcttagaat gcattggcat taagcctaca    960

aagcatactc ccataatata caagtatgat ctcaatccat aaatttcaac acaatattca   1020

cacaatctaa aacaacaact ctatgcataa ctatactcca tagtccagat ggagcctgaa   1080

aattatagta atttaaaact taaggagaga tataagatag aagatggggc aaatacaacc   1140

atggctctta gcaaagtcaa gttgaatgat acactcaaca aagatcaact tctgtcatcc   1200

agcaaataca ccatccaacg gagcacagga gatagtattg atactcctaa ttatgatgtg   1260

cagaaacaca tcaataagtt atgtggcatg ttattaatca cagaagatgc taatcataaa   1320

ttcactgggt taataggtat gttatatgcg atgtctaggt taggaagaga agacaccata   1380

aaaatactca gagatgcggg atatcatgta aaagcaaatg gagtagatgt aacaacacat   1440

cgtcaagaca ttaatggaaa agaaatgaaa tttgaagtgt taacattggc aagcttaaca   1500

actgaaattc aaatcaacat tgagatagaa tctagaaaat cctacaaaaa aatgctaaaa   1560

gaaatgggag aggtagctcc agaatacagg catgactctc ctgattgtgg gatgataata   1620

ttatgtatag cagcattagt aataactaaa ttagcagcag gggacagatc tggtcttaca   1680
```

```
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcagt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aacctttttc ctctacatca gtgtgttaat tcatacaaac tttctaccta   4080
```

cattcttcac ttcaccatca caatcacaaa cactctgtgg ttcaaccaat caaacaaaac 4140
ttatctgaag tcccagatca tcccaagtca ttgtttatca gatctagtac tcaaataagt 4200
taataaaaaa tatacacatg gggcaaataa tcattggagg aaatccaact aatcacaata 4260
tctgttaaca tagacaagtc cacacaccat acagaatcaa ccaatggaaa atacatccat 4320
aacaatagaa ttctcaagca aattctggcc ttactttaca ctaatacaca tgatcacaac 4380
aataatctct ttgctaatca taatctccat catgattgca atactaaaca aactttgtga 4440
atataacgta ttccataaca aaacctttga gttaccaaga gctcgagtca acacatagca 4500
ttcatcaatc caacagccca aaacagtaac cttgcattta aaaatgaaca acccctacct 4560
ctttacaaca cctcattaac atcccaccat gcaaaccact atccatacta taaagtagtt 4620
aattaaaaat agtcataaca atgaactagg atatcaagac taacaataac attggggcaa 4680
atgcaaacat gtccaaaaac aaggaccaac gcaccgctaa gacattagaa aggacctggg 4740
acactctcaa tcatttatta ttcatatcat cgtgcttata taagttaaat cttaaatctg 4800
tagcacaaat cacattatcc attctggcaa tgataatctc aacttcactt ataattgcag 4860
ccatcatatt catagcctcg gcaaaccaca aagtcacacc aacaactgca atcatacaag 4920
atgcaacaag ccagatcaag aacacaaccc caacatacct cacccagaat cctcagcttg 4980
gaatcagtcc ctctaatccg tctgaaatta catcacaaat caccaccata ctagcttcaa 5040
caacaccagg agtcaagtca accctgcaat ccacaacagt caagaccaaa aacacaacaa 5100
caactcaaac acaacccagc aagcccacca caaaacaacg ccaaaacaaa ccaccaagca 5160
aacccaataa tgattttcac tttgaagtgt tcaactttgt accctgcagc atatgcagca 5220
acaatccaac ctgctgggct atctgcaaaa gaataccaaa caaaaaacca ggaaagaaaa 5280
ccactaccaa gcccacaaaa aaaccaaccc tcaagacaac caaaaaagat cccaaacctc 5340
aaaccactaa atcaaaggaa gtacccacca ccaagcccac agaagagcca accatcaaca 5400
ccaccaaaac aaacatcata actacactac tcacctccaa caccacagga aatccagaac 5460
tcacaagtca aatggaaacc ttccactcaa cttcctccga aggcaatcca agcccttctc 5520
aagtctctac aacatccgag tacccatcac aaccttcatc tccacccaac acaccacgcc 5580
agtagttact taaaaacata ttatcacaaa aggccttgac caacttaaac agaatcaaaa 5640
taaactctgg ggcaaataac aatggagttg ctaatcctca aagcaaatgc aattaccaca 5700
atcctcactg cagtcacatt ttgttttgct tctggtcaaa acatcactga agaattttat 5760
caatcaacat gcagtgcagt tagcaaaggc tatcttagtg ctctgagaac tggttggtat 5820
accagtgtta taactataga attaagtaat atcaagaaaa ataagtgtaa tggaacagat 5880
gctaaggtaa aattgataaa acaagaatta gataaatata aaaatgctgt aacagaattg 5940
cagttgctca tgcaaagcac acaagcaaca aacaatcgag ccagaagaga actaccaagg 6000
tttatgaatt atacactcaa caatgccaaa aaaaccaatg taacattaag caagaaaagg 6060
aaaagaagat ttcttggttt tttgttaggt gttggatctg caatcgccag tggcgttgct 6120
gtatctaagg tcctgcacct agaaggggaa gtgaacaaga tcaaaagtgc tctactatcc 6180
acaaacaagg ctgtagtcag cttatcaaat ggagttagtg ttttaaccag caaagtgtta 6240
gacctcaaaa actatataga taaacaattg ttacctattg tgaacaagca aagctgcagc 6300
atatcaaata tagaaactgt gatagagttc caacaaaaga acaacagact actagagatt 6360
accagggaat ttagtgttaa tgcaggcgta actacacctg taagcactta catgttaact 6420
aatagtgaat tattgtcatt aatcaatgat atgcctataa caaatgatca gaaaaagtta 6480
atgtccaaca atgttcaaat agttagacag caaagttact ctatcatgtc cataataaaa 6540
gaggaagtct tagcatatgt agtacaatta ccactatatg gtgttataga tacaccctgt 6600
tggaaactac acacatcccc tctatgtaca accaacacaa aagaagggtc caacatctgt 6660
ttaacaagaa ctgacagagg atggtactgt gacaatgcag gatcagtatc tttcttccca 6720
caagctgaaa catgtaaagt tcaatcaaat cgagtatttt gtgacacaat gaacagttta 6780
acattaccaa gtgaagtaaa tctctgcaat gttgacatat tcaaccccaa atatgattgt 6840
aaaattatga cttcaaaaac agatgtaagc agctccgtta tcacatctct aggagccatt 6900
gtgtcatgct atggcaaaac taaatgtaca gcatccaata aaaatcgtgg aatcataaag 6960
acattttcta acgggtgcga ttatgtatca aataaagggg tggacactgt gtctgtaggt 7020
aacacattat attatgtaaa taagcaagaa ggtaaaagtc tctatgtaaa aggtgaacca 7080
ataataaatt tctatgaccc attagtattc ccctctgatg aatttgatgc atcaatatct 7140
caagtcaacg agaagattaa ccagagccta gcatttattc gtaaatccga tgaattatta 7200
cataatgtaa atgctggtaa atccaccaca aatatcatga taactactat aattatagtg 7260
attatagtaa tattgttatc attaattgct gttggactgc tcttatactg taaggccaga 7320
agcacaccag tcacactaag caaagatcaa ctgagtggta taaataatat tgcatttagt 7380
aactaaataa aaatagcacc taatcatgtt cttacaatgg tttactatct gctcatagac 7440
aacccatctg tcattggatt ttcttaaaat ctgaacttca tcgaaactct catctataaa 7500
ccatctcact tacactattt aagtagattc ctagtttata gttatataaa acacaattgc 7560
atgccagatt aacttaccat ctgtaaaaat gaaaactggg gcaaatatgt cacgaaggaa 7620
tccttgcaaa tttgaaattc gaggtcattg cttaaatggt aagaggtgtc attttagtca 7680
taattatttt gaatggccac cccatgcact gcttgtaaga caaaacttta tgttaaacag 7740
aatacttaag tctatggata aaagtataga taccttatca gaaataagtg gagctgcaga 7800
gttggacaga acagaagagt atgctcttgg tgtagttgga gtgctagaga gttatatagg 7860
atcaataaac aatataacta aacaatcagc atgtgttgcc atgagcaaac tcctcactga 7920
actcaatagt gatgatatca aaaagctgag ggacaatgaa gagctaaatt cacccaagat 7980
aagagtgtac aatactgtca tatcatatat tgaaagcaac aggaaaaaca ataaacaaac 8040
tatccatctg ttaaaaagat tgccagcaga cgtattgaag aaaaccatca aaaacacatt 8100
ggatatccat aagagcataa ccatcaacaa cccaaaagaa tcaactgtta gtgatacaaa 8160
tgaccatgcc aaaaataatg atactacctg acaaatatcc ttgtagtata acttccatac 8220
taataacaag tagatgtaga gttactatgt ataatcaaaa gaacacacta tatttcaatc 8280
aaaacaaccc aaataaccat atgtactcac cgaatcaaac attcaatgaa atccattgga 8340
cctctcaaga attgattgac acaattcaaa attttctaca acatctaggt attattgagg 8400
atatatatac aatatatata ttagtgtcat aacactcaat tctaacactc accacatcgt 8460
tacattatta attcaaacaa ttcaagttgt gggacaaaat ggatcccatt attaatggaa 8520
attctgctaa tgtttatcta accgatagtt atttaaaagg tgttatctct ttctcagagt 8580
gtaatgcttt aggaagttac atattcaatg gtccttatct caaaaatgat tataccaact 8640
taattagtag acaaaatcca ttaatagaac acatgaatct aaagaaacta aatataacac 8700
agtccttaat atctaagtat cataaaggtg aaataaaatt agaagaacct acttattttc 8760
agtcattact tatgacatac aagagtatga cctcgtcaga acagattgct accactaatt 8820

```
tacttaaaaa gataataaga agagctatag aaataagtga tgtcaaagtc tatgctatat   8880
tgaataaact agggcttaaa gaaaaggaca agattaaatc caacaatgga caagatgaag   8940
acaactcagt tattacgacc ataatcaaag atgatatact ttcagctgtt aaagataatc   9000
aatctcatct taaagcagac aaaaatcact ctacaaaaca aaaagacaca atcaaaacaa   9060
cactcttgaa gaaattgatg tgttcaatgc aacatcctcc atcatggtta atacattggt   9120
ttaacttata cacaaaatta aacaacatat taacacagta tcgatcaaat gaggtaaaaa   9180
accatgggtt tacattgata gataatcaaa ctcttagtgg atttcaattt attttgaacc   9240
aatatggttg tatagtttat cataaggaac tcaaaagaat tactgtgaca acctataatc   9300
aattcttgac atggaaagat attagcctta gtagattaaa tgtttgttta attacatgga   9360
ttagtaactg cttgaacaca ttaaataaaa gcttaggctt aagatgcgga ttcaataatg   9420
ttatcttgac acaactattc ctttatggag attgtatact aaagctattt cacaatgagg   9480
ggttctacat aataaaagag gtagagggat ttattatgtc tctaatttta aatataacag   9540
aagaagatca attcagaaaa cgattttata atagtatgct caacaacatc acagatgctg   9600
ctaataaagc tcagaaaaat ctgctatcaa gagtatgtca tacattatta gataagacag   9660
tgtccgataa tataataaat ggcagatgga taattctatt aagtaagttc cttaaattaa   9720
ttaagcttgc aggtgacaat aaccttaaca atctgagtga actatatttt ttgttcagaa   9780
tatttggaca cccaatggta gatgaaagac aagccatgga tgctgttaaa attaattgca   9840
atgagaccaa attttacttg ttaagcagtc tgagtatgtt aagaggtgcc tttatatata   9900
gaattataaa agggtttgta aataattaca acagatggcc tactttaaga aatgctattg   9960
ttttaccctt aagatggtta acttactata aactaaacac ttatccttct ttgttggaac  10020
ttacagaaag agatttgatt gtgttatcag gactacgttt ctatcgtgag tttcggttgc  10080
ctaaaaaagt ggatcttgaa atgattataa atgataaagc tatatcacct cctaaaaatt  10140
tgatatggac tagtttccct agaaattaca tgccatcaca catacaaaac tatatagaac  10200
atgaaaaatt aaaatttccc gagagtgata aatcaagaag agtattagag tattatttaa  10260
gagataacaa attcaatgaa tgtgatttat acaactgtgt agttaatcaa agttatctca  10320
acaaccctaa tcatgtggta tcattgacag gcaaagaaag agaactcagt gtaggtagaa  10380
tgtttgcaat gcaaccggga atgttcagac aggttcaaat attggcagag aaaatgatag  10440
ctgaaaacat tttacaattc tttcctgaaa gtcttacaag atatggtgat ctagaactac  10500
aaaaaatatt agaactgaaa gcaggaataa gtaacaaatc aaatcgctac aatgataatt  10560
acaacaatta cattagtaag tgctctatca tcacagatct cagcaaattc aatcaagcat  10620
ttcgatatga aacgtcatgt atttgtagtg atgtgctgga tgaactgcat ggtgtacaat  10680
ctctattttc ctggttacat ttaactattc ctcatgtcac aataatatgc acatataggc  10740
atgcaccccc ctatatagga gatcatattg tagatcttaa caatgtagat gaacaaagtg  10800
gattatatag atatcacatg ggtggcatcg aagggtggtg tcaaaaacta tggaccatag  10860
aagctatatc actattggat ctaatatctc tcaaagggaa attctcaatt actgctttaa  10920
ttaatggtga caatcaatca atagatataa gcaaaccaat cagactcatg gaaggtcaaa  10980
ctcatgctca agcagattat ttgctagcat taaatagcct taaattactg tataaagagt  11040
atgcaggcat aggccacaaa ttaaaaggaa ctgagactta tatatcacga gatatgcaat  11100
ttatgagtaa aacaattcaa cataacggtg tatattaccc agctagtata aagaaagtcc  11160
```

```
taagagtggg accgtggata aacactatac ttgatgattt caaagtgagt ctagaatcta  11220
taggtagttt gacacaagaa ttagaatata gaggtgaaag tctattatgc agtttaatat  11280
ttagaaatgt atggttatat aatcagattg ctctacaatt aaaaaatcat gcattatgta  11340
acaataaact atatttggac atattaaagg ttctgaaaca cttaaaaacc tttttaatc  11400
ttgataatat tgatacagca ttaacattgt atatgaattt acccatgtta tttggtggtg  11460
gtgatcccaa cttgttatat cgaagtttct atagaagaac tcctgacttc ctcacagagg  11520
ctatagttca ctctgtgttc atacttagtt attatacaaa ccatgactta aaagataaac  11580
ttcaagatct gtcagatgat agattgaata agttcttaac atgcataatc acgtttgaca  11640
aaaaccctaa tgctgaattc gtaacattga tgagagatcc tcaagcttta gggtctgaga  11700
gacaagctaa aattactagc gaaatcaata gactggcagt tacagaggtt ttgagtacag  11760
ctccaaacaa aatattctcc aaaagtgcac aacattatac tactacagag atagatctaa  11820
atgatattat gcaaaatata gaacctacat atcctcatgg gctaagagtt gtttatgaaa  11880
gtttaccctt ttataaagca gagaaaatag taaatcttat atcaggtaca aaatctataa  11940
ctaacatact ggaaaaaact tctgccatag acttaacaga tattgataga gccactgaga  12000
tgatgaggaa aaacataact ttgcttataa ggatacttcc attggattgt aacagagata  12060
aaagagagat attgagtatg gaaaacctaa gtattactga attaagcaaa tatgttaggg  12120
aaagatcttg gtctttatcc aatatagttg gtgttacatc acccagtatc atgtatacaa  12180
tggacatcaa atatactaca agcactatat ctagtggcat aattatagag aaatataatg  12240
ttaacagttt aacacgtggt gagagaggac ccactaaacc atgggttggt tcatctacac  12300
aagagaaaaa aacaatgcca gtttataata gacaagtctt aaccaaaaaa cagagagatc  12360
aaatagatct attagcaaaa ttggattggg tgtatgcatc tatagataac aaggatgaat  12420
tcatggaaga actcagcata ggaacccttg ggttaacata tgaaaaggcc aagaaattat  12480
ttccacaata tttaagtgtc aattatttgc atcgccttac agtcagtagt agaccatgtg  12540
aattccctgc atcaatacca gcttatagaa caacaaatta tcactttgac actagcccta  12600
ttaatcgcat attaacagaa aagtatggtg atgaagatat tgacatagta ttccaaaact  12660
gtataagctt tggccttagt ttaatgtcag tagtagaaca atttactaat gtatgtccta  12720
acagaattat tctcatacct aagcttaatg agatacattt gatgaaacct cccatattca  12780
caggtgatgt tgatattcac aagttaaaac aagtgataca aaaacagcat atgtttttac  12840
cagacaaaat aagtttgact caatatgtgg aattattctt aagtaataaa acactcaaat  12900
ctggatctca tgttaattct aatttaatat tggcacataa aatatctgac tattttcata  12960
atacttacat tttaagtact aatttagctg gacattggat tctgattata caacttatga  13020
aagattctaa aggtattttt gaaaaagatt ggggagaggg atatataact gatcatatgt  13080
ttattaattt gaaagttttc ttcaatgctt ataagaccta tctcttgtgt tttcataaag  13140
gttatggcaa agcaaagctg gagtgtgata tgaacacttc agatcttcta tgtgtattgg  13200
aattaataga cagtagttat tggaagtcta tgtctaaggt atttttagaa caaaaagtta  13260
tcaaatacat tcttagccaa gatgcaagtt tacatagagt aaaaggatgt catagcttca  13320
aattatggtt tcttaaacgt cttaatgtag cagaattcac agtttgccct tgggttgtta  13380
acatagatta tcatccaaca catatgaaag caatattaac ttatatagat cttgttagaa  13440
tgggattgat aaatatagat agaatacaca ttaaaaataa acacaaattc aatgatgaat  13500
tttatacttc taatctcttc tacattaatt ataacttctc agataatact catctattaa  13560
```

```
ctaaacatat aaggattgct aattctgaat tagaaaataa ttacaacaaa ttatatcatc  13620

ctacaccaga aaccctagag aatatactag ccaatccgat taaaagtaat gacaaaaaga  13680

cactgaatga ctattgtata ggtaaaaatg ttgactcaat aatgttacca ttgttatcta  13740

ataagaagct tattaaatcg tctgcaatga ttagaaccaa ttacagcaaa caagatttgt  13800

ataatttatt ccctatggtt gtgattgata gaattataga tcattcaggc aatacagcca  13860

aatccaacca actttacact actacttccc accaaatatc cttagtgcac aatagcacat  13920

cactttactg catgcttcct tggcatcata ttaatagatt caattttgta tttagttcta  13980

caggttgtaa aattagtata gagtatattt taaaagatct taaaattaaa gatcccaatt  14040

gtatagcatt cataggtgaa ggagcaggga atttattatt gcgtacagta gtggaacttc  14100

atcctgacat aagatatatt tacagaagtc tgaaagattg caatgatcat agtttaccta  14160

ttgagttttt aaggctgtac aatggacata tcaacattga ttatggtgaa aatttgacca  14220

ttcctgctac agatgcaacc aacaacattc attggtctta tttacatata aagtttgctg  14280

aacctatcag tctttttgtc tgtgatgccg aattgtctgt aacagtcaac tggagtaaaa  14340

ttataataga atggagcaag catgtaagaa agtgcaagta ctgttcctca gttaataaat  14400

gtatgttaat agtaaaatat catgctcaag atgatattga tttcaaatta gacaatataa  14460

ctatattaaa aacttatgta tgcttaggca gtaagttaaa gggatcggag gtttacttag  14520

tccttacaat aggtcctgcg aatatattcc cagtatttaa tgtagtacaa aatgctaaat  14580

tgatactatc aagaaccaaa aatttcatca tgcctaagaa agctgataaa gagtctattg  14640

atgcaaatat taaaagtttg ataccctttc tttgttaccc tataacaaaa aaaggaatta  14700

atactgcatt gtcaaaacta aagagtgttg ttagtggaga tatactatca tattctatag  14760

ctggacgtaa tgaagttttc agcaataaac ttataaatca taagcatatg aacatcttaa  14820

aatggttcaa tcatgtttta aatttcagat caacagaact aaactataac catttatata  14880

tggtagaatc tacatatcct tacctaagtg aattgttaaa cagcttgaca accaatgaac  14940

ttaaaaaact gattaaaatc acaggtagtc tgttatacaa ctttcataat gaataatgaa  15000

taaagatctt ataataaaaa ttcccatagc tatacactaa cactgtattc aattatagtt  15060

attaaaaatt aaaaatcata taattttta aataactttt agtgaactaa tcctaaagtt  15120

atcattttaa tcttggagga ataaatttaa accctaatct aattggttta tatgtgtatt  15180

aactaaatta cgagatatta gtttttgaca cttttttct cgt                    15223
```

<210> SEQ ID NO 2
<211> LENGTH: 14582
<212> TYPE: DNA
<213> ORGANISM: Artificial Sequence
<220> FEATURE:
<223> OTHER INFORMATION: Recombinant RSV sequence

<400> SEQUENCE: 2

```
acgggaaaaa atgcgtacaa caaacttgca taaaccaaaa aaatggggca aataagaatt     60

tgataagtac cacttaaatt taactccctt ggttagagat ggacacaacc cacaatgata    120

atacaccaca aagactgatg atcacagaca tgagaccgtt gtcacttgag accataataa    180

catcactaac cagagacatc ataacacaca aatttatata cttgataaat catgaatgca    240

tagtgagaaa acttgatgaa agacaggcca catttacatt cctggtcaac tatgaaatga    300

aactattaca caaagtagga agcactaaat ataaaaaata tactgaatac aacacaaaat    360
```

-continued

```
atggcacttt ccctatgcca atattcatca atcatgatgg gttcttagaa tgcattggca    420
ttaagcctac aaagcatact cccataatat acaagtatga tctcaatcca taaatttcaa    480
cacaatattc acacaatcta aaacaacaac tctatgcata actatactcc atagtccaga    540
tggagcctga aaattatagt aatttaaaac ttaaggagag atataagata gaagatgggg    600
caaatacaac catggctctt agcaaagtca agttgaatga tacactcaac aaagatcaac    660
ttctgtcatc cagcaaatac accatccaac ggagcacagg agatagtatt gatactccta    720
attatgatgt gcagaaacac atcaataagt tatgtggcat gttattaatc acagaagatg    780
ctaatcataa attcactggg ttaataggta tgttatatgc gatgtctagg ttaggaagag    840
aagacaccat aaaaatactc agagatgcgg gatatcatgt aaaagcaaat ggagtagatg    900
taacaacaca tcgtcaagac attaatggaa aagaaatgaa atttgaagtg ttaacattgg    960
caagcttaac aactgaaatt caaatcaaca ttgagataga atctagaaaa tcctacaaaa   1020
aaatgctaaa agaaatggga gaggtagctc cagaatacag gcatgactct cctgattgtg   1080
ggatgataat attatgtata gcagcattag taataactaa attagcagca ggggacagat   1140
ctggtcttac agccgtgatt aggagagcta ataatgtcct aaaaaatgaa atgaaacgtt   1200
acaaaggctt actacccaag gacatagcca acagcttcta tgaagtgttt gaaaaacatc   1260
cccactttat agatgttttt gttcattttg gtatagcaca atcttctacc agaggtggca   1320
gtagagttga agggattttt gcaggattgt ttatgaatgc ctatggtgca gggcaagtga   1380
tgttacggtg gggagtctta gcaaaatcag ttaaaaatat tatgttagga catgctagtg   1440
tgcaagcaga aatggaacaa gttgttgagg tttatgaata tgcccaaaaa ttgggtggtg   1500
aagcaggatt ctaccatata ttgaacaacc caaaagcatc attattatct ttgactcaat   1560
ttcctcactt ctccagtgta gtattaggca atgctgctgg cctaggcata atgggagagt   1620
acagaggtac accgaggaat caagatctat atgatgcagc aaaggcatat gctgaacaac   1680
tcaaagaaaa tggtgtgatt aactacagtg tactagactt gacagcagaa gaactagagg   1740
ctatcaaaca tcagcttaat ccaaaagata atgatgtaga gctttgagtt aataaaaaat   1800
ggggcaaata aatcatcatg gaaaagtttg ctcctgaatt ccatggagaa gatgcaaaca   1860
acagggctac taaattccta gaatcaataa agggcaaatt cacatcaccc aaagatccca   1920
agaaaaaaga tagtatcata tctgtcaact caatagatat agaagtaacc aaagaaagcc   1980
ctataacatc aaattcaact attatcaacc caacaaatga gacagatgat actgcaggga   2040
acaagcccaa ttatcaaaga aaacctctag taagtttcaa agaagaccct acaccaagtg   2100
ataatccctt ttctaaacta tacaaagaaa ccatagaaac atttgataac aatgaagaag   2160
aatccagcta ttcatacgaa gaaataaatg atcagacaaa cgataatata acagcaagat   2220
tagataggat tgatgaaaaa ttaagtgaaa tactaggaat gcttcacaca ttagtagtgg   2280
caagtgcagg acctacatct gctcgggatg gtataagaga tgccatggtt ggtttaagag   2340
aagaaatgat agaaaaaatc agaactgaag cattaatgac caatgacaga ttagaagcta   2400
tggcaagact caggaatgag gaaagtgaaa agatggcaaa agacacatca gatgaagtgt   2460
ctctcaatcc aacatcagag aaattgaaca acctattgga agggaatgat agtgacaatg   2520
atctatcact tgaagatttc tgattagtta ccaatcttca catcaacaca caataccaac   2580
agaagaccaa caaactaacc aacccaatca tccaaccaaa catccatccg ccaatcagcc   2640
aaacagccaa caaaacaacc agccaatcca aaactaacca cccggaaaaa atctataata   2700
tagttacaaa aaaaggaaag ggtggggcaa atatggaaac atacgtgaac aagcttcacg   2760
```

aaggctccac atacacagct gctgttcaat acaatgtctt agaaaaagac gatgaccctg 2820
catcacttac aatatgggtg cccatgttcc aatcatctat gccagcagat ttacttataa 2880
aagaactagc taatgtcaac atactagtga aacaaatatc cacacccaag ggaccttcac 2940
taagagtcat gataaactca agaagtgcag tgctagcaca aatgcccagc aaatttacca 3000
tatgcgctaa tgtgtccttg gatgaaagaa gcaaactagc atatgatgta accacaccct 3060
gtgaaatcaa ggcatgtagt ctaacatgcc taaaatcaaa aaatatgttg actacagtta 3120
aagatctcac tatgaagaca ctcaacccta cacatgatat tattgcttta tgtgaatttg 3180
aaaacatagt aacatcaaaa aaagtcataa taccaacata cctaagatcc atcagtgtca 3240
gaaataaaga tctgaacaca cttgaaaata taacaaccac tgaattcaaa aatgctatca 3300
caaatgcaaa aatcatccct tactcaggat tactattagt catcacagtg actgacaaca 3360
aaggagcatt caaatacata aagccacaaa gtcaattcat agtagatctt ggagcttacc 3420
tagaaaaaga aagtatatat tatgttacca caaattggaa gcacacagct acacgatttg 3480
caatcaaacc catggaagat taaccttttt cctctacatc agtgtgttaa ttcatacaaa 3540
ctttctacct acattcttca cttcaccatc acaatcacaa acactctgtg gttcaaccaa 3600
tcaaacaaaa cttatctgaa gtcccagatc atcccaagtc attgtttatc agatctagta 3660
ctcaaataag ttaataaaaa atatacacat ggggcaaata atcattggag gaaatccaac 3720
taatcacaat atctgttaac atagacaagt ccacacacca tacagaatca accaatggaa 3780
aatacatcca taacaataga attctcaagc aaattctggc cttactttac actaatacac 3840
atgatcacaa caataatctc tttgctaatc ataatctcca tcatgattgc aatactaaac 3900
aaactttgtg aatataacgt attccataac aaaacctttg agttaccaag agctcgagtt 3960
aatacttgat aaagtagtta attaaaaata gtcataacaa tgaactagga tatcaagact 4020
aacaataaca ttggggcaaa tgcaaacatg tccaaaaaca aggaccaacg caccgctaag 4080
acattagaaa ggacctggga cactctcaat catttattat tcatatcatc gtgcttatat 4140
aagttaaatc ttaaatctgt agcacaaatc acattatcca ttctggcaat gataatctca 4200
acttcactta taattgcagc catcatattc atagcctcgg caaaccacaa agtcacacca 4260
acaactgcaa tcatacaaga tgcaacaagc cagatcaaga acacaacccc aacataccte 4320
acccagaatc ctcagcttgg aatcagtccc tctaatccgt ctgaaattac atcacaaatc 4380
accaccatac tagcttcaac aacaccagga gtcaagtcaa ccctgcaatc cacaacagtc 4440
aagaccaaaa acacaacaac aactcaaaca caacccagca agcccaccac aaaacaacgc 4500
caaaacaaac caccaagcaa acccaataat gattttcact ttgaagtgtt caactttgta 4560
ccctgcagca tatgcagcaa caatccaacc tgctgggcta tctgcaaaag aataccaaac 4620
aaaaaaccag gaaagaaaac cactaccaag cccacaaaaa aaccaaccct caagacaacc 4680
aaaaaagatc ccaaacctca aaccactaaa tcaaaggaag tacccaccac caagcccaca 4740
gaagagccaa ccatcaacac caccaaaaca aacatcataa ctacactact cacctccaac 4800
accacaggaa atccagaact cacaagtcaa atggaaacct tccactcaac ttcctccgaa 4860
ggcaatccaa gcccttctca agtctctaca acatccgagt acccatcaca accttcatct 4920
ccacccaaca caccacgcca gtagttactt aaaaacatat tatcacaaaa ggccttgacc 4980
aacttaaaca gaatcaaaat aaactctggg gcaaataaca atggagttgc taatcctcaa 5040
agcaaatgca attaccacaa tcctcactgc agtcacattt tgttttgctt ctggtcaaaa 5100

```
catcactgaa gaattttatc aatcaacatg cagtgcagtt agcaaaggct atcttagtgc   5160
tctgagaact ggttggtata ccagtgttat aactatagaa ttaagtaata tcaagaaaaa   5220
taagtgtaat ggaacagatg ctaaggtaaa attgataaaa caagaattag ataaatataa   5280
aaatgctgta acagaattgc agttgctcat gcaaagcaca caagcaacaa acaatcgagc   5340
cagaagagaa ctaccaaggt ttatgaatta tacactcaac aatgccaaaa aaaccaatgt   5400
aacattaagc aagaaaagga aaagaagatt tcttggtttt ttgttaggtg ttggatctgc   5460
aatcgccagt ggcgttgctg tatctaaggt cctgcaccta gaaggggaag tgaacaagat   5520
caaaagtgct ctactatcca caaacaaggc tgtagtcagc ttatcaaatg gagttagtgt   5580
tttaaccagc aaagtgttag acctcaaaaa ctatatagat aaacaattgt tacctattgt   5640
gaacaagcaa agctgcagca tatcaaatat agaaactgtg atagagttcc aacaaaagaa   5700
caacagacta ctagagatta ccagggaatt tagtgttaat gcaggcgtaa ctacacctgt   5760
aagcacttac atgttaacta atagtgaatt attgtcatta atcaatgata tgcctataac   5820
aaatgatcag aaaaagttaa tgtccaacaa tgttcaaata gttagacagc aaagttactc   5880
tatcatgtcc ataataaaag aggaagtctt agcatatgta gtacaattac cactatatgg   5940
tgttatagat acaccctgtt ggaaactaca cacatcccct ctatgtacaa ccaacacaaa   6000
agaagggtcc aacatctgtt taacaagaac tgacagagga tggtactgtg acaatgcagg   6060
atcagtatct ttcttcccac aagctgaaac atgtaaagtt caatcaaatc gagtattttg   6120
tgacacaatg aacagtttaa cattaccaag tgaagtaaat ctctgcaatg ttgacatatt   6180
caaccccaaa tatgattgta aaattatgac ttcaaaaaca gatgtaagca gctccgttat   6240
cacatctcta ggagccattg tgtcatgcta tggcaaaact aaatgtacag catccaataa   6300
aaatcgtgga atcataaaga cattttctaa cgggtgcgat tatgtatcaa ataaaggggt   6360
ggacactgtg tctgtaggta acacattata ttatgtaaat aagcaagaag gtaaaagtct   6420
ctatgtaaaa ggtgaaccaa taataaattt ctatgaccca ttagtattcc cctctgatga   6480
atttgatgca tcaatatctc aagtcaacga gaagattaac cagagcctag catttattcg   6540
taaatccgat gaattattac ataatgtaaa tgctggtaaa tccaccacaa atatcatgat   6600
aactactata attatagtga ttatagtaat attgttatca ttaattgctg ttggactgct   6660
cttatactgt aaggccagaa gcacaccagt cacactaagc aaagatcaac tgagtggtat   6720
aaataatatt gcatttagta actaaataaa aatagcacct aatcatgttc ttacaatggt   6780
ttactatctg ctcatagaca acccatctgt cattggattt tcttaaaatc tgaacttcat   6840
cgaaactctc atctataaac catctcactt acactattta agtagattcc tagtttatag   6900
ttatataaaa cacaattgca tgccagatta acttaccatc tgtaaaaatg aaaactgggg   6960
caaatatgtc acgaaggaat ccttgcaaat ttgaaattcg aggtcattgc ttaaatggta   7020
agaggtgtca ttttagtcat aattattttg aatggccacc ccatgcactg cttgtaagac   7080
aaaactttat gttaaacaga atacttaagt ctatggataa aagtatagat accttatcag   7140
aaataagtgg agctgcagag ttggacagaa cagaagagta tgctcttggt gtagttggag   7200
tgctagagag ttatatagga tcaataaaca atataactaa acaatcagca tgtgttgcca   7260
tgagcaaact cctcactgaa ctcaatagtg atgatatcaa aaagctgagg gacaatgaag   7320
agctaaattc acccaagata agagtgtaca atactgtcat atcatatatt gaaagcaaca   7380
ggaaaaacaa taaacaaact atccatctgt taaaaagatt gccagcagac gtattgaaga   7440
aaaccatcaa aaacacattg gatatccata agagcataac catcaacaac ccaaaagaat   7500
```

caactgttag tgatacaaat gaccatgcca aaaataatga tactacctga caaatatcct 7560
tgtagtataa cttccatact aataacaagt agatgtagag ttactatgta taatcaaaag 7620
aacacactat atttcaatca aaacaaccca aataaccata tgtactcacc gaatcaaaca 7680
ttcaatgaaa tccattggac ctctcaagaa ttgattgaca caattcaaaa ttttctacaa 7740
catctaggta ttattgagga tatatataca atatatatat tagtgtcata acactcaatt 7800
ctaacactca ccacatcgtt acattattaa ttcaaacaat tcaagttgtg ggacaaaatg 7860
gatcccatta ttaatggaaa ttctgctaat gtttatctaa ccgatagtta tttaaaaggt 7920
gttatctctt tctcagagtg taatgcttta ggaagttaca tattcaatgg tccttatctc 7980
aaaaatgatt ataccaactt aattagtaga caaaatccat taatagaaca catgaatcta 8040
aagaaactaa atataacaca gtccttaata tctaagtatc ataaaggtga aataaaatta 8100
gaagaaccta cttattttca gtcattactt atgacataca agagtatgac ctcgtcagaa 8160
cagattgcta ccactaattt acttaaaaag ataataagaa gagctataga aataagtgat 8220
gtcaaagtct atgctatatt gaataaacta gggcttaaag aaaaggacaa gattaaatcc 8280
aacaatggac aagatgaaga caactcagtt attacgacca taatcaaaga tgatatactt 8340
tcagctgtta aagataatca atctcatctt aaagcagaca aaaatcactc tacaaaacaa 8400
aaagacacaa tcaaaacaac actcttgaag aaattgatgt gttcaatgca acatcctcca 8460
tcatggttaa tacattggtt taacttatac acaaaattaa acaacatatt aacacagtat 8520
cgatcaaatg aggtaaaaaa ccatgggttt acattgatag ataatcaaac tcttagtgga 8580
tttcaattta ttttgaacca atatggttgt atagtttatc ataaggaact caaaagaatt 8640
actgtgacaa cctataatca attcttgaca tggaaagata ttagccttag tagattaaat 8700
gtttgtttaa ttacatggat tagtaactgc ttgaacacat taaataaaag cttaggctta 8760
agatgcggat tcaataatgt tatcttgaca caactattcc tttatggaga ttgtatacta 8820
aagctatttc acaatgaggg gttctacata ataaaagagg tagagggatt tattatgtct 8880
ctaattttaa atataacaga agaagatcaa ttcagaaaac gattttataa tagtatgctc 8940
aacaacatca cagatgctgc taataaagct cagaaaaatc tgctatcaag agtatgtcat 9000
acattattag ataagacagt gtccgataat ataataaatg gcagatggat aattctatta 9060
agtaagttcc ttaaattaat taagcttgca ggtgacaata accttaacaa tctgagtgaa 9120
ctatattttt tgttcagaat atttggacac ccaatggtag atgaaagaca agccatggat 9180
gctgttaaaa ttaattgcaa tgagaccaaa ttttacttgt taagcagtct gagtatgtta 9240
agaggtgcct ttatatatag aattataaaa gggtttgtaa ataattacaa cagatggcct 9300
actttaagaa atgctattgt tttaccctta agatggttaa cttactataa actaaacact 9360
tatccttctt tgttggaact tacagaaaga gatttgattg tgttatcagg actacgtttc 9420
tatcgtgagt ttcggttgcc taaaaaagtg gatcttgaaa tgattataaa tgataaagct 9480
atatcacctc ctaaaaattt gatatggact agtttcccta gaaattacat gccatcacac 9540
atacaaaact atatagaaca tgaaaaatta aaattttccg agagtgataa atcaagaaga 9600
gtattagagt attatttaag agataacaaa ttcaatgaat gtgatttata caactgtgta 9660
gttaatcaaa gttatctcaa caaccctaat catgtggtat cattgacagg caaagaaaga 9720
gaactcagtg taggtagaat gtttgcaatg caaccgggaa tgttcagaca ggttcaaata 9780
ttggcagaga aaatgatagc tgaaaacatt ttacaattct ttcctgaaag tcttacaaga 9840

```
tatggtgatc tagaactaca aaaaatatta gaactgaaag caggaataag taacaaatca   9900
aatcgctaca atgataatta caacaattac attagtaagt gctctatcat cacagatctc   9960
agcaaattca atcaagcatt tcgatatgaa acgtcatgta tttgtagtga tgtgctggat  10020
gaactgcatg gtgtacaatc tctattttcc tggttacatt taactattcc tcatgtcaca  10080
ataaatatgca catataggca tgcacccccc tatataggag atcatattgt agatcttaac  10140
aatgtagatg aacaaagtgg attatataga tatcacatgg gtggcatcga agggtggtgt  10200
caaaaactat ggaccataga agctatatca ctattggatc taatatctct caaagggaaa  10260
ttctcaatta ctgctttaat taatggtgac aatcaatcaa tagatataag caaaccaatc  10320
agactcatgg aaggtcaaac tcatgctcaa gcagattatt tgctagcatt aaatagcctt  10380
aaattactgt ataaagagta tgcaggcata ggccacaaat taaaaggaac tgagacttat  10440
atatcacgag atatgcaatt tatgagtaaa acaattcaac ataacggtgt atattaccca  10500
gctagtataa agaaagtcct aagagtggga ccgtggataa acactatact tgatgatttc  10560
aaagtgagtc tagaatctat aggtagtttg acacaagaat tagaatatag aggtgaaagt  10620
ctattatgca gtttaatatt tagaaatgta tggttatata atcagattgc tctacaatta  10680
aaaaatcatg cattatgtaa caataaacta tatttggaca tattaaaggt tctgaaacac  10740
ttaaaaacct tttttaatct tgataatatt gatacagcat taacattgta tatgaattta  10800
cccatgttat ttggtggtgg tgatcccaac ttgttatatc gaagtttcta tagaagaact  10860
cctgacttcc tcacagaggc tatagttcac tctgtgttca tacttagtta ttatacaaac  10920
catgacttaa aagataaact tcaagatctg tcagatgata gattgaataa gttcttaaca  10980
tgcataatca cgtttgacaa aaaccctaat gctgaattcg taacattgat gagagatcct  11040
caagctttag ggtctgagag acaagctaaa attactagcg aaatcaatag actggcagtt  11100
acagaggttt tgagtacagc tccaaacaaa atattctcca aaagtgcaca acattatact  11160
actacagaga tagatctaaa tgatattatg caaaatatag aacctacata tcctcatggg  11220
ctaagagttg tttatgaaag tttacccttt tataaagcag agaaaatagt aaatcttata  11280
tcaggtacaa aatctataac taacatactg gaaaaaactt ctgccataga cttaacagat  11340
attgatagag ccactgagat gatgaggaaa aacataactt tgcttataag gatacttcca  11400
ttggattgta acagagataa aagagagata ttgagtatgg aaaacctaag tattactgaa  11460
ttaagcaaat atgttaggga aagatcttgg tctttatcca atatagttgg tgttacatca  11520
cccagtatca tgtatacaat ggacatcaaa tatactacaa gcactatatc tagtggcata  11580
attatagaga aatataatgt taacagttta acacgtggtg agagaggacc cactaaacca  11640
tgggttggtt catctacaca agagaaaaaa acaatgccag tttataatag acaagtctta  11700
accaaaaaac agagagatca aatagatcta ttagcaaaat tggattgggt gtatgcatct  11760
atagataaca aggatgaatt catggaagaa ctcagcatag gaacccttgg gttaacatat  11820
gaaaaggcca agaaattatt tccacaatat ttaagtgtca attatttgca tcgccttaca  11880
gtcagtagta gaccatgtga attccctgca tcaataccag cttatagaac aacaaattat  11940
cactttgaca ctagccctat taatcgcata ttaacagaaa agtatggtga tgaagatatt  12000
gacatagtat tccaaaactg tataagcttt ggccttagtt taatgtcagt agtagaacaa  12060
tttactaatg tatgtcctaa cagaattatt ctcataccta agcttaatga gatacatttg  12120
atgaaacctc ccatattcac aggtgatgtt gatattcaca agttaaaaca agtgatacaa  12180
aaacagcata tgtttttacc agacaaaata agtttgactc aatatgtgga attattctta  12240
```

agtaataaaa cactcaaatc tggatctcat gttaattcta atttaatatt ggcacataaa 12300
atatctgact attttcataa tacttacatt ttaagtacta atttagctgg acattggatt 12360
ctgattatac aacttatgaa agattctaaa ggtatttttg aaaaagattg gggagaggga 12420
tatataactg atcatatgtt tattaatttg aaagttttct tcaatgctta taagacctat 12480
ctcttgtgtt ttcataaagg ttatggcaaa gcaaagctgg agtgtgatat gaacacttca 12540
gatcttctat gtgtattgga attaatagac agtagttatt ggaagtctat gtctaaggta 12600
tttttagaac aaaaagttat caaatacatt cttagccaag atgcaagttt acatagagta 12660
aaaggatgtc atagcttcaa attatggttt cttaaacgtc ttaatgtagc agaattcaca 12720
gtttgccctt gggttgttaa catagattat catccaacac atatgaaagc aatattaact 12780
tatatagatc ttgttagaat gggattgata aatatagata gaatacacat taaaaataaa 12840
cacaaattca atgatgaatt ttatacttct aatctcttct acattaatta taacttctca 12900
gataatactc atctattaac taaacatata aggattgcta attctgaatt agaaaataat 12960
tacaacaaat tatatcatcc tacaccagaa accctagaga atatactagc caatccgatt 13020
aaaagtaatg acaaaaagac actgaatgac tattgtatag gtaaaaatgt tgactcaata 13080
atgttaccat tgttatctaa taagaagctt attaaatcgt ctgcaatgat tagaaccaat 13140
tacagcaaac aagatttgta taatttattc cctatggttg tgattgatag aattatagat 13200
cattcaggca atacagccaa atccaaccaa ctttacacta ctacttccca ccaaatatcc 13260
ttagtgcaca atagcacatc actttactgc atgcttcctt ggcatcatat taatagattc 13320
aattttgtat ttagttctac aggttgtaaa attagtatag agtatatttt aaaagatctt 13380
aaaattaaag atcccaattg tatagcattc ataggtgaag gagcagggaa tttattattg 13440
cgtacagtag tggaacttca tcctgacata agatatattt acagaagtct gaaagattgc 13500
aatgatcata gtttacctat tgagttttta aggctgtaca atggacatat caacattgat 13560
tatggtgaaa atttgaccat tcctgctaca gatgcaacca acaacattca ttggtcttat 13620
ttacatataa agtttgctga acctatcagt ctttttgtct gtgatgccga attgtctgta 13680
acagtcaact ggagtaaaat tataatagaa tggagcaagc atgtaagaaa gtgcaagtac 13740
tgttcctcag ttaataaatg tatgttaata gtaaaatatc atgctcaaga tgatattgat 13800
ttcaaattag acaatataac tatattaaaa acttatgtat gcttaggcag taagttaaag 13860
ggatcggagg tttacttagt ccttacaata ggtcctgcga atatattccc agtatttaat 13920
gtagtacaaa atgctaaatt gatactatca agaaccaaaa atttcatcat gcctaagaaa 13980
gctgataaag agtctattga tgcaaatatt aaaagtttga taccctttct ttgttaccct 14040
ataacaaaaa aaggaattaa tactgcattg tcaaaactaa agagtgttgt tagtggagat 14100
atactatcat attctatagc tggacgtaat gaagttttca gcaataaact tataaatcat 14160
aagcatatga acatcttaaa atggttcaat catgttttaa atttcagatc aacagaacta 14220
aactataacc atttatatat ggtagaatct acatatcctt acctaagtga attgttaaac 14280
agcttgacaa ccaatgaact taaaaaactg attaaaatca caggtagtct gttatacaac 14340
tttcataatg aataatgaat aaagatctta taataaaaat tcccatagct atacactaac 14400
actgtattca attatagtta ttaaaaatta aaaatcatat aattttttaa ataactttta 14460
gtgaactaat cctaaagtta tcattttaat cttggaggaa taaatttaaa ccctaatcta 14520
attggtttat atgtgtatta actaaattac gagatattag tttttgacac ttttttctc 14580 gt 14582

<210> SEQ ID NO 3
<211> LENGTH: 14348
<212> TYPE: DNA
<213> ORGANISM: Artificial Sequence
<220> FEATURE:
<223> OTHER INFORMATION: Recombinant RSV sequence

<400> SEQUENCE: 3
acgggaaaaa atgcgtacaa caaacttgca taaaccaaaa aaatggggca aataagaatt 60
tgataagtac cacttaaatt taactcctcg agttcaccat ggagttgcta atcctcaaag 120
caaatgcaat taccacaatc ctcactgcag tcacattttg ttttgcttct ggtcaaaaca 180
tcactgaaga attttatcaa tcaacatgca gtgcagttag caaaggctat cttagtgctc 240
tgagaactgg ttggtatacc agtgttataa ctatagaatt aagtaatatc aagaaaaata 300
agtgtaatgg aacagatgct aaggtaaaat tgataaaaca agaattagat aaatataaaa 360
atgctgtaac agaattgcag ttgctcatgc aaagcacaca agcaacaaac aatcgagcca 420
gaagagaact accaaggttt atgaattata cactcaacaa tgccaaaaaa accaatgtaa 480
cattaagcaa gaaaaggaaa agaagatttc ttggtttttt gttaggtgtt ggatctgcaa 540
tcgccagtgg cgttgctgta tctaaggtcc tgcacctaga aggggaagtg aacaagatca 600
aaagtgctct actatccaca aacaaggctg tagtcagctt atcaaatgga gttagtgttt 660
taaccagcaa agtgttagac ctcaaaaact atatagataa acaattgtta cctattgtga 720
acaagcaaag ctgcagcata tcaaatatag aaactgtgat agagttccaa caaaagaaca 780
acagactact agagattacc agggaattta gtgttaatgc aggcgtaact acacctgtaa 840
gcacttacat gttaactaat agtgaattat tgtcattaat caatgatatg cctataacaa 900
atgatcagaa aaagttaatg tccaacaatg ttcaaatagt tagacagcaa agttactcta 960
tcatgtccat aataaaagag gaagtcttag catatgtagt acaattacca ctatatggtg 1020
ttatagatac accctgttgg aaactacaca catcccctct atgtacaacc aacacaaaag 1080
aagggtccaa catctgttta acaagaactg acagaggatg gtactgtgac aatgcaggat 1140
cagtatcttt cttcccacaa gctgaaacat gtaaagttca atcaaatcga gtattttgtg 1200
acacaatgaa cagtttaaca ttaccaagtg aagtaaatct ctgcaatgtt gacatattca 1260
accccaaata tgattgtaaa attatgactt caaaaacaga tgtaagcagc tccgttatca 1320
catctctagg agccattgtg tcatgctatg gcaaaactaa atgtacagca tccaataaaa 1380
atcgtggaat cataaagaca ttttctaacg ggtgcgatta tgtatcaaat aaaggggtgg 1440
acactgtgtc tgtaggtaac acattatatt atgtaaataa gcaagaaggt aaaagtctct 1500
atgtaaaagg tgaaccaata ataaatttct atgacccatt agtattcccc tctgatgaat 1560
ttgatgcatc aatatctcaa gtcaacgaga agattaacca gagcctagca tttattcgta 1620
aatccgatga attattacat aatgtaaatg ctggtaaatc caccacaaat atcatgataa 1680
ctactataat tatagtgatt atagtaatat tgttatcatt aattgctgtt ggactgctct 1740
tatactgtaa ggccagaagc acaccagtca cactaagcaa agatcaactg agtggtataa 1800
ataatattgc atttagtaac taaagtagtt aattaaaaat ggggcaaata caaccatgtc 1860
caaaaacaag gaccaacgca ccgctaagac attagaaagg acctgggaca ctctcaatca 1920
tttattattc atatcatcgt gcttatataa gttaaatctt aaatctgtag cacaaatcac 1980
attatccatt ctggcaatga taatctcaac ttcacttata attgcagcca tcatattcat 2040

```
agcctcggca aaccacaaag tcacaccaac aactgcaatc atacaagatg caacaagcca   2100
gatcaagaac acaaccccaa catacctcac ccagaatcct cagcttggaa tcagtccctc   2160
taatccgtct gaaattacat cacaaatcac caccatacta gcttcaacaa caccaggagt   2220
caagtcaacc ctgcaatcca caacagtcaa gaccaaaaac acaacaacaa ctcaaacaca   2280
acccagcaag cccaccacaa aacaacgcca aaacaaacca ccaagcaaac ccaataatga   2340
ttttcacttt gaagtgttca actttgtacc ctgcagcata tgcagcaaca atccaacctg   2400
ctgggctatc tgcaaaagaa taccaaacaa aaaaccagga aagaaaacca ctaccaagcc   2460
cacaaaaaaa ccaaccctca agacaaccaa aaaagatccc aaacctcaaa ccactaaatc   2520
aaaggaagta cccaccacca agcccacaga agagccaacc atcaacacca ccaaaacaaa   2580
catcataact acactactca cctccaacac cacaggaaat ccagaactca caagtcaaat   2640
ggaaaccttc cactcaactt cctccgaagg caatccaagc ccttctcaag tctctacaac   2700
atccgagtac ccatcacaac cttcatctcc acccaacaca ccacgccagt agttaataaa   2760
aaatggggca aatactcgag ttagagatgg acacaaccca caatgataat acaccacaaa   2820
gactgatgat cacagacatg agaccgttgt cacttgagac cataataaca tcactaacca   2880
gagacatcat aacacacaaa tttatatact tgataaatca tgaatgcata gtgagaaaac   2940
ttgatgaaag acaggccaca tttacattcc tggtcaacta tgaaatgaaa ctattacaca   3000
aagtaggaag cactaaatat aaaaaatata ctgaatacaa cacaaaatat ggcactttcc   3060
ctatgccaat attcatcaat catgatgggt tcttagaatg cattggcatt aagcctacaa   3120
agcatactcc cataatatac aagtatgatc tcaatccata aatttcaaca caatattcac   3180
acaatctaaa acaacaactc tatgcataac tatactccat agtccagatg gagcctgaaa   3240
attatagtaa tttaaaactt aaggagagat ataagataga agatggggca aatacaacca   3300
tggctcttag caaagtcaag ttgaatgata cactcaacaa agatcaactt ctgtcatcca   3360
gcaaatacac catccaacgg agcacaggag atagtattga tactcctaat tatgatgtgc   3420
agaaacacat caataagtta tgtggcatgt tattaatcac agaagatgct aatcataaat   3480
tcactgggtt aataggtatg ttatatgcga tgtctaggtt aggaagagaa gacaccataa   3540
aaatactcag agatgcggga tatcatgtaa aagcaaatgg agtagatgta acaacacatc   3600
gtcaagacat taatggaaaa gaaatgaaat ttgaagtgtt aacattggca agcttaacaa   3660
ctgaaattca aatcaacatt gagatagaat ctagaaaatc ctacaaaaaa atgctaaaag   3720
aaatgggaga ggtagctcca gaatacaggc atgactctcc tgattgtggg atgataatat   3780
tatgtatagc agcattagta ataactaaat tagcagcagg ggacagatct ggtcttacag   3840
ccgtgattag gagagctaat aatgtcctaa aaaatgaaat gaaacgttac aaaggcttac   3900
tacccaagga catagccaac agcttctatg aagtgtttga aaaacatccc cactttatag   3960
atgtttttgt tcattttggt atagcacaat cttctaccag aggtggcagt agagttgaag   4020
ggatttttgc aggattgttt atgaatgcct atggtgcagg gcaagtgatg ttacggtggg   4080
gagtcttagc aaaatcggtt aaaaatatta tgttaggaca tgctagtgtg caagcagaaa   4140
tggaacaagt tgttgaggtt tatgaatatg cccaaaaatt gggtggtgaa gcaggattct   4200
accatatatt gaacaaccca aaagcatcat tattatcttt gactcaattt cctcacttct   4260
ccagtgtagt attaggcaat gctgctggcc taggcataat gggagagtac agaggtacac   4320
cgaggaatca agatctatat gatgcagcaa aggcatatgc tgaacaactc aaagaaaatg   4380
```

-continued

```
gtgtgattaa ctacagtgta ctagacttga cagcagaaga actagaggct atcaaacatc   4440
agcttaatcc aaaagataat gatgtagagc tttgagttaa taaaaaatgg ggcaaataaa   4500
tcatcatgga aaagtttgct cctgaattcc atggagaaga tgcaaacaac agggctacta   4560
aattcctaga atcaataaag ggcaaattca catcacccaa agatcccaag aaaaaagata   4620
gtatcatatc tgtcaactca atagatatag aagtaaccaa agaaagccct ataacatcaa   4680
attcaactat tatcaaccca acaaatgaga cagatgatac tgcagggaac aagcccaatt   4740
atcaaagaaa acctctagta agtttcaaag aagaccctac accaagtgat aatccctttt   4800
ctaaactata caaagaaacc atagaaacat ttgataacaa tgaagaagaa tccagctatt   4860
catacgaaga aataaatgat cagacaaacg ataatataac agcaagatta gataggattg   4920
atgaaaaatt aagtgaaata ctaggaatgc ttcacacatt agtagtggca agtgcaggac   4980
ctacatctgc tcgggatggt ataagagatg ccatggttgg tttaagagaa gaaatgatag   5040
aaaaaatcag aactgaagca ttaatgacca atgacagatt agaagctatg gcaagactca   5100
ggaatgagga aagtgaaaag atggcaaaag acacatcaga tgaagtgtct ctcaatccaa   5160
catcagagaa attgaacaac ctattggaag ggaatgatag tgacaatgat ctatcacttg   5220
aagatttctg attagttacc aatcttcaca tcaacacaca ataccaacag aagaccaaca   5280
aactaaccaa cccaatcatc caaccaaaca tccatccgcc aatcagccaa acagccaaca   5340
aaacaaccag ccaatccaaa actaaccacc cggaaaaaat ctataatata gttacaaaaa   5400
aaggaaaggg tggggcaaat atggaaacat acgtgaacaa gcttcacgaa ggctccacat   5460
acacagctgc tgttcaatac aatgtcttag aaaaagacga tgaccctgca tcacttacaa   5520
tatgggtgcc catgttccaa tcatctatgc cagcagattt acttataaaa gaactagcta   5580
atgtcaacat actagtgaaa caaatatcca cacccaaggg accttcacta agagtcatga   5640
taaactcaag aagtgcagtg ctagcacaaa tgcccagcaa atttaccata tgcgctaatg   5700
tgtccttgga tgaaagaagc aaactagcat atgatgtaac cacaccctgt gaaatcaagg   5760
catgtagtct aacatgccta aaatcaaaaa atatgttgac tacagttaaa gatctcacta   5820
tgaagacact caaccctaca catgatatta ttgctttatg tgaatttgaa aacatagtaa   5880
catcaaaaaa agtcataata ccaacatacc taagatccat cagtgtcaga aataaagatc   5940
tgaacacact tgaaaatata acaaccactg aattcaaaaa tgctatcaca aatgcaaaaa   6000
tcatccctta ctcaggatta ctattagtca tcacagtgac tgacaacaaa ggagcattca   6060
aatacataaa gccacaaagt caattcatag tagatcttgg agcttaccta gaaaaagaaa   6120
gtatatatta tgttaccaca aattggaagc acacagctac acgatttgca atcaaaccca   6180
tggaagatta accttttttcc tctacatcag tgtgttaatt catacaaact ttctacctac   6240
attcttcact tcaccatcac aatcacaaac actctgtggt tcaaccaatc aaacaaaact   6300
tatctgaagt cccagatcat cccaagtcat tgtttatcag atctagtact caaataagtt   6360
aataaaaaat atacacatgg ggcaaataat cattggagga aatccaacta atcacaatat   6420
ctgttaacat agacaagtcc acacaccata cagaatcaac caatggaaaa tacatccata   6480
acaatagaat tctcaagcaa attctggcct tactttacac taatacacat gatcacaaca   6540
ataatctctt tgctaatcat aatctccatc atgattgcaa tactaaacaa actttgtgaa   6600
tataacgtat tccataacaa aacctttgag ttaccaagag ctcgagttaa tacttgataa   6660
agtagttaat taaaaacaca attgcatgcc agattaactt accatctgta aaatgaaaa    6720
ctggggcaaa tatgtcacga aggaatcctt gcaaatttga aattcgaggt cattgcttaa   6780
```

atggtaagag gtgtcatttt agtcataatt attttgaatg gccaccccat gcactgcttg 6840
taagacaaaa ctttatgtta aacagaatac ttaagtctat ggataaaagt atagatacct 6900
tatcagaaat aagtggagct gcagagttgg acagaacaga agagtatgct cttggtgtag 6960
ttggagtgct agagagttat ataggatcaa taaacaatat aactaaacaa tcagcatgtg 7020
ttgccatgag caaactcctc actgaactca atagtgatga tatcaaaaag ctgagggaca 7080
atgaagagct aaattcaccc aagataagag tgtacaatac tgtcatatca tatattgaaa 7140
gcaacaggaa aaacaataaa caaactatcc atctgttaaa aagattgcca gcagacgtat 7200
tgaagaaaac catcaaaaac acattggata tccataagag cataaccatc aacaacccaa 7260
aagaatcaac tgttagtgat acaaatgacc atgccaaaaa taatgatact acctgacaaa 7320
tatccttgta gtataacttc catactaata acaagtagat gtagagttac tatgtataat 7380
caaaagaaca cactatattt caatcaaaac aacccaaata accatatgta ctcaccgaat 7440
caaacattca atgaaatcca ttggacctct caagaattga ttgacacaat tcaaaatttt 7500
ctacaacatc taggtattat tgaggatata tatacaatat atatattagt gtcataacac 7560
tcaattctaa cactcaccac atcgttacat tattaattca aacaattcaa gttgtgggac 7620
aaaatggatc ccattattaa tggaaattct gctaatgttt atctaaccga tagttattta 7680
aaaggtgtta tctctttctc agagtgtaat gctttaggaa gttacatatt caatggtcct 7740
tatctcaaaa atgattatac caacttaatt agtagacaaa atccattaat agaacacatg 7800
aatctaaaga aactaaatat aacacagtcc ttaatatcta agtatcataa aggtgaaata 7860
aaattagaag aacctactta ttttcagtca ttacttatga catacaagag tatgacctcg 7920
tcagaacaga ttgctaccac taatttactt aaaaagataa taagaagagc tatagaaata 7980
agtgatgtca aagtctatgc tatattgaat aaactagggc ttaaagaaaa ggacaagatt 8040
aaatccaaca atggacaaga tgaagacaac tcagttatta cgaccataat caaagatgat 8100
atactttcag ctgttaaaga taatcaatct catcttaaag cagacaaaaa tcactctaca 8160
aaacaaaaag acacaatcaa aacaacactc ttgaagaaat tgatgtgttc aatgcaacat 8220
cctccatcat ggttaataca ttggtttaac ttatacacaa aattaaacaa catattaaca 8280
cagtatcgat caaatgaggt aaaaaaccat gggtttacat tgatagataa tcaaactctt 8340
agtggatttc aatttatttt gaaccaatat ggttgtatag tttatcataa ggaactcaaa 8400
agaattactg tgacaaccta taatcaattc ttgacatgga aagatattag ccttagtaga 8460
ttaaatgttt gtttaattac atggattagt aactgcttga acacattaaa taaaagctta 8520
ggcttaagat gcggattcaa taatgttatc ttgacacaac tattccttta tggagattgt 8580
atactaaagc tatttcacaa tgaggggttc tacataataa aagaggtaga gggatttatt 8640
atgtctctaa ttttaaatat aacagaagaa gatcaattca gaaaacgatt ttataatagt 8700
atgctcaaca acatcacaga tgctgctaat aaagctcaga aaaatctgct atcaagagta 8760
tgtcatacat tattagataa gacagtgtcc gataatataa taaatggcag atggataatt 8820
ctattaagta agttccttaa attaattaag cttgcaggtg acaataacct taacaatctg 8880
agtgaactat attttttgtt cagaatattt ggacacccaa tggtagatga aagacaagcc 8940
atggatgctg ttaaaattaa ttgcaatgag accaaatttt acttgttaag cagtctgagt 9000
atgttaagag gtgcctttat atatagaatt ataaaagggt ttgtaaataa ttacaacaga 9060
tggcctactt taagaaatgc tattgtttta cccttaagat ggttaactta ctataaacta 9120
aacacttatc cttctttgtt ggaacttaca gaaagagatt tgattgtgtt atcaggacta 9180
cgtttctatc gtgagtttcg gttgcctaaa aaagtggatc ttgaaatgat tataaatgat 9240
aaagctatat cacctcctaa aaatttgata tggactagtt tccctagaaa ttacatgcca 9300
tcacacatac aaaactatat agaacatgaa aaattaaaat tttccgagag tgataaatca 9360
agaagagtat tagagtatta tttaagagat aacaaattca atgaatgtga tttatacaac 9420
tgtgtagtta atcaaagtta tctcaacaac cctaatcatg tggtatcatt gacaggcaaa 9480
gaaagagaac tcagtgtagg tagaatgttt gcaatgcaac cgggaatgtt cagacaggtt 9540
caaatattgg cagagaaaat gatagctgaa aacattttac aattctttcc tgaaagtctt 9600
acaagatatg gtgatctaga actacaaaaa atattagaac tgaaagcagg aataagtaac 9660
aaatcaaatc gctacaatga taattacaac aattacatta gtaagtgctc tatcatcaca 9720
gatctcagca aattcaatca agcatttcga tatgaaacgt catgtatttg tagtgatgtg 9780
ctggatgaac tgcatggtgt acaatctcta ttttcctggt tacatttaac tattcctcat 9840
gtcacaataa tatgcacata taggcatgca ccccccctata taggagatca tattgtagat 9900
cttaacaatg tagatgaaca aagtggatta tatagatatc acatgggtgg catcgaaggg 9960
tggtgtcaaa aactatggac catagaagct atatcactat tggatctaat atctctcaaa 10020
gggaaattct caattactgc tttaattaat ggtgacaatc aatcaataga tataagcaaa 10080
ccaatcagac tcatggaagg tcaaactcat gctcaagcag attatttgct agcattaaat 10140
agccttaaat tactgtataa agagtatgca ggcataggcc acaaattaaa aggaactgag 10200
acttatatat cacgagatat gcaatttatg agtaaaacaa ttcaacataa cggtgtatat 10260
tacccagcta gtataaagaa agtcctaaga gtgggaccgt ggataaacac tatacttgat 10320
gatttcaaag tgagtctaga atctataggt agtttgacac aagaattaga atatagaggt 10380
gaaagtctat tatgcagttt aatatttaga aatgtatggt tatataatca gattgctcta 10440
caattaaaaa atcatgcatt atgtaacaat aaactatatt tggacatatt aaaggttctg 10500
aaacacttaa aaaccttttt taatcttgat aatattgata cagcattaac attgtatatg 10560
aatttaccca tgttatttgg tggtggtgat cccaacttgt tatatcgaag tttctataga 10620
agaactcctg acttcctcac agaggctata gttcactctg tgttcatact tagttattat 10680
acaaaccatg acttaaaaga taaacttcaa gatctgtcag atgatagatt gaataagttc 10740
ttaacatgca taatcacgtt tgacaaaaac cctaatgctg aattcgtaac attgatgaga 10800
gatcctcaag ctttagggtc tgagagacaa gctaaaatta ctagcgaaat caatagactg 10860
gcagttacag aggttttgag tacagctcca aacaaaatat tctccaaaag tgcacaacat 10920
tatactacta cagagataga tctaaatgat attatgcaaa atatagaacc tacatatcct 10980
catgggctaa gagttgttta tgaaagttta cccttttata aagcagagaa aatagtaaat 11040
cttatatcag gtacaaaatc tataactaac atactggaaa aaacttctgc catagactta 11100
acagatattg atagagccac tgagatgatg aggaaaaaca taactttgct tataaggata 11160
cttccattgg attgtaacag agataaaaga gagatattga gtatggaaaa cctaagtatt 11220
actgaattaa gcaaatatgt tagggaaaga tcttggtctt tatccaatat agttggtgtt 11280
acatcaccca gtatcatgta tacaatggac atcaaatata ctacaagcac tatatctagt 11340
ggcataatta tagagaaata taatgttaac agtttaacac gtggtgagag aggacccact 11400
aaaccatggg ttggttcatc tacacaagag aaaaaaacaa tgccagttta taatagacaa 11460
gtcttaacca aaaaacagag agatcaaata gatctattag caaaattgga ttgggtgtat 11520
gcatctatag ataacaagga tgaattcatg gaagaactca gcataggaac ccttgggtta 11580
acatatgaaa aggccaagaa attatttcca caatatttaa gtgtcaatta tttgcatcgc 11640
cttacagtca gtagtagacc atgtgaattc cctgcatcaa taccagctta tagaacaaca 11700
aattatcact ttgacactag ccctattaat cgcatattaa cagaaaagta tggtgatgaa 11760
gatattgaca tagtattcca aaactgtata agctttggcc ttagtttaat gtcagtagta 11820
gaacaattta ctaatgtatg tcctaacaga attattctca tacctaagct taatgagata 11880
catttgatga aacctcccat attcacaggt gatgttgata ttcacaagtt aaaacaagtg 11940
atacaaaaac agcatatgtt tttaccagac aaaataagtt tgactcaata tgtggaatta 12000
ttcttaagta ataaaacact caaatctgga tctcatgtta attctaattt aatattggca 12060
cataaaatat ctgactattt tcataatact tacattttaa gtactaattt agctggacat 12120
tggattctga ttatacaact tatgaaagat tctaaaggta tttttgaaaa agattgggga 12180
gagggatata taactgatca tatgtttatt aatttgaaag ttttcttcaa tgcttataag 12240
acctatctct tgtgttttca taaaggttat ggcaaagcaa agctggagtg tgatatgaac 12300
acttcagatc ttctatgtgt attggaatta atagacagta gttattggaa gtctatgtct 12360
aaggtatttt tagaacaaaa agttatcaaa tacattctta gccaagatgc aagtttacat 12420
agagtaaaag gatgtcatag cttcaaatta tggtttctta aacgtcttaa tgtagcagaa 12480
ttcacagttt gcccttgggt tgttaacata gattatcatc caacacatat gaaagcaata 12540
ttaacttata tagatcttgt tagaatggga ttgataaata tagatagaat acacattaaa 12600
aataaacaca aattcaatga tgaattttat acttctaatc tcttctacat taattataac 12660
ttctcagata atactcatct attaactaaa catataagga ttgctaattc tgaattagaa 12720
aataattaca acaaattata tcatcctaca ccagaaaccc tagagaatat actagccaat 12780
ccgattaaaa gtaatgacaa aaagacactg aatgactatt gtataggtaa aaatgttgac 12840
tcaataatgt taccattgtt atctaataag aagcttatta aatcgtctgc aatgattaga 12900
accaattaca gcaaacaaga tttgtataat ttattcccta tggttgtgat tgatagaatt 12960
atagatcatt caggcaatac agccaaatcc aaccaacttt acactactac ttcccaccaa 13020
atatccttag tgcacaatag cacatcactt tactgcatgc ttccttggca tcatattaat 13080
agattcaatt ttgtatttag ttctacaggt tgtaaaatta gtatagagta tattttaaaa 13140
gatcttaaaa ttaaagatcc caattgtata gcattcatag gtgaaggagc agggaattta 13200
ttattgcgta cagtagtgga acttcatcct gacataagat atatttacag aagtctgaaa 13260
gattgcaatg atcatagttt acctattgag tttttaaggc tgtacaatgg acatatcaac 13320
attgattatg gtgaaaattt gaccattcct gctacagatg caaccaacaa cattcattgg 13380
tcttatttac atataaagtt tgctgaacct atcagtcttt ttgtctgtga tgccgaattg 13440
tctgtaacag tcaactggag taaaattata atagaatgga gcaagcatgt aagaaagtgc 13500
aagtactgtt cctcagttaa taaatgtatg ttaatagtaa aatatcatgc tcaagatgat 13560
attgatttca aattagacaa tataactata ttaaaaactt atgtatgctt aggcagtaag 13620
ttaaagggat cggaggttta cttagtcctt acaataggtc ctgcgaatat attcccagta 13680
tttaatgtag tacaaaatgc taaattgata ctatcaagaa ccaaaaattt catcatgcct 13740
aagaaagctg ataaagagtc tattgatgca aatattaaaa gtttgatacc ctttctttgt 13800
taccctataa caaaaaaagg aattaatact gcattgtcaa aactaaagag tgttgttagt 13860
ggagatatac tatcatattc tatagctgga cgtaatgaag ttttcagcaa taaacttata 13920
aatcataagc atatgaacat cttaaaatgg ttcaatcatg ttttaaattt cagatcaaca 13980
gaactaaact ataaccattt atatatggta gaatctacat atccttacct aagtgaattg 14040
ttaaacagct tgacaaccaa tgaacttaaa aaactgatta aaatcacagg tagtctgtta 14100
tacaactttc ataatgaata atgaataaag atcttataat aaaaattccc atagctatac 14160
actaacactg tattcaatta tagttattaa aaattaaaaa tcatataatt ttttaaataa 14220
cttttagtga actaatccta aagttatcat tttaatcttg gaggaataaa tttaaaccct 14280
aatctaattg gtttatatgt gtattaacta aattacgaga tattagtttt tgacactttt 14340
tttctcgt 14348

<210> SEQ ID NO 4
<211> LENGTH: 14348
<212> TYPE: DNA
<213> ORGANISM: Artificial Sequence
<220> FEATURE:
<223> OTHER INFORMATION: Recombinant RSV sequence

<400> SEQUENCE: 4
acgggaaaaa atgcgtacaa caaacttgca taaaccaaaa aaatggggca aataagaatt 60
tgataagtac cacttaaatt taactcctcg agttcaccat ggagctcctc attctcaaag 120
ccaacgcaat cacaacaatt ctgaccgccg tcacattctg ctttgcctcc ggacagaaca 180
tcacagaaga gttttaccaa agtacatgca gcgccgtgag caaaggctac ctgtccgccc 240
tgaggacagg gtggtacaca tccgtgatta ccattgagct gagtaatatc aagaagaaca 300
agtgcaacgg cactgatgcc aaagtgaagc tcattaaaca ggaactcgat aagtacaaga 360
acgccgtgac tgagctccag ctgctgatgc agtcaactca ggctacaaac aacagagccc 420
ggagggagct gcccaggttt atgaactaca ccctgaacaa cgccaagaag accaacgtga 480
cattgagcaa gaagaggaag cggcggttcc tggggttctt gctaggtgtg ggcagcgcta 540
ttgcttctgg cgtcgccgtc tccaaggtgc tgcacctgga aggcgaagtg aataagatta 600
agtccgcact gcttagcacc aataaggccg tcgtgagcct gtctaacgga gtgagtgtgc 660
tcacaagcaa ggtcctcgat ctcaagaact acattgataa gcagctcctg cccatcgtca 720
acaagcagtc atgctccatt agtaacatcg agaccgtgat tgaatttcaa cagaagaaca 780
accggctcct ggagattact agggagttca gcgtgaacgc cggggtgaca acaccagtct 840
ccacctatat gcttaccaac agcgagttgc tctccctgat taacgatatg ccaattacaa 900
acgaccagaa gaagctgatg tcaaacaacg tccagattgt ccggcagcag tcctactcaa 960
tcatgtccat tattaaggag gaggtcctgg cttacgtcgt gcagctgcct ctttatgggg 1020
tgatcgacac cccttgctgg aagctccata catcccctct gtgcactacc aacaccaagg 1080
aggggtccaa catctgcttg acaagaaccg atcgcggctg gtactgcgat aacgcaggca 1140
gtgtctcctt ctttccccag gccgagactt gtaaggtgca gtctaaccgc gtcttctgcg 1200
acaccatgaa cagcctgacc cttcccagcg aggtgaacct ttgtaacgtg gacatcttca 1260
acccaaagta tgattgtaag attatgacta gcaaaaccga tgtcagcagc agcgtgatca 1320
ctagcctggg cgctatcgtc agctgctacg gaaagactaa gtgcaccgcc agcaacaaga 1380
acagaggcat catcaagacc ttcagtaatg gatgtgacta cgtgtccaac aaaggggtgg 1440
atacagtgag cgtgggaaac acattgtact acgtgaacaa acaggagggg aagtccttgt 1500
acgtgaaggg tgagcccatt atcaacttct acgaccctct cgtgttccca tcagacgagt 1560
ttgacgcctc catctcccag gtgaacgaga agatcaatca gtcactggcc tttattagga 1620
aatccgacga gctgctgcac aacgtcaacg ccggaaagtc taccactaac atcatgatca 1680
ccacaatcat cattgtgatc atcgtcatcc tcctgagctt gatcgctgtc gggttgctgt 1740
tgtactgcaa ggcccggtcc acacccgtga ctctgagcaa ggaccagctg tctggcatta 1800
acaacatcgc ctttagcaac taaagtagtt aattaaaaat ggggcaaata caaccatgtc 1860
caaaaacaag gaccaacgca ccgctaagac attagaaagg acctgggaca ctctcaatca 1920
tttattattc atatcatcgt gcttatataa gttaaatctt aaatctgtag cacaaatcac 1980
attatccatt ctggcaatga taatctcaac ttcacttata attgcagcca tcatattcat 2040
agcctcggca aaccacaaag tcacaccaac aactgcaatc atacaagatg caacaagcca 2100
gatcaagaac acaaccccaa catacctcac ccagaatcct cagcttggaa tcagtccctc 2160
taatccgtct gaaattacat cacaaatcac caccatacta gcttcaacaa caccaggagt 2220
caagtcaacc ctgcaatcca caacagtcaa gaccaaaaac acaacaacaa ctcaaacaca 2280
acccagcaag cccaccacaa aacaacgcca aaacaaacca ccaagcaaac ccaataatga 2340
ttttcacttt gaagtgttca actttgtacc ctgcagcata tgcagcaaca atccaacctg 2400
ctgggctatc tgcaaaagaa taccaaacaa aaaaccagga aagaaaacca ctaccaagcc 2460
cacaaaaaaa ccaaccctca agacaaccaa aaaagatccc aaacctcaaa ccactaaatc 2520
aaaggaagta cccaccacca agcccacaga agagccaacc atcaacacca ccaaaacaaa 2580
catcataact acactactca cctccaacac cacaggaaat ccagaactca caagtcaaat 2640
ggaaaccttc cactcaactt cctccgaagg caatccaagc ccttctcaag tctctacaac 2700
atccgagtac ccatcacaac cttcatctcc acccaacaca ccacgccagt agttaataaa 2760
aaatggggca aatactcgag ttagagatgg acacaaccca caatgataat acaccacaaa 2820
gactgatgat cacagacatg agaccgttgt cacttgagac cataataaca tcactaacca 2880
gagacatcat aacacacaaa tttatatact tgataaatca tgaatgcata gtgagaaaac 2940
ttgatgaaag acaggccaca tttacattcc tggtcaacta tgaaatgaaa ctattacaca 3000
aagtaggaag cactaaatat aaaaaatata ctgaatacaa cacaaaatat ggcactttcc 3060
ctatgccaat attcatcaat catgatgggt tcttagaatg cattggcatt aagcctacaa 3120
agcatactcc cataatatac aagtatgatc tcaatccata aatttcaaca caatattcac 3180
acaatctaaa acaacaactc tatgcataac tatactccat agtccagatg gagcctgaaa 3240
attatagtaa tttaaaactt aaggagagat ataagataga agatggggca aatacaacca 3300
tggctcttag caaagtcaag ttgaatgata cactcaacaa agatcaactt ctgtcatcca 3360
gcaaatacac catccaacgg agcacaggag atagtattga tactcctaat tatgatgtgc 3420
agaaacacat caataagtta tgtggcatgt tattaatcac agaagatgct aatcataaat 3480
tcactgggtt aataggtatg ttatatgcga tgtctaggtt aggaagagaa gacaccataa 3540
aaatactcag agatgcggga tatcatgtaa aagcaaatgg agtagatgta acaacacatc 3600
gtcaagacat taatggaaaa gaaatgaaat ttgaagtgtt aacattggca agcttaacaa 3660
ctgaaattca aatcaacatt gagatagaat ctagaaaatc ctacaaaaaa atgctaaaag 3720
aaatgggaga ggtagctcca gaatacaggc atgactctcc tgattgtggg atgataatat 3780
tatgtatagc agcattagta ataactaaat tagcagcagg ggacagatct ggtcttacag 3840
ccgtgattag gagagctaat aatgtcctaa aaaatgaaat gaaacgttac aaaggcttac 3900
tacccaagga catagccaac agcttctatg aagtgtttga aaaacatccc cactttatag 3960
atgtttttgt tcattttggt atagcacaat cttctaccag aggtggcagt agagttgaag 4020
ggatttttgc aggattgttt atgaatgcct atggtgcagg gcaagtgatg ttacggtggg 4080
gagtcttagc aaaatcggtt aaaaatatta tgttaggaca tgctagtgtg caagcagaaa 4140
tggaacaagt tgttgaggtt tatgaatatg cccaaaaatt gggtggtgaa gcaggattct 4200
accatatatt gaacaaccca aaagcatcat tattatcttt gactcaattt cctcacttct 4260
ccagtgtagt attaggcaat gctgctggcc taggcataat gggagagtac agaggtacac 4320
cgaggaatca agatctatat gatgcagcaa aggcatatgc tgaacaactc aaagaaaatg 4380
gtgtgattaa ctacagtgta ctagacttga cagcagaaga actagaggct atcaaacatc 4440
agcttaatcc aaaagataat gatgtagagc tttgagttaa taaaaaatgg ggcaaataaa 4500
tcatcatgga aaagtttgct cctgaattcc atggagaaga tgcaaacaac agggctacta 4560
aattcctaga atcaataaag ggcaaattca catcacccaa agatcccaag aaaaaagata 4620
gtatcatatc tgtcaactca atagatatag aagtaaccaa agaaagccct ataacatcaa 4680
attcaactat tatcaaccca acaaatgaga cagatgatac tgcagggaac aagcccaatt 4740
atcaaagaaa acctctagta agtttcaaag aagaccctac accaagtgat aatccctttt 4800
ctaaactata caaagaaacc atagaaacat ttgataacaa tgaagaagaa tccagctatt 4860
catacgaaga aataaatgat cagacaaacg ataatataac agcaagatta gataggattg 4920
atgaaaaatt aagtgaaata ctaggaatgc ttcacacatt agtagtggca agtgcaggac 4980
ctacatctgc tcgggatggt ataagagatg ccatggttgg tttaagagaa gaaatgatag 5040
aaaaaatcag aactgaagca ttaatgacca atgacagatt agaagctatg gcaagactca 5100
ggaatgagga aagtgaaaag atggcaaaag acacatcaga tgaagtgtct ctcaatccaa 5160
catcagagaa attgaacaac ctattggaag ggaatgatag tgacaatgat ctatcacttg 5220
aagatttctg attagttacc aatcttcaca tcaacacaca ataccaacag aagaccaaca 5280
aactaaccaa cccaatcatc caaccaaaca tccatccgcc aatcagccaa acagccaaca 5340
aaacaaccag ccaatccaaa actaaccacc cggaaaaaat ctataatata gttacaaaaa 5400
aaggaaaggg tggggcaaat atggaaacat acgtgaacaa gcttcacgaa ggctccacat 5460
acacagctgc tgttcaatac aatgtcttag aaaaagacga tgaccctgca tcacttacaa 5520
tatgggtgcc catgttccaa tcatctatgc cagcagattt acttataaaa gaactagcta 5580
atgtcaacat actagtgaaa caaatatcca cacccaaggg accttcacta agagtcatga 5640
taaactcaag aagtgcagtg ctagcacaaa tgcccagcaa atttaccata tgcgctaatg 5700
tgtccttgga tgaaagaagc aaactagcat atgatgtaac cacaccctgt gaaatcaagg 5760
catgtagtct aacatgccta aaatcaaaaa atatgttgac tacagttaaa gatctcacta 5820
tgaagacact caaccctaca catgatatta ttgctttatg tgaatttgaa aacatagtaa 5880
catcaaaaaa agtcataata ccaacatacc taagatccat cagtgtcaga aataaagatc 5940
tgaacacact tgaaaatata acaaccactg aattcaaaaa tgctatcaca aatgcaaaaa 6000
tcatccctta ctcaggatta ctattagtca tcacagtgac tgacaacaaa ggagcattca 6060
aatacataaa gccacaaagt caattcatag tagatcttgg agcttaccta gaaaaagaaa 6120
gtatatatta tgttaccaca aattggaagc acacagctac acgatttgca atcaaaccca 6180
tggaagatta accttttttcc tctacatcag tgtgttaatt catacaaact ttctacctac 6240
attcttcact tcaccatcac aatcacaaac actctgtggt tcaaccaatc aaacaaaact 6300

```
tatctgaagt cccagatcat cccaagtcat tgtttatcag atctagtact caaataagtt   6360
aataaaaaat atacacatgg ggcaaataat cattggagga aatccaacta atcacaatat   6420
ctgttaacat agacaagtcc acacaccata cagaatcaac caatggaaaa tacatccata   6480
acaatagaat tctcaagcaa attctggcct tactttacac taatacacat gatcacaaca   6540
ataatctctt tgctaatcat aatctccatc atgattgcaa tactaaacaa actttgtgaa   6600
tataacgtat tccataacaa aacctttgag ttaccaagag ctcgagttaa tacttgataa   6660
agtagttaat taaaaacaca attgcatgcc agattaactt accatctgta aaaatgaaaa   6720
ctggggcaaa tatgtcacga aggaatcctt gcaaatttga aattcgaggt cattgcttaa   6780
atggtaagag gtgtcatttt agtcataatt attttgaatg gccaccccat gcactgcttg   6840
taagacaaaa ctttatgtta aacagaatac ttaagtctat ggataaaagt atagatacct   6900
tatcagaaat aagtggagct gcagagttgg acagaacaga agagtatgct cttggtgtag   6960
ttggagtgct agagagttat ataggatcaa taaacaatat aactaaacaa tcagcatgtg   7020
ttgccatgag caaactcctc actgaactca atagtgatga tatcaaaaag ctgagggaca   7080
atgaagagct aaattcaccc aagataagag tgtacaatac tgtcatatca tatattgaaa   7140
gcaacaggaa aaacaataaa caaactatcc atctgttaaa aagattgcca gcagacgtat   7200
tgaagaaaac catcaaaaac acattggata tccataagag cataaccatc aacaacccaa   7260
aagaatcaac tgttagtgat acaaatgacc atgccaaaaa taatgatact acctgacaaa   7320
tatccttgta gtataacttc catactaata acaagtagat gtagagttac tatgtataat   7380
caaaagaaca cactatattt caatcaaaac aacccaaata accatatgta ctcaccgaat   7440
caaacattca atgaaatcca ttggacctct caagaattga ttgacacaat tcaaaatttt   7500
ctacaacatc taggtattat tgaggatata tatacaatat atatattagt gtcataacac   7560
tcaattctaa cactcaccac atcgttacat tattaattca aacaattcaa gttgtgggac   7620
aaaatggatc ccattattaa tggaaattct gctaatgttt atctaaccga tagttattta   7680
aaaggtgtta tctctttctc agagtgtaat gctttaggaa gttacatatt caatggtcct   7740
tatctcaaaa atgattatac caacttaatt agtagacaaa atccattaat agaacacatg   7800
aatctaaaga aactaaatat aacacagtcc ttaatatcta agtatcataa aggtgaaata   7860
aaattagaag aacctactta ttttcagtca ttacttatga catacaagag tatgacctcg   7920
tcagaacaga ttgctaccac taatttactt aaaaagataa taagaagagc tatagaaata   7980
agtgatgtca aagtctatgc tatattgaat aaactagggc ttaaagaaaa ggacaagatt   8040
aaatccaaca atggacaaga tgaagacaac tcagttatta cgaccataat caaagatgat   8100
atactttcag ctgttaaaga taatcaatct catcttaaag cagacaaaaa tcactctaca   8160
aaacaaaaag acacaatcaa aacaacactc ttgaagaaat tgatgtgttc aatgcaacat   8220
cctccatcat ggttaataca ttggtttaac ttatacacaa aattaaacaa catattaaca   8280
cagtatcgat caaatgaggt aaaaaaccat gggtttacat tgatagataa tcaaactctt   8340
agtggatttc aatttatttt gaaccaatat ggttgtatag tttatcataa ggaactcaaa   8400
agaattactg tgacaaccta taatcaattc ttgacatgga aagatattag ccttagtaga   8460
ttaaatgttt gtttaattac atggattagt aactgcttga acacattaaa taaaagctta   8520
ggcttaagat gcggattcaa taatgttatc ttgacacaac tattccttta tggagattgt   8580
atactaaagc tatttcacaa tgaggggttc tacataataa aagaggtaga gggatttatt   8640
```

atgtctctaa ttttaaatat aacagaagaa gatcaattca gaaaacgatt ttataatagt 8700
atgctcaaca acatcacaga tgctgctaat aaagctcaga aaaatctgct atcaagagta 8760
tgtcatacat tattagataa gacagtgtcc gataatataa taaatggcag atggataatt 8820
ctattaagta agttccttaa attaattaag cttgcaggtg acaataacct taacaatctg 8880
agtgaactat attttttgtt cagaatattt ggacacccaa tggtagatga aagacaagcc 8940
atggatgctg ttaaaattaa ttgcaatgag accaaatttt acttgttaag cagtctgagt 9000
atgttaagag gtgcctttat atatagaatt ataaaagggt ttgtaaataa ttacaacaga 9060
tggcctactt taagaaatgc tattgtttta cccttaagat ggttaactta ctataaacta 9120
aacacttatc cttctttgtt ggaacttaca gaaagagatt tgattgtgtt atcaggacta 9180
cgtttctatc gtgagtttcg gttgcctaaa aaagtggatc ttgaaatgat tataaatgat 9240
aaagctatat cacctcctaa aaatttgata tggactagtt tccctagaaa ttacatgcca 9300
tcacacatac aaaactatat agaacatgaa aaattaaaat tttccgagag tgataaatca 9360
agaagagtat tagagtatta tttaagagat aacaaattca atgaatgtga tttatacaac 9420
tgtgtagtta atcaaagtta tctcaacaac cctaatcatg tggtatcatt gacaggcaaa 9480
gaaagagaac tcagtgtagg tagaatgttt gcaatgcaac cgggaatgtt cagacaggtt 9540
caaatattgg cagagaaaat gatagctgaa aacattttac aattctttcc tgaaagtctt 9600
acaagatatg gtgatctaga actacaaaaa atattagaac tgaaagcagg aataagtaac 9660
aaatcaaatc gctacaatga taattacaac aattacatta gtaagtgctc tatcatcaca 9720
gatctcagca aattcaatca agcatttcga tatgaaacgt catgtatttg tagtgatgtg 9780
ctggatgaac tgcatggtgt acaatctcta ttttcctggt tacatttaac tattcctcat 9840
gtcacaataa tatgcacata taggcatgca cccccctata taggagatca tattgtagat 9900
cttaacaatg tagatgaaca aagtggatta tatagatatc acatgggtgg catcgaaggg 9960
tggtgtcaaa aactatggac catagaagct atatcactat tggatctaat atctctcaaa 10020
gggaaattct caattactgc tttaattaat ggtgacaatc aatcaataga tataagcaaa 10080
ccaatcagac tcatggaagg tcaaactcat gctcaagcag attatttgct agcattaaat 10140
agccttaaat tactgtataa agagtatgca ggcataggcc acaaattaaa aggaactgag 10200
acttatatat cacgagatat gcaatttatg agtaaaacaa ttcaacataa cggtgtatat 10260
tacccagcta gtataaagaa agtcctaaga gtgggaccgt ggataaacac tatacttgat 10320
gatttcaaag tgagtctaga atctataggt agtttgacac aagaattaga atatagaggt 10380
gaaagtctat tatgcagttt aatatttaga aatgtatggt tatataatca gattgctcta 10440
caattaaaaa atcatgcatt atgtaacaat aaactatatt tggacatatt aaaggttctg 10500
aaacacttaa aaaccttttt taatcttgat aatattgata cagcattaac attgtatatg 10560
aatttaccca tgttatttgg tggtggtgat cccaacttgt tatatcgaag tttctataga 10620
agaactcctg acttcctcac agaggctata gttcactctg tgttcatact tagttattat 10680
acaaaccatg acttaaaaga taaacttcaa gatctgtcag atgatagatt gaataagttc 10740
ttaacatgca taatcacgtt tgacaaaaac cctaatgctg aattcgtaac attgatgaga 10800
gatcctcaag ctttagggtc tgagagacaa gctaaaatta ctagcgaaat caatagactg 10860
gcagttacag aggttttgag tacagctcca aacaaaatat tctccaaaag tgcacaacat 10920
tatactacta cagagataga tctaaatgat attatgcaaa atatagaacc tacatatcct 10980
catgggctaa gagttgttta tgaaagttta cccttttata aagcagagaa aatagtaaat 11040
cttatatcag gtacaaaatc tataactaac atactggaaa aaacttctgc catagactta 11100
acagatattg atagagccac tgagatgatg aggaaaaaca taactttgct tataaggata 11160
cttccattgg attgtaacag agataaaaga gagatattga gtatggaaaa cctaagtatt 11220
actgaattaa gcaaatatgt tagggaaaga tcttggtctt tatccaatat agttggtgtt 11280
acatcaccca gtatcatgta tacaatggac atcaaatata ctacaagcac tatatctagt 11340
ggcataatta tagagaaata taatgttaac agtttaacac gtggtgagag aggacccact 11400
aaaccatggg ttggttcatc tacacaagag aaaaaaacaa tgccagttta taatagacaa 11460
gtcttaacca aaaaacagag agatcaaata gatctattag caaaattgga ttgggtgtat 11520
gcatctatag ataacaagga tgaattcatg gaagaactca gcataggaac ccttgggtta 11580
acatatgaaa aggccaagaa attatttcca caatatttaa gtgtcaatta tttgcatcgc 11640
cttacagtca gtagtagacc atgtgaattc cctgcatcaa taccagctta tagaacaaca 11700
aattatcact ttgacactag ccctattaat cgcatattaa cagaaaagta tggtgatgaa 11760
gatattgaca tagtattcca aaactgtata agctttggcc ttagtttaat gtcagtagta 11820
gaacaattta ctaatgtatg tcctaacaga attattctca tacctaagct taatgagata 11880
catttgatga aacctcccat attcacaggt gatgttgata ttcacaagtt aaaacaagtg 11940
atacaaaaac agcatatgtt tttaccagac aaaataagtt tgactcaata tgtggaatta 12000
ttcttaagta ataaaacact caaatctgga tctcatgtta attctaattt aatattggca 12060
cataaaatat ctgactattt tcataatact tacattttaa gtactaattt agctggacat 12120
tggattctga ttatacaact tatgaaagat tctaaaggta tttttgaaaa agattgggga 12180
gagggatata taactgatca tatgtttatt aatttgaaag ttttcttcaa tgcttataag 12240
acctatctct tgtgttttca taaaggttat ggcaaagcaa agctggagtg tgatatgaac 12300
acttcagatc ttctatgtgt attggaatta atagacagta gttattggaa gtctatgtct 12360
aaggtatttt tagaacaaaa agttatcaaa tacattctta gccaagatgc aagtttacat 12420
agagtaaaag gatgtcatag cttcaaatta tggtttctta aacgtcttaa tgtagcagaa 12480
ttcacagttt gcccttgggt tgttaacata gattatcatc caacacatat gaaagcaata 12540
ttaacttata tagatcttgt tagaatggga ttgataaata tagatagaat acacattaaa 12600
aataaacaca aattcaatga tgaattttat acttctaatc tcttctacat taattataac 12660
ttctcagata atactcatct attaactaaa catataagga ttgctaattc tgaattagaa 12720
aataattaca acaaattata tcatcctaca ccagaaaccc tagagaatat actagccaat 12780
ccgattaaaa gtaatgacaa aaagacactg aatgactatt gtataggtaa aaatgttgac 12840
tcaataatgt taccattgtt atctaataag aagcttatta aatcgtctgc aatgattaga 12900
accaattaca gcaaacaaga tttgtataat ttattcccta tggttgtgat tgatagaatt 12960
atagatcatt caggcaatac agccaaatcc aaccaacttt acactactac ttcccaccaa 13020
atatccttag tgcacaatag cacatcactt tactgcatgc ttccttggca tcatattaat 13080
agattcaatt ttgtatttag ttctacaggt tgtaaaatta gtatagagta tattttaaaa 13140
gatcttaaaa ttaaagatcc caattgtata gcattcatag gtgaaggagc agggaattta 13200
ttattgcgta cagtagtgga acttcatcct gacataagat atatttacag aagtctgaaa 13260
gattgcaatg atcatagttt acctattgag tttttaaggc tgtacaatgg acatatcaac 13320
attgattatg gtgaaaattt gaccattcct gctacagatg caaccaacaa cattcattgg 13380

```
tcttatttac atataaagtt tgctgaacct atcagtcttt ttgtctgtga tgccgaattg  13440

tctgtaacag tcaactggag taaaattata atagaatgga gcaagcatgt aagaaagtgc  13500

aagtactgtt cctcagttaa taaatgtatg ttaatagtaa aatatcatgc tcaagatgat  13560

attgatttca aattagacaa tataactata ttaaaaactt atgtatgctt aggcagtaag  13620

ttaaagggat cggaggttta cttagtcctt acaataggtc ctgcgaatat attcccagta  13680

tttaatgtag tacaaaatgc taaattgata ctatcaagaa ccaaaaattt catcatgcct  13740

aagaaagctg ataaagagtc tattgatgca aatattaaaa gtttgatacc ctttctttgt  13800

taccctataa caaaaaaagg aattaatact gcattgtcaa aactaaagag tgttgttagt  13860

ggagatatac tatcatattc tatagctgga cgtaatgaag ttttcagcaa taaacttata  13920

aatcataagc atatgaacat cttaaaatgg ttcaatcatg ttttaaattt cagatcaaca  13980

gaactaaact ataaccattt atatatggta gaatctacat atccttacct aagtgaattg  14040

ttaaacagct tgacaaccaa tgaacttaaa aaactgatta aatcacagg tagtctgtta  14100

tacaactttc ataatgaata atgaataaag atcttataat aaaaattccc atagctatac  14160

actaacactg tattcaatta tagttattaa aaattaaaaa tcatataatt ttttaaataa  14220

cttttagtga actaatccta aagttatcat tttaatcttg gaggaataaa tttaaaccct  14280

aatctaattg gtttatatgt gtattaacta aattacgaga tattagtttt tgacactttt  14340

tttctcgt                                                          14348
```

<210> SEQ ID NO 5
<211> LENGTH: 14582
<212> TYPE: DNA
<213> ORGANISM: Artificial Sequence
<220> FEATURE:
<223> OTHER INFORMATION: Recombinant RSV sequence

<400> SEQUENCE: 5

```
acgggaaaaa atgcgtacaa caaacttgca taaaccaaaa aaatggggca aataagaatt     60

tgataagtac cacttaaatt taactccctt ggttagagat ggacacaacc cacaatgata    120

atacaccaca aagactgatg atcacagaca tgagaccgtt gtcacttgag accataataa    180

catcactaac cagagacatc ataacacaca aatttatata cttgataaat catgaatgca    240

tagtgagaaa acttgatgaa agacaggcca catttacatt cctggtcaac tatgaaatga    300

aactattaca caaagtagga agcactaaat ataaaaaata tactgaatac aacacaaaat    360

atggcacttt ccctatgcca atattcatca atcatgatgg gttcttagaa tgcattggca    420

ttaagcctac aaagcatact cccataatat acaagtatga tctcaatcca taaatttcaa    480

cacaatattc acacaatcta aaacaacaac tctatgcata actatactcc atagtccaga    540

tggagcctga aaattatagt aatttaaaac ttaaggagag atataagata gaagatgggg    600

caaatacaac catggctctt agcaaagtca agttgaatga tacactcaac aaagatcaac    660

ttctgtcatc cagcaaatac accatccaac ggagcacagg agatagtatt gatactccta    720

attatgatgt gcagaaacac atcaataagt tatgtggcat gttattaatc acagaagatg    780

ctaatcataa attcactggg ttaataggta tgttatatgc gatgtctagg ttaggaagag    840

aagacaccat aaaaatactc agagatgcgg gatatcatgt aaaagcaaat ggagtagatg    900

taacaacaca tcgtcaagac attaatggaa aagaaatgaa atttgaagtg ttaacattgg    960

caagcttaac aactgaaatt caaatcaaca ttgagataga atctagaaaa tcctacaaaa   1020

aaatgctaaa agaaatggga gaggtagctc cagaatacag gcatgactct cctgattgtg   1080
```

ggatgataat attatgtata gcagcattag taataactaa attagcagca ggggacagat 1140
ctggtcttac agccgtgatt aggagagcta ataatgtcct aaaaaatgaa atgaaacgtt 1200
acaaaggctt actacccaag gacatagcca acagcttcta tgaagtgttt gaaaaacatc 1260
cccactttat agatgttttt gttcattttg gtatagcaca atcttctacc agaggtggca 1320
gtagagttga agggattttt gcaggattgt ttatgaatgc ctatggtgca gggcaagtga 1380
tgttacggtg gggagtctta gcaaaatcag ttaaaaatat tatgttagga catgctagtg 1440
tgcaagcaga aatggaacaa gttgttgagg tttatgaata tgcccaaaaa ttgggtggtg 1500
aagcaggatt ctaccatata ttgaacaacc caaaagcatc attattatct ttgactcaat 1560
ttcctcactt ctccagtgta gtattaggca atgctgctgg cctaggcata atgggagagt 1620
acagaggtac accgaggaat caagatctat atgatgcagc aaaggcatat gctgaacaac 1680
tcaaagaaaa tggtgtgatt aactacagtg tactagactt gacagcagaa gaactagagg 1740
ctatcaaaca tcagcttaat ccaaaagata atgatgtaga gctttgagtt aataaaaaat 1800
ggggcaaata aatcatcatg gaaaagtttg ctcctgaatt ccatggagaa gatgcaaaca 1860
acagggctac taaattccta gaatcaataa agggcaaatt cacatcaccc aaagatccca 1920
agaaaaaaga tagtatcata tctgtcaact caatagatat agaagtaacc aaagaaagcc 1980
ctataacatc aaattcaact attatcaacc caacaaatga gacagatgat actgcaggga 2040
acaagcccaa ttatcaaaga aaacctctag taagtttcaa agaagaccct acaccaagtg 2100
ataatccctt ttctaaacta tacaaagaaa ccatagaaac atttgataac aatgaagaag 2160
aatccagcta ttcatacgaa gaaataaatg atcagacaaa cgataatata acagcaagat 2220
tagataggat tgatgaaaaa ttaagtgaaa tactaggaat gcttcacaca ttagtagtgg 2280
caagtgcagg acctacatct gctcgggatg gtataagaga tgccatggtt ggtttaagag 2340
aagaaatgat agaaaaaatc agaactgaag cattaatgac caatgacaga ttagaagcta 2400
tggcaagact caggaatgag gaaagtgaaa agatggcaaa agacacatca gatgaagtgt 2460
ctctcaatcc aacatcagag aaattgaaca acctattgga agggaatgat agtgacaatg 2520
atctatcact tgaagatttc tgattagtta ccaatcttca catcaacaca caataccaac 2580
agaagaccaa caaactaacc aacccaatca tccaaccaaa catccatccg ccaatcagcc 2640
aaacagccaa caaaacaacc agccaatcca aaactaacca cccggaaaaa atctataata 2700
tagttacaaa aaaaggaaag ggtggggcaa atatggaaac atacgtgaac aagcttcacg 2760
aaggctccac atacacagct gctgttcaat acaatgtctt agaaaaagac gatgaccctg 2820
catcacttac aatatgggtg cccatgttcc aatcatctat gccagcagat ttacttataa 2880
aagaactagc taatgtcaac atactagtga aacaaatatc cacacccaag ggaccttcac 2940
taagagtcat gataaactca agaagtgcag tgctagcaca aatgcccagc aaatttacca 3000
tatgcgctaa tgtgtccttg gatgaaagaa gcaaactagc atatgatgta accacaccct 3060
gtgaaatcaa ggcatgtagt ctaacatgcc taaaatcaaa aaatatgttg actacagtta 3120
aagatctcac tatgaagaca ctcaacccta cacatgatat tattgcttta tgtgaatttg 3180
aaaacatagt aacatcaaaa aaagtcataa taccaacata cctaagatcc atcagtgtca 3240
gaaataaaga tctgaacaca cttgaaaata taacaaccac tgaattcaaa aatgctatca 3300
caaatgcaaa aatcatccct tactcaggat tactattagt catcacagtg actgacaaca 3360
aaggagcatt caaatacata aagccacaaa gtcaattcat agtagatctt ggagcttacc 3420

```
tagaaaaaga aagtatatat tatgttacca caaattggaa gcacacagct acacgatttg   3480
caatcaaacc catggaagat taacctttt cctctacatc agtgtgttaa ttcatacaaa    3540
ctttctacct acattcttca cttcaccatc acaatcacaa acactctgtg gttcaaccaa   3600
tcaaacaaaa cttatctgaa gtcccagatc atcccaagtc attgtttatc agatctagta   3660
ctcaaataag ttaataaaaa atatacacat ggggcaaata atcattggag gaaatccaac   3720
taatcacaat atctgttaac atagacaagt ccacacacca tacagaatca accaatggaa   3780
aatacatcca taacaataga attctcaagc aaattctggc cttactttac actaatacac   3840
atgatcacaa caataatctc tttgctaatc ataatctcca tcatgattgc aatactaaac   3900
aaactttgtg aatataacgt attccataac aaaacctttg agttaccaag agctcgagtt   3960
aatacttgat aaagtagtta attaaaaata gtcataacaa tgaactagga tatcaagact   4020
aacaataaca ttggggcaaa tgcaaacatg tccaaaaaca aggaccaacg caccgctaag   4080
acattagaaa ggacctggga cactctcaat catttattat tcatatcatc gtgcttatat   4140
aagttaaatc ttaaatctgt agcacaaatc acattatcca ttctggcaat gataatctca   4200
acttcactta taattgcagc catcatattc atagcctcgg caaaccacaa agtcacacca   4260
acaactgcaa tcatacaaga tgcaacaagc cagatcaaga acacaacccc aacatacctc   4320
acccagaatc ctcagcttgg aatcagtccc tctaatccgt ctgaaattac atcacaaatc   4380
accaccatac tagcttcaac aacaccagga gtcaagtcaa ccctgcaatc cacaacagtc   4440
aagaccaaaa acacaacaac aactcaaaca caacccagca agcccaccac aaaacaacgc   4500
caaaacaaac caccaagcaa acccaataat gattttcact ttgaagtgtt caactttgta   4560
ccctgcagca tatgcagcaa caatccaacc tgctgggcta tctgcaaaag aataccaaac   4620
aaaaaaccag gaaagaaaac cactaccaag cccacaaaaa aaccaaccct caagacaacc   4680
aaaaaagatc ccaaacctca aaccactaaa tcaaaggaag tacccaccac caagcccaca   4740
gaagagccaa ccatcaacac caccaaaaca aacatcataa ctacactact cacctccaac   4800
accacaggaa atccagaact cacaagtcaa atggaaacct tccactcaac ttcctccgaa   4860
ggcaatccaa gcccttctca agtctctaca acatccgagt acccatcaca accttcatct   4920
ccacccaaca caccacgcca gtagttactt aaaaacatat tatcacaaaa ggccttgacc   4980
aacttaaaca gaatcaaaat aaactctggg gcaaataaca atggagttgc taatcctcaa   5040
agcaaatgca attaccacaa tcctcactgc agtcacattt tgttttgctt ctggtcaaaa   5100
catcactgaa gaattttatc aatcaacatg cagtgcagtt agcaaaggct atcttagtgc   5160
tctgagaact ggttggtata ccagtgttat aactatagaa ttaagtaata tcaagaaaaa   5220
taagtgtaat ggaacagatg ctaaggtaaa attgataaaa caagaattag ataaatataa   5280
aaatgctgta acagaattgc agttgctcat gcaaagcaca caagcaacaa acaatcgagc   5340
cagaagagaa ctaccaaggt ttatgaatta tacactcaac aatgccaaaa aaaccaatgt   5400
aacattaagc aagaaaagga aaagaagatt tcttggtttt ttgttaggtg ttggatctgc   5460
aatcgccagt ggcgttgctg tatctaaggt cctgcaccta gaaggggaag tgaacaagat   5520
caaaagtgct ctactatcca caaacaaggc tgtagtcagc ttatcaaatg gagttagtgt   5580
tttaaccagc aaagtgttag acctcaaaaa ctatatagat aaacaattgt tacctattgt   5640
gaacaagcaa agctgcagca tatcaaatat agaaactgtg atagagttcc aacaaaagaa   5700
caacagacta ctagagatta ccagggaatt tagtgttaat gcaggcgtaa ctacacctgt   5760
aagcacttac atgttaacta atagtgaatt attgtcatta atcaatgata tgcctataac   5820
```

```
aaatgatcag aaaaagttaa tgtccaacaa tgttcaaata gttagacagc aaagttactc   5880
tatcatgtcc ataataaaag aggaagtctt agcatatgta gtacaattac cactatatgg   5940
tgttatagat acaccctgtt ggaaactaca cacatcccct ctatgtacaa ccaacacaaa   6000
agaagggtcc aacatctgtt taacaagaac tgacagagga tggtactgtg acaatgcagg   6060
atcagtatct ttcttcccac aagctgaaac atgtaaagtt caatcaaatc gagtattttg   6120
tgacacaatg aacagtttaa cattaccaag tgaagtaaat ctctgcaatg ttgacatatt   6180
caaccccaaa tatgattgta aaattatgac ttcaaaaaca gatgtaagca gctccgttat   6240
cacatctcta ggagccattg tgtcatgcta tggcaaaact aaatgtacag catccaataa   6300
aaatcgtgga atcataaaga cattttctaa cgggtgcgat tatgtatcaa ataaaggggt   6360
ggacactgtg tctgtaggta acacattata ttatgtaaat aagcaagaag gtaaaagtct   6420
ctatgtaaaa ggtgaaccaa taataaattt ctatgaccca ttagtattcc cctctgatga   6480
atttgatgca tcaatatctc aagtcaacga gaagattaac cagagcctag catttattcg   6540
taaatccgat gaattattac ataatgtaaa tgctggtaaa tccaccacaa atatcatgat   6600
aactactata attatagtga ttatagtaat attgttatca ttaattgctg ttggactgct   6660
cttatactgt aaggccagaa gcacaccagt cacactaagc aaagatcaac tgagtggtat   6720
aaataatatt gcatttagta actaaataaa aatagcacct aatcatgttc ttacaatggt   6780
ttactatctg ctcatagaca acccatctgt cattggattt tcttaaaatc tgaacttcat   6840
cgaaactctc atctataaac catctcactt acactattta agtagattcc tagtttatag   6900
ttatataaaa cacaattgca tgccagatta acttaccatc tgtaaaaatg aaaactgggg   6960
caaatatgtc acgaaggaat ccttgcaaat ttgaaattcg aggtcattgc ttaaatggta   7020
agaggtgtca ttttagtcat aattattttg aatggccacc ccatgcactg cttgtaagac   7080
aaaactttat gttaaacaga atacttaagt ctatggataa aagtatagat accttatcag   7140
aaataagtgg agctgcagag ttggacagaa cagaagagta tgctcttggt gtagttggag   7200
tgctagagag ttatatagga tcaataaaca atataactaa acaatcagca tgtgttgcca   7260
tgagcaaact cctcactgaa ctcaatagtg atgatatcaa aaagctgagg gacaatgaag   7320
agctaaattc acccaagata agagtgtaca atactgtcat atcatatatt gaaagcaaca   7380
ggaaaaacaa taaacaaact atccatctgt taaaaagatt gccagcagac gtattgaaga   7440
aaaccatcaa aaacacattg gatatccata agagcataac catcaacaac ccaaaagaat   7500
caactgttag tgatacaaat gaccatgcca aaaataatga tactacctga caaatatcct   7560
tgtagtataa cttccatact aataacaagt agatgtagag ttactatgta taatcaaaag   7620
aacacactat atttcaatca aaacaaccca aataaccata tgtactcacc gaatcaaaca   7680
ttcaatgaaa tccattggac ctctcaagaa ttgattgaca caattcaaaa ttttctacaa   7740
catctaggta ttattgagga tatatataca atatatatat tagtgtcata acactcaatt   7800
ctaacactca ccacatcgtt acattattaa ttcaaacaat tcaagttgtg ggacaaaatg   7860
gatcccatta ttaatggaaa ttctgctaat gtttatctaa ccgatagtta tttaaaaggt   7920
gttatctctt tctcagagtg taatgcttta ggaagttaca tattcaatgg tccttatctc   7980
aaaaatgatt ataccaactt aattagtaga caaaatccat taatagaaca catgaatcta   8040
aagaaactaa atataacaca gtccttaata tctaagtatc ataaaggtga aataaaatta   8100
gaagaaccta cttattttca gtcattactt atgacataca agagtatgac ctcgtcagaa   8160
```

cagattgcta ccactaattt acttaaaaag ataataagaa gagctataga aataagtgat 8220
gtcaaagtct atgctatatt gaataaacta gggcttaaag aaaaggacaa gattaaatcc 8280
aacaatggac aagatgaaga caactcagtt attacgacca taatcaaaga tgatatactt 8340
tcagctgtta aagataatca atctcatctt aaagcagaca aaaatcactc tacaaaacaa 8400
aaagacacaa tcaaaacaac actcttgaag aaattgatgt gttcaatgca acatcctcca 8460
tcatggttaa tacattggtt taacttatac acaaaattaa acaacatatt aacacagtat 8520
cgatcaaatg aggtaaaaaa ccatgggttt acattgatag ataatcaaac tcttagtgga 8580
tttcaattta ttttgaacca atatggttgt atagtttatc ataaggaact caaaagaatt 8640
actgtgacaa cctataatca attcttgaca tggaaagata ttagccttag tagattaaat 8700
gtttgtttaa ttacatggat tagtaactgc ttgaacacat taaataaaag cttaggctta 8760
agatgcggat tcaataatgt tatcttgaca caactattcc tttatggaga ttgtatacta 8820
aagctatttc acaatgaggg gttctacata ataaaagagg tagagggatt tattatgtct 8880
ctaattttaa atataacaga agaagatcaa ttcagaaaac gattttataa tagtatgctc 8940
aacaacatca cagatgctgc taataaagct cagaaaaatc tgctatcaag agtatgtcat 9000
acattattag ataagacagt gtccgataat ataataaatg gcagatggat aattctatta 9060
agtaagttcc ttaaattaat taagcttgca ggtgacaata accttaacaa tctgagtgaa 9120
ctatattttt tgttcagaat atttggacac ccaatggtag atgaaagaca agccatggat 9180
gctgttaaaa ttaattgcaa tgagaccaaa ttttacttgt taagcagtct gagtatgtta 9240
agaggtgcct ttatatatag aattataaaa gggtttgtaa ataattacaa cagatggcct 9300
actttaagaa atgctattgt tttaccctta agatggttaa cttactataa actaaacact 9360
tatccttctt tgttggaact tacagaaaga gatttgattg tgttatcagg actacgtttc 9420
tatcgtgagt ttcggttgcc taaaaaagtg gatcttgaaa tgattataaa tgataaagct 9480
atatcacctc ctaaaaattt gatatggact agtttcccta gaaattacat gccatcacac 9540
atacaaaact atatagaaca tgaaaaatta aaattttccg agagtgataa atcaagaaga 9600
gtattagagt attatttaag agataacaaa ttcaatgaat gtgatttata caactgtgta 9660
gttaatcaaa gttatctcaa caaccctaat catgtggtat cattgacagg caaagaaaga 9720
gaactcagtg taggtagaat gtttgcaatg caaccgggaa tgttcagaca ggttcaaata 9780
ttggcagaga aaatgatagc tgaaaacatt ttacaattct ttcctgaaag tcttacaaga 9840
tatggtgatc tagaactaca aaaaatatta gaactgaaag caggaataag taacaaatca 9900
aatcgctaca atgataatta caacaattac attagtaagt gctctatcat cacagatctc 9960
agcaaattca atcaagcatt tcgatatgaa acgtcatgta tttgtagtga tgtgctggat 10020
gaactgcatg gtgtacaatc tctattttcc tggttacatt taactattcc tcatgtcaca 10080 ataaatatgca catataggca tgcacccccc tatataggag atcatattgt agatcttaac 10140
aatgtagatg aacaaagtgg attatataga tatcacatgg gtggcatcga agggtggtgt 10200
caaaaactat ggaccataga agctatatca ctattggatc taatatctct caaagggaaa 10260
ttctcaatta ctgctttaat taatggtgac aatcaatcaa tagatataag caaaccaatc 10320
agactcatgg aaggtcaaac tcatgctcaa gcagattatt tgctagcatt aaatagcctt 10380
aaattactgt ataaagagta tgcaggcata ggccacaaat taaaaggaac tgagacttat 10440
atatcacgag atatgcaatt tatgagtaaa acaattcaac ataacggtgt atattaccca 10500
gctagtataa agaaagtcct aagagtggga ccgtggataa acactatact tgatgatttc 10560

```
aaagtgagtc tagaatctat aggtagtttg acacaagaat tagaatatag aggtgaaagt  10620
ctattatgca gtttaatatt tagaaatgta tggttatata atcagattgc tctacaatta  10680
aaaaatcatg cattatgtaa caataaacta tatttggaca tattaaaggt tctgaaacac  10740
ttaaaaacct tttttaatct tgataatatt gatacagcat taacattgta tatgaattta  10800
cccatgttat ttggtggtgg tgatcccaac ttgttatatc gaagtttcta tagaagaact  10860
cctgacttcc tcacagaggc tatagttcac tctgtgttca tacttagtta ttatacaaac  10920
catgacttaa aagataaact tcaagatctg tcagatgata gattgaataa gttcttaaca  10980
tgcataatca cgtttgacaa aaaccctaat gctgaattcg taacattgat gagagatcct  11040
caagctttag ggtctgagag acaagctaaa attactagcg aaatcaatag actggcagtt  11100
acagaggttt tgagtacagc tccaaacaaa atattctcca aaagtgcaca acattatact  11160
actacagaga tagatctaaa tgatattatg caaaatatag aacctacata tcctcatggg  11220
ctaagagttg tttatgaaag tttacccttt tataaagcag agaaaatagt aaatcttata  11280
tcaggtacaa aatctataac taacatactg gaaaaaactt ctgccataga cttaacagat  11340
attgatagag ccactgagat gatgaggaaa aacataactt tgcttataag gatacttcca  11400
ttggattgta acagagataa aagagagata ttgagtatgg aaaacctaag tattactgaa  11460
ttaagcaaat atgttaggga aagatcttgg tctttatcca atatagttgg tgttacatca  11520
cccagtatca tgtatacaat ggacatcaaa tatactacaa gcactatatc tagtggcata  11580
attatagaga aatataatgt taacagttta acacgtggtg agagaggacc cactaaacca  11640
tgggttggtt catctacaca agagaaaaaa acaatgccag tttataatag acaagtctta  11700
accaaaaaac agagagatca aatagatcta ttagcaaaat tggattgggt gtatgcatct  11760
atagataaca aggatgaatt catggaagaa ctctcaatag gaacccttgg gttaacaaaa  11820
gaaaaggcca agaaattatt tccacaatat ttaagtgtca attatttgca tcgccttaca  11880
gtcagtagta gaccatgtga attccctgca tcaataccag cttatagaac aacaaattat  11940
cactttgaca ctagccctat taatcgcata ttaacagaaa agtatggtga tgaagatatt  12000
gacatagtat tccaaaactg tataagcttt ggccttagtt taatgtcagt agtagaacaa  12060
tttactaatg tatgtcctaa cagaattatt ctcataccta agcttaatga gatacatttg  12120
atgaaacctc ccatattcac aggtgatgtt gatattcaca agttaaaaca agtgatacaa  12180
aaacagcata tgtttttacc agacaaaata agtttgactc aatatgtgga attattctta  12240
agtaataaaa cactcaaatc tggatctcat gttaattcta atttaatatt ggcacataaa  12300
atatctgact attttcataa tacttacatt ttaagtacta atttagctgg acattggatt  12360
ctgattatac aacttatgaa agattctaaa ggtatttttg aaaaagattg gggagaggga  12420
tatataactg atcatatgtt tattaatttg aaagttttct tcaatgctta taagacctat  12480
ctcttgtgtt ttcataaagg ttatggcaaa gcaaagctgg agtgtgatat gaacacttca  12540
gatcttctat gtgtattgga attaatagac agtagttatt ggaagtctat gtctaaggta  12600
tttttagaac aaaaagttat caaatacatt cttagccaag atgcaagttt acatagagta  12660
aaaggatgtc atagcttcaa attatggttt cttaaacgtc ttaatgtagc agaattcaca  12720
gtttgccctt gggttgttaa catagattat catccaacac atatgaaagc aatattaact  12780
tatatagatc ttgttagaat gggattgata aatatagata gaatacacat taaaaataaa  12840
cacaaattca atgatgaatt ttatacttct aatctcttct acattaatta taacttctca  12900
```

```
gataatactc atctattaac taaacatata aggattgcta attctgaatt agaaaataat  12960
tacaacaaat tatatcatcc tacaccagaa accctagaga atatactagc caatccgatt  13020
aaaagtaatg acaaaaagac actgaatgac tattgtatag gtaaaaatgt tgactcaata  13080
atgttaccat tgttatctaa taagaagctt attaaatcgt ctgcaatgat tagaaccaat  13140
tacagcaaac aagatttgta taatttattc cctatggttg tgattgatag aattatagat  13200
cattcaggca atacagccaa atccaaccaa ctttacacta ctacttccca ccaaatatcc  13260
ttagtgcaca atagcacatc actttactgc atgcttcctt ggcatcatat taatagattc  13320
aattttgtat ttagttctac aggttgtaaa attagtatag agtatatttt aaaagatctt  13380
aaaattaaag atcccaattg tatagcattc ataggtgaag gagcagggaa tttattattg  13440
cgtacagtag tggaacttca tcctgacata agatatattt acagaagtct gaaagattgc  13500
aatgatcata gtttacctat tgagttttta aggctgtaca atggacatat caacattgat  13560
tatggtgaaa atttgaccat tcctgctaca gatgcaacca acaacattca ttggtcttat  13620
ttacatataa agtttgctga acctatcagt ctttttgtct gtgatgccga attgtctgta  13680
acagtcaact ggagtaaaat tataatagaa tggagcaagc atgtaagaaa gtgcaagtac  13740
tgttcctcag ttaataaatg tatgttaata gtaaaatatc atgctcaaga tgatattgat  13800
ttcaaattag acaatataac tatattaaaa acttatgtat gcttaggcag taagttaaag  13860
ggatcggagg tttacttagt ccttacaata ggtcctgcga atatattccc agtatttaat  13920
gtagtacaaa atgctaaatt gatactatca agaaccaaaa atttcatcat gcctaagaaa  13980
gctgataaag agtctattga tgcaaatatt aaaagtttga taccctttct ttgttaccct  14040
ataacaaaaa aaggaattaa tactgcattg tcaaaactaa agagtgttgt tagtggagat  14100
atactatcat attctatagc tggacgtaat gaagttttca gcaataaact tataaatcat  14160
aagcatatga acatcttaaa atggttcaat catgttttaa atttcagatc aacagaacta  14220
aactataacc atttatatat ggtagaatct acatatcctt acctaagtga attgttaaac  14280
agcttgacaa ccaatgaact taaaaaactg attaaaatca caggtagtct gttatacaac  14340
tttcataatg aataatgaat aaagatctta taataaaaat tcccatagct atacactaac  14400
actgtattca attatagtta ttaaaaatta aaaatcatat aattttttaa ataactttta  14460
gtgaactaat cctaaagtta tcattttaat cttggaggaa taaatttaaa ccctaatcta  14520
attggtttat atgtgtatta actaaattac gagatattag tttttgacac tttttttctc  14580
gt                                                                 14582
```

```
<210> SEQ ID NO 6
<211> LENGTH: 14348
<212> TYPE: DNA
<213> ORGANISM: Artificial Sequence
<220> FEATURE:
<223> OTHER INFORMATION: Recombinant RSV sequence

<400> SEQUENCE: 6

acgggaaaaa atgcgtacaa caaacttgca taaaccaaaa aaatggggca aataagaatt     60
tgataagtac cacttaaatt taactcctcg agttcaccat ggagttgcta atcctcaaag    120
caaatgcaat taccacaatc ctcactgcag tcacattttg ttttgcttct ggtcaaaaca    180
tcactgaaga attttatcaa tcaacatgca gtgcagttag caaaggctat cttagtgctc    240
tgagaactgg ttggtatacc agtgttataa ctatagaatt aagtaatatc aagaaaaata    300
agtgtaatgg aacagatgct aaggtaaaat tgataaaaca agaattagat aaatataaaa    360
```

```
atgctgtaac agaattgcag ttgctcatgc aaagcacaca agcaacaaac aatcgagcca    420
gaagagaact accaaggttt atgaattata cactcaacaa tgccaaaaaa accaatgtaa    480
cattaagcaa gaaaaggaaa agaagatttc ttggtttttt gttaggtgtt ggatctgcaa    540
tcgccagtgg cgttgctgta tctaaggtcc tgcacctaga aggggaagtg aacaagatca    600
aaagtgctct actatccaca aacaaggctg tagtcagctt atcaaatgga gttagtgttt    660
taaccagcaa agtgttagac ctcaaaaact atatagataa acaattgtta cctattgtga    720
acaagcaaag ctgcagcata tcaaatatag aaactgtgat agagttccaa caaaagaaca    780
acagactact agagattacc agggaattta gtgttaatgc aggcgtaact acacctgtaa    840
gcacttacat gttaactaat agtgaattat tgtcattaat caatgatatg cctataacaa    900
atgatcagaa aaagttaatg tccaacaatg ttcaaatagt tagacagcaa agttactcta    960
tcatgtccat aataaaagag gaagtcttag catatgtagt acaattacca ctatatggtg   1020
ttatagatac accctgttgg aaactacaca catcccctct atgtacaacc aacacaaaag   1080
aagggtccaa catctgttta acaagaactg acagaggatg gtactgtgac aatgcaggat   1140
cagtatcttt cttcccacaa gctgaaacat gtaaagttca atcaaatcga gtattttgtg   1200
acacaatgaa cagtttaaca ttaccaagtg aagtaaatct ctgcaatgtt gacatattca   1260
accccaaata tgattgtaaa attatgactt caaaaacaga tgtaagcagc tccgttatca   1320
catctctagg agccattgtg tcatgctatg gcaaaactaa atgtacagca tccaataaaa   1380
atcgtggaat cataaagaca ttttctaacg ggtgcgatta tgtatcaaat aaaggggtgg   1440
acactgtgtc tgtaggtaac acattatatt atgtaaataa gcaagaaggt aaaagtctct   1500
atgtaaaagg tgaaccaata ataaatttct atgacccatt agtattcccc tctgatgaat   1560
ttgatgcatc aatatctcaa gtcaacgaga agattaacca gagcctagca tttattcgta   1620
aatccgatga attattacat aatgtaaatg ctggtaaatc caccacaaat atcatgataa   1680
ctactataat tatagtgatt atagtaatat tgttatcatt aattgctgtt ggactgctct   1740
tatactgtaa ggccagaagc acaccagtca cactaagcaa agatcaactg agtggtataa   1800
ataatattgc atttagtaac taaagtagtt aattaaaaat ggggcaaata caaccatgtc   1860
caaaaacaag gaccaacgca ccgctaagac attagaaagg acctgggaca ctctcaatca   1920
tttattattc atatcatcgt gcttatataa gttaaatctt aaatctgtag cacaaatcac   1980
attatccatt ctggcaatga taatctcaac ttcacttata attgcagcca tcatattcat   2040
agcctcggca aaccacaaag tcacaccaac aactgcaatc atacaagatg caacaagcca   2100
gatcaagaac acaaccccaa catacctcac ccagaatcct cagcttggaa tcagtccctc   2160
taatccgtct gaaattacat cacaaatcac caccatacta gcttcaacaa caccaggagt   2220
caagtcaacc ctgcaatcca caacagtcaa gaccaaaaac acaacaacaa ctcaaacaca   2280
acccagcaag cccaccacaa aacaacgcca aaacaaacca ccaagcaaac ccaataatga   2340
ttttcacttt gaagtgttca actttgtacc ctgcagcata tgcagcaaca atccaacctg   2400
ctgggctatc tgcaaaagaa taccaaacaa aaaaccagga aagaaaacca ctaccaagcc   2460
cacaaaaaaa ccaaccctca agacaaccaa aaaagatccc aaacctcaaa ccactaaatc   2520
aaaggaagta cccaccacca agcccacaga agagccaacc atcaacacca ccaaaacaaa   2580
catcataact acactactca cctccaacac cacaggaaat ccagaactca caagtcaaat   2640
ggaaaccttc cactcaactt cctccgaagg caatccaagc ccttctcaag tctctacaac   2700
```

```
atccgagtac ccatcacaac cttcatctcc acccaacaca ccacgccagt agttaataaa   2760
aaatggggca aatactcgag ttagagatgg acacaaccca caatgataat acaccacaaa   2820
gactgatgat cacagacatg agaccgttgt cacttgagac cataataaca tcactaacca   2880
gagacatcat aacacacaaa tttatatact tgataaatca tgaatgcata gtgagaaaac   2940
ttgatgaaag acaggccaca tttacattcc tggtcaacta tgaaatgaaa ctattacaca   3000
aagtaggaag cactaaatat aaaaaatata ctgaatacaa cacaaaatat ggcactttcc   3060
ctatgccaat attcatcaat catgatgggt tcttagaatg cattggcatt aagcctacaa   3120
agcatactcc cataatatac aagtatgatc tcaatccata aatttcaaca caatattcac   3180
acaatctaaa acaacaactc tatgcataac tatactccat agtccagatg gagcctgaaa   3240
attatagtaa tttaaaactt aaggagagat ataagataga agatggggca aatacaacca   3300
tggctcttag caaagtcaag ttgaatgata cactcaacaa agatcaactt ctgtcatcca   3360
gcaaatacac catccaacgg agcacaggag atagtattga tactcctaat tatgatgtgc   3420
agaaacacat caataagtta tgtggcatgt tattaatcac agaagatgct aatcataaat   3480
tcactgggtt aataggtatg ttatatgcga tgtctaggtt aggaagagaa gacaccataa   3540
aaatactcag agatgcggga tatcatgtaa aagcaaatgg agtagatgta acaacacatc   3600
gtcaagacat taatggaaaa gaaatgaaat ttgaagtgtt aacattggca agcttaacaa   3660
ctgaaattca aatcaacatt gagatagaat ctagaaaatc ctacaaaaaa atgctaaaag   3720
aaatgggaga ggtagctcca gaatacaggc atgactctcc tgattgtggg atgataaatat   3780
tatgtatagc agcattagta ataactaaat tagcagcagg ggacagatct ggtcttacag   3840
ccgtgattag gagagctaat aatgtcctaa aaaatgaaat gaaacgttac aaaggcttac   3900
tacccaagga catagccaac agcttctatg aagtgtttga aaaacatccc cactttatag   3960
atgtttttgt tcattttggt atagcacaat cttctaccag aggtggcagt agagttgaag   4020
ggatttttgc aggattgttt atgaatgcct atggtgcagg gcaagtgatg ttacggtggg   4080
gagtcttagc aaaatcggtt aaaaatatta tgttaggaca tgctagtgtg caagcagaaa   4140
tggaacaagt tgttgaggtt tatgaatatg cccaaaaatt gggtggtgaa gcaggattct   4200
accatatatt gaacaaccca aaagcatcat tattatcttt gactcaattt cctcacttct   4260
ccagtgtagt attaggcaat gctgctggcc taggcataat gggagagtac agaggtacac   4320
cgaggaatca agatctatat gatgcagcaa aggcatatgc tgaacaactc aaagaaaatg   4380
gtgtgattaa ctacagtgta ctagacttga cagcagaaga actagaggct atcaaacatc   4440
agcttaatcc aaaagataat gatgtagagc tttgagttaa taaaaaatgg ggcaaataaa   4500
tcatcatgga aaagtttgct cctgaattcc atggagaaga tgcaaacaac agggctacta   4560
aattcctaga atcaataaag ggcaaattca catcacccaa agatcccaag aaaaaagata   4620
gtatcatatc tgtcaactca atagatatag aagtaaccaa agaaagccct ataacatcaa   4680
attcaactat tatcaaccca acaaatgaga cagatgatac tgcagggaac aagcccaatt   4740
atcaaagaaa acctctagta agtttcaaag aagaccctac accaagtgat aatccctttt   4800
ctaaactata caaagaaacc atagaaacat ttgataacaa tgaagaagaa tccagctatt   4860
catacgaaga aataaatgat cagacaaacg ataatataac agcaagatta gataggattg   4920
atgaaaaatt aagtgaaata ctaggaatgc ttcacacatt agtagtggca agtgcaggac   4980
ctacatctgc tcgggatggt ataagagatg ccatggttgg tttaagagaa gaaatgatag   5040
aaaaaatcag aactgaagca ttaatgacca atgacagatt agaagctatg gcaagactca   5100
```

```
ggaatgagga aagtgaaaag atggcaaaag acacatcaga tgaagtgtct ctcaatccaa   5160
catcagagaa attgaacaac ctattggaag ggaatgatag tgacaatgat ctatcacttg   5220
aagatttctg attagttacc aatcttcaca tcaacacaca ataccaacag aagaccaaca   5280
aactaaccaa cccaatcatc caaccaaaca tccatccgcc aatcagccaa acagccaaca   5340
aaacaaccag ccaatccaaa actaaccacc cggaaaaaat ctataatata gttacaaaaa   5400
aaggaaaggg tggggcaaat atggaaacat acgtgaacaa gcttcacgaa ggctccacat   5460
acacagctgc tgttcaatac aatgtcttag aaaaagacga tgaccctgca tcacttacaa   5520
tatgggtgcc catgttccaa tcatctatgc cagcagattt acttataaaa gaactagcta   5580
atgtcaacat actagtgaaa caaatatcca cacccaaggg accttcacta agagtcatga   5640
taaactcaag aagtgcagtg ctagcacaaa tgcccagcaa atttaccata tgcgctaatg   5700
tgtccttgga tgaaagaagc aaactagcat atgatgtaac cacaccctgt gaaatcaagg   5760
catgtagtct aacatgccta aaatcaaaaa atatgttgac tacagttaaa gatctcacta   5820
tgaagacact caaccctaca catgatatta ttgctttatg tgaatttgaa aacatagtaa   5880
catcaaaaaa agtcataata ccaacatacc taagatccat cagtgtcaga aataaagatc   5940
tgaacacact tgaaaatata acaaccactg aattcaaaaa tgctatcaca aatgcaaaaa   6000
tcatccctta ctcaggatta ctattagtca tcacagtgac tgacaacaaa ggagcattca   6060
aatacataaa gccacaaagt caattcatag tagatcttgg agcttaccta gaaaaagaaa   6120
gtatatatta tgttaccaca aattggaagc acacagctac acgatttgca atcaaaccca   6180
tggaagatta accttttttcc tctacatcag tgtgttaatt catacaaact ttctacctac   6240
attcttcact tcaccatcac aatcacaaac actctgtggt tcaaccaatc aaacaaaact   6300
tatctgaagt cccagatcat cccaagtcat tgtttatcag atctagtact caaataagtt   6360
aataaaaaat atacacatgg ggcaaataat cattggagga aatccaacta atcacaatat   6420
ctgttaacat agacaagtcc acacaccata cagaatcaac caatggaaaa tacatccata   6480
acaatagaat tctcaagcaa attctggcct tactttacac taatacacat gatcacaaca   6540
ataatctctt tgctaatcat aatctccatc atgattgcaa tactaaacaa actttgtgaa   6600
tataacgtat tccataacaa aacctttgag ttaccaagag ctcgagttaa tacttgataa   6660
agtagttaat taaaaacaca attgcatgcc agattaactt accatctgta aaaatgaaaa   6720
ctggggcaaa tatgtcacga aggaatcctt gcaaatttga aattcgaggt cattgcttaa   6780
atggtaagag gtgtcatttt agtcataatt attttgaatg gccacccccat gcactgcttg   6840
taagacaaaa ctttatgtta aacagaatac ttaagtctat ggataaaagt atagatacct   6900
tatcagaaat aagtggagct gcagagttgg acagaacaga agagtatgct cttggtgtag   6960
ttggagtgct agagagttat ataggatcaa taaacaatat aactaaacaa tcagcatgtg   7020
ttgccatgag caaactcctc actgaactca atagtgatga tatcaaaaag ctgagggaca   7080
atgaagagct aaattcaccc aagataagag tgtacaatac tgtcatatca tatattgaaa   7140
gcaacaggaa aaacaataaa caaactatcc atctgttaaa aagattgcca gcagacgtat   7200
tgaagaaaac catcaaaaac acattggata tccataagag cataaccatc aacaacccaa   7260
aagaatcaac tgttagtgat acaaatgacc atgccaaaaa taatgatact acctgacaaa   7320
tatccttgta gtataacttc catactaata acaagtagat gtagagttac tatgtataat   7380
caaaagaaca cactatattt caatcaaaac aacccaaata accatatgta ctcaccgaat   7440
```

caaacattca atgaaatcca ttggacctct caagaattga ttgacacaat tcaaaatttt 7500
ctacaacatc taggtattat tgaggatata tatacaatat atatattagt gtcataacac 7560
tcaattctaa cactcaccac atcgttacat tattaattca aacaattcaa gttgtgggac 7620
aaaatggatc ccattattaa tggaaattct gctaatgttt atctaaccga tagttattta 7680
aaaggtgtta tctctttctc agagtgtaat gctttaggaa gttacatatt caatggtcct 7740
tatctcaaaa atgattatac caacttaatt agtagacaaa atccattaat agaacacatg 7800
aatctaaaga aactaaatat aacacagtcc ttaatatcta agtatcataa aggtgaaata 7860
aaattagaag aacctactta ttttcagtca ttacttatga catacaagag tatgacctcg 7920
tcagaacaga ttgctaccac taatttactt aaaaagataa taagaagagc tatagaaata 7980
agtgatgtca aagtctatgc tatattgaat aaactagggc ttaaagaaaa ggacaagatt 8040
aaatccaaca atggacaaga tgaagacaac tcagttatta cgaccataat caaagatgat 8100
atactttcag ctgttaaaga taatcaatct catcttaaag cagacaaaaa tcactctaca 8160
aaacaaaaag acacaatcaa aacaacactc ttgaagaaat tgatgtgttc aatgcaacat 8220
cctccatcat ggttaataca ttggtttaac ttatacacaa aattaaacaa catattaaca 8280
cagtatcgat caaatgaggt aaaaaaccat gggtttacat tgatagataa tcaaactctt 8340
agtggatttc aatttatttt gaaccaatat ggttgtatag tttatcataa ggaactcaaa 8400
agaattactg tgacaaccta taatcaattc ttgacatgga aagatattag ccttagtaga 8460
ttaaatgttt gtttaattac atggattagt aactgcttga acacattaaa taaaagctta 8520
ggcttaagat gcggattcaa taatgttatc ttgacacaac tattccttta tggagattgt 8580
atactaaagc tatttcacaa tgaggggttc tacataataa aagaggtaga gggatttatt 8640
atgtctctaa ttttaaatat aacagaagaa gatcaattca gaaaacgatt ttataatagt 8700
atgctcaaca acatcacaga tgctgctaat aaagctcaga aaaatctgct atcaagagta 8760
tgtcatacat tattagataa gacagtgtcc gataatataa taaatggcag atggataatt 8820
ctattaagta agttccttaa attaattaag cttgcaggtg acaataacct taacaatctg 8880
agtgaactat atttttgtt cagaatattt ggacacccaa tggtagatga aagacaagcc 8940
atggatgctg ttaaaattaa ttgcaatgag accaaatttt acttgttaag cagtctgagt 9000
atgttaagag gtgcctttat atatagaatt ataaaagggt ttgtaaataa ttacaacaga 9060
tggcctactt taagaaatgc tattgtttta cccttaagat ggttaactta ctataaacta 9120
aacacttatc cttctttgtt ggaacttaca gaaagagatt tgattgtgtt atcaggacta 9180
cgtttctatc gtgagtttcg gttgcctaaa aaagtggatc ttgaaatgat tataaatgat 9240
aaagctatat cacctcctaa aaatttgata tggactagtt tccctagaaa ttacatgcca 9300
tcacacatac aaaactatat agaacatgaa aaattaaaat tttccgagag tgataaatca 9360
agaagagtat tagagtatta tttaagagat aacaaattca atgaatgtga tttatacaac 9420
tgtgtagtta atcaaagtta tctcaacaac cctaatcatg tggtatcatt gacaggcaaa 9480
gaaagagaac tcagtgtagg tagaatgttt gcaatgcaac cgggaatgtt cagacaggtt 9540
caaatattgg cagagaaaat gatagctgaa aacattttac aattctttcc tgaaagtctt 9600
acaagatatg gtgatctaga actacaaaaa atattagaac tgaaagcagg aataagtaac 9660
aaatcaaatc gctacaatga taattacaac aattacatta gtaagtgctc tatcatcaca 9720
gatctcagca aattcaatca agcatttcga tatgaaacgt catgtatttg tagtgatgtg 9780
ctggatgaac tgcatggtgt acaatctcta ttttcctggt tacatttaac tattcctcat 9840

```
gtcacaataa tatgcacata taggcatgca ccccccctata taggagatca tattgtagat   9900
cttaacaatg tagatgaaca aagtggatta tatagatatc acatgggtgg catcgaaggg   9960
tggtgtcaaa aactatggac catagaagct atatcactat tggatctaat atctctcaaa  10020
gggaaattct caattactgc tttaattaat ggtgacaatc aatcaataga tataagcaaa  10080
ccaatcagac tcatggaagg tcaaactcat gctcaagcag attatttgct agcattaaat  10140
agccttaaat tactgtataa agagtatgca ggcataggcc acaaattaaa aggaactgag  10200
acttatatat cacgagatat gcaatttatg agtaaaacaa ttcaacataa cggtgtatat  10260
tacccagcta gtataaagaa agtcctaaga gtgggaccgt ggataaacac tatacttgat  10320
gatttcaaag tgagtctaga atctataggt agtttgacac aagaattaga atatagaggt  10380
gaaagtctat tatgcagttt aatatttaga aatgtatggt tatataatca gattgctcta  10440
caattaaaaa atcatgcatt atgtaacaat aaactatatt tggacatatt aaaggttctg  10500
aaacacttaa aaaccttttt taatcttgat aatattgata cagcattaac attgtatatg  10560
aatttaccca tgttatttgg tggtggtgat cccaacttgt tatatcgaag tttctataga  10620
agaactcctg acttcctcac agaggctata gttcactctg tgttcatact tagttattat  10680
acaaaccatg acttaaaaga taaacttcaa gatctgtcag atgatagatt gaataagttc  10740
ttaacatgca taatcacgtt tgacaaaaac cctaatgctg aattcgtaac attgatgaga  10800
gatcctcaag ctttagggtc tgagagacaa gctaaaatta ctagcgaaat caatagactg  10860
gcagttacag aggttttgag tacagctcca aacaaaatat tctccaaaag tgcacaacat  10920
tatactacta cagagataga tctaaatgat attatgcaaa atatagaacc tacatatcct  10980
catgggctaa gagttgttta tgaaagttta ccccttttata aagcagagaa aatagtaaat  11040
cttatatcag gtacaaaatc tataactaac atactggaaa aaacttctgc catagactta  11100
acagatattg atagagccac tgagatgatg aggaaaaaca taactttgct tataaggata  11160
cttccattgg attgtaacag agataaaaga gagatattga gtatggaaaa cctaagtatt  11220
actgaattaa gcaaatatgt tagggaaaga tcttggtctt tatccaatat agttggtgtt  11280
acatcaccca gtatcatgta tacaatggac atcaaatata ctacaagcac tatatctagt  11340
ggcataatta tagagaaata taatgttaac agtttaacac gtggtgagag aggacccact  11400
aaaccatggg ttggttcatc tacacaagag aaaaaaacaa tgccagttta taatagacaa  11460
gtcttaacca aaaaacagag agatcaaata gatctattag caaaattgga ttgggtgtat  11520
gcatctatag ataacaagga tgaattcatg gaagaactct caataggaac ccttgggtta  11580
acaaaagaaa aggccaagaa attatttcca caatatttaa gtgtcaatta tttgcatcgc  11640
cttacagtca gtagtagacc atgtgaattc cctgcatcaa taccagctta tagaacaaca  11700
aattatcact ttgacactag ccctattaat cgcatattaa cagaaaagta tggtgatgaa  11760
gatattgaca tagtattcca aaactgtata agctttggcc ttagtttaat gtcagtagta  11820
gaacaattta ctaatgtatg tcctaacaga attattctca tacctaagct taatgagata  11880
catttgatga aacctcccat attcacaggt gatgttgata ttcacaagtt aaaacaagtg  11940
atacaaaaac agcatatgtt tttaccagac aaaataagtt tgactcaata tgtggaatta  12000
ttcttaagta ataaaacact caaatctgga tctcatgtta attctaattt aatattggca  12060
cataaaatat ctgactattt tcataatact tacattttaa gtactaattt agctggacat  12120
tggattctga ttatacaact tatgaaagat tctaaaggta tttttgaaaa agattgggga  12180
```

gagggatata taactgatca tatgtttatt aatttgaaag ttttcttcaa tgcttataag 12240
acctatctct tgtgttttca taaaggttat ggcaaagcaa agctggagtg tgatatgaac 12300
acttcagatc ttctatgtgt attggaatta atagacagta gttattggaa gtctatgtct 12360
aaggtatttt tagaacaaaa agttatcaaa tacattctta gccaagatgc aagtttacat 12420
agagtaaaag gatgtcatag cttcaaatta tggtttctta aacgtcttaa tgtagcagaa 12480
ttcacagttt gcccttgggt tgttaacata gattatcatc caacacatat gaaagcaata 12540
ttaacttata tagatcttgt tagaatggga ttgataaata tagatagaat acacattaaa 12600
aataaacaca aattcaatga tgaattttat acttctaatc tcttctacat taattataac 12660
ttctcagata atactcatct attaactaaa catataagga ttgctaattc tgaattagaa 12720
aataattaca acaaattata tcatcctaca ccagaaaccc tagagaatat actagccaat 12780
ccgattaaaa gtaatgacaa aaagacactg aatgactatt gtataggtaa aaatgttgac 12840
tcaataatgt taccattgtt atctaataag aagcttatta aatcgtctgc aatgattaga 12900
accaattaca gcaaacaaga tttgtataat ttattcccta tggttgtgat tgatagaatt 12960
atagatcatt caggcaatac agccaaatcc aaccaacttt acactactac ttcccaccaa 13020
atatccttag tgcacaatag cacatcactt tactgcatgc ttccttggca tcatattaat 13080
agattcaatt ttgtatttag ttctacaggt tgtaaaatta gtatagagta tattttaaaa 13140
gatcttaaaa ttaaagatcc caattgtata gcattcatag gtgaaggagc agggaattta 13200
ttattgcgta cagtagtgga acttcatcct gacataagat atatttacag aagtctgaaa 13260
gattgcaatg atcatagttt acctattgag tttttaaggc tgtacaatgg acatatcaac 13320
attgattatg gtgaaaattt gaccattcct gctacagatg caaccaacaa cattcattgg 13380
tcttatttac atataaagtt tgctgaacct atcagtcttt ttgtctgtga tgccgaattg 13440
tctgtaacag tcaactggag taaaattata atagaatgga gcaagcatgt aagaaagtgc 13500
aagtactgtt cctcagttaa taaatgtatg ttaatagtaa aatatcatgc tcaagatgat 13560
attgatttca aattagacaa tataactata ttaaaaactt atgtatgctt aggcagtaag 13620
ttaaagggat cggaggttta cttagtcctt acaataggtc ctgcgaatat attcccagta 13680
tttaatgtag tacaaaatgc taaattgata ctatcaagaa ccaaaaattt catcatgcct 13740
aagaaagctg ataaagagtc tattgatgca aatattaaaa gtttgatacc ctttctttgt 13800
taccctataa caaaaaaagg aattaatact gcattgtcaa aactaaagag tgttgttagt 13860
ggagatatac tatcatattc tatagctgga cgtaatgaag ttttcagcaa taaacttata 13920
aatcataagc atatgaacat cttaaaatgg ttcaatcatg ttttaaattt cagatcaaca 13980
gaactaaact ataaccattt atatatggta gaatctacat atccttacct aagtgaattg 14040
ttaaacagct tgacaaccaa tgaacttaaa aaactgatta aaatcacagg tagtctgtta 14100
tacaactttc ataatgaata atgaataaag atcttataat aaaaattccc atagctatac 14160
actaacactg tattcaatta tagttattaa aaattaaaaa tcatataatt ttttaaataa 14220
cttttagtga actaatccta aagttatcat tttaatcttg gaggaataaa tttaaaccct 14280
aatctaattg gtttatatgt gtattaacta aattacgaga tattagtttt tgacactttt 14340
tttctcgt 14348

<210> SEQ ID NO 7
<211> LENGTH: 14348
<212> TYPE: DNA
<213> ORGANISM: Artificial Sequence
<220> FEATURE:
<223> OTHER INFORMATION: Recombinant RSV sequence

<400> SEQUENCE: 7

```
acgggaaaaa atgcgtacaa caaacttgca taaaccaaaa aaatggggca aataagaatt     60
tgataagtac cacttaaatt taactcctcg agttcaccat ggagctcctc attctcaaag    120
ccaacgcaat cacaacaatt ctgaccgccg tcacattctg ctttgcctcc ggacagaaca    180
tcacagaaga gttttaccaa agtacatgca gcgccgtgag caaaggctac ctgtccgccc    240
tgaggacagg gtggtacaca tccgtgatta ccattgagct gagtaatatc aagaagaaca    300
agtgcaacgg cactgatgcc aaagtgaagc tcattaaaca ggaactcgat aagtacaaga    360
acgccgtgac tgagctccag ctgctgatgc agtcaactca ggctacaaac aacagagccc    420
ggagggagct gcccaggttt atgaactaca ccctgaacaa cgccaagaag accaacgtga    480
cattgagcaa gaagaggaag cggcggttcc tggggttctt gctaggtgtg ggcagcgcta    540
ttgcttctgg cgtcgccgtc tccaaggtgc tgcacctgga aggcgaagtg aataagatta    600
agtccgcact gcttagcacc aataaggccg tcgtgagcct gtctaacgga gtgagtgtgc    660
tcacaagcaa ggtcctcgat ctcaagaact acattgataa gcagctcctg cccatcgtca    720
acaagcagtc atgctccatt agtaacatcg agaccgtgat tgaatttcaa cagaagaaca    780
accggctcct ggagattact agggagttca gcgtgaacgc cggggtgaca acaccagtct    840
ccacctatat gcttaccaac agcgagttgc tctccctgat taacgatatg ccaattacaa    900
acgaccagaa gaagctgatg tcaaacaacg tccagattgt ccggcagcag tcctactcaa    960
tcatgtccat tattaaggag gaggtcctgg cttacgtcgt gcagctgcct ctttatgggg   1020
tgatcgacac cccttgctgg aagctccata catcccctct gtgcactacc aacaccaagg   1080
aggggtccaa catctgcttg acaagaaccg atcgcggctg gtactgcgat aacgcaggca   1140
gtgtctcctt ctttccccag gccgagactt gtaaggtgca gtctaaccgc gtcttctgcg   1200
acaccatgaa cagcctgacc cttcccagcg aggtgaacct ttgtaacgtg gacatcttca   1260
acccaaagta tgattgtaag attatgacta gcaaaaccga tgtcagcagc agcgtgatca   1320
ctagcctggg cgctatcgtc agctgctacg gaaagactaa gtgcaccgcc agcaacaaga   1380
acagaggcat catcaagacc ttcagtaatg gatgtgacta cgtgtccaac aaaggggtgg   1440
atacagtgag cgtgggaaac acattgtact acgtgaacaa acaggagggg aagtccttgt   1500
acgtgaaggg tgagcccatt atcaacttct acgaccctct cgtgttccca tcagacgagt   1560
ttgacgcctc catctcccag gtgaacgaga agatcaatca gtcactggcc tttattagga   1620
aatccgacga gctgctgcac aacgtcaacg ccggaaagtc taccactaac atcatgatca   1680
ccacaatcat cattgtgatc atcgtcatcc tcctgagctt gatcgctgtc gggttgctgt   1740
tgtactgcaa ggcccggtcc acacccgtga ctctgagcaa ggaccagctg tctggcatta   1800
acaacatcgc ctttagcaac taaagtagtt aattaaaaat ggggcaaata caaccatgtc   1860
caaaaacaag gaccaacgca ccgctaagac attagaaagg acctgggaca ctctcaatca   1920
tttattattc atatcatcgt gcttatataa gttaaatctt aaatctgtag cacaaatcac   1980
attatccatt ctggcaatga taatctcaac ttcacttata attgcagcca tcatattcat   2040
agcctcggca aaccacaaag tcacaccaac aactgcaatc atacaagatg caacaagcca   2100
gatcaagaac acaaccccaa catacctcac ccagaatcct cagcttggaa tcagtccctc   2160
taatccgtct gaaattacat cacaaatcac caccatacta gcttcaacaa caccaggagt   2220
```

```
caagtcaacc ctgcaatcca caacagtcaa gaccaaaaac acaacaacaa ctcaaacaca   2280
acccagcaag cccaccacaa aacaacgcca aaacaaacca ccaagcaaac ccaataatga   2340
ttttcacttt gaagtgttca actttgtacc ctgcagcata tgcagcaaca atccaacctg   2400
ctgggctatc tgcaaaagaa taccaaacaa aaaaccagga aagaaaacca ctaccaagcc   2460
cacaaaaaaa ccaaccctca agacaaccaa aaaagatccc aaacctcaaa ccactaaatc   2520
aaaggaagta cccaccacca agcccacaga agagccaacc atcaacacca ccaaaacaaa   2580
catcataact acactactca cctccaacac cacaggaaat ccagaactca caagtcaaat   2640
ggaaaccttc cactcaactt cctccgaagg caatccaagc ccttctcaag tctctacaac   2700
atccgagtac ccatcacaac cttcatctcc acccaacaca ccacgccagt agttaataaa   2760
aaatggggca aatactcgag ttagagatgg acacaaccca caatgataat acaccacaaa   2820
gactgatgat cacagacatg agaccgttgt cacttgagac cataataaca tcactaacca   2880
gagacatcat aacacacaaa tttatatact tgataaatca tgaatgcata gtgagaaaac   2940
ttgatgaaag acaggccaca tttacattcc tggtcaacta tgaaatgaaa ctattacaca   3000
aagtaggaag cactaaatat aaaaaatata ctgaatacaa cacaaaatat ggcactttcc   3060
ctatgccaat attcatcaat catgatgggt tcttagaatg cattggcatt aagcctacaa   3120
agcatactcc cataatatac aagtatgatc tcaatccata aatttcaaca caatattcac   3180
acaatctaaa acaacaactc tatgcataac tatactccat agtccagatg gagcctgaaa   3240
attatagtaa tttaaaactt aaggagagat ataagataga agatggggca aatacaacca   3300
tggctcttag caaagtcaag ttgaatgata cactcaacaa agatcaactt ctgtcatcca   3360
gcaaatacac catccaacgg agcacaggag atagtattga tactcctaat tatgatgtgc   3420
agaaacacat caataagtta tgtggcatgt tattaatcac agaagatgct aatcataaat   3480
tcactgggtt aataggtatg ttatatgcga tgtctaggtt aggaagagaa gacaccataa   3540
aaatactcag agatgcggga tatcatgtaa aagcaaatgg agtagatgta acaacacatc   3600
gtcaagacat taatggaaaa gaaatgaaat ttgaagtgtt aacattggca agcttaacaa   3660
ctgaaattca aatcaacatt gagatagaat ctagaaaatc ctacaaaaaa atgctaaaag   3720
aaatgggaga ggtagctcca gaatacaggc atgactctcc tgattgtggg atgataatat   3780
tatgtatagc agcattagta ataactaaat tagcagcagg ggacagatct ggtcttacag   3840
ccgtgattag gagagctaat aatgtcctaa aaaatgaaat gaaacgttac aaaggcttac   3900
tacccaagga catagccaac agcttctatg aagtgtttga aaaacatccc cactttatag   3960
atgtttttgt tcattttggt atagcacaat cttctaccag aggtggcagt agagttgaag   4020
ggatttttgc aggattgttt atgaatgcct atggtgcagg gcaagtgatg ttacggtggg   4080
gagtcttagc aaaatcggtt aaaaatatta tgttaggaca tgctagtgtg caagcagaaa   4140
tggaacaagt tgttgaggtt tatgaatatg cccaaaaatt gggtggtgaa gcaggattct   4200
accatatatt gaacaaccca aaagcatcat tattatcttt gactcaattt cctcacttct   4260
ccagtgtagt attaggcaat gctgctggcc taggcataat gggagagtac agaggtacac   4320
cgaggaatca agatctatat gatgcagcaa aggcatatgc tgaacaactc aaagaaaatg   4380
gtgtgattaa ctacagtgta ctagacttga cagcagaaga actagaggct atcaaacatc   4440
agcttaatcc aaaagataat gatgtagagc tttgagttaa taaaaaatgg ggcaaataaa   4500
tcatcatgga aaagtttgct cctgaattcc atggagaaga tgcaaacaac agggctacta   4560
aattcctaga atcaataaag ggcaaattca catcacccaa agatcccaag aaaaaagata   4620
```

```
gtatcatatc tgtcaactca atagatatag aagtaaccaa agaaagccct ataacatcaa   4680
attcaactat tatcaaccca acaaatgaga cagatgatac tgcagggaac aagcccaatt   4740
atcaaagaaa acctctagta agtttcaaag aagaccctac accaagtgat aatccctttt   4800
ctaaactata caaagaaacc atagaaacat ttgataacaa tgaagaagaa tccagctatt   4860
catacgaaga aataaatgat cagacaaacg ataatataac agcaagatta gataggattg   4920
atgaaaaatt aagtgaaata ctaggaatgc ttcacacatt agtagtggca agtgcaggac   4980
ctacatctgc tcgggatggt ataagagatg ccatggttgg tttaagagaa gaaatgatag   5040
aaaaaatcag aactgaagca ttaatgacca atgacagatt agaagctatg gcaagactca   5100
ggaatgagga aagtgaaaag atggcaaaag acacatcaga tgaagtgtct ctcaatccaa   5160
catcagagaa attgaacaac ctattggaag ggaatgatag tgacaatgat ctatcacttg   5220
aagatttctg attagttacc aatcttcaca tcaacacaca ataccaacag aagaccaaca   5280
aactaaccaa cccaatcatc caaccaaaca tccatccgcc aatcagccaa acagccaaca   5340
aaacaaccag ccaatccaaa actaaccacc cggaaaaaat ctataatata gttacaaaaa   5400
aaggaaaggg tggggcaaat atggaaacat acgtgaacaa gcttcacgaa ggctccacat   5460
acacagctgc tgttcaatac aatgtcttag aaaaagacga tgaccctgca tcacttacaa   5520
tatgggtgcc catgttccaa tcatctatgc cagcagattt acttataaaa gaactagcta   5580
atgtcaacat actagtgaaa caaatatcca cacccaaggg accttcacta agagtcatga   5640
taaactcaag aagtgcagtg ctagcacaaa tgcccagcaa atttaccata tgcgctaatg   5700
tgtccttgga tgaaagaagc aaactagcat atgatgtaac cacaccctgt gaaatcaagg   5760
catgtagtct aacatgccta aaatcaaaaa atatgttgac tacagttaaa gatctcacta   5820
tgaagacact caaccctaca catgatatta ttgctttatg tgaatttgaa aacatagtaa   5880
catcaaaaaa agtcataata ccaacatacc taagatccat cagtgtcaga aataaagatc   5940
tgaacacact tgaaaatata acaaccactg aattcaaaaa tgctatcaca aatgcaaaaa   6000
tcatccctta ctcaggatta ctattagtca tcacagtgac tgacaacaaa ggagcattca   6060
aatacataaa gccacaaagt caattcatag tagatcttgg agcttaccta gaaaaagaaa   6120
gtatatatta tgttaccaca aattggaagc acacagctac acgatttgca atcaaaccca   6180
tggaagatta accttttcc tctacatcag tgtgttaatt catacaaact ttctacctac   6240
attcttcact tcaccatcac aatcacaaac actctgtggt tcaaccaatc aaacaaaact   6300
tatctgaagt cccagatcat cccaagtcat tgtttatcag atctagtact caaataagtt   6360
aataaaaaat atacacatgg ggcaaataat cattggagga aatccaacta atcacaatat   6420
ctgttaacat agacaagtcc acacaccata cagaatcaac caatggaaaa tacatccata   6480
acaatagaat tctcaagcaa attctggcct tactttacac taatacacat gatcacaaca   6540
ataatctctt tgctaatcat aatctccatc atgattgcaa tactaaacaa actttgtgaa   6600
tataacgtat tccataacaa aacctttgag ttaccaagag ctcgagttaa tacttgataa   6660
agtagttaat taaaaacaca attgcatgcc agattaactt accatctgta aaaatgaaaa   6720
ctggggcaaa tatgtcacga aggaatcctt gcaaatttga aattcgaggt cattgcttaa   6780
atggtaagag gtgtcatttt agtcataatt attttgaatg gccacccccat gcactgcttg   6840
taagacaaaa ctttatgtta aacagaatac ttaagtctat ggataaaagt atagatacct   6900
tatcagaaat aagtggagct gcagagttgg acagaacaga agagtatgct cttggtgtag   6960
```

-continued

```
ttggagtgct agagagttat ataggatcaa taaacaatat aactaaacaa tcagcatgtg   7020
ttgccatgag caaactcctc actgaactca atagtgatga tatcaaaaag ctgagggaca   7080
atgaagagct aaattcaccc aagataagag tgtacaatac tgtcatatca tatattgaaa   7140
gcaacaggaa aaacaataaa caaactatcc atctgttaaa aagattgcca gcagacgtat   7200
tgaagaaaac catcaaaaac acattggata tccataagag cataaccatc aacaacccaa   7260
aagaatcaac tgttagtgat acaaatgacc atgccaaaaa taatgatact acctgacaaa   7320
tatccttgta gtataacttc catactaata acaagtagat gtagagttac tatgtataat   7380
caaaagaaca cactatattt caatcaaaac aacccaaata accatatgta ctcaccgaat   7440
caaacattca atgaaatcca ttggacctct caagaattga ttgacacaat tcaaaatttt   7500
ctacaacatc taggtattat tgaggatata tatacaatat atatattagt gtcataacac   7560
tcaattctaa cactcaccac atcgttacat tattaattca aacaattcaa gttgtgggac   7620
aaaatggatc ccattattaa tggaaattct gctaatgttt atctaaccga tagttattta   7680
aaaggtgtta tctctttctc agagtgtaat gctttaggaa gttacatatt caatggtcct   7740
tatctcaaaa atgattatac caacttaatt agtagacaaa atccattaat agaacacatg   7800
aatctaaaga aactaaatat aacacagtcc ttaatatcta agtatcataa aggtgaaata   7860
aaattagaag aacctactta ttttcagtca ttacttatga catacaagag tatgacctcg   7920
tcagaacaga ttgctaccac taatttactt aaaaagataa taagaagagc tatagaaata   7980
agtgatgtca aagtctatgc tatattgaat aaactagggc ttaaagaaaa ggacaagatt   8040
aaatccaaca atggacaaga tgaagacaac tcagttatta cgaccataat caaagatgat   8100
atactttcag ctgttaaaga taatcaatct catcttaaag cagacaaaaa tcactctaca   8160
aaacaaaaag acacaatcaa aacaacactc ttgaagaaat tgatgtgttc aatgcaacat   8220
cctccatcat ggttaataca ttggtttaac ttatacacaa aattaaacaa catattaaca   8280
cagtatcgat caaatgaggt aaaaaaccat gggtttacat tgatagataa tcaaactctt   8340
agtggatttc aatttatttt gaaccaatat ggttgtatag tttatcataa ggaactcaaa   8400
agaattactg tgacaaccta taatcaattc ttgacatgga aagatattag ccttagtaga   8460
ttaaatgttt gtttaattac atggattagt aactgcttga acacattaaa taaaagctta   8520
ggcttaagat gcggattcaa taatgttatc ttgacacaac tattccttta tggagattgt   8580
atactaaagc tatttcacaa tgaggggttc tacataataa aagaggtaga gggatttatt   8640
atgtctctaa ttttaaatat aacagaagaa gatcaattca gaaaacgatt ttataatagt   8700
atgctcaaca acatcacaga tgctgctaat aaagctcaga aaaatctgct atcaagagta   8760
tgtcatacat tattagataa gacagtgtcc gataaatataa taaatggcag atggataatt   8820
ctattaagta agttccttaa attaattaag cttgcaggtg acaataacct taacaatctg   8880
agtgaactat atttttgtt cagaatattt ggacacccaa tggtagatga aagacaagcc   8940
atggatgctg ttaaaattaa ttgcaatgag accaaatttt acttgttaag cagtctgagt   9000
atgttaagag gtgcctttat atatagaatt ataaaagggt ttgtaaataa ttacaacaga   9060
tggcctactt taagaaatgc tattgtttta cccttaagat ggttaactta ctataaacta   9120
aacacttatc cttctttgtt ggaacttaca gaaagagatt tgattgtgtt atcaggacta   9180
cgtttctatc gtgagtttcg gttgcctaaa aaagtggatc ttgaaatgat tataaatgat   9240
aaagctatat cacctcctaa aaatttgata tggactagtt tccctagaaa ttacatgcca   9300
tcacacatac aaaactatat agaacatgaa aaattaaaat tttccgagag tgataaatca   9360
```

agaagagtat tagagtatta tttaagagat aacaaattca atgaatgtga tttatacaac 9420
tgtgtagtta atcaaagtta tctcaacaac cctaatcatg tggtatcatt gacaggcaaa 9480
gaaagagaac tcagtgtagg tagaatgttt gcaatgcaac cgggaatgtt cagacaggtt 9540
caaatattgg cagagaaaat gatagctgaa aacattttac aattctttcc tgaaagtctt 9600
acaagatatg gtgatctaga actacaaaaa atattagaac tgaaagcagg aataagtaac 9660
aaatcaaatc gctacaatga taattacaac aattacatta gtaagtgctc tatcatcaca 9720
gatctcagca aattcaatca agcatttcga tatgaaacgt catgtatttg tagtgatgtg 9780
ctggatgaac tgcatggtgt acaatctcta ttttcctggt tacatttaac tattcctcat 9840
gtcacaataa tatgcacata taggcatgca ccccccctata taggagatca tattgtagat 9900
cttaacaatg tagatgaaca aagtggatta tatagatatc acatgggtgg catcgaaggg 9960
tggtgtcaaa aactatggac catagaagct atatcactat tggatctaat atctctcaaa 10020
gggaaattct caattactgc tttaattaat ggtgacaatc aatcaataga tataagcaaa 10080
ccaatcagac tcatggaagg tcaaactcat gctcaagcag attatttgct agcattaaat 10140
agccttaaat tactgtataa agagtatgca ggcataggcc acaaattaaa aggaactgag 10200
acttatatat cacgagatat gcaatttatg agtaaaacaa ttcaacataa cggtgtatat 10260
tacccagcta gtataaagaa agtcctaaga gtgggaccgt ggataaacac tatacttgat 10320
gatttcaaag tgagtctaga atctataggt agtttgacac aagaattaga atatagaggt 10380
gaaagtctat tatgcagttt aatatttaga aatgtatggt tatataatca gattgctcta 10440
caattaaaaa atcatgcatt atgtaacaat aaactatatt tggacatatt aaaggttctg 10500
aaacacttaa aaaccttttt taatcttgat aatattgata cagcattaac attgtatatg 10560
aatttaccca tgttatttgg tggtggtgat cccaacttgt tatatcgaag tttctataga 10620
agaactcctg acttcctcac agaggctata gttcactctg tgttcatact tagttattat 10680
acaaaccatg acttaaaaga taaacttcaa gatctgtcag atgatagatt gaataagttc 10740
ttaacatgca taatcacgtt tgacaaaaac cctaatgctg aattcgtaac attgatgaga 10800
gatcctcaag ctttagggtc tgagagacaa gctaaaatta ctagcgaaat caatagactg 10860
gcagttacag aggttttgag tacagctcca aacaaaaatat tctccaaaag tgcacaacat 10920
tatactacta cagagataga tctaaatgat attatgcaaa atatagaacc tacatatcct 10980
catgggctaa gagttgttta tgaaagttta cccttttata aagcagagaa aatagtaaat 11040
cttatatcag gtacaaaatc tataactaac atactggaaa aaacttctgc catagactta 11100
acagatattg atagagccac tgagatgatg aggaaaaaca taactttgct tataaggata 11160
cttccattgg attgtaacag agataaaaga gagatattga gtatggaaaa cctaagtatt 11220
actgaattaa gcaaatatgt tagggaaaga tcttggtctt tatccaatat agttggtgtt 11280
acatcaccca gtatcatgta tacaatggac atcaaatata ctacaagcac tatatctagt 11340
ggcataatta tagagaaata taatgttaac agtttaacac gtggtgagag aggacccact 11400
aaaccatggg ttggttcatc tacacaagag aaaaaaacaa tgccagttta taatagacaa 11460
gtcttaacca aaaaacagag agatcaaata gatctattag caaaattgga ttgggtgtat 11520
gcatctatag ataacaagga tgaattcatg gaagaactct caataggaac ccttgggtta 11580
acaaaagaaa aggccaagaa attatttcca caatatttaa gtgtcaatta tttgcatcgc 11640
cttacagtca gtagtagacc atgtgaattc cctgcatcaa taccagctta tagaacaaca 11700

-continued aattatcact ttgacactag ccctattaat cgcatattaa cagaaaagta tggtgatgaa 11760
gatattgaca tagtattcca aaactgtata agctttggcc ttagtttaat gtcagtagta 11820
gaacaattta ctaatgtatg tcctaacaga attattctca tacctaagct taatgagata 11880
catttgatga aacctcccat attcacaggt gatgttgata ttcacaagtt aaaacaagtg 11940
atacaaaaac agcatatgtt tttaccagac aaaataagtt tgactcaata tgtggaatta 12000
ttcttaagta ataaaacact caaatctgga tctcatgtta attctaattt aatattggca 12060
cataaaatat ctgactattt tcataatact tacattttaa gtactaattt agctggacat 12120
tggattctga ttatacaact tatgaaagat tctaaaggta tttttgaaaa agattgggga 12180
gagggatata taactgatca tatgtttatt aatttgaaag ttttcttcaa tgcttataag 12240
acctatctct tgtgttttca taaaggttat ggcaaagcaa agctggagtg tgatatgaac 12300
acttcagatc ttctatgtgt attggaatta atagacagta gttattggaa gtctatgtct 12360
aaggtatttt tagaacaaaa agttatcaaa tacattctta gccaagatgc aagtttacat 12420
agagtaaaag gatgtcatag cttcaaatta tggtttctta aacgtcttaa tgtagcagaa 12480
ttcacagttt gcccttgggt tgttaacata gattatcatc caacacatat gaaagcaata 12540
ttaacttata tagatcttgt tagaatggga ttgataaata tagatagaat acacattaaa 12600
aataaacaca aattcaatga tgaattttat acttctaatc tcttctacat taattataac 12660
ttctcagata atactcatct attaactaaa catataagga ttgctaattc tgaattagaa 12720
aataattaca acaaattata tcatcctaca ccagaaaccc tagagaatat actagccaat 12780
ccgattaaaa gtaatgacaa aaagacactg aatgactatt gtataggtaa aaatgttgac 12840
tcaataatgt taccattgtt atctaataag aagcttatta aatcgtctgc aatgattaga 12900
accaattaca gcaaacaaga tttgtataat ttattcccta tggttgtgat tgatagaatt 12960
atagatcatt caggcaatac agccaaatcc aaccaacttt acactactac ttcccaccaa 13020
atatccttag tgcacaatag cacatcactt tactgcatgc ttccttggca tcatattaat 13080
agattcaatt ttgtatttag ttctacaggt tgtaaaatta gtatagagta tattttaaaa 13140
gatcttaaaa ttaaagatcc caattgtata gcattcatag gtgaaggagc agggaattta 13200
ttattgcgta cagtagtgga acttcatcct gacataagat atatttacag aagtctgaaa 13260
gattgcaatg atcatagttt acctattgag tttttaaggc tgtacaatgg acatatcaac 13320
attgattatg gtgaaaattt gaccattcct gctacagatg caaccaacaa cattcattgg 13380
tcttatttac atataaagtt tgctgaacct atcagtcttt ttgtctgtga tgccgaattg 13440
tctgtaacag tcaactggag taaaattata atagaatgga gcaagcatgt aagaaagtgc 13500
aagtactgtt cctcagttaa taaatgtatg ttaatagtaa aatatcatgc tcaagatgat 13560
attgatttca aattagacaa tataactata ttaaaaactt atgtatgctt aggcagtaag 13620
ttaaagggat cggaggttta cttagtcctt acaataggtc ctgcgaatat attcccagta 13680
tttaatgtag tacaaaatgc taaattgata ctatcaagaa ccaaaaattt catcatgcct 13740
aagaaagctg ataaagagtc tattgatgca aatattaaaa gtttgatacc ctttctttgt 13800
taccctataa caaaaaaagg aattaatact gcattgtcaa aactaaagag tgttgttagt 13860
ggagatatac tatcatattc tatagctgga cgtaatgaag ttttcagcaa taaacttata 13920
aatcataagc atatgaacat cttaaaatgg ttcaatcatg ttttaaattt cagatcaaca 13980
gaactaaact ataaccattt atatatggta gaatctacat atccttacct aagtgaattg 14040
ttaaacagct tgacaaccaa tgaacttaaa aaactgatta aaatcacagg tagtctgtta 14100

```
tacaactttc ataatgaata atgaataaag atcttataat aaaaattccc atagctatac  14160

actaacactg tattcaatta tagttattaa aaattaaaaa tcatataatt ttttaaataa  14220

cttttagtga actaatccta aagttatcat tttaatcttg gaggaataaa tttaaaccct  14280

aatctaattg gtttatatgt gtattaacta aattacgaga tattagtttt tgacactttt  14340

tttctcgt                                                           14348
```

<210> SEQ ID NO 8
<211> LENGTH: 14579
<212> TYPE: DNA
<213> ORGANISM: Artificial Sequence
<220> FEATURE:
<223> OTHER INFORMATION: Recombinant RSV sequence

<400> SEQUENCE: 8

```
acgggaaaaa atgcgtacaa caaacttgca taaaccaaaa aaatggggca aataagaatt     60

tgataagtac cacttaaatt taactccctt ggttagagat ggacacaacc cacaatgata    120

atacaccaca aagactgatg atcacagaca tgagaccgtt gtcacttgag accataataa    180

catcactaac cagagacatc ataacacaca aatttatata cttgataaat catgaatgca    240

tagtgagaaa acttgatgaa agacaggcca catttacatt cctggtcaac tatgaaatga    300

aactattaca caaagtagga agcactaaat ataaaaaata tactgaatac aacacaaaat    360

atggcacttt ccctatgcca atattcatca atcatgatgg gttcttagaa tgcattggca    420

ttaagcctac aaagcatact cccataatat acaagtatga tctcaatcca taaatttcaa    480

cacaatattc acacaatcta aaacaacaac tctatgcata actatactcc atagtccaga    540

tggagcctga aaattatagt aatttaaaac ttaaggagag atataagata gaagatgggg    600

caaatacaac catggctctt agcaaagtca agttgaatga tacactcaac aaagatcaac    660

ttctgtcatc cagcaaatac accatccaac ggagcacagg agatagtatt gatactccta    720

attatgatgt gcagaaacac atcaataagt tatgtggcat gttattaatc acagaagatg    780

ctaatcataa attcactggg ttaataggta tgttatatgc gatgtctagg ttaggaagag    840

aagacaccat aaaaatactc agagatgcgg gatatcatgt aaaagcaaat ggagtagatg    900

taacaacaca tcgtcaagac attaatggaa aagaaatgaa atttgaagtg ttaacattgg    960

caagcttaac aactgaaatt caaatcaaca ttgagataga atctagaaaa tcctacaaaa   1020

aaatgctaaa agaaatggga gaggtagctc cagaatacag gcatgactct cctgattgtg   1080

ggatgataat attatgtata gcagcattag taataactaa attagcagca ggggacagat   1140

ctggtcttac agccgtgatt aggagagcta ataatgtcct aaaaaatgaa atgaaacgtt   1200

acaaaggctt actacccaag gacatagcca acagcttcta tgaagtgttt gaaaaacatc   1260

cccactttat agatgttttt gttcattttg gtatagcaca atcttctacc agaggtggca   1320

gtagagttga agggattttt gcaggattgt ttatgaatgc ctatggtgca gggcaagtga   1380

tgttacggtg gggagtctta gcaaaatcag ttaaaaatat tatgttagga catgctagtg   1440

tgcaagcaga aatggaacaa gttgttgagg tttatgaata tgcccaaaaa ttgggtggtg   1500

aagcaggatt ctaccatata ttgaacaacc caaaagcatc attattatct ttgactcaat   1560

ttcctcactt ctccagtgta gtattaggca atgctgctgg cctaggcata atgggagagt   1620

acagaggtac accgaggaat caagatctat atgatgcagc aaaggcatat gctgaacaac   1680

tcaaagaaaa tggtgtgatt aactacagtg tactagactt gacagcagaa gaactagagg   1740
```

```
ctatcaaaca tcagcttaat ccaaaagata atgatgtaga gctttgagtt aataaaaaat   1800
ggggcaaata aatcatcatg gaaaagtttg ctcctgaatt ccatggagaa gatgcaaaca   1860
acagggctac taaattccta gaatcaataa agggcaaatt cacatcaccc aaagatccca   1920
agaaaaaaga tagtatcata tctgtcaact caatagatat agaagtaacc aaagaaagcc   1980
ctataacatc aaattcaact attatcaacc caacaaatga gacagatgat actgcaggga   2040
acaagcccaa ttatcaaaga aaacctctag taagtttcaa agaagaccct acaccaagtg   2100
ataatccctt ttctaaacta tacaaagaaa ccatagaaac atttgataac aatgaagaag   2160
aatccagcta ttcatacgaa gaaataaatg atcagacaaa cgataatata acagcaagat   2220
tagataggat tgatgaaaaa ttaagtgaaa tactaggaat gcttcacaca ttagtagtgg   2280
caagtgcagg acctacatct gctcgggatg gtataagaga tgccatggtt ggtttaagag   2340
aagaaatgat agaaaaaatc agaactgaag cattaatgac caatgacaga ttagaagcta   2400
tggcaagact caggaatgag gaaagtgaaa agatggcaaa agacacatca gatgaagtgt   2460
ctctcaatcc aacatcagag aaattgaaca acctattgga agggaatgat agtgacaatg   2520
atctatcact tgaagatttc tgattagtta ccaatcttca catcaacaca caataccaac   2580
agaagaccaa caaactaacc aacccaatca tccaaccaaa catccatccg ccaatcagcc   2640
aaacagccaa caaaacaacc agccaatcca aaactaacca cccggaaaaa atctataata   2700
tagttacaaa aaaaggaaag ggtggggcaa atatggaaac atacgtgaac aagcttcacg   2760
aaggctccac atacacagct gctgttcaat acaatgtctt agaaaaagac gatgaccctg   2820
catcacttac aatatgggtg cccatgttcc aatcatctat gccagcagat ttacttataa   2880
aagaactagc taatgtcaac atactagtga aacaaatatc cacacccaag ggaccttcac   2940
taagagtcat gataaactca agaagtgcag tgctagcaca aatgcccagc aaatttacca   3000
tatgcgctaa tgtgtccttg gatgaaagaa gcaaactagc atatgatgta accacaccct   3060
gtgaaatcaa ggcatgtagt ctaacatgcc taaaatcaaa aaatatgttg actacagtta   3120
aagatctcac tatgaagaca ctcaacccta cacatgatat tattgcttta tgtgaatttg   3180
aaaacatagt aacatcaaaa aaagtcataa taccaacata cctaagatcc atcagtgtca   3240
gaaataaaga tctgaacaca cttgaaaata taacaaccac tgaattcaaa aatgctatca   3300
caaatgcaaa aatcatccct tactcaggat tactattagt catcacagtg actgacaaca   3360
aaggagcatt caaatacata aagccacaaa gtcaattcat agtagatctt ggagcttacc   3420
tagaaaaaga aagtatatat tatgttacca caaattggaa gcacacagct acacgatttg   3480
caatcaaacc catggaagat taaccttttt cctctacatc agtgtgttaa ttcatacaaa   3540
ctttctacct acattcttca cttcaccatc acaatcacaa acactctgtg gttcaaccaa   3600
tcaaacaaaa cttatctgaa gtcccagatc atcccaagtc attgtttatc agatctagta   3660
ctcaaataag ttaataaaaa atatacacat ggggcaaata atcattggag gaaatccaac   3720
taatcacaat atctgttaac atagacaagt ccacacacca tacagaatca accaatggaa   3780
aatacatcca taacaataga attctcaagc aaattctggc cttactttac actaatacac   3840
atgatcacaa caataatctc tttgctaatc ataatctcca tcatgattgc aatactaaac   3900
aaactttgtg aatataacgt attccataac aaaacctttg agttaccaag agctcgagtt   3960
aatacttgat aaagtagtta attaaaaata gtcataacaa tgaactagga tatcaagact   4020
aacaataaca ttggggcaaa tgcaaacatg tccaaaaaca aggaccaacg caccgctaag   4080
acattagaaa ggacctggga cactctcaat catttattat tcatatcatc gtgcttatat   4140
```

aagttaaatc ttaaatctgt agcacaaatc acattatcca ttctggcaat gataatctca 4200
acttcactta taattgcagc catcatattc atagcctcgg caaaccacaa agtcacacca 4260
acaactgcaa tcatacaaga tgcaacaagc cagatcaaga acacaacccc aacatacctc 4320
acccagaatc ctcagcttgg aatcagtccc tctaatccgt ctgaaattac atcacaaatc 4380
accaccatac tagcttcaac aacaccagga gtcaagtcaa ccctgcaatc cacaacagtc 4440
aagaccaaaa acacaacaac aactcaaaca caacccagca agcccaccac aaaacaacgc 4500
caaaacaaac caccaagcaa acccaataat gattttcact ttgaagtgtt caactttgta 4560
ccctgcagca tatgcagcaa caatccaacc tgctgggcta tctgcaaaag aataccaaac 4620
aaaaaaccag gaaagaaaac cactaccaag cccacaaaaa aaccaaccct caagacaacc 4680
aaaaaagatc ccaaacctca aaccactaaa tcaaaggaag tacccaccac caagcccaca 4740
gaagagccaa ccatcaacac caccaaaaca aacatcataa ctacactact cacctccaac 4800
accacaggaa atccagaact cacaagtcaa atggaaacct tccactcaac ttcctccgaa 4860
ggcaatccaa gcccttctca agtctctaca acatccgagt acccatcaca accttcatct 4920
ccacccaaca caccacgcca gtagttactt aaaaacatat tatcacaaaa ggccttgacc 4980
aacttaaaca gaatcaaaat aaactctggg gcaaataaca atggagttgc taatcctcaa 5040
agcaaatgca attaccacaa tcctcactgc agtcacattt tgttttgctt ctggtcaaaa 5100
catcactgaa gaattttatc aatcaacatg cagtgcagtt agcaaaggct atcttagtgc 5160
tctgagaact ggttggtata ccagtgttat aactatagaa ttaagtaata tcaagaaaaa 5220
taagtgtaat ggaacagatg ctaaggtaaa attgataaaa caagaattag ataaatataa 5280
aaatgctgta acagaattgc agttgctcat gcaaagcaca caagcaacaa acaatcgagc 5340
cagaagagaa ctaccaaggt ttatgaatta tacactcaac aatgccaaaa aaaccaatgt 5400
aacattaagc aagaaaagga aaagaagatt tcttggtttt ttgttaggtg ttggatctgc 5460
aatcgccagt ggcgttgctg tatctaaggt cctgcaccta gaaggggaag tgaacaagat 5520
caaaagtgct ctactatcca caaacaaggc tgtagtcagc ttatcaaatg gagttagtgt 5580
tttaaccagc aaagtgttag acctcaaaaa ctatatagat aaacaattgt tacctattgt 5640
gaacaagcaa agctgcagca tatcaaatat agaaactgtg atagagttcc aacaaaagaa 5700
caacagacta ctagagatta ccagggaatt tagtgttaat gcaggcgtaa ctacacctgt 5760
aagcacttac atgttaacta atagtgaatt attgtcatta atcaatgata tgcctataac 5820
aaatgatcag aaaaagttaa tgtccaacaa tgttcaaata gttagacagc aaagttactc 5880
tatcatgtcc ataataaaag aggaagtctt agcatatgta gtacaattac cactatatgg 5940
tgttatagat acaccctgtt ggaaactaca cacatcccct ctatgtacaa ccaacacaaa 6000
agaagggtcc aacatctgtt taacaagaac tgacagagga tggtactgtg acaatgcagg 6060
atcagtatct ttcttcccac aagctgaaac atgtaaagtt caatcaaatc gagtattttg 6120
tgacacaatg aacagtttaa cattaccaag tgaagtaaat ctctgcaatg ttgacatatt 6180
caaccccaaa tatgattgta aaattatgac ttcaaaaaca gatgtaagca gctccgttat 6240
cacatctcta ggagccattg tgtcatgcta tggcaaaact aaatgtacag catccaataa 6300
aaatcgtgga atcataaaga cattttctaa cgggtgcgat tatgtatcaa ataaaggggt 6360
ggacactgtg tctgtaggta acacattata ttatgtaaat aagcaagaag gtaaaagtct 6420
ctatgtaaaa ggtgaaccaa taataaattt ctatgaccca ttagtattcc cctctgatga 6480
atttgatgca tcaatatctc aagtcaacga gaagattaac cagagcctag catttattcg 6540
taaatccgat gaattattac ataatgtaaa tgctggtaaa tccaccacaa atatcatgat 6600
aactactata attatagtga ttatagtaat attgttatca ttaattgctg ttggactgct 6660
cttatactgt aaggccagaa gcacaccagt cacactaagc aaagatcaac tgagtggtat 6720
aaataatatt gcatttagta actaaataaa aatagcacct aatcatgttc ttacaatggt 6780
ttactatctg ctcatagaca acccatctgt cattggattt tcttaaaatc tgaacttcat 6840
cgaaactctc atctataaac catctcactt acactattta agtagattcc tagtttatag 6900
ttatataaaa cacaattgca tgccagatta acttaccatc tgtaaaaatg aaaactgggg 6960
caaatatgtc acgaaggaat ccttgcaaat ttgaaattcg aggtcattgc ttaaatggta 7020
agaggtgtca ttttagtcat aattattttg aatggccacc ccatgcactg cttgtaagac 7080
aaaactttat gttaaacaga atacttaagt ctatggataa aagtatagat accttatcag 7140
aaataagtgg agctgcagag ttggacagaa cagaagagta tgctcttggt gtagttggag 7200
tgctagagag ttatatagga tcaataaaca atataactaa acaatcagca tgtgttgcca 7260
tgagcaaact cctcactgaa ctcaatagtg atgatatcaa aaagctgagg gacaatgaag 7320
agctaaattc acccaagata agagtgtaca atactgtcat atcatatatt gaaagcaaca 7380
ggaaaaacaa taaacaaact atccatctgt taaaaagatt gccagcagac gtattgaaga 7440
aaaccatcaa aaacacattg gatatccata agagcataac catcaacaac ccaaaagaat 7500
caactgttag tgatacaaat gaccatgcca aaaataatga tactacctga caaatatcct 7560
tgtagtataa cttccatact aataacaagt agatgtagag ttactatgta taatcaaaag 7620
aacacactat atttcaatca aaacaaccca aataaccata tgtactcacc gaatcaaaca 7680
ttcaatgaaa tccattggac ctctcaagaa ttgattgaca caattcaaaa ttttctacaa 7740
catctaggta ttattgagga tatatataca atatatatat tagtgtcata acactcaatt 7800
ctaacactca ccacatcgtt acattattaa ttcaaacaat tcaagttgtg ggacaaaatg 7860
gatcccatta ttaatggaaa ttctgctaat gtttatctaa ccgatagtta tttaaaaggt 7920
gttatctctt tctcagagtg taatgcttta ggaagttaca tattcaatgg tccttatctc 7980
aaaaatgatt ataccaactt aattagtaga caaaatccat taatagaaca catgaatcta 8040
aagaaactaa atataacaca gtccttaata tctaagtatc ataaaggtga aataaaatta 8100
gaagaaccta cttattttca gtcattactt atgacataca agagtatgac ctcgtcagaa 8160
cagattgcta ccactaattt acttaaaaag ataataagaa gagctataga aataagtgat 8220
gtcaaagtct atgctatatt gaataaacta gggcttaaag aaaaggacaa gattaaatcc 8280
aacaatggac aagatgaaga caactcagtt attacgacca taatcaaaga tgatatactt 8340
tcagctgtta aagataatca atctcatctt aaagcagaca aaaatcactc tacaaaacaa 8400
aaagacacaa tcaaaacaac actcttgaag aaattgatgt gttcaatgca acatcctcca 8460
tcatggttaa tacattggtt taacttatac acaaaattaa acaacatatt aacacagtat 8520
cgatcaaatg aggtaaaaaa ccatgggttt acattgatag ataatcaaac tcttagtgga 8580
tttcaattta ttttgaacca atatggttgt atagtttatc ataaggaact caaaagaatt 8640
actgtgacaa cctataatca attcttgaca tggaaagata ttagccttag tagattaaat 8700
gtttgtttaa ttacatggat tagtaactgc ttgaacacat taaataaaag cttaggctta 8760
agatgcggat tcaataatgt tatcttgaca caactattcc tttatggaga ttgtatacta 8820
aagctatttc acaatgaggg gttctacata ataaaagagg tagagggatt tattatgtct 8880
ctaattttaa atataacaga agaagatcaa ttcagaaaac gattttataa tagtatgctc 8940
aacaacatca cagatgctgc taataaagct cagaaaaatc tgctatcaag agtatgtcat 9000
acattattag ataagacagt gtccgataat ataataaatg gcagatggat aattctatta 9060
agtaagttcc ttaaattaat taagcttgca ggtgacaata accttaacaa tctgagtgaa 9120
ctatattttt tgttcagaat atttggacac ccaatggtag atgaaagaca agccatggat 9180
gctgttaaaa ttaattgcaa tgagaccaaa ttttacttgt taagcagtct gagtatgtta 9240
agaggtgcct ttatatatag aattataaaa gggtttgtaa ataattacaa cagatggcct 9300
actttaagaa atgctattgt tttaccctta agatggttaa cttactataa actaaacact 9360
tatccttctt tgttggaact tacagaaaga gatttgattg tgttatcagg actacgtttc 9420
tatcgtgagt ttcggttgcc taaaaaagtg gatcttgaaa tgattataaa tgataaagct 9480
atatcacctc ctaaaaattt gatatggact agtttcccta gaaattacat gccatcacac 9540
atacaaaact atatagaaca tgaaaaatta aaattttccg agagtgataa atcaagaaga 9600
gtattagagt attatttaag agataacaaa ttcaatgaat gtgatttata caactgtgta 9660
gttaatcaaa gttatctcaa caaccctaat catgtggtat cattgacagg caaagaaaga 9720
gaactcagtg taggtagaat gtttgcaatg caaccgggaa tgttcagaca ggttcaaata 9780
ttggcagaga aaatgatagc tgaaaacatt ttacaattct ttcctgaaag tcttacaaga 9840
tatggtgatc tagaactaca aaaaatatta gaactgaaag caggaataag taacaaatca 9900
aatcgctaca atgataatta caacaattac attagtaagt gctctatcat cacagatctc 9960
agcaaattca atcaagcatt tcgatatgaa acgtcatgta tttgtagtga tgtgctggat 10020
gaactgcatg gtgtacaatc tctattttcc tggttacatt taactattcc tcatgtcaca 10080
ataaatatgca catataggca tgcacccccc tatataggag atcatattgt agatcttaac 10140
aatgtagatg aacaaagtgg attatataga tatcacatgg gtggcatcga agggtggtgt 10200
caaaaactat ggaccataga agctatatca ctattggatc taatatctct caaagggaaa 10260
ttctcaatta ctgctttaat taatggtgac aatcaatcaa tagatataag caaaccaatc 10320
agactcatgg aaggtcaaac tcatgctcaa gcagattatt tgctagcatt aaatagcctt 10380
aaattactgt ataaagagta tgcaggcata ggccacaaat taaaaggaac tgagacttat 10440
atatcacgag atatgcaatt tatgagtaaa acaattcaac ataacggtgt atattaccca 10500
gctagtataa agaaagtcct aagagtggga ccgtggataa acactatact tgatgatttc 10560
aaagtgagtc tagaatctat aggtagtttg acacaagaat tagaatatag aggtgaaagt 10620
ctattatgca gtttaatatt tagaaatgta tggttatata atcagattgc tctacaatta 10680
aaaaatcatg cattatgtaa caataaacta tatttggaca tattaaaggt tctgaaacac 10740
ttaaaaacct tttttaatct tgataatatt gatacagcat taacattgta tatgaattta 10800
cccatgttat ttggtggtgg tgatcccaac ttgttatatc gaagtttcta tagaagaact 10860
cctgacttcc tcacagaggc tatagttcac tctgtgttca tacttagtta ttatacaaac 10920
catgacttaa aagataaact tcaagatctg tcagatgata gattgaataa gttcttaaca 10980
tgcataatca cgtttgacaa aaaccctaat gctgaattcg taacattgat gagagatcct 11040
caagctttag ggtctgagag acaagctaaa attactagcg aaatcaatag actggcagtt 11100
acagaggttt tgagtacagc tccaaacaaa atattctcca aaagtgcaca acattatact 11160
actacagaga tagatctaaa tgatattatg caaaatatag aacctacata tcctcatggg 11220
ctaagagttg tttatgaaag tttacccttt tataaagcag agaaaatagt aaatcttata 11280
tcaggtacaa aatctataac taacatactg gaaaaaactt ctgccataga cttaacagat 11340
attgatagag ccactgagat gatgaggaaa aacataactt tgcttataag gatacttcca 11400
ttggattgta acagagataa aagagagata ttgagtatgg aaaacctaag tattactgaa 11460
ttaagcaaat atgttaggga aagatcttgg tctttatcca atatagttgg tgttacatca 11520
cccagtatca tgtatacaat ggacatcaaa tatactacaa gcactatatc tagtggcata 11580
attatagaga aatataatgt taacagttta acacgtggtg agagaggacc cactaaacca 11640
tgggttggtt catctacaca agagaaaaaa acaatgccag tttataatag acaagtctta 11700
accaaaaaac agagagatca aatagatcta ttagcaaaat tggattgggt gtatgcatct 11760
atagataaca aggatgaatt catggaagaa ctcctgggaa cccttgggtt aacatatgaa 11820
aaggccaaga aattatttcc acaatattta agtgtcaatt atttgcatcg ccttacagtc 11880
agtagtagac catgtgaatt ccctgcatca ataccagctt atagaacaac aaattatcac 11940
tttgacacta gccctattaa tcgcatatta acagaaaagt atggtgatga agatattgac 12000
atagtattcc aaaactgtat aagctttggc cttagtttaa tgtcagtagt agaacaattt 12060
actaatgtat gtcctaacag aattattctc atacctaagc ttaatgagat acatttgatg 12120
aaacctccca tattcacagg tgatgttgat attcacaagt taaaacaagt gatacaaaaa 12180
cagcatatgt ttttaccaga caaaataagt ttgactcaat atgtggaatt attcttaagt 12240
aataaaacac tcaaatctgg atctcatgtt aattctaatt taatattggc acataaaata 12300
tctgactatt ttcataatac ttacatttta agtactaatt tagctggaca ttggattctg 12360
attatacaac ttatgaaaga ttctaaaggt atttttgaaa aagattgggg agagggatat 12420
ataactgatc atatgtttat taatttgaaa gttttcttca atgcttataa gacctatctc 12480
ttgtgttttc ataaaggtta tggcaaagca aagctggagt gtgatatgaa cacttcagat 12540
cttctatgtg tattggaatt aatagacagt agttattgga agtctatgtc taaggtattt 12600
ttagaacaaa aagttatcaa atacattctt agccaagatg caagtttaca tagagtaaaa 12660
ggatgtcata gcttcaaatt atggtttctt aaacgtctta atgtagcaga attcacagtt 12720
tgcccttggg ttgttaacat agattatcat ccaacacata tgaaagcaat attaacttat 12780
atagatcttg ttagaatggg attgataaat atagatagaa tacacattaa aaataaacac 12840
aaattcaatg atgaatttta tacttctaat ctcttctaca ttaattataa cttctcagat 12900
aatactcatc tattaactaa acatataagg attgctaatt ctgaattaga aaataattac 12960
aacaaattat atcatcctac accagaaacc ctagagaata tactagccaa tccgattaaa 13020
agtaatgaca aaaagacact gaatgactat tgtataggta aaaatgttga ctcaataatg 13080
ttaccattgt tatctaataa gaagcttatt aaatcgtctg caatgattag aaccaattac 13140
agcaaacaag atttgtataa tttattccct atggttgtga ttgatagaat tatagatcat 13200
tcaggcaata cagccaaatc caaccaactt tacactacta cttcccacca aatatcctta 13260
gtgcacaata gcacatcact ttactgcatg cttccttggc atcatattaa tagattcaat 13320
tttgtattta gttctacagg ttgtaaaatt agtatagagt atattttaaa agatcttaaa 13380
attaaagatc ccaattgtat agcattcata ggtgaaggag cagggaattt attattgcgt 13440
acagtagtgg aacttcatcc tgacataaga tatatttaca gaagtctgaa agattgcaat 13500
gatcatagtt tacctattga gtttttaagg ctgtacaatg gacatatcaa cattgattat 13560
ggtgaaaatt tgaccattcc tgctacagat gcaaccaaca acattcattg gtcttattta 13620
catataaagt ttgctgaacc tatcagtctt tttgtctgtg atgccgaatt gtctgtaaca 13680
gtcaactgga gtaaaattat aatagaatgg agcaagcatg taagaaagtg caagtactgt 13740
tcctcagtta ataaatgtat gttaatagta aaatatcatg ctcaagatga tattgatttc 13800
aaattagaca atataactat attaaaaact tatgtatgct taggcagtaa gttaaaggga 13860
tcggaggttt acttagtcct tacaataggt cctgcgaata tattcccagt atttaatgta 13920
gtacaaaatg ctaaattgat actatcaaga accaaaaatt tcatcatgcc taagaaagct 13980
gataaagagt ctattgatgc aaatattaaa agtttgatac cctttctttg ttaccctata 14040
acaaaaaaag gaattaatac tgcattgtca aaactaaaga gtgttgttag tggagatata 14100
ctatcatatt ctatagctgg acgtaatgaa gttttcagca ataaacttat aaatcataag 14160
catatgaaca tcttaaaatg gttcaatcat gttttaaatt tcagatcaac agaactaaac 14220
tataaccatt tatatatggt agaatctaca tatccttacc taagtgaatt gttaaacagc 14280
ttgacaacca atgaacttaa aaaactgatt aaaatcacag gtagtctgtt atacaacttt 14340
cataatgaat aatgaataaa gatcttataa taaaaattcc catagctata cactaacact 14400
gtattcaatt atagttatta aaaattaaaa atcatataat tttttaaata acttttagtg 14460
aactaatcct aaagttatca ttttaatctt ggaggaataa atttaaaccc taatctaatt 14520
ggtttatatg tgtattaact aaattacgag atattagttt ttgacacttt ttttctcgt 14579

<210> SEQ ID NO 9
<211> LENGTH: 14345
<212> TYPE: DNA
<213> ORGANISM: Artificial Sequence
<220> FEATURE:
<223> OTHER INFORMATION: Recombinant RSV sequence

<400> SEQUENCE: 9
acgggaaaaa atgcgtacaa caaacttgca taaaccaaaa aaatggggca aataagaatt 60
tgataagtac cacttaaatt taactcctcg agttcaccat ggagttgcta atcctcaaag 120
caaatgcaat taccacaatc ctcactgcag tcacattttg ttttgcttct ggtcaaaaca 180
tcactgaaga attttatcaa tcaacatgca gtgcagttag caaaggctat cttagtgctc 240
tgagaactgg ttggtatacc agtgttataa ctatagaatt aagtaatatc aagaaaaata 300
agtgtaatgg aacagatgct aaggtaaaat tgataaaaca agaattagat aaatataaaa 360
atgctgtaac agaattgcag ttgctcatgc aaagcacaca agcaacaaac aatcgagcca 420
gaagagaact accaaggttt atgaattata cactcaacaa tgccaaaaaa accaatgtaa 480
cattaagcaa gaaaaggaaa agaagatttc ttggtttttt gttaggtgtt ggatctgcaa 540
tcgccagtgg cgttgctgta tctaaggtcc tgcacctaga aggggaagtg aacaagatca 600
aaagtgctct actatccaca aacaaggctg tagtcagctt atcaaatgga gttagtgttt 660
taaccagcaa agtgttagac ctcaaaaact atatagataa acaattgtta cctattgtga 720
acaagcaaag ctgcagcata tcaaatatag aaactgtgat agagttccaa caaaagaaca 780
acagactact agagattacc agggaattta gtgttaatgc aggcgtaact acacctgtaa 840
gcacttacat gttaactaat agtgaattat tgtcattaat caatgatatg cctataacaa 900
atgatcagaa aaagttaatg tccaacaatg ttcaaatagt tagacagcaa agttactcta 960
tcatgtccat aataaaagag gaagtcttag catatgtagt acaattacca ctatatggtg 1020
ttatagatac accctgttgg aaactacaca catcccctct atgtacaacc aacacaaaag 1080
aagggtccaa catctgttta acaagaactg acagaggatg gtactgtgac aatgcaggat 1140
cagtatcttt cttcccacaa gctgaaacat gtaaagttca atcaaatcga gtattttgtg 1200
acacaatgaa cagtttaaca ttaccaagtg aagtaaatct ctgcaatgtt gacatattca 1260
accccaaata tgattgtaaa attatgactt caaaaacaga tgtaagcagc tccgttatca 1320
catctctagg agccattgtg tcatgctatg gcaaaactaa atgtacagca tccaataaaa 1380
atcgtggaat cataaagaca ttttctaacg ggtgcgatta tgtatcaaat aaaggggtgg 1440
acactgtgtc tgtaggtaac acattatatt atgtaaataa gcaagaaggt aaaagtctct 1500
atgtaaaagg tgaaccaata ataaatttct atgacccatt agtattcccc tctgatgaat 1560
ttgatgcatc aatatctcaa gtcaacgaga agattaacca gagcctagca tttattcgta 1620
aatccgatga attattacat aatgtaaatg ctggtaaatc caccacaaat atcatgataa 1680
ctactataat tatagtgatt atagtaatat tgttatcatt aattgctgtt ggactgctct 1740
tatactgtaa ggccagaagc acaccagtca cactaagcaa agatcaactg agtggtataa 1800
ataatattgc atttagtaac taaagtagtt aattaaaaat ggggcaaata caaccatgtc 1860
caaaaacaag gaccaacgca ccgctaagac attagaaagg acctgggaca ctctcaatca 1920
tttattattc atatcatcgt gcttatataa gttaaatctt aaatctgtag cacaaatcac 1980
attatccatt ctggcaatga taatctcaac ttcacttata attgcagcca tcatattcat 2040
agcctcggca aaccacaaag tcacaccaac aactgcaatc atacaagatg caacaagcca 2100
gatcaagaac acaaccccaa catacctcac ccagaatcct cagcttggaa tcagtccctc 2160
taatccgtct gaaattacat cacaaatcac caccatacta gcttcaacaa caccaggagt 2220
caagtcaacc ctgcaatcca caacagtcaa gaccaaaaac acaacaacaa ctcaaacaca 2280
acccagcaag cccaccacaa aacaacgcca aaacaaacca ccaagcaaac ccaataatga 2340
ttttcacttt gaagtgttca actttgtacc ctgcagcata tgcagcaaca atccaacctg 2400
ctgggctatc tgcaaaagaa taccaaacaa aaaaccagga aagaaaacca ctaccaagcc 2460
cacaaaaaaa ccaaccctca agacaaccaa aaaagatccc aaacctcaaa ccactaaatc 2520
aaaggaagta cccaccacca agcccacaga agagccaacc atcaacacca ccaaaacaaa 2580
catcataact acactactca cctccaacac cacaggaaat ccagaactca caagtcaaat 2640
ggaaaccttc cactcaactt cctccgaagg caatccaagc ccttctcaag tctctacaac 2700
atccgagtac ccatcacaac cttcatctcc acccaacaca ccacgccagt agttaataaa 2760
aaatggggca aatactcgag ttagagatgg acacaaccca caatgataat acaccacaaa 2820
gactgatgat cacagacatg agaccgttgt cacttgagac cataataaca tcactaacca 2880
gagacatcat aacacacaaa tttatatact tgataaatca tgaatgcata gtgagaaaac 2940
ttgatgaaag acaggccaca tttacattcc tggtcaacta tgaaatgaaa ctattacaca 3000
aagtaggaag cactaaatat aaaaaatata ctgaatacaa cacaaaatat ggcactttcc 3060
ctatgccaat attcatcaat catgatgggt tcttagaatg cattggcatt aagcctacaa 3120
agcatactcc cataatatac aagtatgatc tcaatccata aatttcaaca caatattcac 3180
acaatctaaa acaacaactc tatgcataac tatactccat agtccagatg gagcctgaaa 3240
attatagtaa tttaaaactt aaggagagat ataagataga agatggggca aatacaacca 3300
tggctcttag caaagtcaag ttgaatgata cactcaacaa agatcaactt ctgtcatcca 3360
gcaaatacac catccaacgg agcacaggag atagtattga tactcctaat tatgatgtgc 3420
agaaacacat caataagtta tgtggcatgt tattaatcac agaagatgct aatcataaat 3480
tcactgggtt aataggtatg ttatatgcga tgtctaggtt aggaagagaa gacaccataa 3540
aaatactcag agatgcggga tatcatgtaa aagcaaatgg agtagatgta acaacacatc 3600
gtcaagacat taatggaaaa gaaatgaaat ttgaagtgtt aacattggca agcttaacaa 3660
ctgaaattca aatcaacatt gagatagaat ctagaaaatc ctacaaaaaa atgctaaaag 3720
aaatgggaga ggtagctcca gaatacaggc atgactctcc tgattgtggg atgataatat 3780
tatgtatagc agcattagta ataactaaat tagcagcagg ggacagatct ggtcttacag 3840
ccgtgattag gagagctaat aatgtcctaa aaaatgaaat gaaacgttac aaaggcttac 3900
tacccaagga catagccaac agcttctatg aagtgtttga aaaacatccc cactttatag 3960
atgtttttgt tcattttggt atagcacaat cttctaccag aggtggcagt agagttgaag 4020
ggatttttgc aggattgttt atgaatgcct atggtgcagg gcaagtgatg ttacggtggg 4080
gagtcttagc aaaatcggtt aaaaatatta tgttaggaca tgctagtgtg caagcagaaa 4140
tggaacaagt tgttgaggtt tatgaatatg cccaaaaatt gggtggtgaa gcaggattct 4200
accatatatt gaacaaccca aaagcatcat tattatcttt gactcaattt cctcacttct 4260
ccagtgtagt attaggcaat gctgctggcc taggcataat gggagagtac agaggtacac 4320
cgaggaatca agatctatat gatgcagcaa aggcatatgc tgaacaactc aaagaaaatg 4380
gtgtgattaa ctacagtgta ctagacttga cagcagaaga actagaggct atcaaacatc 4440
agcttaatcc aaaagataat gatgtagagc tttgagttaa taaaaaatgg ggcaaataaa 4500
tcatcatgga aaagtttgct cctgaattcc atggagaaga tgcaaacaac agggctacta 4560
aattcctaga atcaataaag ggcaaattca catcacccaa agatcccaag aaaaaagata 4620
gtatcatatc tgtcaactca atagatatag aagtaaccaa agaaagccct ataacatcaa 4680
attcaactat tatcaaccca acaaatgaga cagatgatac tgcagggaac aagcccaatt 4740
atcaaagaaa acctctagta agtttcaaag aagaccctac accaagtgat aatccctttt 4800
ctaaactata caaagaaacc atagaaacat ttgataacaa tgaagaagaa tccagctatt 4860
catacgaaga aataaatgat cagacaaacg ataatataac agcaagatta gataggattg 4920
atgaaaaatt aagtgaaata ctaggaatgc ttcacacatt agtagtggca agtgcaggac 4980
ctacatctgc tcgggatggt ataagagatg ccatggttgg tttaagagaa gaaatgatag 5040
aaaaaatcag aactgaagca ttaatgacca atgacagatt agaagctatg gcaagactca 5100
ggaatgagga aagtgaaaag atggcaaaag acacatcaga tgaagtgtct ctcaatccaa 5160
catcagagaa attgaacaac ctattggaag ggaatgatag tgacaatgat ctatcacttg 5220
aagatttctg attagttacc aatcttcaca tcaacacaca ataccaacag aagaccaaca 5280
aactaaccaa cccaatcatc caaccaaaca tccatccgcc aatcagccaa acagccaaca 5340
aaacaaccag ccaatccaaa actaaccacc cggaaaaaat ctataatata gttacaaaaa 5400
aaggaaaggg tggggcaaat atggaaacat acgtgaacaa gcttcacgaa ggctccacat 5460
acacagctgc tgttcaatac aatgtcttag aaaaagacga tgaccctgca tcacttacaa 5520
tatgggtgcc catgttccaa tcatctatgc cagcagattt acttataaaa gaactagcta 5580
atgtcaacat actagtgaaa caaatatcca cacccaaggg accttcacta agagtcatga 5640
taaactcaag aagtgcagtg ctagcacaaa tgcccagcaa atttaccata tgcgctaatg 5700
tgtccttgga tgaaagaagc aaactagcat atgatgtaac cacaccctgt gaaatcaagg 5760
catgtagtct aacatgccta aaatcaaaaa atatgttgac tacagttaaa gatctcacta 5820
tgaagacact caaccctaca catgatatta ttgctttatg tgaatttgaa aacatagtaa 5880
catcaaaaaa agtcataata ccaacatacc taagatccat cagtgtcaga aataaagatc 5940
tgaacacact tgaaaatata acaaccactg aattcaaaaa tgctatcaca aatgcaaaaa 6000
tcatccctta ctcaggatta ctattagtca tcacagtgac tgacaacaaa ggagcattca 6060
aatacataaa gccacaaagt caattcatag tagatcttgg agcttaccta gaaaaagaaa 6120
gtatatatta tgttaccaca aattggaagc acacagctac acgatttgca atcaaaccca 6180
tggaagatta accttttcc tctacatcag tgtgttaatt catacaaact ttctacctac 6240
attcttcact tcaccatcac aatcacaaac actctgtggt tcaaccaatc aaacaaaact 6300
tatctgaagt cccagatcat cccaagtcat tgtttatcag atctagtact caaataagtt 6360
aataaaaaat atacacatgg ggcaaataat cattggagga aatccaacta atcacaatat 6420
ctgttaacat agacaagtcc acacaccata cagaatcaac caatggaaaa tacatccata 6480
acaatagaat tctcaagcaa attctggcct tactttacac taatacacat gatcacaaca 6540
ataatctctt tgctaatcat aatctccatc atgattgcaa tactaaacaa actttgtgaa 6600
tataacgtat tccataacaa aacctttgag ttaccaagag ctcgagttaa tacttgataa 6660
agtagttaat taaaaacaca attgcatgcc agattaactt accatctgta aaaatgaaaa 6720
ctggggcaaa tatgtcacga aggaatcctt gcaaatttga aattcgaggt cattgcttaa 6780
atggtaagag gtgtcatttt agtcataatt attttgaatg gccacccccat gcactgcttg 6840
taagacaaaa ctttatgtta aacagaatac ttaagtctat ggataaaagt atagatacct 6900
tatcagaaat aagtggagct gcagagttgg acagaacaga agagtatgct cttggtgtag 6960
ttggagtgct agagagttat ataggatcaa taaacaatat aactaaacaa tcagcatgtg 7020
ttgccatgag caaactcctc actgaactca atagtgatga tatcaaaaag ctgagggaca 7080
atgaagagct aaattcaccc aagataagag tgtacaatac tgtcatatca tatattgaaa 7140
gcaacaggaa aaacaataaa caaactatcc atctgttaaa aagattgcca gcagacgtat 7200
tgaagaaaac catcaaaaac acattggata tccataagag cataaccatc aacaacccaa 7260
aagaatcaac tgttagtgat acaaatgacc atgccaaaaa taatgatact acctgacaaa 7320
tatccttgta gtataacttc catactaata acaagtagat gtagagttac tatgtataat 7380
caaaagaaca cactatattt caatcaaaac aacccaaata accatatgta ctcaccgaat 7440
caaacattca atgaaatcca ttggacctct caagaattga ttgacacaat tcaaaatttt 7500
ctacaacatc taggtattat tgaggatata tatacaatat atatattagt gtcataacac 7560
tcaattctaa cactcaccac atcgttacat tattaattca aacaattcaa gttgtgggac 7620
aaaatggatc ccattattaa tggaaattct gctaatgttt atctaaccga tagttattta 7680
aaaggtgtta tctctttctc agagtgtaat gctttaggaa gttacatatt caatggtcct 7740
tatctcaaaa atgattatac caacttaatt agtagacaaa atccattaat agaacacatg 7800
aatctaaaga aactaaatat aacacagtcc ttaatatcta agtatcataa aggtgaaata 7860
aaattagaag aacctactta ttttcagtca ttacttatga catacaagag tatgacctcg 7920
tcagaacaga ttgctaccac taatttactt aaaaagataa taagaagagc tatagaaata 7980
agtgatgtca aagtctatgc tatattgaat aaactagggc ttaaagaaaa ggacaagatt 8040
aaatccaaca atggacaaga tgaagacaac tcagttatta cgaccataat caaagatgat 8100
atactttcag ctgttaaaga taatcaatct catcttaaag cagacaaaaa tcactctaca 8160
aaacaaaaag acacaatcaa aacaacactc ttgaagaaat tgatgtgttc aatgcaacat 8220

```
cctccatcat ggttaataca ttggtttaac ttatacacaa aattaaacaa catattaaca   8280
cagtatcgat caaatgaggt aaaaaaccat gggtttacat tgatagataa tcaaactctt   8340
agtggatttc aatttatttt gaaccaatat ggttgtatag tttatcataa ggaactcaaa   8400
agaattactg tgacaaccta taatcaattc ttgacatgga aagatattag ccttagtaga   8460
ttaaatgttt gtttaattac atggattagt aactgcttga acacattaaa taaaagctta   8520
ggcttaagat gcggattcaa taatgttatc ttgacacaac tattccttta tggagattgt   8580
atactaaagc tatttcacaa tgaggggttc tacataataa aagaggtaga gggatttatt   8640
atgtctctaa ttttaaatat aacagaagaa gatcaattca gaaaacgatt ttataatagt   8700
atgctcaaca acatcacaga tgctgctaat aaagctcaga aaaatctgct atcaagagta   8760
tgtcatacat tattagataa gacagtgtcc gataatataa taaatggcag atggataatt   8820
ctattaagta agttccttaa attaattaag cttgcaggtg acaataacct taacaatctg   8880
agtgaactat attttttgtt cagaatattt ggacacccaa tggtagatga aagacaagcc   8940
atggatgctg ttaaaattaa ttgcaatgag accaaatttt acttgttaag cagtctgagt   9000
atgttaagag gtgcctttat atatagaatt ataaaagggt ttgtaaataa ttacaacaga   9060
tggcctactt taagaaatgc tattgtttta cccttaagat ggttaactta ctataaacta   9120
aacacttatc cttctttgtt ggaacttaca gaaagagatt tgattgtgtt atcaggacta   9180
cgtttctatc gtgagtttcg gttgcctaaa aaagtggatc ttgaaatgat tataaatgat   9240
aaagctatat cacctcctaa aaatttgata tggactagtt tccctagaaa ttacatgcca   9300
tcacacatac aaaactatat agaacatgaa aaattaaaat tttccgagag tgataaatca   9360
agaagagtat tagagtatta tttaagagat aacaaattca atgaatgtga tttatacaac   9420
tgtgtagtta atcaaagtta tctcaacaac cctaatcatg tggtatcatt gacaggcaaa   9480
gaaagagaac tcagtgtagg tagaatgttt gcaatgcaac cgggaatgtt cagacaggtt   9540
caaatattgg cagagaaaat gatagctgaa aacattttac aattctttcc tgaaagtctt   9600
acaagatatg gtgatctaga actacaaaaa atattagaac tgaaagcagg aataagtaac   9660
aaatcaaatc gctacaatga taattacaac aattacatta gtaagtgctc tatcatcaca   9720
gatctcagca aattcaatca agcatttcga tatgaaacgt catgtatttg tagtgatgtg   9780
ctggatgaac tgcatggtgt acaatctcta ttttcctggt tacatttaac tattcctcat   9840
gtcacaataa tatgcacata taggcatgca ccccccctata taggagatca tattgtagat   9900
cttaacaatg tagatgaaca aagtggatta tatagatatc acatgggtgg catcgaaggg   9960
tggtgtcaaa aactatggac catagaagct atatcactat tggatctaat atctctcaaa  10020
gggaaattct caattactgc tttaattaat ggtgacaatc aatcaataga tataagcaaa  10080
ccaatcagac tcatggaagg tcaaactcat gctcaagcag attatttgct agcattaaat  10140
agccttaaat tactgtataa agagtatgca ggcataggcc acaaattaaa aggaactgag  10200
acttatatat cacgagatat gcaatttatg agtaaaacaa ttcaacataa cggtgtatat  10260
tacccagcta gtataaagaa agtcctaaga gtgggaccgt ggataaacac tatacttgat  10320
gatttcaaag tgagtctaga atctataggt agtttgacac aagaattaga atatagaggt  10380
gaaagtctat tatgcagttt aatatttaga aatgtatggt tatataatca gattgctcta  10440
caattaaaaa atcatgcatt atgtaacaat aaactatatt tggacatatt aaaggttctg  10500
aaacacttaa aaaccttttt taatcttgat aatattgata cagcattaac attgtatatg  10560
```

```
aatttaccca tgttatttgg tggtggtgat cccaacttgt tatatcgaag tttctataga  10620
agaactcctg acttcctcac agaggctata gttcactctg tgttcatact tagttattat  10680
acaaaccatg acttaaaaga taaacttcaa gatctgtcag atgatagatt gaataagttc  10740
ttaacatgca taatcacgtt tgacaaaaac cctaatgctg aattcgtaac attgatgaga  10800
gatcctcaag ctttagggtc tgagagacaa gctaaaatta ctagcgaaat caatagactg  10860
gcagttacag aggttttgag tacagctcca aacaaaatat tctccaaaag tgcacaacat  10920
tatactacta cagagataga tctaaatgat attatgcaaa atatagaacc tacatatcct  10980
catgggctaa gagttgttta tgaaagttta cccttttata aagcagagaa aatagtaaat  11040
cttatatcag gtacaaaatc tataactaac atactggaaa aaacttctgc catagactta  11100
acagatattg atagagccac tgagatgatg aggaaaaaca taactttgct tataaggata  11160
cttccattgg attgtaacag agataaaaga gagatattga gtatggaaaa cctaagtatt  11220
actgaattaa gcaaatatgt tagggaaaga tcttggtctt tatccaatat agttggtgtt  11280
acatcaccca gtatcatgta tacaatggac atcaaatata ctacaagcac tatatctagt  11340
ggcataatta tagagaaata taatgttaac agtttaacac gtggtgagag aggacccact  11400
aaaccatggg ttggttcatc tacacaagag aaaaaaacaa tgccagttta taatagacaa  11460
gtcttaacca aaaaacagag agatcaaata gatctattag caaaattgga ttgggtgtat  11520
gcatctatag ataacaagga tgaattcatg gaagaactcc tgggaaccct tgggttaaca  11580
tatgaaaagg ccaagaaatt atttccacaa tatttaagtg tcaattattt gcatcgcctt  11640
acagtcagta gtagaccatg tgaattccct gcatcaatac cagcttatag aacaacaaat  11700
tatcactttg acactagccc tattaatcgc atattaacag aaaagtatgg tgatgaagat  11760
attgacatag tattccaaaa ctgtataagc tttggcctta gtttaatgtc agtagtagaa  11820
caatttacta atgtatgtcc taacagaatt attctcatac ctaagcttaa tgagatacat  11880
ttgatgaaac ctcccatatt cacaggtgat gttgatattc acaagttaaa acaagtgata  11940
caaaaacagc atatgttttt accagacaaa ataagtttga ctcaatatgt ggaattattc  12000
ttaagtaata aaacactcaa atctggatct catgttaatt ctaatttaat attggcacat  12060
aaaatatctg actattttca taatacttac attttaagta ctaatttagc tggacattgg  12120
attctgatta tacaacttat gaaagattct aaaggtattt ttgaaaaaga ttggggagag  12180
ggatatataa ctgatcatat gtttattaat ttgaaagttt tcttcaatgc ttataagacc  12240
tatctcttgt gttttcataa aggttatggc aaagcaaagc tggagtgtga tatgaacact  12300
tcagatcttc tatgtgtatt ggaattaata gacagtagtt attggaagtc tatgtctaag  12360
gtatttttag aacaaaaagt tatcaaatac attcttagcc aagatgcaag tttacataga  12420
gtaaaaggat gtcatagctt caaattatgg tttcttaaac gtcttaatgt agcagaattc  12480
acagtttgcc cttgggttgt taacatagat tatcatccaa cacatatgaa agcaatatta  12540
acttatatag atcttgttag aatgggattg ataaatatag atagaataca cattaaaaat  12600
aaacacaaat tcaatgatga attttatact tctaatctct tctacattaa ttataacttc  12660
tcagataata ctcatctatt aactaaacat ataaggattg ctaattctga attagaaaat  12720
aattacaaca aattatatca tcctacacca gaaaccctag agaatatact agccaatccg  12780
attaaaagta atgacaaaaa gacactgaat gactattgta taggtaaaaa tgttgactca  12840
ataatgttac cattgttatc taataagaag cttattaaat cgtctgcaat gattagaacc  12900
aattacagca aacaagattt gtataattta ttccctatgg ttgtgattga tagaattata  12960
```

```
gatcattcag gcaatacagc caaatccaac caactttaca ctactacttc ccaccaaata  13020

tccttagtgc acaatagcac atcactttac tgcatgcttc cttggcatca tattaataga  13080

ttcaatttg tatttagttc tacaggttgt aaaattagta tagagtatat tttaaaagat  13140

cttaaaatta aagatcccaa ttgtatagca ttcataggtg aaggagcagg gaatttatta  13200

ttgcgtacag tagtggaact tcatcctgac ataagatata tttacagaag tctgaaagat  13260

tgcaatgatc atagtttacc tattgagttt ttaaggctgt acaatggaca tatcaacatt  13320

gattatggtg aaaatttgac cattcctgct acagatgcaa ccaacaacat tcattggtct  13380

tatttacata taaagtttgc tgaacctatc agtctttttg tctgtgatgc cgaattgtct  13440

gtaacagtca actggagtaa aattataata gaatggagca agcatgtaag aaagtgcaag  13500

tactgttcct cagttaataa atgtatgtta atagtaaaat atcatgctca agatgatatt  13560

gatttcaaat tagacaatat aactatatta aaaacttatg tatgcttagg cagtaagtta  13620

aagggatcgg aggtttactt agtccttaca ataggtcctg cgaatatatt cccagtattt  13680

aatgtagtac aaaatgctaa attgatacta tcaagaacca aaaatttcat catgcctaag  13740

aaagctgata aagagtctat tgatgcaaat attaaaagtt tgataccctt tctttgttac  13800

cctataacaa aaaaaggaat taatactgca ttgtcaaaac taaagagtgt tgttagtgga  13860

gatatactat catattctat agctggacgt aatgaagttt tcagcaataa acttataaat  13920

cataagcata tgaacatctt aaaatggttc aatcatgttt taaatttcag atcaacagaa  13980

ctaaactata accatttata tatggtagaa tctacatatc cttacctaag tgaattgtta  14040

aacagcttga caaccaatga acttaaaaaa ctgattaaaa tcacaggtag tctgttatac  14100

aactttcata atgaataatg aataaagatc ttataataaa aattcccata gctatacact  14160

aacactgtat tcaattatag ttattaaaaa ttaaaaatca tataattttt taaataactt  14220

ttagtgaact aatcctaaag ttatcatttt aatcttggag gaataaattt aaaccctaat  14280

ctaattggtt tatatgtgta ttaactaaat tacgagatat tagtttttga cacttttttt  14340

ctcgt                                                             14345
```

<210> SEQ ID NO 10
<211> LENGTH: 14345
<212> TYPE: DNA
<213> ORGANISM: Artificial Sequence
<220> FEATURE:
<223> OTHER INFORMATION: Recombinabt RSV sequence

<400> SEQUENCE: 10

```
acgggaaaaa atgcgtacaa caaacttgca taaaccaaaa aaatggggca aataagaatt     60

tgataagtac cacttaaatt taactcctcg agttcaccat ggagctcctc attctcaaag    120

ccaacgcaat cacaacaatt ctgaccgccg tcacattctg ctttgcctcc ggacagaaca    180

tcacagaaga gttttaccaa agtacatgca gcgccgtgag caaaggctac ctgtccgccc    240

tgaggacagg gtggtacaca tccgtgatta ccattgagct gagtaatatc aagaagaaca    300

agtgcaacgg cactgatgcc aaagtgaagc tcattaaaca ggaactcgat aagtacaaga    360

acgccgtgac tgagctccag ctgctgatgc agtcaactca ggctacaaac aacagagccc    420

ggagggagct gcccaggttt atgaactaca ccctgaacaa cgccaagaag accaacgtga    480

cattgagcaa gaagaggaag cggcggttcc tggggttctt gctaggtgtg ggcagcgcta    540

ttgcttctgg cgtcgccgtc tccaaggtgc tgcacctgga aggcgaagtg aataagatta    600
```

```
agtccgcact gcttagcacc aataaggccg tcgtgagcct gtctaacgga gtgagtgtgc    660
tcacaagcaa ggtcctcgat ctcaagaact acattgataa gcagctcctg cccatcgtca    720
acaagcagtc atgctccatt agtaacatcg agaccgtgat tgaatttcaa cagaagaaca    780
accggctcct ggagattact agggagttca gcgtgaacgc cggggtgaca acaccagtct    840
ccacctatat gcttaccaac agcgagttgc tctccctgat taacgatatg ccaattacaa    900
acgaccagaa gaagctgatg tcaaacaacg tccagattgt ccggcagcag tcctactcaa    960
tcatgtccat tattaaggag gaggtcctgg cttacgtcgt gcagctgcct ctttatgggg   1020
tgatcgacac cccttgctgg aagctccata catcccctct gtgcactacc aacaccaagg   1080
aggggtccaa catctgcttg acaagaaccg atcgcggctg gtactgcgat aacgcaggca   1140
gtgtctcctt ctttccccag gccgagactt gtaaggtgca gtctaaccgc gtcttctgcg   1200
acaccatgaa cagcctgacc cttcccagcg aggtgaacct ttgtaacgtg gacatcttca   1260
acccaaagta tgattgtaag attatgacta gcaaaaccga tgtcagcagc agcgtgatca   1320
ctagcctggg cgctatcgtc agctgctacg gaaagactaa gtgcaccgcc agcaacaaga   1380
acagaggcat catcaagacc ttcagtaatg gatgtgacta cgtgtccaac aaaggggtgg   1440
atacagtgag cgtgggaaac acattgtact acgtgaacaa acaggagggg aagtccttgt   1500
acgtgaaggg tgagcccatt atcaacttct acgaccctct cgtgttccca tcagacgagt   1560
ttgacgcctc catctcccag gtgaacgaga agatcaatca gtcactggcc tttattagga   1620
aatccgacga gctgctgcac aacgtcaacg ccggaaagtc taccactaac atcatgatca   1680
ccacaatcat cattgtgatc atcgtcatcc tcctgagctt gatcgctgtc gggttgctgt   1740
tgtactgcaa ggcccggtcc acacccgtga ctctgagcaa ggaccagctg tctggcatta   1800
acaacatcgc ctttagcaac taaagtagtt aattaaaaat ggggcaaata caaccatgtc   1860
caaaaacaag gaccaacgca ccgctaagac attagaaagg acctgggaca ctctcaatca   1920
tttattattc atatcatcgt gcttatataa gttaaatctt aaatctgtag cacaaatcac   1980
attatccatt ctggcaatga taatctcaac ttcacttata attgcagcca tcatattcat   2040
agcctcggca aaccacaaag tcacaccaac aactgcaatc atacaagatg caacaagcca   2100
gatcaagaac acaaccccaa catacctcac ccagaatcct cagcttggaa tcagtccctc   2160
taatccgtct gaaattacat cacaaatcac caccatacta gcttcaacaa caccaggagt   2220
caagtcaacc ctgcaatcca caacagtcaa gaccaaaaac acaacaacaa ctcaaacaca   2280
acccagcaag cccaccacaa aacaacgcca aaacaaacca ccaagcaaac ccaataatga   2340
ttttcacttt gaagtgttca actttgtacc ctgcagcata tgcagcaaca atccaacctg   2400
ctgggctatc tgcaaaagaa taccaaacaa aaaaccagga aagaaaacca ctaccaagcc   2460
cacaaaaaaa ccaaccctca agacaaccaa aaaagatccc aaacctcaaa ccactaaatc   2520
aaaggaagta cccaccacca agcccacaga agagccaacc atcaacacca ccaaaacaaa   2580
catcataact acactactca cctccaacac cacaggaaat ccagaactca caagtcaaat   2640
ggaaaccttc cactcaactt cctccgaagg caatccaagc ccttctcaag tctctacaac   2700
atccgagtac ccatcacaac cttcatctcc acccaacaca ccacgccagt agttaataaa   2760
aaatggggca aatactcgag ttagagatgg acacaaccca caatgataat acaccacaaa   2820
gactgatgat cacagacatg agaccgttgt cacttgagac cataataaca tcactaacca   2880
gagacatcat aacacacaaa tttatatact tgataaatca tgaatgcata gtgagaaaac   2940
ttgatgaaag acaggccaca tttacattcc tggtcaacta tgaaatgaaa ctattacaca   3000
```

```
aagtaggaag cactaaatat aaaaaatata ctgaatacaa cacaaaatat ggcactttcc   3060
ctatgccaat attcatcaat catgatgggt tcttagaatg cattggcatt aagcctacaa   3120
agcatactcc cataatatac aagtatgatc tcaatccata aatttcaaca caatattcac   3180
acaatctaaa acaacaactc tatgcataac tatactccat agtccagatg gagcctgaaa   3240
attatagtaa tttaaaactt aaggagagat ataagataga agatggggca aatacaacca   3300
tggctcttag caaagtcaag ttgaatgata cactcaacaa agatcaactt ctgtcatcca   3360
gcaaatacac catccaacgg agcacaggag atagtattga tactcctaat tatgatgtgc   3420
agaaacacat caataagtta tgtggcatgt tattaatcac agaagatgct aatcataaat   3480
tcactgggtt aataggtatg ttatatgcga tgtctaggtt aggaagagaa gacaccataa   3540
aaatactcag agatgcggga tatcatgtaa aagcaaatgg agtagatgta acaacacatc   3600
gtcaagacat taatggaaaa gaaatgaaat ttgaagtgtt aacattggca agcttaacaa   3660
ctgaaattca aatcaacatt gagatagaat ctagaaaatc ctacaaaaaa atgctaaaag   3720
aaatgggaga ggtagctcca gaatacaggc atgactctcc tgattgtggg atgataatat   3780
tatgtatagc agcattagta ataactaaat tagcagcagg ggacagatct ggtcttacag   3840
ccgtgattag gagagctaat aatgtcctaa aaaatgaaat gaaacgttac aaaggcttac   3900
tacccaagga catagccaac agcttctatg aagtgtttga aaaacatccc cactttatag   3960
atgtttttgt tcattttggt atagcacaat cttctaccag aggtggcagt agagttgaag   4020
ggatttttgc aggattgttt atgaatgcct atggtgcagg gcaagtgatg ttacggtggg   4080
gagtcttagc aaaatcggtt aaaaatatta tgttaggaca tgctagtgtg caagcagaaa   4140
tggaacaagt tgttgaggtt tatgaatatg cccaaaaatt gggtggtgaa gcaggattct   4200
accatatatt gaacaaccca aaagcatcat tattatcttt gactcaattt cctcacttct   4260
ccagtgtagt attaggcaat gctgctggcc taggcataat gggagagtac agaggtacac   4320
cgaggaatca agatctatat gatgcagcaa aggcatatgc tgaacaactc aaagaaaatg   4380
gtgtgattaa ctacagtgta ctagacttga cagcagaaga actagaggct atcaaacatc   4440
agcttaatcc aaaagataat gatgtagagc tttgagttaa taaaaaatgg ggcaaataaa   4500
tcatcatgga aaagtttgct cctgaattcc atggagaaga tgcaaacaac agggctacta   4560
aattcctaga atcaataaag ggcaaattca catcacccaa agatcccaag aaaaaagata   4620
gtatcatatc tgtcaactca atagatatag aagtaaccaa agaaagccct ataacatcaa   4680
attcaactat tatcaaccca acaaatgaga cagatgatac tgcagggaac aagcccaatt   4740
atcaaagaaa acctctagta agtttcaaag aagaccctac accaagtgat aatccctttt   4800
ctaaactata caaagaaacc atagaaacat ttgataacaa tgaagaagaa tccagctatt   4860
catacgaaga aataaatgat cagacaaacg ataatataac agcaagatta gataggattg   4920
atgaaaaatt aagtgaaata ctaggaatgc ttcacacatt agtagtggca agtgcaggac   4980
ctacatctgc tcgggatggt ataagagatg ccatggttgg tttaagagaa gaaatgatag   5040
aaaaaatcag aactgaagca ttaatgacca atgacagatt agaagctatg gcaagactca   5100
ggaatgagga aagtgaaaag atggcaaaag acacatcaga tgaagtgtct ctcaatccaa   5160
catcagagaa attgaacaac ctattggaag ggaatgatag tgacaatgat ctatcacttg   5220
aagatttctg attagttacc aatcttcaca tcaacacaca ataccaacag aagaccaaca   5280
aactaaccaa cccaatcatc caaccaaaca tccatccgcc aatcagccaa acagccaaca   5340
```

aaacaaccag ccaatccaaa actaaccacc cggaaaaaat ctataatata gttacaaaaa 5400
aaggaaaggg tggggcaaat atggaaacat acgtgaacaa gcttcacgaa ggctccacat 5460
acacagctgc tgttcaatac aatgtcttag aaaaagacga tgaccctgca tcacttacaa 5520
tatgggtgcc catgttccaa tcatctatgc cagcagattt acttataaaa gaactagcta 5580
atgtcaacat actagtgaaa caaatatcca cacccaaggg accttcacta agagtcatga 5640
taaactcaag aagtgcagtg ctagcacaaa tgcccagcaa atttaccata tgcgctaatg 5700
tgtccttgga tgaaagaagc aaactagcat atgatgtaac cacaccctgt gaaatcaagg 5760
catgtagtct aacatgccta aaatcaaaaa atatgttgac tacagttaaa gatctcacta 5820
tgaagacact caaccctaca catgatatta ttgctttatg tgaatttgaa aacatagtaa 5880
catcaaaaaa agtcataata ccaacatacc taagatccat cagtgtcaga aataaagatc 5940
tgaacacact tgaaaatata acaaccactg aattcaaaaa tgctatcaca aatgcaaaaa 6000
tcatccctta ctcaggatta ctattagtca tcacagtgac tgacaacaaa ggagcattca 6060
aatacataaa gccacaaagt caattcatag tagatcttgg agcttaccta gaaaaagaaa 6120
gtatatatta tgttaccaca aattggaagc acacagctac acgatttgca atcaaaccca 6180
tggaagatta accttttcc tctacatcag tgtgttaatt catacaaact ttctacctac 6240
attcttcact tcaccatcac aatcacaaac actctgtggt tcaaccaatc aaacaaaact 6300
tatctgaagt cccagatcat cccaagtcat tgtttatcag atctagtact caaataagtt 6360
aataaaaaat atacacatgg ggcaaataat cattggagga aatccaacta atcacaatat 6420
ctgttaacat agacaagtcc acacaccata cagaatcaac caatggaaaa tacatccata 6480
acaatagaat tctcaagcaa attctggcct tactttacac taatacacat gatcacaaca 6540
ataatctctt tgctaatcat aatctccatc atgattgcaa tactaaacaa actttgtgaa 6600
tataacgtat tccataacaa aacctttgag ttaccaagag ctcgagttaa tacttgataa 6660
agtagttaat taaaaacaca attgcatgcc agattaactt accatctgta aaaatgaaaa 6720
ctggggcaaa tatgtcacga aggaatcctt gcaaatttga aattcgaggt cattgcttaa 6780
atggtaagag gtgtcatttt agtcataatt attttgaatg gccaccccat gcactgcttg 6840
taagacaaaa ctttatgtta aacagaatac ttaagtctat ggataaaagt atagatacct 6900
tatcagaaat aagtggagct gcagagttgg acagaacaga agagtatgct cttggtgtag 6960
ttggagtgct agagagttat ataggatcaa taaacaatat aactaaacaa tcagcatgtg 7020
ttgccatgag caaactcctc actgaactca atagtgatga tatcaaaaag ctgagggaca 7080
atgaagagct aaattcaccc aagataagag tgtacaatac tgtcatatca tatattgaaa 7140
gcaacaggaa aaacaataaa caaactatcc atctgttaaa aagattgcca gcagacgtat 7200
tgaagaaaac catcaaaaac acattggata tccataagag cataaccatc aacaacccaa 7260
aagaatcaac tgttagtgat acaaatgacc atgccaaaaa taatgatact acctgacaaa 7320
tatccttgta gtataacttc catactaata acaagtagat gtagagttac tatgtataat 7380
caaaagaaca cactatattt caatcaaaac aacccaaata accatatgta ctcaccgaat 7440
caaacattca atgaaatcca ttggacctct caagaattga ttgacacaat tcaaaatttt 7500
ctacaacatc taggtattat tgaggatata tatacaatat atatattagt gtcataacac 7560
tcaattctaa cactcaccac atcgttacat tattaattca aacaattcaa gttgtgggac 7620
aaaatggatc ccattattaa tggaaattct gctaatgttt atctaaccga tagttattta 7680
aaaggtgtta tctctttctc agagtgtaat gctttaggaa gttacatatt caatggtcct 7740

```
tatctcaaaa atgattatac caacttaatt agtagacaaa atccattaat agaacacatg   7800
aatctaaaga aactaaatat aacacagtcc ttaatatcta agtatcataa aggtgaaata   7860
aaattagaag aacctactta ttttcagtca ttacttatga catacaagag tatgacctcg   7920
tcagaacaga ttgctaccac taatttactt aaaaagataa taagaagagc tatagaaata   7980
agtgatgtca aagtctatgc tatattgaat aaactagggc ttaaagaaaa ggacaagatt   8040
aaatccaaca atggacaaga tgaagacaac tcagttatta cgaccataat caaagatgat   8100
atactttcag ctgttaaaga taatcaatct catcttaaag cagacaaaaa tcactctaca   8160
aaacaaaaag acacaatcaa aacaacactc ttgaagaaat tgatgtgttc aatgcaacat   8220
cctccatcat ggttaataca ttggtttaac ttatacacaa aattaaacaa catattaaca   8280
cagtatcgat caaatgaggt aaaaaaccat gggtttacat tgatagataa tcaaactctt   8340
agtggatttc aatttatttt gaaccaatat ggttgtatag tttatcataa ggaactcaaa   8400
agaattactg tgacaaccta taatcaattc ttgacatgga aagatattag ccttagtaga   8460
ttaaatgttt gtttaattac atggattagt aactgcttga acacattaaa taaaagctta   8520
ggcttaagat gcggattcaa taatgttatc ttgacacaac tattccttta tggagattgt   8580
atactaaagc tatttcacaa tgaggggttc tacataataa aagaggtaga gggatttatt   8640
atgtctctaa ttttaaatat aacagaagaa gatcaattca gaaaacgatt ttataatagt   8700
atgctcaaca acatcacaga tgctgctaat aaagctcaga aaaatctgct atcaagagta   8760
tgtcatacat tattagataa gacagtgtcc gataatataa taaatggcag atggataatt   8820
ctattaagta agttccttaa attaattaag cttgcaggtg acaataacct taacaatctg   8880
agtgaactat atttttgttt cagaatattt ggacacccaa tggtagatga aagacaagcc   8940
atggatgctg ttaaaattaa ttgcaatgag accaaatttt acttgttaag cagtctgagt   9000
atgttaagag gtgcctttat atatagaatt ataaaagggt ttgtaaataa ttacaacaga   9060
tggcctactt taagaaatgc tattgtttta cccttaagat ggttaactta ctataaacta   9120
aacacttatc cttctttgtt ggaacttaca gaaagagatt tgattgtgtt atcaggacta   9180
cgtttctatc gtgagtttcg gttgcctaaa aaagtggatc ttgaaatgat tataaatgat   9240
aaagctatat cacctcctaa aaatttgata tggactagtt tccctagaaa ttacatgcca   9300
tcacacatac aaaactatat agaacatgaa aaattaaaat tttccgagag tgataaatca   9360
agaagagtat tagagtatta tttaagagat aacaaattca atgaatgtga tttatacaac   9420
tgtgtagtta atcaaagtta tctcaacaac cctaatcatg tggtatcatt gacaggcaaa   9480
gaaagagaac tcagtgtagg tagaatgttt gcaatgcaac cgggaatgtt cagacaggtt   9540
caaatattgg cagagaaaat gatagctgaa aacattttac aattctttcc tgaaagtctt   9600
acaagatatg gtgatctaga actacaaaaa atattagaac tgaaagcagg aataagtaac   9660
aaatcaaatc gctacaatga taattacaac aattacatta gtaagtgctc tatcatcaca   9720
gatctcagca aattcaatca agcatttcga tatgaaacgt catgtatttg tagtgatgtg   9780
ctggatgaac tgcatggtgt acaatctcta ttttcctggt tacatttaac tattcctcat   9840
gtcacaataa tatgcacata taggcatgca cccccctata taggagatca tattgtagat   9900
cttaacaatg tagatgaaca aagtggatta tatagatatc acatgggtgg catcgaaggg   9960
tggtgtcaaa aactatggac catagaagct atatcactat tggatctaat atctctcaaa  10020
gggaaattct caattactgc tttaattaat ggtgacaatc aatcaataga tataagcaaa  10080
```

ccaatcagac tcatggaagg tcaaactcat gctcaagcag attatttgct agcattaaat 10140
agccttaaat tactgtataa agagtatgca ggcataggcc acaaattaaa aggaactgag 10200
acttatatat cacgagatat gcaatttatg agtaaaacaa ttcaacataa cggtgtatat 10260
tacccagcta gtataaagaa agtcctaaga gtgggaccgt ggataaacac tatacttgat 10320
gatttcaaag tgagtctaga atctataggt agtttgacac aagaattaga atatagaggt 10380
gaaagtctat tatgcagttt aatatttaga aatgtatggt tatataatca gattgctcta 10440
caattaaaaa atcatgcatt atgtaacaat aaactatatt tggacatatt aaaggttctg 10500
aaacacttaa aaaccttttt taatcttgat aatattgata cagcattaac attgtatatg 10560
aatttaccca tgttatttgg tggtggtgat cccaacttgt tatatcgaag tttctataga 10620
agaactcctg acttcctcac agaggctata gttcactctg tgttcatact tagttattat 10680
acaaaccatg acttaaaaga taaacttcaa gatctgtcag atgatagatt gaataagttc 10740
ttaacatgca taatcacgtt tgacaaaaac cctaatgctg aattcgtaac attgatgaga 10800
gatcctcaag ctttagggtc tgagagacaa gctaaaatta ctagcgaaat caatagactg 10860
gcagttacag aggttttgag tacagctcca aacaaaaatat tctccaaaag tgcacaacat 10920
tatactacta cagagataga tctaaatgat attatgcaaa atatagaacc tacatatcct 10980
catgggctaa gagttgttta tgaaagttta cccttttata aagcagagaa aatagtaaat 11040
cttatatcag gtacaaaatc tataactaac atactggaaa aaacttctgc catagactta 11100
acagatattg atagagccac tgagatgatg aggaaaaaca taactttgct tataaggata 11160
cttccattgg attgtaacag agataaaaga gagatattga gtatggaaaa cctaagtatt 11220
actgaattaa gcaaatatgt tagggaaaga tcttggtctt tatccaatat agttggtgtt 11280
acatcaccca gtatcatgta tacaatggac atcaaatata ctacaagcac tatatctagt 11340
ggcataatta tagagaaata taatgttaac agtttaacac gtggtgagag aggacccact 11400
aaaccatggg ttggttcatc tacacaagag aaaaaaacaa tgccagttta taatagacaa 11460
gtcttaacca aaaaacagag agatcaaata gatctattag caaaattgga ttgggtgtat 11520
gcatctatag ataacaagga tgaattcatg gaagaactcc tgggaaccct tgggttaaca 11580
tatgaaaagg ccaagaaatt atttccacaa tatttaagtg tcaattattt gcatcgcctt 11640
acagtcagta gtagaccatg tgaattccct gcatcaatac cagcttatag aacaacaaat 11700
tatcactttg acactagccc tattaatcgc atattaacag aaaagtatgg tgatgaagat 11760
attgacatag tattccaaaa ctgtataagc tttggcctta gtttaatgtc agtagtagaa 11820
caatttacta atgtatgtcc taacagaatt attctcatac ctaagcttaa tgagatacat 11880
ttgatgaaac ctcccatatt cacaggtgat gttgatattc acaagttaaa acaagtgata 11940
caaaaacagc atatgttttt accagacaaa ataagtttga ctcaatatgt ggaattattc 12000
ttaagtaata aaacactcaa atctggatct catgttaatt ctaatttaat attggcacat 12060
aaaatatctg actattttca taatacttac attttaagta ctaatttagc tggacattgg 12120
attctgatta tacaacttat gaaagattct aaaggtattt ttgaaaaaga ttggggagag 12180
ggatatataa ctgatcatat gtttattaat ttgaaagttt tcttcaatgc ttataagacc 12240
tatctcttgt gttttcataa aggttatggc aaagcaaagc tggagtgtga tatgaacact 12300
tcagatcttc tatgtgtatt ggaattaata gacagtagtt attggaagtc tatgtctaag 12360
gtatttttag aacaaaaagt tatcaaatac attcttagcc aagatgcaag tttacataga 12420
gtaaaaggat gtcatagctt caaattatgg tttcttaaac gtcttaatgt agcagaattc 12480
acagtttgcc cttgggttgt taacatagat tatcatccaa cacatatgaa agcaatatta 12540
acttatatag atcttgttag aatgggattg ataaatatag atagaataca cattaaaaat 12600
aaacacaaat tcaatgatga attttatact tctaatctct tctacattaa ttataacttc 12660
tcagataata ctcatctatt aactaaacat ataaggattg ctaattctga attagaaaat 12720
aattacaaca aattatatca tcctacacca gaaaccctag agaatatact agccaatccg 12780
attaaaagta atgacaaaaa gacactgaat gactattgta taggtaaaaa tgttgactca 12840
ataatgttac cattgttatc taataagaag cttattaaat cgtctgcaat gattagaacc 12900
aattacagca aacaagattt gtataattta ttccctatgg ttgtgattga tagaattata 12960
gatcattcag gcaatacagc caaatccaac caactttaca ctactacttc ccaccaaata 13020
tccttagtgc acaatagcac atcactttac tgcatgcttc cttggcatca tattaataga 13080
ttcaattttg tatttagttc tacaggttgt aaaattagta tagagtatat tttaaaagat 13140
cttaaaatta aagatcccaa ttgtatagca ttcataggtg aaggagcagg gaatttatta 13200
ttgcgtacag tagtggaact tcatcctgac ataagatata tttacagaag tctgaaagat 13260
tgcaatgatc atagtttacc tattgagttt ttaaggctgt acaatggaca tatcaacatt 13320
gattatggtg aaaatttgac cattcctgct acagatgcaa ccaacaacat tcattggtct 13380
tatttacata taaagtttgc tgaacctatc agtctttttg tctgtgatgc cgaattgtct 13440
gtaacagtca actggagtaa aattataata gaatggagca agcatgtaag aaagtgcaag 13500
tactgttcct cagttaataa atgtatgtta atagtaaaat atcatgctca agatgatatt 13560
gatttcaaat tagacaatat aactatatta aaaacttatg tatgcttagg cagtaagtta 13620
aagggatcgg aggtttactt agtccttaca ataggtcctg cgaatatatt cccagtattt 13680
aatgtagtac aaaatgctaa attgatacta tcaagaacca aaaatttcat catgcctaag 13740
aaagctgata aagagtctat tgatgcaaat attaaaagtt tgataccctt tctttgttac 13800
cctataacaa aaaaaggaat taatactgca ttgtcaaaac taaagagtgt tgttagtgga 13860
gatatactat catattctat agctggacgt aatgaagttt tcagcaataa acttataaat 13920
cataagcata tgaacatctt aaaatggttc aatcatgttt taaatttcag atcaacagaa 13980
ctaaactata accatttata tatggtagaa tctacatatc cttacctaag tgaattgtta 14040
aacagcttga caaccaatga acttaaaaaa ctgattaaaa tcacaggtag tctgttatac 14100
aactttcata atgaataatg aataaagatc ttataataaa aattcccata gctatacact 14160
aacactgtat tcaattatag ttattaaaaa ttaaaaatca tataattttt taaataactt 14220
ttagtgaact aatcctaaag ttatcatttt aatcttggag gaataaattt aaaccctaat 14280
ctaattggtt tatatgtgta ttaactaaat tacgagatat tagtttttga cacttttttt 14340
ctcgt 14345

<210> SEQ ID NO 11
<211> LENGTH: 14989
<212> TYPE: DNA
<213> ORGANISM: Artificial Sequence
<220> FEATURE:
<223> OTHER INFORMATION: Recombinant RSV sequence

<400> SEQUENCE: 11
acgggaaaaa atgcgtacaa caaacttgca taaaccaaaa aaatggggca aataagaatt 60
tgataagtac cacttaaatt taactccctt ggttagagat gggcagcaat tcattgagta 120

-continued

```
tgataaaagt tagattacaa aatttgtttg acaatgatga agtagcattg ttaaaaataa    180
catgctatac tgataaatta atacatttaa ctaatgcttt ggctaaggca gtgatacata    240
caatcaaatt gaatggcatt gtgtttgtgc atgttattac aagtagtgat atttgcccta    300
ataataatat tgtagtaaaa tccaatttca caacaatgcc agtactacaa aatggaggtt    360
atatatggga aatgatggaa ttaacacatt gctctcaacc taatggtcta ctagatgaca    420
attgtgaaat taaattctcc aaaaaactaa gtgattcaac aatgaccaat tatatgaatc    480
aattatctga attacttgga tttgatctta atccataaat tataattaat atcaactagc    540
aaatcaatgt cactaacacc attagttaat ataaaactta acagaagaca aaaatggggc    600
aaataaatca attcagccaa cccaaccatg gacacaaccc acaatgataa tacaccacaa    660
agactgatga tcacagacat gagaccgttg tcacttgaga ccataataac atcactaacc    720
agagacatca taacacacaa atttatatac ttgataaatc atgaatgcat agtgagaaga    780
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acactcaaca aagatcaact tctgtcatcc   1200
agcaaatacg ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
```

aattcaacta ttatcaaccc aacaaatgag acagatgata ctgcagggaa caagcccaat 2580
tatcaaagaa aacctctagt aagtttcaaa gaagacccta caccaagtga taatcccttt 2640
tctaaactat acaaagaaac catagaaaca tttgataaca atgaagaaga atccagctat 2700
tcatacgaag aaataaatga tcagacaaac gataatataa cagcaagatt agataggatt 2760
gatgaaaaat taagtgaaat actaggaatg cttcacacat tagtagtggc aagtgcagga 2820
cctacatctg ctcgggatgg tataagagat gccatggttg gtttaagaga agaaatgata 2880
gaaaaaatca gaactgaagc attaatgacc aatgacagat tagaagctat ggcaagactc 2940
aggaatgagg aaagtgaaaa gatggcaaaa gacacatcag atgaagtgtc tctcaatcca 3000
acatcagaga aattgaacaa cctattggaa gggaatgata gtgacaatga tctatcactt 3060
gaagatttct gattagttac caatcttcac atcaacacac aataccaaca gaagaccaac 3120
aaactaacca acccaatcat ccaaccaaac atccatccgc caatcagcca aacagccaac 3180
aaaacaacca gccaatccaa aactaaccac ccggaaaaaa tctataatat agttacaaaa 3240
aaaggaaagg gtggggcaaa tatggaaaca tacgtgaaca agcttcacga aggctccaca 3300
tacacagctg ctgttcaata caatgtctta gaaaaagacg atgaccctgc atcacttaca 3360
atatgggtgc ccatgttcca atcatctatg ccagcagatt tacttataaa agaactagct 3420
aatgtcaaca tactagtgaa acaaatatcc acacccaagg gaccttcact aagagtcatg 3480
ataaactcaa gaagtgcagt gctagcacaa atgcccagca aatttaccat atgcgctaat 3540
gtgtccttgg atgaaagaag caaactagca tatgatgtaa ccacaccctg tgaaatcaag 3600
gcatgtagtc taacatgcct aaaatcaaaa aatatgttga ctacagttaa agatctcact 3660
atgaagacac tcaaccctac acatgatatt attgctttat gtgaatttga aaacatagta 3720
acatcaaaaa aagtcataat accaacatac ctaagatcca tcagtgtcag aaataaagat 3780
ctgaacacac ttgaaaatat aacaaccact gaattcaaaa atgctatcac aaatgcaaaa 3840
atcatccctt actcaggatt actattagtc atcacagtga ctgacaacaa aggagcattc 3900
aaatacataa agccacaaag tcaattcata gtagatcttg gagcttacct agaaaaagaa 3960
agtatatatt atgttaccac aaattggaag cacacagcta cacgatttgc aatcaaaccc 4020
atggaagatt aacctttttc ctctacatca gtgtgttaat tcatacaaac tttctaccta 4080
cattcttcac ttcaccatca caatcacaaa cactctgtgg ttcaaccaat caaacaaaac 4140
ttatctgaag tcccagatca tcccaagtca ttgtttatca gatctagtac tcaaataagt 4200
taataaaaaa tatacacatg gggcaaataa tcattggagg aaatccaact aatcacaata 4260
tctgttaaca tagacaagtc cacacaccat acagaatcaa ccaatggaaa atacatccat 4320
aacaatagaa ttctcaagca aattctggcc ttactttaca ctaatacaca tgatcacaac 4380
aataatctct ttgctaatca taatctccat catgattgca atactaaaca aactttgtga 4440
atataacgta ttccataaca aaacctttga gttaccaaga gctcgagtca acacatagca 4500
ttcatcaatc caacagccca aaacagtaac cttgcattta aaaatgaaca acccctacct 4560
ctttacaaca cctcattaac atcccaccat gcaaaccact atccatacta taaagtagtt 4620
aattaaaaat agtcataaca atgaactagg atatcaagac taacaataac attggggcaa 4680
atgcaaacat gtccaaaaac aaggaccaac gcaccgctaa gacattagaa aggacctggg 4740
acactctcaa tcatttatta ttcatatcat cgtgcttata taagttaaat cttaaatctg 4800
tagcacaaat cacattatcc attctggcaa tgataatctc aacttcactt ataattgcag 4860

```
ccatcatatt catagcctcg gcaaaccaca aagtcacacc aacaactgca atcatacaag   4920
atgcaacaag ccagatcaag aacacaaccc caacatacct cacccagaat cctcagcttg   4980
gaatcagtcc ctctaatccg tctgaaatta catcacaaat caccaccata ctagcttcaa   5040
caacaccagg agtcaagtca accctgcaat ccacaacagt caagaccaaa aacacaacaa   5100
caactcaaac acaacccagc aagcccacca caaaacaacg ccaaaacaaa ccaccaagca   5160
aacccaataa tgattttcac tttgaagtgt tcaactttgt accctgcagc atatgcagca   5220
acaatccaac ctgctgggct atctgcaaaa gaataccaaa caaaaaacca ggaaagaaaa   5280
ccactaccaa gcccacaaaa aaaccaaccc tcaagacaac caaaaaagat cccaaacctc   5340
aaaccactaa atcaaaggaa gtacccacca ccaagcccac agaagagcca accatcaaca   5400
ccaccaaaac aaacatcata actacactac tcacctccaa caccacagga aatccagaac   5460
tcacaagtca aatggaaacc ttccactcaa cttcctccga aggcaatcca agcccttctc   5520
aagtctctac aacatccgag tacccatcac aaccttcatc tccacccaac acaccacgcc   5580
agtagttact taaaaacata ttatcacaaa aggccttgac caacttaaac agaatcaaaa   5640
taaactctgg ggcaaataac aatggagttg ctaatcctca aagcaaatgc aattaccaca   5700
atcctcactg cagtcacatt ttgttttgct tctggtcaaa acatcactga agaattttat   5760
caatcaacat gcagtgcagt tagcaaaggc tatcttagtg ctctgagaac tggttggtat   5820
accagtgtta taactataga attaagtaat atcaagaaaa ataagtgtaa tggaacagat   5880
gctaaggtaa aattgataaa acaagaatta gataaatata aaaatgctgt aacagaattg   5940
cagttgctca tgcaaagcac acaagcaaca aacaatcgag ccagaagaga actaccaagg   6000
tttatgaatt atacactcaa caatgccaaa aaaaccaatg taacattaag caagaaaagg   6060
aaaagaagat ttcttggttt tttgttaggt gttggatctg caatcgccag tggcgttgct   6120
gtatctaagg tcctgcacct agaaggggaa gtgaacaaga tcaaaagtgc tctactatcc   6180
acaaacaagg ctgtagtcag cttatcaaat ggagttagtg ttttaaccag caaagtgtta   6240
gacctcaaaa actatataga taaacaattg ttacctattg tgaacaagca aagctgcagc   6300
atatcaaata tagaaactgt gatagagttc caacaaaaga acaacagact actagagatt   6360
accagggaat ttagtgttaa tgcaggcgta actacacctg taagcactta catgttaact   6420
aatagtgaat tattgtcatt aatcaatgat atgcctataa caaatgatca gaaaaagtta   6480
atgtccaaca atgttcaaat agttagacag caaagttact ctatcatgtc cataataaaa   6540
gaggaagtct tagcatatgt agtacaatta ccactatatg gtgttataga tacaccctgt   6600
tggaaactac acacatcccc tctatgtaca accaacacaa aagaagggtc caacatctgt   6660
ttaacaagaa ctgacagagg atggtactgt gacaatgcag gatcagtatc tttcttccca   6720
caagctgaaa catgtaaagt tcaatcaaat cgagtatttt gtgacacaat gaacagttta   6780
acattaccaa gtgaagtaaa tctctgcaat gttgacatat tcaaccccaa atatgattgt   6840
aaaattatga cttcaaaaac agatgtaagc agctccgtta tcacatctct aggagccatt   6900
gtgtcatgct atggcaaaac taaatgtaca gcatccaata aaaatcgtgg aatcataaag   6960
acattttcta acgggtgcga ttatgtatca aataaagggg tggacactgt gtctgtaggt   7020
aacacattat attatgtaaa taagcaagaa ggtaaaagtc tctatgtaaa aggtgaacca   7080
ataataaatt tctatgaccc attagtattc ccctctgatg aatttgatgc atcaatatct   7140
caagtcaacg agaagattaa ccagagccta gcatttattc gtaaatccga tgaattatta   7200
cataatgtaa atgctggtaa atccaccaca aatatcatga taactactat aattatagtg   7260
```

```
attatagtaa tattgttatc attaattgct gttggactgc tcttatactg taaggccaga   7320
agcacaccag tcacactaag caaagatcaa ctgagtggta taaataatat tgcatttagt   7380
aactaaataa aaatagcacc taatcatgtt cttacaatgg tttactatct gctcatagac   7440
aacccatctg tcattggatt ttcttaaaat ctgaacttca tcgaaactct catctataaa   7500
ccatctcact tacactattt aagtagattc ctagtttata gttatataaa acacaattgc   7560
atgccagatt aacttaccat ctgtaaaaat gaaaactggg gcaaatatgt cacgaaggaa   7620
tccttgcaaa tttgaaattc gaggtcattg cttaaatggt aagaggtgtc attttagtca   7680
taattatttt gaatggccac cccatgcact gcttgtaaga caaaacttta tgttaaacag   7740
aatacttaag tctatggata aaagtataga taccttatca gaaataagtg gagctgcaga   7800
gttggacaga acagaagagt atgctcttgg tgtagttgga gtgctagaga gttatatagg   7860
atcaataaac aatataacta aacaatcagc atgtgttgcc atgagcaaac tcctcactga   7920
actcaatagt gatgatatca aaaagctgag ggacaatgaa gagctaaatt cacccaagat   7980
aagagtgtac aatactgtca tatcatatat tgaaagcaac aggaaaaaca ataaacaaac   8040
tatccatctg ttaaaaagat tgccagcaga cgtattgaag aaaaccatca aaaacacatt   8100
ggatatccat aagagcataa ccatcaacaa cccaaaagaa tcaactgtta gtgatacaaa   8160
tgaccatgcc aaaaataatg atactacctg acaaataagc ttcaattcta acactcacca   8220
catcgttaca ttattaattc aaacaattca agttgtggga caaaatggat cccattatta   8280
atggaaattc tgctaatgtt tatctaaccg atagttattt aaaaggtgtt atctctttct   8340
cagagtgtaa tgctttagga agttacatat tcaatggtcc ttatctcaaa aatgattata   8400
ccaacttaat tagtagacaa aatccattaa tagaacacat gaatctaaag aaactaaata   8460
taacacagtc cttaatatct aagtatcata aaggtgaaat aaaattagaa gaacctactt   8520
attttcagtc attacttatg acatacaaga gtatgacctc gtcagaacag attgctacca   8580
ctaatttact taaaaagata ataagaagag ctatagaaat aagtgatgtc aaagtctatg   8640
ctatattgaa taaactaggg cttaaagaaa aggacaagat taaatccaac aatggacaag   8700
atgaagacaa ctcagttatt acgaccataa tcaaagatga tatactttca gctgttaaag   8760
ataatcaatc tcatcttaaa gcagacaaaa atcactctac aaaacaaaaa gacacaatca   8820
aaacaacact cttgaagaaa ttgatgtgtt caatgcaaca tcctccatca tggttaatac   8880
attggtttaa cttatacaca aaattaaaca acatattaac acagtatcga tcaaatgagg   8940
taaaaaacca tgggtttaca ttgatagata atcaaactct tagtggattt caatttattt   9000
tgaaccaata tggttgtata gtttatcata aggaactcaa aagaattact gtgacaacct   9060
ataatcaatt cttgacatgg aaagatatta gccttagtag attaaatgtt tgtttaatta   9120
catggattag taactgcttg aacacattaa ataaaagctt aggcttaaga tgcggattca   9180
ataatgttat cttgacacaa ctattccttt atggagattg tatactaaag ctatttcaca   9240
atgaggggtt ctacataata aaagaggtag agggatttat tatgtctcta attttaaata   9300
taacagaaga agatcaattc agaaaacgat tttataatag tatgctcaac aacatcacag   9360
atgctgctaa taaagctcag aaaaatctgc tatcaagagt atgtcataca ttattagata   9420
agacagtgtc cgataatata ataaatggca gatggataat tctattaagt aagttcctta   9480
aattaattaa gcttgcaggt gacaataacc ttaacaatct gagtgaacta tattttttgt   9540
tcagaatatt tggacaccca atggtagatg aaagacaagc catggatgct gttaaaatta   9600
```

attgcaatga gaccaaattt tacttgttaa gcagtctgag tatgttaaga ggtgccttta 9660
tatatagaat tataaaaggg tttgtaaata attacaacag atggcctact ttaagaaatg 9720
ctattgtttt acccttaaga tggttaactt actataaact aaacacttat ccttctttgt 9780
tggaacttac agaaagagat ttgattgtgt tatcaggact acgtttctat cgtgagtttc 9840
ggttgcctaa aaaagtggat cttgaaatga ttataaatga taaagctata tcacctccta 9900
aaaatttgat atggactagt ttccctagaa attacatgcc atcacacata caaaactata 9960
tagaacatga aaaattaaaa ttttccgaga gtgataaatc aagaagagta ttagagtatt 10020
atttaagaga taacaaattc aatgaatgtg atttatacaa ctgtgtagtt aatcaaagtt 10080
atctcaacaa ccctaatcat gtggtatcat tgacaggcaa agaaagagaa ctcagtgtag 10140
gtagaatgtt tgcaatgcaa ccgggaatgt tcagacaggt tcaaatattg gcagagaaaa 10200
tgatagctga aaacatttta caattctttc ctgaaagtct tacaagatat ggtgatctag 10260
aactacaaaa aatattagaa ctgaaagcag gaataagtaa caaatcaaat cgctacaatg 10320
ataattacaa caattacatt agtaagtgct ctatcatcac agatctcagc aaattcaatc 10380
aagcatttcg atatgaaacg tcatgtattt gtagtgatgt gctggatgaa ctgcatggtg 10440
tacaatctct attttcctgg ttacatttaa ctattcctca tgtcacaata atatgcacat 10500
ataggcatgc accccctat ataggagatc atattgtaga tcttaacaat gtagatgaac 10560
aaagtggatt atatagatat cacatgggtg gcatcgaagg gtggtgtcaa aaactatgga 10620
ccatagaagc tatatcacta ttggatctaa tatctctcaa agggaaattc tcaattactg 10680
ctttaattaa tggtgacaat caatcaatag atataagcaa accaatcaga ctcatggaag 10740
gtcaaactca tgctcaagca gattatttgc tagcattaaa tagccttaaa ttactgtata 10800
aagagtatgc aggcataggc cacaaattaa aaggaactga gacttatata tcacgagata 10860
tgcaatttat gagtaaaaca attcaacata acggtgtata ttacccagct agtataaaga 10920
aagtcctaag agtgggaccg tggataaaca ctatacttga tgatttcaaa gtgagtctag 10980
aatctatagg tagtttgaca caagaattag aatatagagg tgaaagtcta ttatgcagtt 11040
taatatttag aaatgtatgg ttatataatc agattgctct acaattaaaa aatcatgcat 11100
tatgtaacaa taaactatat ttggacatat taaaggttct gaaacactta aaaacctttt 11160
ttaatcttga taatattgat acagcattaa cattgtatat gaatttaccc atgttatttg 11220
gtggtggtga tcccaacttg ttatatcgaa gtttctatag aagaactcct gacttcctca 11280
cagaggctat agttcactct gtgttcatac ttagttatta tacaaaccat gacttaaaag 11340
ataaacttca agatctgtca gatgatagat tgaataagtt cttaacatgc ataatcacgt 11400
ttgacaaaaa ccctaatgct gaattcgtaa cattgatgag agatcctcaa gctttagggt 11460
ctgagagaca agctaaaatt actagcgaaa tcaatagact ggcagttaca gaggttttga 11520
gtacagctcc aaacaaaata ttctccaaaa gtgcacaaca ttatactact acagagatag 11580
atctaaatga tattatgcaa aatatagaac ctacatatcc tcatgggcta agagttgttt 11640
atgaaagttt acccttttat aaagcagaga aaatagtaaa tcttatatca ggtacaaaat 11700
ctataactaa catactggaa aaaacttctg ccatagactt aacagatatt gatagagcca 11760
ctgagatgat gaggaaaaac ataactttgc ttataaggat acttccattg gattgtaaca 11820
gagataaaag agagatattg agtatggaaa acctaagtat tactgaatta agcaaatatg 11880
ttagggaaag atcttggtct ttatccaata tagttggtgt tacatcaccc agtatcatgt 11940
atacaatgga catcaaatat actacaagca ctatatctag tggcataatt atagagaaat 12000
ataatgttaa cagtttaaca cgtggtgaga gaggacccac taaaccatgg gttggttcat 12060
ctacacaaga gaaaaaaaca atgccagttt ataatagaca agtcttaacc aaaaaacaga 12120
gagatcaaat agatctatta gcaaaattgg attgggtgta tgcatctata gataacaagg 12180
atgaattcat ggaagaactc agcataggaa cccttgggtt aacatatgaa aaggccaaga 12240
aattatttcc acaatattta agtgtcaatt atttgcatcg ccttacagtc agtagtagac 12300
catgtgaatt ccctgcatca ataccagctt atagaacaac aaattatcac tttgacacta 12360
gccctattaa tcgcatatta acagaaaagt atggtgatga agatattgac atagtattcc 12420
aaaactgtat aagctttggc cttagtttaa tgtcagtagt agaacaattt actaatgtat 12480
gtcctaacag aattattctc atacctaagc ttaatgagat acatttgatg aaacctccca 12540
tattcacagg tgatgttgat attcacaagt taaaacaagt gatacaaaaa cagcatatgt 12600
ttttaccaga caaaataagt ttgactcaat atgtggaatt attcttaagt aataaaacac 12660
tcaaatctgg atctcatgtt aattctaatt taatattggc acataaaata tctgactatt 12720
ttcataatac ttacatttta agtactaatt tagctggaca ttggattctg attatacaac 12780
ttatgaaaga ttctaaaggt atttttgaaa aagattgggg agagggatat ataactgatc 12840
atatgtttat taatttgaaa gtttcttca atgcttataa gacctatctc ttgtgttttc 12900
ataaaggtta tggcaaagca aagctggagt gtgatatgaa cacttcagat cttctatgtg 12960
tattggaatt aatagacagt agttattgga agtctatgtc taaggtattt ttagaacaaa 13020
aagttatcaa atacattctt agccaagatg caagtttaca tagagtaaaa ggatgtcata 13080
gcttcaaatt atggtttctt aaacgtctta atgtagcaga attcacagtt tgcccttggg 13140
ttgttaacat agattatcat ccaacacata tgaaagcaat attaacttat atagatcttg 13200
ttagaatggg attgataaat atagatagaa tacacattaa aaataaacac aaattcaatg 13260
atgaatttta tacttctaat ctcttctaca ttaattataa cttctcagat aatactcatc 13320
tattaactaa acatataagg attgctaatt ctgaattaga aaataattac aacaaattat 13380
atcatcctac accagaaacc ctagagaata tactagccaa tccgattaaa agtaatgaca 13440
aaaagacact gaatgactat tgtataggta aaaatgttga ctcaataatg ttaccattgt 13500
tatctaataa gaagcttatt aaatcgtctg caatgattag aaccaattac agcaaacaag 13560
atttgtataa tttattccct atggttgtga ttgatagaat tatagatcat tcaggcaata 13620
cagccaaatc caaccaactt tacactacta cttcccacca aatatcctta gtgcacaata 13680
gcacatcact ttactgcatg cttccttggc atcatattaa tagattcaat tttgtattta 13740
gttctacagg ttgtaaaatt agtatagagt atattttaaa agatcttaaa attaaagatc 13800
ccaattgtat agcattcata ggtgaaggag cagggaattt attattgcgt acagtagtgg 13860
aacttcatcc tgacataaga tatatttaca gaagtctgaa agattgcaat gatcatagtt 13920
tacctattga gtttttaagg ctgtacaatg gacatatcaa cattgattat ggtgaaaatt 13980
tgaccattcc tgctacagat gcaaccaaca acattcattg gtcttattta catataaagt 14040
ttgctgaacc tatcagtctt tttgtctgtg atgccgaatt gtctgtaaca gtcaactgga 14100
gtaaaattat aatagaatgg agcaagcatg taagaaagtg caagtactgt tcctcagtta 14160
ataaatgtat gttaatagta aaatatcatg ctcaagatga tattgatttc aaattagaca 14220
atataactat attaaaaact tatgtatgct taggcagtaa gttaaaggga tcggaggttt 14280
acttagtcct tacaataggt cctgcgaata tattcccagt atttaatgta gtacaaaatg 14340

```
ctaaattgat actatcaaga accaaaaatt tcatcatgcc taagaaagct gataaagagt  14400

ctattgatgc aaatattaaa agtttgatac cctttctttg ttaccctata acaaaaaaag  14460

gaattaatac tgcattgtca aaactaaaga gtgttgttag tggagatata ctatcatatt  14520

ctatagctgg acgtaatgaa gttttcagca ataaacttat aaatcataag catatgaaca  14580

tcttaaaatg gttcaatcat gttttaaatt tcagatcaac agaactaaac tataaccatt  14640

tatatatggt agaatctaca tatccttacc taagtgaatt gttaaacagc ttgacaacca  14700

atgaacttaa aaaactgatt aaaatcacag gtagtctgtt atacaacttt cataatgaat  14760

aatgaataaa gatcttataa taaaaattcc catagctata cactaacact gtattcaatt  14820

atagttatta aaaattaaaa atcatataat tttttaaata acttttagtg aactaatcct  14880

aaagttatca ttttaatctt ggaggaataa atttaaaccc taatctaatt ggtttatatg  14940

tgtattaact aaattacgag atattagttt ttgacacttt ttttctcgt              14989
```

<210> SEQ ID NO 12
<211> LENGTH: 14988
<212> TYPE: DNA
<213> ORGANISM: Artificial Sequence
<220> FEATURE:
<223> OTHER INFORMATION: Recombinant RSV sequence

<400> SEQUENCE: 12

```
acgggaaaaa atgcgtacaa caaacttgca taaaccaaaa aaatggggca aataagaatt     60

tgataagtac cacttaaatt taactccctt ggttagagat gggcagcaat tcattgagta    120

tgataaaagt tagattacaa aatttgtttg acaatgatga agtagcattg ttaaaaataa    180

catgctatac tgataaatta atacatttaa ctaatgcttt ggctaaggca gtgatacata    240

caatcaaatt gaatggcatt gtgtttgtgc atgttattac aagtagtgat atttgcccta    300

ataataatat tgtagtaaaa tccaatttca caacaatgcc agtactacaa aatggaggtt    360

atatatggga aatgatggaa ttaacacatt gctctcaacc taacggtcta ctagatgaca    420

attgtgaaat taaattctcc aaaaaactaa gtgattcaac aatgaccaat tatatgaatc    480

aattatctga attacttgga tttgatctta atccataaat tataattaat atcaactagc    540

aaatcaatgt cactaacacc attagttaat ataaaactta acagaagaca aaaatggggc    600

aaataaatca attcagccaa cccaaccatg gacacaaccc acaatgataa tacaccacaa    660

agactgatga tcacagacat gagaccgttg tcacttgaga ccataataac atcactaacc    720

agagacatca taacacacaa atttatatac ttgataaatc atgaatgcat agtgagaaga    780

cttgatgaaa gacaggccac atttacattc ctggtcaact atgaaatgaa actattacac    840

aaagtaggaa gcactaaata taaaaaatat actgaataca acacaaaata tggcactttc    900

cctatgccaa tattcatcaa tcatgatggg ttcttagaat gcattggcat taagcctaca    960

aagcatactc ccataatata caagtatgat ctcaatccat aaatttcaac acaatattca   1020

cacaatctaa aacaacaact ctatgcataa ctatactcca tagtccagat ggagcctgaa   1080

aattatagta atttaaaatt aaggagagat ataagataga agatggggca aatacaaaga   1140

tggctcttag caaagtcaag ttgaatgata cactcaacaa ggatcaactt ctgtcatcca   1200

gcaaatacgc catccaacgg agcacaggag atagtattga tactcctaat tatgatgtgc   1260

agaaacacat caataagtta tgtggcatgt tattaatcac agaagatgct aatcataaat   1320

tcactgggtt aataggtatg ttatatgcga tgtctaggtt aggaagagaa gacaccataa   1380

aaatactcag agatgcggga tatcatgtaa aagcaaatgg agtagatgta acaacacatc   1440
```

```
gtcaagacat taatggaaaa gaaatgaaat ttgaagtgtt aacattggca agcttaacaa   1500
ctgaaattca aatcaacatt gagatagaat ctagaaaatc ctacaaaaaa atgctaaaag   1560
aaatgggaga ggtagctcca gaatacaggc atgactctcc tgattgtggg atgataatat   1620
tatgtatagc agcattagta ataactaaat tagcagcagg ggacagatct ggtcttacag   1680
ccgtgattag gagagctaat aatgtcctaa aaaatgaaat gaaacgttac aaaggcttac   1740
tacccaagga catagccaac agcttctatg aagtgtttga aaaacatccc cactttatag   1800
atgtttttgt tcattttggt atagcacaat cttctaccag aggtggcagt agagttgaag   1860
ggatttttgc aggattgttt atgaatgcct atggtgcagg gcaagtgatg ttacggtggg   1920
gagtcttagc aaaatcggtt aaaaatatta tgttaggaca tgctagtgtg caagcagaaa   1980
tggaacaagt tgttgaggtt tatgaatatg cccaaaaatt gggtggtgaa gcaggattct   2040
accatatatt gaacaaccca aaagcatcat tattatcttt gactcaattt cctcacttct   2100
ccagtgtagt attaggcaat gctgctggcc taggcataat gggagagtac agaggtacac   2160
cgaggaatca agatctatat gatgcagcaa aggcatatgc tgaacaactc aaagaaaatg   2220
gtgtgattaa ctacagtgta ctagacttga cagcagaaga actagaggct atcaaacatc   2280
agcttaatcc aaaagataat gatgtagagc tttgagttaa taaaaaatgg ggcaaataaa   2340
tcatcatgga aaagtttgct cctgaattcc atggagaaga tgcaaacaac agggctacta   2400
aattcctaga atcaataaag ggcaaattca catcacccaa agatcccaag aaaaaagata   2460
gtatcatatc tgtcaactca atagatatag aagtaaccaa agaaagccct ataacatcaa   2520
attcaactat tatcaaccca acaaatgaga cagatgatac tgcagggaac aagcccaatt   2580
atcaaagaaa acctctagta agtttcaaag aagaccctac accaagtgat aatccctttt   2640
ctaaactata caaagaaacc atagaaacat ttgataacaa tgaagaagaa tccagctatt   2700
catacgaaga aataaatgat cagacaaacg ataatataac agcaagatta gataggattg   2760
atgaaaaatt aagtgaaata ctaggaatgc ttcacacatt agtagtggca agtgcaggac   2820
ctacatctgc tcgggatggt ataagagatg ccatggttgg tttaagagaa gaaatgatag   2880
aaaaaatcag aactgaagca ttaatgacca atgacagatt agaagctatg gcaagactca   2940
ggaatgagga aagtgaaaag atggcaaaag acacatcaga tgaagtgtct ctcaatccaa   3000
catcagagaa attgaacaac ctattggaag ggaatgatag tgacaatgat ctatcacttg   3060
aagatttctg attagttacc aatcttcaca tcaacacaca ataccaacag aagaccaaca   3120
aactaaccaa cccaatcatc caaccaaaca tccatccgcc aatcagccaa acagccaaca   3180
aaacaaccag ccaatccaaa actaaccacc cggaaaaaat ctataatata gttacaaaaa   3240
aaggaaaggg tggggcaaat atggaaacat acgtgaacaa gcttcacgaa ggctccacat   3300
acacagctgc tgttcaatac aatgtcttag aaaaagacga tgaccctgca tcacttacaa   3360
tatgggtgcc catgttccaa tcatctatgc cagcagattt acttataaaa gaactagcta   3420
atgtcaacat actagtgaaa caaatatcca cacccaaggg accttcacta agagtcatga   3480
taaactcaag aagtgcagtg ctagcacaaa tgcccagcaa atttaccata tgcgctaatg   3540
tgtccttgga tgaaagaagc aaactagcat atgatgtaac cacaccctgt gaaatcaagg   3600
catgtagtct aacatgccta aaatcaaaaa atatgttgac tacagttaaa gatctcacta   3660
tgaagacact caaccctaca catgatatta ttgctttatg tgaatttgaa aacatagtaa   3720
catcaaaaaa agtcataata ccaacatacc taagatccat cagtgtcaga aataaagatc   3780
```

tgaacacact tgaaaatata acaaccactg aattcaaaaa tgctatcaca aatgcaaaaa 3840
tcatccctta ctcaggatta ctattagtca tcacagtgac tgacaacaaa ggagcattca 3900
aatacataaa gccacaaagt caattcatag tagatcttgg agcttaccta gaaaaagaaa 3960
gtatatatta tgttaccaca aattggaagc acacagctac acgatttgca atcaaaccca 4020
tggaagatta accttttcc tctacatcag tgtgttaatt catacaaact ttctacctac 4080
attcttcact tcaccatcac aatcacaaac actctgtggt tcaaccaatc aaacaaaact 4140
tatctgaagt cccagatcat cccaagtcat tgtttatcag atctagtact caaataagtt 4200
aataaaaaat atacacatgg ggcaaataat cattggagga aatccaacta atcacaatat 4260
ctgttaacat agacaagtcc acacaccata cagaatcaac caatggaaaa tacatccata 4320
acaatagaat tctcaagcaa attctggcct tactttacac taatacacat gatcacaaca 4380
ataatctctt tgctaatcat aatctccatc atgattgcaa tactaaacaa actttgtgaa 4440
tataacgtat tccataacaa aacctttgag ttaccaagag ctcgagtcaa cacatagcat 4500
tcatcaatcc aacagcccaa aacagtaacc ttgcatttaa aaatgaacaa cccctacctc 4560
tttacaacac ctcattaaca tcccaccatg caaaccacta tccatactat aaagtagtta 4620
attaaaaata gtcataacaa tgaactagga tatcaagact aacaataaca ttggggcaaa 4680
tgcaaacatg tccaaaaaca aggaccaacg caccgctaag acattagaaa ggacctggga 4740
cactctcaat catttattat tcatatcatc gtgcttatat aagttaaatc ttaaatctgt 4800
agcacaaatc acattatcca ttctggcaat gataatctca acttcactta taattgcagc 4860
catcatattc atagcctcgg caaaccacaa agtcacacca acaactgcaa tcatacaaga 4920
tgcaacaagc cagatcaaga acacaacccc aacatacctc acccagaatc ctcagcttgg 4980
aatcagtccc tctaatccgt ctgaaattac atcacaaatc accaccatac tagcttcaac 5040
aacaccagga gtcaagtcaa ccctgcaatc cacaacagtc aagaccaaaa acacaacaac 5100
aactcaaaca caacccagca agcccaccac aaaacaacgc caaaacaaac caccaagcaa 5160
acccaataat gattttcact ttgaagtgtt caactttgta ccctgcagca tatgcagcaa 5220
caatccaacc tgctgggcta tctgcaaaag aataccaaac aaaaaaccag gaaagaaaac 5280
cactaccaag cccacaaaaa aaccaaccct caagacaacc aaaaaagatc ccaaacctca 5340
aaccactaaa tcaaaggaag tacccaccac caagcccaca gaagagccaa ccatcaacac 5400
caccaaaaca aacatcataa ctacactact cacctccaac accacaggaa atccagaact 5460
cacaagtcaa atggaaacct tccactcaac ttcctccgaa ggcaatccaa gcccttctca 5520
agtctctaca acatccgagt acccatcaca accttcatct ccacccaaca caccacgcca 5580
gtagttactt aaaaacatat tatcacaaaa agccatgacc aacttaaaca gaatcaaagt 5640
aaactctggg gcaaataaca atggagttgc taatcctcaa agcaaatgca attaccacaa 5700
tcctcactgc agtcacattt tgttttgctt ctggtcaaaa catcactgaa gaattttatc 5760
aatcaacatg cagtgcagtt agcaaaggct atcttagtgc tctgagaact ggttggtata 5820
ccagtgttat aactatagaa ttaagtaata tcaagaaaaa taagtgtaat ggaacagatg 5880
ctaaggtaaa attgataaaa caagaattag ataaatataa aaatgctgta acagaattgc 5940
agttgctcat gcaaagcaca caagcaacaa acaatcgagc cagaagagaa ctaccaaggt 6000
ttatgaatta tacactcaac aatgccaaaa aaaccaatgt aacattaagc aagaaaagga 6060
aaagaagatt tcttggtttt ttgttaggtg ttggatctgc aatcgccagt ggcgttgctg 6120
tatctaaggt cctgcaccta gaaggggaag tgaacaagat caaaagtgct ctactatcca 6180
caaacaaggc tgtagtcagc ttatcaaatg gagtcagtgt cttaaccagc aaagtgttag 6240
acctcaaaaa ctatatagat aaacaattgt tacctattgt gaacaagcaa agctgcagca 6300
tatcaaatat agaaactgtg atagagttcc aacaaaagaa caacagacta ctagagatta 6360
ccagggaatt tagtgttaat gcaggtgtaa ctacacctgt aagcacttac atgttaacta 6420
atagtgaatt attgtcatta atcaatgata tgcctataac aaatgatcag aaaaagttaa 6480
tgtccaacaa tgttcaaata gttagacagc aaagttactc tatcatgtcc ataataaaag 6540
aggaagtctt agcatatgta gtacaattac cactatatgg tgttatagat acaccctgtt 6600
ggaaactaca cacatcccct ctatgtacaa ccaacacaaa agaagggtcc aacatctgtt 6660
taacaagaac tgacagagga tggtactgtg acaatgcagg atcagtatct ttcttcccac 6720
aagctgaaac atgtaaagtt caatcaaatc gagtattttg tgacacaatg aacagtttaa 6780
cattaccaag tgaagtaaat ctctgcaatg ttgacatatt caaccccaaa tatgattgta 6840
aaattatgac ttcaaaaaca gatgtaagca gctccgttat cacatctcta ggagccattg 6900
tgtcatgcta tggcaaaact aaatgtacag catccaataa aaatcgtgga atcataaaga 6960
cattttctaa cgggtgcgat tatgtatcaa ataaaggggt ggacactgtg tctgtaggta 7020
acacattata ttatgtaaat aagcaagaag gtaaaagtct ctatgtaaaa ggtgaaccaa 7080
taataaattt ctatgaccca ttagtattcc cctctgatga atttgatgca tcaatatctc 7140
aagtcaacga gaagattaac cagagcctag catttattcg taaatccgat gaattattac 7200
ataatgtaaa tgccggtaaa tccaccacaa atatcatgat aactactata attatagtga 7260
ttatagtaat attgttatca ttaattgctg ttggactgct cttatactgt aaggccagaa 7320
gcacaccagt cacactaagc aaagatcaac tgagtggtat aaataatatt gcatttagta 7380
actaaataaa aatagcacct aatcatgttc ttacaatggt ttactatctg ctcatagaca 7440
acccatctgt cattggattt tcttaaaatc tgaacttcat tgaaactctc atctataaac 7500
catctcactt acactattta agtagattcc tagtttatag ttatataaaa cacaattgaa 7560
tgccagatta acttaccatc tgtaaaaatg aaaactgggg caaatatgtc acgaaggaat 7620
ccttgcaaat ttgaaattcg aggtcattgc ttaaatggta agaggtgtca ttttagtcat 7680
aattattttg aatggccacc gcatgcactg cttgtaagac aaaactttat gttaaacaga 7740
atacttaagt ctatggataa aagtatagat accttatcag aaataagtgg agctgcagag 7800
ttggacagaa cagaagagta tgctcttggt gtagttggag tgctagagag ttatatagga 7860
tcaataaaca atataactaa acaatcagca tgtgttgcca tgagcaaact cctcactgaa 7920
ctcaatagtg atgatatcaa aaagctgagg gacaatgaag agctaaattc acccaagata 7980
agagtgtaca atactgtcat atcatatatt gaaagcaaca ggaaaaacaa taaacaaact 8040
atccatctgt taaaaagatt gccagcagac gtattgaaga aaaccatcaa aaacacattg 8100
gatatccata agagcataac catcaacaac ccaaaagaat caactgttag tgatacaaat 8160
gaccatgcca aaaataatga tactacctga caaataacgt tcaattctaa cactcaccac 8220
atcgttacat tattaattca aacaattcaa gttgtgggac aaaatggatc ccattattaa 8280
tggaaattct gctaatgttt atctaaccga tagttattta aaaggtgtta tctctttctc 8340
agagtgtaat gctttaggaa gttacatatt caatggtcct tatctcaaaa atgattatac 8400
caacttaatt agtagacaaa atccattaat agaacacatg aatctaaaga aactaaatat 8460
aacacagtcc ttaatatcta agtatcataa aggtgaaata aaattagaag aacctactta 8520

```
ttttcagtca ttacttatga catacaagag tatgacctcg tcagaacaga ttgctaccac   8580
taatttactt aaaaagataa taagaagagc tatagaaata agtgatgtca aagtctatgc   8640
tatattgaat aaactagggc ttaaagaaaa ggacaagatt aaatccaaca atggacaaga   8700
tgaagacaac tcagttatta cgaccataat caaagatgat atactttcag ctgttaaaga   8760
taatcaatct catcttaaag cagacaaaaa tcactctaca aaacaaaaag acacaatcaa   8820
aacaacactc ttgaagaaat tgatgtgttc aatgcaacat cctccatcat ggttaataca   8880
ttggtttaac ttatacacaa aattaaacaa catattaaca cagtatcgat caaatgaggt   8940
aaaaaaccat gggtttacat tgatagataa tcaaactctt agtggatttc aatttatttt   9000
gaaccaatat ggttgtatag tttatcataa ggaactcaaa agaattactg tgacaaccta   9060
taatcaattc ttgacatgga aagatattag ccttagtaga ttaaatgttt gtttaattac   9120
atggattagt aactgcttga acacattaaa taaaagctta ggcttaagat gcggattcaa   9180
taatgttatc ttgacacaac tattccttta tggagattgt atactaaagc tatttcacaa   9240
tgaggggttc tacataataa aagaggtaga gggatttatt atgtctctaa ttttaaatat   9300
aacagaagaa gatcaattca gaaaacgatt ttataatagt atgctcaaca acatcacaga   9360
tgctgctaat aaagctcaga aaaatctgct atcaagagta tgtcatacat tattagataa   9420
gacagtgtcc gataatataa taaatggcag atggataatt ctattaagta agttccttaa   9480
attaattaag cttgcaggtg acaataacct taacaatctg agtgaactat atttttgtt   9540
cagaatattt ggacacccaa tggtagatga aagacaagcc atggatgctg ttaaaattaa   9600
ttgcaatgag accaaatttt acttgttaag cagtctgagt atgttaagag gtgcctttat   9660
atatagaatt ataaaagggt ttgtaaataa ttacaacaga tggcctactt taagaaatgc   9720
tattgtttta cccttaagat ggttaactta ctataaacta aacacttatc cttctttgtt   9780
ggaacttaca gaaagagatt tgattgtgtt atcaggacta cgtttctatc gtgagtttcg   9840
gttgcctaaa aaagtggatc ttgaaatgat tataaatgat aaagctatat cacctcctaa   9900
aaatttgata tggactagtt tccctagaaa ttacatgcca tcacacatac aaaactatat   9960
agaacatgaa aaattaaaat tttccgagag tgataaatca agaagagtat tagagtatta  10020
tttaagagat aacaaattca atgaatgtga tttatacaac tgtgtagtta atcaaagtta  10080
tctcaacaac cctaatcatg tggtatcatt gacaggcaaa gaaagagaac tcagtgtagg  10140
tagaatgttt gcaatgcaac cgggaatgtt cagacaggtt caaatattgg cagagaaaat  10200
gatagctgaa aacattttac aattctttcc tgaaagtctt acaagatatg gtgatctaga  10260
actacaaaaa atattagaat tgaaagcagg aataagtaac aaatcaaatc gctacaatga  10320
taattacaac aattacatta gtaagtgctc tatcatcaca gatctcagca aattcaatca  10380
agcatttcga tatgaaacgt catgtatttg tagtgatgtg ctggatgaac tgcatggtgt  10440
acaatctcta ttttcctggt tacatttaac tattcctcat gtcacaataa tatgcacata  10500
taggcatgca ccccccctata taggagatca tattgtagat cttaacaatg tagatgaaca  10560
aagtggatta tatagatatc acatgggtgg catcgaaggg tggtgtcaaa aactatggac  10620
catagaagct atatcactat tggatctaat atctctcaaa gggaaattct caattactgc  10680
tttaattaat ggtgacaatc aatcaataga tataagcaaa ccaatcagac tcatggaagg  10740
tcaaactcat gctcaagcag attatttgct agcattaaat agccttaaat tactgtataa  10800
agagtatgca ggcataggcc acaaattaaa aggaactgag acttatatat cacgagatat  10860
gcaatttatg agtaaaacaa ttcaacataa cggtgtatat tacccagcta gtataaagaa  10920
```

agtcctaaga gtgggaccgt ggataaacac tatacttgat gatttcaaag tgagtctaga 10980
atctataggt agtttgacac aagaattaga atatagaggt gaaagtctat tatgcagttt 11040
aatatttaga aatgtatggt tatataatca gattgctcta caattaaaaa atcatgcatt 11100
atgtaacaat aaactatatt tggacatatt aaaggttctg aaacacttaa aaaccttttt 11160
taatcttgat aatattgata cagcattaac attgtatatg aatttaccca tgttatttgg 11220
tggtggtgat cccaacttgt tatatcgaag tttctataga agaactcctg acttcctcac 11280
agaggctata gttcactctg tgttcatact tagttattat acaaaccatg acttaaaaga 11340
taaacttcaa gatctgtcag atgatagatt gaataagttc ttaacatgca taatcacgtt 11400
tgacaaaaac cctaatgctg aattcgtaac attgatgaga gatcctcaag ctttagggtc 11460
tgagagacaa gctaaaatta ctagcgaaat caatagactg gcagttacag aggttttgag 11520
tacagctcca aacaaaatat tctccaaaag tgcacaacat tatactacta cagagataga 11580
tctaaatgat attatgcaaa atatagaacc tacatatcct catgggctaa gagttgttta 11640
tgaaagttta cccttttata aagcagagaa aatagtaaat cttatatcag gtacaaaatc 11700
tataactaac atactggaaa aaacttctgc catagactta acagatattg atagagccac 11760
tgagatgatg aggaaaaaca taactttgct tataaggata cttccattgg attgtaacag 11820
agataaaaga gagatattga gtatggaaaa cctaagtatt actgaattaa gcaaatatgt 11880
tagggaaaga tcttggtctt tatccaatat agttggtgtt acatcaccca gtatcatgta 11940
tacaatggac atcaaatata ctacaagcac tatatctagt ggcataatta tagagaaata 12000
taatgttaac agtttaacac gtggtgagag aggacccact aaaccatggg ttggttcatc 12060
tacacaagag aaaaaaacaa tgccagttta taatagacaa gtcttaacca aaaaacagag 12120
agatcaaata gatctattag caaaattgga ttgggtgtat gcatctatag ataacaagga 12180
tgaattcatg gaagaactca gcataggaac ccttgggtta acatatgaaa aggccaagaa 12240
attatttcca caatatttaa gtgtcaatta tttgcatcgc cttacagtca gtagtagacc 12300
atgtgaattc cctgcatcaa taccagctta tagaacaaca aattatcact ttgacactag 12360
ccctattaat cgcatattaa cagaaaagta tggtgatgaa gatattgaca tagtattcca 12420
aaactgtata agctttggcc ttagtttaat gtcagtagta gaacaattta ctaatgtatg 12480
tcctaacaga attattctca tacctaagct taatgagata catttgatga aacctcccat 12540
attcacaggt gatgttgata ttcacaagtt aaaacaagtg atacaaaaac agcatatgtt 12600
tttaccagac aaaataagtt tgactcaata tgtggaatta ttcttaagta ataaaacact 12660
caaatctgga tctcatgtta attctaattt aatattggca cataaaatat ctgactattt 12720
tcataatact tacattttaa gtactaattt agctggacat tggattctga ttatacaact 12780
tatgaaagat tctaaaggta tttttgaaaa agattgggga gagggatata taactgatca 12840
tatgtttatt aatttgaaag ttttcttcaa tgcttataag acctatctct tgtgttttca 12900
taaaggttat ggcaaagcaa agctggagtg tgatatgaac acttcagatc ttctatgtgt 12960
attggaatta atagacagta gttattggaa gtctatgtct aaggtatttt tagaacaaaa 13020
agttatcaaa tacattctta gccaagatgc aagtttacat agagtaaaag gatgtcatag 13080
cttcaaatta tggtttctta aacgtcttaa tgtagcagaa ttcacagttt gcccttgggt 13140
tgttaacata gattatcatc caacacatat gaaagcaata ttaacttata tagatcttgt 13200
tagaatggga ttgataaata tagatagaat acacattaaa aataaacaca aattcaatga 13260

```
tgaattttat acttctaatc tcttctacat taattataac ttctcagata atactcatct  13320
attaactaaa catataagga ttgctaattc tgaattagaa aataattaca acaaattata  13380
tcatcctaca ccagaaacac tagagaatat actagccaat ccgattaaaa gtaatgacaa  13440
aaagacactg aatgactatt gtataggtaa aaatgttgac tcaataatgt taccattgtt  13500
atctaataag aagcttatta aatcgtctgc aatgattaga accaattaca gcaaacaaga  13560
tttgtataat ttattcccta tggttgtgat tgatagaatt atagatcatt caggcaatac  13620
agccaaatcc aaccaacttt acactactac ttcccaccaa atatccttag tgcacaatag  13680
cacatcactt tactgcatgc ttccttggca tcatattaat agattcaatt ttgtatttag  13740
ttctacaggt tgtaaaatta gtatagagta tattttaaaa gatcttaaaa ttaaagatcc  13800
caattgtata gcattcatag gtgaaggagc agggaattta ttattgcgta cagtagtgga  13860
acttcatcct gacataagat atatttacag aagtctgaaa gattgcaatg atcatagttt  13920
acctattgag tttttaaggc tgtacaatgg acatatcaac attgattatg gtgaaaattt  13980
gaccattcct gctacagatg caaccaacaa cattcattgg tcttatttac atataaagtt  14040
tgctgaacct atcagtcttt ttgtctgtga tgccgaattg tctgtaacag tcaactggag  14100
taaaattata atagaatgga gcaagcatgt aagaaagtgc aagtactgtt cctcagttaa  14160
taaatgtatg ttaatagtaa aatatcatgc tcaagatgat attgatttca aattagacaa  14220
tataactata ttaaaaactt atgtatgctt aggcagtaag ttaaagggat cggaggttta  14280
cttagtcctt acaataggtc ctgcgaatat attcccagta tttaatgtag tacaaaatgc  14340
taaattgata ctatcaagaa ccaaaaattt catcatgcct aagaaagctg ataaagagtc  14400
tattgatgca aatattaaaa gtttgatacc ctttctttgt taccctataa caaaaaaagg  14460
aattaatact gcattgtcaa aactaaagag tgttgttagt ggagatatac tatcatattc  14520
tatagctgga cgtaatgaag ttttcagcaa taaacttata aatcataagc atatgaacat  14580
cttaaaatgg ttcaatcatg ttttaaattt cagatcaaca gaactaaact ataaccattt  14640
atatatggta gaatctacat atccttacct aagtgaattg ttaaacagct tgacaaccaa  14700
tgaacttaaa aaactgatta aaatcacagg tagtctgtta tacaactttc ataatgaata  14760
atgaataaag atcttataat aaaaattccc atagctatac actaacactg tattcaatta  14820
tagttattaa aaattaaaaa tcatataatt ttttaaataa cttttagtga actaatccta  14880
aagttatcat tttaatcttg gaggaataaa tttaaaccct aatctaattg gtttatatgt  14940
gtattaacta aattacgaga tattagtttt tgacactttt tttctcgt              14988
```

<210> SEQ ID NO 13
<211> LENGTH: 2165
<212> TYPE: PRT
<213> ORGANISM: Respiratory Syncytial Virus

<400> SEQUENCE: 13

```
Met Asp Pro Ile Ile Asn Gly Asn Ser Ala Asn Val Tyr Leu Thr Asp
1               5                   10                  15

Ser Tyr Leu Lys Gly Val Ile Ser Phe Ser Glu Cys Asn Ala Leu Gly
            20                  25                  30

Ser Tyr Ile Phe Asn Gly Pro Tyr Leu Lys Asn Asp Tyr Thr Asn Leu
        35                  40                  45

Ile Ser Arg Gln Asn Pro Leu Ile Glu His Met Asn Leu Lys Lys Leu
    50                  55                  60

Asn Ile Thr Gln Ser Leu Ile Ser Lys Tyr His Lys Gly Glu Ile Lys
```

```
65                  70                  75                  80

Leu Glu Glu Pro Thr Tyr Phe Gln Ser Leu Leu Met Thr Tyr Lys Ser
                85                  90                  95

Met Thr Ser Ser Glu Gln Ile Ala Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Asn His Gly Phe Thr Leu Ile Asp Asn Gln Thr Leu Ser
225                 230                 235                 240

Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
    290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365

Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Ile Asn Cys Asn
        435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495
```

```
Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
        515                 520                 525

Lys Lys Val Asp Leu Glu Met Ile Ile Asn Asp Lys Ala Ile Ser Pro
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asn Gln Ser Tyr Leu Asn
        595                 600                 605

Asn Pro Asn His Val Val Ser Leu Thr Gly Lys Glu Arg Glu Leu Ser
    610                 615                 620

Val Gly Arg Met Phe Ala Met Gln Pro Gly Met Phe Arg Gln Val Gln
625                 630                 635                 640

Ile Leu Ala Glu Lys Met Ile Ala Glu Asn Ile Leu Gln Phe Phe Pro
                645                 650                 655

Glu Ser Leu Thr Arg Tyr Gly Asp Leu Glu Leu Gln Lys Ile Leu Glu
            660                 665                 670

Leu Lys Ala Gly Ile Ser Asn Lys Ser Asn Arg Tyr Asn Asp Asn Tyr
        675                 680                 685

Asn Asn Tyr Ile Ser Lys Cys Ser Ile Ile Thr Asp Leu Ser Lys Phe
    690                 695                 700

Asn Gln Ala Phe Arg Tyr Glu Thr Ser Cys Ile Cys Ser Asp Val Leu
705                 710                 715                 720

Asp Glu Leu His Gly Val Gln Ser Leu Phe Ser Trp Leu His Leu Thr
                725                 730                 735

Ile Pro His Val Thr Ile Ile Cys Thr Tyr Arg His Ala Pro Pro Tyr
            740                 745                 750

Ile Gly Asp His Ile Val Asp Leu Asn Asn Val Asp Glu Gln Ser Gly
        755                 760                 765

Leu Tyr Arg Tyr His Met Gly Gly Ile Glu Gly Trp Cys Gln Lys Leu
    770                 775                 780

Trp Thr Ile Glu Ala Ile Ser Leu Leu Asp Leu Ile Ser Leu Lys Gly
785                 790                 795                 800

Lys Phe Ser Ile Thr Ala Leu Ile Asn Gly Asp Asn Gln Ser Ile Asp
                805                 810                 815

Ile Ser Lys Pro Ile Arg Leu Met Glu Gly Gln Thr His Ala Gln Ala
            820                 825                 830

Asp Tyr Leu Leu Ala Leu Asn Ser Leu Lys Leu Leu Tyr Lys Glu Tyr
        835                 840                 845

Ala Gly Ile Gly His Lys Leu Lys Gly Thr Glu Thr Tyr Ile Ser Arg
    850                 855                 860

Asp Met Gln Phe Met Ser Lys Thr Ile Gln His Asn Gly Val Tyr Tyr
865                 870                 875                 880

Pro Ala Ser Ile Lys Lys Val Leu Arg Val Gly Pro Trp Ile Asn Thr
                885                 890                 895

Ile Leu Asp Asp Phe Lys Val Ser Leu Glu Ser Ile Gly Ser Leu Thr
            900                 905                 910
```

Gln Glu Leu Glu Tyr Arg Gly Glu Ser Leu Leu Cys Ser Leu Ile Phe
915 920 925

Arg Asn Val Trp Leu Tyr Asn Gln Ile Ala Leu Gln Leu Lys Asn His
930 935 940

Ala Leu Cys Asn Asn Lys Leu Tyr Leu Asp Ile Leu Lys Val Leu Lys
945 950 955 960

His Leu Lys Thr Phe Phe Asn Leu Asp Asn Ile Asp Thr Ala Leu Thr
965 970 975

Leu Tyr Met Asn Leu Pro Met Leu Phe Gly Gly Gly Asp Pro Asn Leu
980 985 990

Leu Tyr Arg Ser Phe Tyr Arg Arg Thr Pro Asp Phe Leu Thr Glu Ala
995 1000 1005

Ile Val His Ser Val Phe Ile Leu Ser Tyr Tyr Thr Asn His Asp
1010 1015 1020

Leu Lys Asp Lys Leu Gln Asp Leu Ser Asp Asp Arg Leu Asn Lys
1025 1030 1035

Phe Leu Thr Cys Ile Ile Thr Phe Asp Lys Asn Pro Asn Ala Glu
1040 1045 1050

Phe Val Thr Leu Met Arg Asp Pro Gln Ala Leu Gly Ser Glu Arg
1055 1060 1065

Gln Ala Lys Ile Thr Ser Glu Ile Asn Arg Leu Ala Val Thr Glu
1070 1075 1080

Val Leu Ser Thr Ala Pro Asn Lys Ile Phe Ser Lys Ser Ala Gln
1085 1090 1095

His Tyr Thr Thr Thr Glu Ile Asp Leu Asn Asp Ile Met Gln Asn
1100 1105 1110

Ile Glu Pro Thr Tyr Pro His Gly Leu Arg Val Val Tyr Glu Ser
1115 1120 1125

Leu Pro Phe Tyr Lys Ala Glu Lys Ile Val Asn Leu Ile Ser Gly
1130 1135 1140

Thr Lys Ser Ile Thr Asn Ile Leu Glu Lys Thr Ser Ala Ile Asp
1145 1150 1155

Leu Thr Asp Ile Asp Arg Ala Thr Glu Met Met Arg Lys Asn Ile
1160 1165 1170

Thr Leu Leu Ile Arg Ile Leu Pro Leu Asp Cys Asn Arg Asp Lys
1175 1180 1185

Arg Glu Ile Leu Ser Met Glu Asn Leu Ser Ile Thr Glu Leu Ser
1190 1195 1200

Lys Tyr Val Arg Glu Arg Ser Trp Ser Leu Ser Asn Ile Val Gly
1205 1210 1215

Val Thr Ser Pro Ser Ile Met Tyr Thr Met Asp Ile Lys Tyr Thr
1220 1225 1230

Thr Ser Thr Ile Ser Ser Gly Ile Ile Ile Glu Lys Tyr Asn Val
1235 1240 1245

Asn Ser Leu Thr Arg Gly Glu Arg Gly Pro Thr Lys Pro Trp Val
1250 1255 1260

Gly Ser Ser Thr Gln Glu Lys Lys Thr Met Pro Val Tyr Asn Arg
1265 1270 1275

Gln Val Leu Thr Lys Lys Gln Arg Asp Gln Ile Asp Leu Leu Ala
1280 1285 1290

Lys Leu Asp Trp Val Tyr Ala Ser Ile Asp Asn Lys Asp Glu Phe
1295 1300 1305

Met Glu Glu Leu Ser Ile Gly Thr Leu Gly Leu Thr Tyr Glu Lys

```
    1310                1315                1320

Ala Lys  Lys Leu Phe Pro Gln  Tyr Leu Ser Val Asn  Tyr Leu His
    1325                1330                1335

Arg Leu  Thr Val Ser Ser Arg  Pro Cys Glu Phe Pro  Ala Ser Ile
    1340                1345                1350

Pro Ala  Tyr Arg Thr Thr Asn  Tyr His Phe Asp Thr  Ser Pro Ile
    1355                1360                1365

Asn Arg  Ile Leu Thr Glu Lys  Tyr Gly Asp Glu Asp  Ile Asp Ile
    1370                1375                1380

Val Phe  Gln Asn Cys Ile Ser  Phe Gly Leu Ser Leu  Met Ser Val
    1385                1390                1395

Val Glu  Gln Phe Thr Asn Val  Cys Pro Asn Arg Ile  Ile Leu Ile
    1400                1405                1410

Pro Lys  Leu Asn Glu Ile His  Leu Met Lys Pro Pro  Ile Phe Thr
    1415                1420                1425

Gly Asp  Val Asp Ile His Lys  Leu Lys Gln Val Ile  Gln Lys Gln
    1430                1435                1440

His Met  Phe Leu Pro Asp Lys  Ile Ser Leu Thr Gln  Tyr Val Glu
    1445                1450                1455

Leu Phe  Leu Ser Asn Lys Thr  Leu Lys Ser Gly Ser  His Val Asn
    1460                1465                1470

Ser Asn  Leu Ile Leu Ala His  Lys Ile Ser Asp Tyr  Phe His Asn
    1475                1480                1485

Thr Tyr  Ile Leu Ser Thr Asn  Leu Ala Gly His Trp  Ile Leu Ile
    1490                1495                1500

Ile Gln  Leu Met Lys Asp Ser  Lys Gly Ile Phe Glu  Lys Asp Trp
    1505                1510                1515

Gly Glu  Gly Tyr Ile Thr Asp  His Met Phe Ile Asn  Leu Lys Val
    1520                1525                1530

Phe Phe  Asn Ala Tyr Lys Thr  Tyr Leu Leu Cys Phe  His Lys Gly
    1535                1540                1545

Tyr Gly  Lys Ala Lys Leu Glu  Cys Asp Met Asn Thr  Ser Asp Leu
    1550                1555                1560

Leu Cys  Val Leu Glu Leu Ile  Asp Ser Ser Tyr Trp  Lys Ser Met
    1565                1570                1575

Ser Lys  Val Phe Leu Glu Gln  Lys Val Ile Lys Tyr  Ile Leu Ser
    1580                1585                1590

Gln Asp  Ala Ser Leu His Arg  Val Lys Gly Cys His  Ser Phe Lys
    1595                1600                1605

Leu Trp  Phe Leu Lys Arg Leu  Asn Val Ala Glu Phe  Thr Val Cys
    1610                1615                1620

Pro Trp  Val Val Asn Ile Asp  Tyr His Pro Thr His  Met Lys Ala
    1625                1630                1635

Ile Leu  Thr Tyr Ile Asp Leu  Val Arg Met Gly Leu  Ile Asn Ile
    1640                1645                1650

Asp Arg  Ile His Ile Lys Asn  Lys His Lys Phe Asn  Asp Glu Phe
    1655                1660                1665

Tyr Thr  Ser Asn Leu Phe Tyr  Ile Asn Tyr Asn Phe  Ser Asp Asn
    1670                1675                1680

Thr His  Leu Leu Thr Lys His  Ile Arg Ile Ala Asn  Ser Glu Leu
    1685                1690                1695

Glu Asn  Asn Tyr Asn Lys Leu  Tyr His Pro Thr Pro  Glu Thr Leu
    1700                1705                1710
```

```
Glu Asn Ile Leu Ala Asn Pro Ile Lys Ser Asn Asp Lys Lys Thr
    1715                1720                1725

Leu Asn Asp Tyr Cys Ile Gly Lys Asn Val Asp Ser Ile Met Leu
    1730                1735                1740

Pro Leu Leu Ser Asn Lys Lys Leu Ile Lys Ser Ser Ala Met Ile
    1745                1750                1755

Arg Thr Asn Tyr Ser Lys Gln Asp Leu Tyr Asn Leu Phe Pro Met
    1760                1765                1770

Val Val Ile Asp Arg Ile Ile Asp His Ser Gly Asn Thr Ala Lys
    1775                1780                1785

Ser Asn Gln Leu Tyr Thr Thr Thr Ser His Gln Ile Ser Leu Val
    1790                1795                1800

His Asn Ser Thr Ser Leu Tyr Cys Met Leu Pro Trp His His Ile
    1805                1810                1815

Asn Arg Phe Asn Phe Val Phe Ser Ser Thr Gly Cys Lys Ile Ser
    1820                1825                1830

Ile Glu Tyr Ile Leu Lys Asp Leu Lys Ile Lys Asp Pro Asn Cys
    1835                1840                1845

Ile Ala Phe Ile Gly Glu Gly Ala Gly Asn Leu Leu Leu Arg Thr
    1850                1855                1860

Val Val Glu Leu His Pro Asp Ile Arg Tyr Ile Tyr Arg Ser Leu
    1865                1870                1875

Lys Asp Cys Asn Asp His Ser Leu Pro Ile Glu Phe Leu Arg Leu
    1880                1885                1890

Tyr Asn Gly His Ile Asn Ile Asp Tyr Gly Glu Asn Leu Thr Ile
    1895                1900                1905

Pro Ala Thr Asp Ala Thr Asn Asn Ile His Trp Ser Tyr Leu His
    1910                1915                1920

Ile Lys Phe Ala Glu Pro Ile Ser Leu Phe Val Cys Asp Ala Glu
    1925                1930                1935

Leu Ser Val Thr Val Asn Trp Ser Lys Ile Ile Ile Glu Trp Ser
    1940                1945                1950

Lys His Val Arg Lys Cys Lys Tyr Cys Ser Ser Val Asn Lys Cys
    1955                1960                1965

Met Leu Ile Val Lys Tyr His Ala Gln Asp Asp Ile Asp Phe Lys
    1970                1975                1980

Leu Asp Asn Ile Thr Ile Leu Lys Thr Tyr Val Cys Leu Gly Ser
    1985                1990                1995

Lys Leu Lys Gly Ser Glu Val Tyr Leu Val Leu Thr Ile Gly Pro
    2000                2005                2010

Ala Asn Ile Phe Pro Val Phe Asn Val Val Gln Asn Ala Lys Leu
    2015                2020                2025

Ile Leu Ser Arg Thr Lys Asn Phe Ile Met Pro Lys Lys Ala Asp
    2030                2035                2040

Lys Glu Ser Ile Asp Ala Asn Ile Lys Ser Leu Ile Pro Phe Leu
    2045                2050                2055

Cys Tyr Pro Ile Thr Lys Lys Gly Ile Asn Thr Ala Leu Ser Lys
    2060                2065                2070

Leu Lys Ser Val Val Ser Gly Asp Ile Leu Ser Tyr Ser Ile Ala
    2075                2080                2085

Gly Arg Asn Glu Val Phe Ser Asn Lys Leu Ile Asn His Lys His
    2090                2095                2100
```

Met Asn Ile Leu Lys Trp Phe Asn His Val Leu Asn Phe Arg Ser
2105 2110 2115

Thr Glu Leu Asn Tyr Asn His Leu Tyr Met Val Glu Ser Thr Tyr
2120 2125 2130

Pro Tyr Leu Ser Glu Leu Leu Asn Ser Leu Thr Thr Asn Glu Leu
2135 2140 2145

Lys Lys Leu Ile Lys Ile Thr Gly Ser Leu Leu Tyr Asn Phe His
2150 2155 2160

Asn Glu
2165

<210> SEQ ID NO 14
<211> LENGTH: 1725
<212> TYPE: PRT
<213> ORGANISM: Respiratory Syncytial Virus

<400> SEQUENCE: 14

Ala Thr Gly Gly Ala Gly Thr Thr Gly Cys Thr Ala Ala Thr Cys Cys
1 5 10 15

Thr Cys Ala Ala Ala Gly Cys Ala Ala Ala Thr Gly Cys Ala Ala Thr
20 25 30

Thr Ala Cys Cys Ala Cys Ala Ala Thr Cys Cys Thr Cys Ala Cys Thr
35 40 45

Gly Cys Ala Gly Thr Cys Ala Cys Ala Thr Thr Thr Thr Gly Thr Thr
50 55 60

Thr Thr Gly Cys Thr Thr Cys Thr Gly Gly Thr Cys Ala Ala Ala Ala
65 70 75 80

Cys Ala Thr Cys Ala Cys Thr Gly Ala Ala Gly Ala Ala Thr Thr Thr
85 90 95

Thr Ala Thr Cys Ala Ala Thr Cys Ala Ala Cys Ala Thr Gly Cys Ala
100 105 110

Gly Thr Gly Cys Ala Gly Thr Thr Ala Gly Cys Ala Ala Gly Gly
115 120 125

Cys Thr Ala Thr Cys Thr Thr Ala Gly Thr Gly Cys Thr Cys Thr Gly
130 135 140

Ala Gly Ala Ala Cys Thr Gly Gly Thr Thr Gly Gly Thr Ala Thr Ala
145 150 155 160

Cys Cys Ala Gly Thr Gly Thr Thr Ala Thr Ala Ala Cys Thr Ala Thr
165 170 175

Ala Gly Ala Ala Thr Thr Ala Ala Gly Thr Ala Ala Thr Ala Thr Cys
180 185 190

Ala Ala Gly Ala Ala Ala Ala Ala Thr Ala Ala Gly Thr Gly Thr Ala
195 200 205

Ala Thr Gly Gly Ala Ala Cys Ala Gly Ala Thr Gly Cys Thr Ala Ala
210 215 220

Gly Gly Thr Ala Ala Ala Ala Thr Thr Gly Ala Thr Ala Ala Ala Ala
225 230 235 240

Cys Ala Ala Gly Ala Ala Thr Thr Ala Gly Ala Thr Ala Ala Ala Thr
245 250 255

Ala Thr Ala Ala Ala Ala Ala Thr Gly Cys Thr Gly Thr Ala Ala Cys
260 265 270

Ala Gly Ala Ala Thr Thr Gly Cys Ala Gly Thr Thr Gly Cys Thr Cys
275 280 285

Ala Thr Gly Cys Ala Ala Ala Gly Cys Ala Cys Ala Cys Ala Ala Gly
290 295 300

```
Cys Ala Ala Cys Ala Ala Ala Cys Ala Ala Thr Cys Gly Ala Gly Cys
305                 310                 315                 320

Cys Ala Gly Ala Ala Gly Ala Gly Ala Ala Cys Thr Ala Cys Cys Ala
                325                 330                 335

Ala Gly Gly Thr Thr Thr Ala Thr Gly Ala Ala Thr Thr Ala Thr Ala
            340                 345                 350

Cys Ala Cys Thr Cys Ala Ala Cys Ala Ala Thr Gly Cys Cys Ala Ala
        355                 360                 365

Ala Ala Ala Ala Ala Cys Cys Ala Ala Thr Gly Thr Ala Ala Cys Ala
    370                 375                 380

Thr Thr Ala Ala Gly Cys Ala Ala Gly Ala Ala Ala Ala Gly Gly Ala
385                 390                 395                 400

Ala Ala Ala Gly Ala Ala Gly Ala Thr Thr Thr Cys Thr Thr Gly Gly
                405                 410                 415

Thr Thr Thr Thr Thr Thr Gly Thr Thr Ala Gly Gly Thr Gly Thr Thr
            420                 425                 430

Gly Gly Ala Thr Cys Thr Gly Cys Ala Ala Thr Cys Gly Cys Cys Ala
        435                 440                 445

Gly Thr Gly Gly Cys Gly Thr Thr Gly Cys Thr Gly Thr Ala Thr Cys
    450                 455                 460

Thr Ala Ala Gly Gly Thr Cys Cys Thr Gly Cys Ala Cys Cys Thr Ala
465                 470                 475                 480

Gly Ala Ala Gly Gly Gly Gly Ala Ala Gly Thr Gly Ala Ala Cys Ala
                485                 490                 495

Ala Gly Ala Thr Cys Ala Ala Ala Ala Gly Thr Gly Cys Thr Cys Thr
            500                 505                 510

Ala Cys Thr Ala Thr Cys Cys Ala Cys Ala Ala Ala Cys Ala Ala Gly
        515                 520                 525

Gly Cys Thr Gly Thr Ala Gly Thr Cys Ala Gly Cys Thr Thr Ala Thr
    530                 535                 540

Cys Ala Ala Ala Thr Gly Gly Ala Gly Thr Thr Ala Gly Thr Gly Thr
545                 550                 555                 560

Thr Thr Thr Ala Ala Cys Cys Ala Gly Cys Ala Ala Ala Gly Thr Gly
                565                 570                 575

Thr Thr Ala Gly Ala Cys Cys Thr Cys Ala Ala Ala Ala Ala Cys Thr
            580                 585                 590

Ala Thr Ala Thr Ala Gly Ala Thr Ala Ala Ala Cys Ala Ala Thr Thr
        595                 600                 605

Gly Thr Thr Ala Cys Cys Thr Ala Thr Thr Gly Thr Gly Ala Ala Cys
    610                 615                 620

Ala Ala Gly Cys Ala Ala Ala Gly Cys Thr Gly Cys Ala Gly Cys Ala
625                 630                 635                 640

Thr Ala Thr Cys Ala Ala Ala Thr Ala Thr Ala Gly Ala Ala Ala Cys
                645                 650                 655

Thr Gly Thr Gly Ala Thr Ala Gly Ala Gly Thr Thr Cys Cys Ala Ala
            660                 665                 670

Cys Ala Ala Ala Ala Gly Ala Ala Cys Ala Ala Cys Ala Gly Ala Cys
        675                 680                 685

Thr Ala Cys Thr Ala Gly Ala Gly Ala Thr Thr Ala Cys Cys Ala Gly
    690                 695                 700

Gly Gly Ala Ala Thr Thr Thr Ala Gly Thr Gly Thr Thr Ala Ala Thr
705                 710                 715                 720
```

Gly Cys Ala Gly Gly Cys Gly Thr Ala Ala Cys Thr Ala Cys Ala Cys
725 730 735

Cys Thr Gly Thr Ala Ala Gly Cys Ala Cys Thr Thr Ala Cys Ala Thr
740 745 750

Gly Thr Thr Ala Ala Cys Thr Ala Ala Thr Ala Gly Thr Gly Ala Ala
755 760 765

Thr Thr Ala Thr Thr Gly Thr Cys Ala Thr Thr Ala Ala Thr Cys Ala
770 775 780

Ala Thr Gly Ala Thr Ala Thr Gly Cys Cys Thr Ala Thr Ala Ala Cys
785 790 795 800

Ala Ala Ala Thr Gly Ala Thr Cys Ala Gly Ala Ala Ala Ala Ala Gly
805 810 815

Thr Thr Ala Ala Thr Gly Thr Cys Cys Ala Ala Cys Ala Ala Thr Gly
820 825 830

Thr Thr Cys Ala Ala Ala Thr Ala Gly Thr Thr Ala Gly Ala Cys Ala
835 840 845

Gly Cys Ala Ala Ala Gly Thr Thr Ala Cys Thr Cys Thr Ala Thr Cys
850 855 860

Ala Thr Gly Thr Cys Cys Ala Thr Ala Ala Thr Ala Ala Ala Ala Gly
865 870 875 880

Ala Gly Gly Ala Ala Gly Thr Cys Thr Thr Ala Gly Cys Ala Thr Ala
885 890 895

Thr Gly Thr Ala Gly Thr Ala Cys Ala Ala Thr Thr Ala Cys Cys Ala
900 905 910

Cys Thr Ala Thr Ala Thr Gly Gly Thr Gly Thr Thr Ala Thr Ala Gly
915 920 925

Ala Thr Ala Cys Ala Cys Cys Cys Thr Gly Thr Thr Gly Gly Ala Ala
930 935 940

Ala Cys Thr Ala Cys Ala Cys Ala Cys Ala Thr Cys Cys Cys Cys Thr
945 950 955 960

Cys Thr Ala Thr Gly Thr Ala Cys Ala Ala Cys Cys Ala Ala Cys Ala
965 970 975

Cys Ala Ala Ala Ala Gly Ala Ala Gly Gly Gly Thr Cys Cys Ala Ala
980 985 990

Cys Ala Thr Cys Thr Gly Thr Thr Thr Ala Ala Cys Ala Ala Gly Ala
995 1000 1005

Ala Cys Thr Gly Ala Cys Ala Gly Ala Gly Gly Ala Thr Gly Gly
1010 1015 1020

Thr Ala Cys Thr Gly Thr Gly Ala Cys Ala Ala Thr Gly Cys Ala
1025 1030 1035

Gly Gly Ala Thr Cys Ala Gly Thr Ala Thr Cys Thr Thr Thr Cys
1040 1045 1050

Thr Thr Cys Cys Cys Ala Cys Ala Ala Gly Cys Thr Gly Ala Ala
1055 1060 1065

Ala Cys Ala Thr Gly Thr Ala Ala Ala Gly Thr Thr Cys Ala Ala
1070 1075 1080

Thr Cys Ala Ala Ala Thr Cys Gly Ala Gly Thr Ala Thr Thr Thr
1085 1090 1095

Thr Gly Thr Gly Ala Cys Ala Cys Ala Ala Thr Gly Ala Ala Cys
1100 1105 1110

Ala Gly Thr Thr Thr Ala Ala Cys Ala Thr Thr Ala Cys Cys Ala
1115 1120 1125

Ala Gly Thr Gly Ala Ala Gly Thr Ala Ala Ala Thr Cys Thr Cys

```
    1130                1135                1140

Thr Gly  Cys Ala Ala Thr Gly  Thr Thr Gly Ala Cys  Ala Thr Ala
    1145                1150                1155

Thr Thr  Cys Ala Ala Cys Cys  Cys Cys Ala Ala Ala  Thr Ala Thr
    1160                1165                1170

Gly Ala  Thr Thr Gly Thr Ala  Ala Ala Ala Thr Thr  Ala Thr Gly
    1175                1180                1185

Ala Cys  Thr Thr Cys Ala Ala  Ala Ala Ala Cys Ala  Gly Ala Thr
    1190                1195                1200

Gly Thr  Ala Ala Gly Cys Ala  Gly Cys Thr Cys Cys  Gly Thr Thr
    1205                1210                1215

Ala Thr  Cys Ala Cys Ala Thr  Cys Thr Cys Thr Ala  Gly Gly Ala
    1220                1225                1230

Gly Cys  Cys Ala Thr Thr Gly  Thr Gly Thr Cys Ala  Thr Gly Cys
    1235                1240                1245

Thr Ala  Thr Gly Gly Cys Ala  Ala Ala Ala Cys Thr  Ala Ala Ala
    1250                1255                1260

Thr Gly  Thr Ala Cys Ala Gly  Cys Ala Thr Cys Cys  Ala Ala Thr
    1265                1270                1275

Ala Ala  Ala Ala Ala Thr Cys  Gly Thr Gly Gly Ala  Ala Thr Cys
    1280                1285                1290

Ala Thr  Ala Ala Ala Gly Ala  Cys Ala Thr Thr Thr  Thr Cys Thr
    1295                1300                1305

Ala Ala  Cys Gly Gly Gly Thr  Gly Cys Gly Ala Thr  Thr Ala Thr
    1310                1315                1320

Gly Thr  Ala Thr Cys Ala Ala  Ala Thr Ala Ala Ala  Gly Gly Gly
    1325                1330                1335

Gly Thr  Gly Gly Ala Cys Ala  Cys Thr Gly Thr Gly  Thr Cys Thr
    1340                1345                1350

Gly Thr  Ala Gly Gly Thr Ala  Ala Cys Ala Cys Ala  Thr Thr Ala
    1355                1360                1365

Thr Ala  Thr Thr Ala Thr Gly  Thr Ala Ala Ala Thr  Ala Ala Gly
    1370                1375                1380

Cys Ala  Ala Gly Ala Ala Gly  Gly Thr Ala Ala Ala  Ala Gly Thr
    1385                1390                1395

Cys Thr  Cys Thr Ala Thr Gly  Thr Ala Ala Ala Ala  Gly Gly Thr
    1400                1405                1410

Gly Ala  Ala Cys Cys Ala Ala  Thr Ala Ala Thr Ala  Ala Ala Thr
    1415                1420                1425

Thr Thr  Cys Thr Ala Thr Gly  Ala Cys Cys Cys Ala  Thr Thr Ala
    1430                1435                1440

Gly Thr  Ala Thr Thr Cys Cys  Cys Cys Thr Cys Thr  Gly Ala Thr
    1445                1450                1455

Gly Ala  Ala Thr Thr Thr Gly  Ala Thr Gly Cys Ala  Thr Cys Ala
    1460                1465                1470

Ala Thr  Ala Thr Cys Thr Cys  Ala Ala Gly Thr Cys  Ala Ala Cys
    1475                1480                1485

Gly Ala  Gly Ala Ala Gly Ala  Thr Thr Ala Ala Cys  Cys Ala Gly
    1490                1495                1500

Ala Gly  Cys Cys Thr Ala Gly  Cys Ala Thr Thr Thr  Ala Thr Thr
    1505                1510                1515

Cys Gly  Thr Ala Ala Ala Thr  Cys Cys Gly Ala Thr  Gly Ala Ala
    1520                1525                1530
```

```
Thr Thr  Ala Thr Thr Ala Cys  Ala Thr Ala Ala Thr  Gly Thr Ala
    1535                 1540                 1545

Ala Ala  Thr Gly Cys Thr Gly  Gly Thr Ala Ala Ala  Thr Cys Cys
    1550                 1555                 1560

Ala Cys  Cys Ala Cys Ala Ala  Ala Thr Ala Thr Cys  Ala Thr Gly
    1565                 1570                 1575

Ala Thr  Ala Ala Cys Thr Ala  Cys Thr Ala Thr Ala  Ala Thr Thr
    1580                 1585                 1590

Ala Thr  Ala Gly Thr Gly Ala  Thr Thr Ala Thr Ala  Gly Thr Ala
    1595                 1600                 1605

Ala Thr  Ala Thr Thr Gly Thr  Thr Ala Thr Cys Ala  Thr Thr Ala
    1610                 1615                 1620

Ala Thr  Thr Gly Cys Thr Gly  Thr Thr Gly Gly Ala  Cys Thr Gly
    1625                 1630                 1635

Cys Thr  Cys Thr Thr Ala Thr  Ala Cys Thr Gly Thr  Ala Ala Gly
    1640                 1645                 1650

Gly Cys  Cys Ala Gly Ala Ala  Gly Cys Ala Cys Ala  Cys Cys Ala
    1655                 1660                 1665

Gly Thr  Cys Ala Cys Ala Cys  Thr Ala Ala Gly Cys  Ala Ala Ala
    1670                 1675                 1680

Gly Ala  Thr Cys Ala Ala Cys  Thr Gly Ala Gly Thr  Gly Gly Thr
    1685                 1690                 1695

Ala Thr  Ala Ala Ala Thr Ala  Ala Thr Ala Thr Thr  Gly Cys Ala
    1700                 1705                 1710

Thr Thr  Thr Ala Gly Thr Ala  Ala Cys Thr Ala Ala
    1715                 1720                 1725


<210> SEQ ID NO 15
<211> LENGTH: 1725
<212> TYPE: PRT
<213> ORGANISM: Respiratory Syncytial Virus

<400> SEQUENCE: 15

Ala Thr Gly Gly Ala Gly Cys Thr Cys Cys Thr Cys Ala Thr Thr Cys
1               5                   10                  15

Thr Cys Ala Ala Ala Gly Cys Cys Ala Ala Cys Gly Cys Ala Ala Thr
            20                  25                  30

Cys Ala Cys Ala Ala Cys Ala Ala Thr Thr Cys Thr Gly Ala Cys Cys
        35                  40                  45

Gly Cys Cys Gly Thr Cys Ala Cys Ala Thr Thr Cys Thr Gly Cys Thr
    50                  55                  60

Thr Thr Gly Cys Cys Thr Cys Cys Gly Gly Ala Cys Ala Gly Ala Ala
65                  70                  75                  80

Cys Ala Thr Cys Ala Cys Ala Gly Ala Ala Gly Ala Gly Thr Thr Thr
                85                  90                  95

Thr Ala Cys Cys Ala Ala Ala Gly Thr Ala Cys Ala Thr Gly Cys Ala
            100                 105                 110

Gly Cys Gly Cys Cys Gly Thr Gly Ala Gly Cys Ala Ala Ala Gly Gly
        115                 120                 125

Cys Thr Ala Cys Cys Thr Gly Thr Cys Cys Gly Cys Cys Cys Thr Gly
    130                 135                 140

Ala Gly Gly Ala Cys Ala Gly Gly Gly Thr Gly Gly Thr Ala Cys Ala
145                 150                 155                 160

Cys Ala Thr Cys Cys Gly Thr Gly Ala Thr Thr Ala Cys Cys Ala Thr
```

```
                165                 170                 175

Thr Gly Ala Gly Cys Thr Gly Ala Gly Thr Ala Ala Thr Ala Thr Cys
            180                 185                 190

Ala Ala Gly Ala Ala Gly Ala Ala Cys Ala Ala Gly Thr Gly Cys Ala
        195                 200                 205

Ala Cys Gly Gly Cys Ala Cys Thr Gly Ala Thr Gly Cys Cys Ala Ala
    210                 215                 220

Ala Gly Thr Gly Ala Ala Gly Cys Thr Cys Ala Thr Thr Ala Ala Ala
225                 230                 235                 240

Cys Ala Gly Gly Ala Ala Cys Thr Cys Gly Ala Thr Ala Ala Gly Thr
                245                 250                 255

Ala Cys Ala Ala Gly Ala Ala Cys Gly Cys Cys Gly Thr Gly Ala Cys
            260                 265                 270

Thr Gly Ala Gly Cys Thr Cys Cys Ala Gly Cys Thr Gly Cys Thr Gly
        275                 280                 285

Ala Thr Gly Cys Ala Gly Thr Cys Ala Ala Cys Thr Cys Ala Gly Gly
    290                 295                 300

Cys Thr Ala Cys Ala Ala Ala Cys Ala Ala Cys Ala Gly Ala Gly Cys
305                 310                 315                 320

Cys Cys Gly Gly Ala Gly Gly Gly Ala Gly Cys Thr Gly Cys Cys Cys
                325                 330                 335

Ala Gly Gly Thr Thr Thr Ala Thr Gly Ala Ala Cys Thr Ala Cys Ala
            340                 345                 350

Cys Cys Cys Thr Gly Ala Ala Cys Ala Ala Cys Gly Cys Cys Ala Ala
        355                 360                 365

Gly Ala Ala Gly Ala Cys Cys Ala Ala Cys Gly Thr Gly Ala Cys Ala
    370                 375                 380

Thr Thr Gly Ala Gly Cys Ala Ala Gly Ala Ala Gly Ala Gly Gly Ala
385                 390                 395                 400

Ala Gly Cys Gly Gly Cys Gly Gly Thr Thr Cys Cys Thr Gly Gly Gly
                405                 410                 415

Gly Thr Thr Cys Thr Thr Gly Cys Thr Ala Gly Gly Thr Gly Thr Gly
            420                 425                 430

Gly Gly Cys Ala Gly Cys Gly Cys Thr Ala Thr Thr Gly Cys Thr Thr
        435                 440                 445

Cys Thr Gly Gly Cys Gly Thr Cys Gly Cys Cys Gly Thr Cys Thr Cys
    450                 455                 460

Cys Ala Ala Gly Gly Thr Gly Cys Thr Gly Cys Ala Cys Cys Thr Gly
465                 470                 475                 480

Gly Ala Ala Gly Gly Cys Gly Ala Ala Gly Thr Gly Ala Ala Thr Ala
                485                 490                 495

Ala Gly Ala Thr Thr Ala Ala Gly Thr Cys Cys Gly Cys Ala Cys Thr
            500                 505                 510

Gly Cys Thr Thr Ala Gly Cys Ala Cys Cys Ala Ala Thr Ala Ala Gly
        515                 520                 525

Gly Cys Cys Gly Thr Cys Gly Thr Gly Ala Gly Cys Cys Thr Gly Thr
    530                 535                 540

Cys Thr Ala Ala Cys Gly Gly Ala Gly Thr Gly Ala Gly Thr Gly Thr
545                 550                 555                 560

Gly Cys Thr Cys Ala Cys Ala Ala Gly Cys Ala Ala Gly Gly Thr Cys
                565                 570                 575

Cys Thr Cys Gly Ala Thr Cys Thr Cys Ala Ala Gly Ala Ala Cys Thr
            580                 585                 590
```

Ala Cys Ala Thr Thr Gly Ala Thr Ala Ala Gly Cys Ala Gly Cys Thr
595 600 605

Cys Cys Thr Gly Cys Cys Cys Ala Thr Cys Gly Thr Cys Ala Ala Cys
610 615 620

Ala Ala Gly Cys Ala Gly Thr Cys Ala Thr Gly Cys Thr Cys Cys Ala
625 630 635 640

Thr Thr Ala Gly Thr Ala Ala Cys Ala Thr Cys Gly Ala Gly Ala Cys
645 650 655

Cys Gly Thr Gly Ala Thr Thr Gly Ala Ala Thr Thr Thr Cys Ala Ala
660 665 670

Cys Ala Gly Ala Ala Gly Ala Ala Cys Ala Ala Cys Cys Gly Gly Cys
675 680 685

Thr Cys Cys Thr Gly Gly Ala Gly Ala Thr Thr Ala Cys Thr Ala Gly
690 695 700

Gly Gly Ala Gly Thr Thr Cys Ala Gly Cys Gly Thr Gly Ala Ala Cys
705 710 715 720

Gly Cys Cys Gly Gly Gly Gly Thr Gly Ala Cys Ala Ala Cys Ala Cys
725 730 735

Cys Ala Gly Thr Cys Thr Cys Cys Ala Cys Cys Thr Ala Thr Ala Thr
740 745 750

Gly Cys Thr Thr Ala Cys Cys Ala Ala Cys Ala Gly Cys Gly Ala Gly
755 760 765

Thr Thr Gly Cys Thr Cys Thr Cys Cys Cys Thr Gly Ala Thr Thr Ala
770 775 780

Ala Cys Gly Ala Thr Ala Thr Gly Cys Cys Ala Ala Thr Thr Ala Cys
785 790 795 800

Ala Ala Ala Cys Gly Ala Cys Cys Ala Gly Ala Ala Gly Ala Ala Gly
805 810 815

Cys Thr Gly Ala Thr Gly Thr Cys Ala Ala Ala Cys Ala Ala Cys Gly
820 825 830

Thr Cys Cys Ala Gly Ala Thr Thr Gly Thr Cys Cys Gly Gly Cys Ala
835 840 845

Gly Cys Ala Gly Thr Cys Cys Thr Ala Cys Thr Cys Ala Ala Thr Cys
850 855 860

Ala Thr Gly Thr Cys Cys Ala Thr Thr Ala Thr Thr Ala Ala Gly Gly
865 870 875 880

Ala Gly Gly Ala Gly Gly Thr Cys Cys Thr Gly Gly Cys Thr Thr Ala
885 890 895

Cys Gly Thr Cys Gly Thr Gly Cys Ala Gly Cys Thr Gly Cys Cys Thr
900 905 910

Cys Thr Thr Thr Ala Thr Gly Gly Gly Gly Thr Gly Ala Thr Cys Gly
915 920 925

Ala Cys Ala Cys Cys Cys Cys Thr Thr Gly Cys Thr Gly Gly Ala Ala
930 935 940

Gly Cys Thr Cys Cys Ala Thr Ala Cys Ala Thr Cys Cys Cys Cys Thr
945 950 955 960

Cys Thr Gly Thr Gly Cys Ala Cys Thr Ala Cys Cys Ala Ala Cys Ala
965 970 975

Cys Cys Ala Ala Gly Gly Ala Gly Gly Gly Gly Thr Cys Cys Ala Ala
980 985 990

Cys Ala Thr Cys Thr Gly Cys Thr Thr Gly Ala Cys Ala Ala Gly Ala
995 1000 1005

Ala Cys Cys Gly Ala Thr Cys Gly Cys Gly Gly Cys Thr Gly Gly
1010 1015 1020

Thr Ala Cys Thr Gly Cys Gly Ala Thr Ala Ala Cys Gly Cys Ala
1025 1030 1035

Gly Gly Cys Ala Gly Thr Gly Thr Cys Thr Cys Cys Thr Thr Cys
1040 1045 1050

Thr Thr Thr Cys Cys Cys Cys Ala Gly Gly Cys Cys Gly Ala Gly
1055 1060 1065

Ala Cys Thr Thr Gly Thr Ala Ala Gly Gly Thr Gly Cys Ala Gly
1070 1075 1080

Thr Cys Thr Ala Ala Cys Cys Gly Cys Gly Thr Cys Thr Thr Cys
1085 1090 1095

Thr Gly Cys Gly Ala Cys Ala Cys Cys Ala Thr Gly Ala Ala Cys
1100 1105 1110

Ala Gly Cys Cys Thr Gly Ala Cys Cys Cys Thr Thr Cys Cys Cys
1115 1120 1125

Ala Gly Cys Gly Ala Gly Gly Thr Gly Ala Ala Cys Cys Thr Thr
1130 1135 1140

Thr Gly Thr Ala Ala Cys Gly Thr Gly Gly Ala Cys Ala Thr Cys
1145 1150 1155

Thr Thr Cys Ala Ala Cys Cys Cys Ala Ala Ala Gly Thr Ala Thr
1160 1165 1170

Gly Ala Thr Thr Gly Thr Ala Ala Gly Ala Thr Thr Ala Thr Gly
1175 1180 1185

Ala Cys Thr Ala Gly Cys Ala Ala Ala Ala Cys Cys Gly Ala Thr
1190 1195 1200

Gly Thr Cys Ala Gly Cys Ala Gly Cys Ala Gly Cys Gly Thr Gly
1205 1210 1215

Ala Thr Cys Ala Cys Thr Ala Gly Cys Cys Thr Gly Gly Gly Cys
1220 1225 1230

Gly Cys Thr Ala Thr Cys Gly Thr Cys Ala Gly Cys Thr Gly Cys
1235 1240 1245

Thr Ala Cys Gly Gly Ala Ala Ala Gly Ala Cys Thr Ala Ala Gly
1250 1255 1260

Thr Gly Cys Ala Cys Cys Gly Cys Cys Ala Gly Cys Ala Ala Cys
1265 1270 1275

Ala Ala Gly Ala Ala Cys Ala Gly Ala Gly Gly Cys Ala Thr Cys
1280 1285 1290

Ala Thr Cys Ala Ala Gly Ala Cys Cys Thr Thr Cys Ala Gly Thr
1295 1300 1305

Ala Ala Thr Gly Gly Ala Thr Gly Thr Gly Ala Cys Thr Ala Cys
1310 1315 1320

Gly Thr Gly Thr Cys Cys Ala Ala Cys Ala Ala Ala Gly Gly Gly
1325 1330 1335

Gly Thr Gly Gly Ala Thr Ala Cys Ala Gly Thr Gly Ala Gly Cys
1340 1345 1350

Gly Thr Gly Gly Gly Ala Ala Ala Cys Ala Cys Ala Thr Thr Gly
1355 1360 1365

Thr Ala Cys Thr Ala Cys Gly Thr Gly Ala Ala Cys Ala Ala Ala
1370 1375 1380

Cys Ala Gly Gly Ala Gly Gly Gly Gly Ala Ala Gly Thr Cys Cys
1385 1390 1395

Thr Thr Gly Thr Ala Cys Gly Thr Gly Ala Ala Gly Gly Gly Thr 1400 1405 1410

Gly Ala Gly Cys Cys Cys Ala Thr Thr Ala Thr Cys Ala Ala Cys
1415 1420 1425

Thr Thr Cys Thr Ala Cys Gly Ala Cys Cys Cys Thr Cys Thr Cys
1430 1435 1440

Gly Thr Gly Thr Thr Cys Cys Cys Ala Thr Cys Ala Gly Ala Cys
1445 1450 1455

Gly Ala Gly Thr Thr Thr Gly Ala Cys Gly Cys Cys Thr Cys Cys
1460 1465 1470

Ala Thr Cys Thr Cys Cys Cys Ala Gly Gly Thr Gly Ala Ala Cys
1475 1480 1485

Gly Ala Gly Ala Ala Gly Ala Thr Cys Ala Ala Thr Cys Ala Gly
1490 1495 1500

Thr Cys Ala Cys Thr Gly Gly Cys Cys Thr Thr Thr Ala Thr Thr
1505 1510 1515

Ala Gly Gly Ala Ala Ala Thr Cys Cys Gly Ala Cys Gly Ala Gly
1520 1525 1530

Cys Thr Gly Cys Thr Gly Cys Ala Cys Ala Ala Cys Gly Thr Cys
1535 1540 1545

Ala Ala Cys Gly Cys Cys Gly Gly Ala Ala Ala Gly Thr Cys Thr
1550 1555 1560

Ala Cys Cys Ala Cys Thr Ala Ala Cys Ala Thr Cys Ala Thr Gly
1565 1570 1575

Ala Thr Cys Ala Cys Cys Ala Cys Ala Ala Thr Cys Ala Thr Cys
1580 1585 1590

Ala Thr Thr Gly Thr Gly Ala Thr Cys Ala Thr Cys Gly Thr Cys
1595 1600 1605

Ala Thr Cys Cys Thr Cys Cys Thr Gly Ala Gly Cys Thr Thr Gly
1610 1615 1620

Ala Thr Cys Gly Cys Thr Gly Thr Cys Gly Gly Gly Thr Thr Gly
1625 1630 1635

Cys Thr Gly Thr Thr Gly Thr Ala Cys Thr Gly Cys Ala Ala Gly
1640 1645 1650

Gly Cys Cys Cys Gly Gly Thr Cys Cys Ala Cys Ala Cys Cys Cys
1655 1660 1665

Gly Thr Gly Ala Cys Thr Cys Thr Gly Ala Gly Cys Ala Ala Gly
1670 1675 1680

Gly Ala Cys Cys Ala Gly Cys Thr Gly Thr Cys Thr Gly Gly Cys
1685 1690 1695

Ala Thr Thr Ala Ala Cys Ala Ala Cys Ala Thr Cys Gly Cys Cys
1700 1705 1710

Thr Thr Thr Ala Gly Cys Ala Ala Cys Thr Ala Ala
1715 1720 1725

<210> SEQ ID NO 16
<211> LENGTH: 17214
<212> TYPE: DNA
<213> ORGANISM: Artificial Sequence
<220> FEATURE:
<223> OTHER INFORMATION: Recombinant RSV sequence

<400> SEQUENCE: 16
accaaacaag agaagagact ggtttgggaa tattaattca aataaaaatt aacttaggat 60
taaagaactt taccgaaagg taaggggaaa gaaatcctaa gagcttagcc atgttgagtc 120

```
tattcgacac attcagtgcg cgtaggcagg agaacataac gaaatcagct ggtggggctg    180
ttattcccgg gcaaaaaaac actgtgtcta tatttgctct tggaccatca ataacagatg    240
acaatgataa aatgacattg gctcttctct ttttgtctca ttctttagac aatgaaaagc    300
agcatgcgca aagagctgga tttttagttt ctctgttatc aatggcttat gccaacccag    360
aattatattt aacatcaaat ggtagtaatg cagatgttaa atatgttatc tacatgatag    420
agaaagaccc aggaagacag aaatatggtg ggtttgtcgt caagactaga gagatggttt    480
atgaaaagac aactgattgg atgttcggga gtgatcttga gtatgatcaa gacaatatgt    540
tgcaaaatgg tagaagcact tctacaatcg aggatcttgt tcatactttt ggatatccat    600
cgtgtcttgg agcccttata atccaagttt ggataatact tgttaaggct ataaccagta    660
tatcaggatt gaggaaagga ttctttactc ggttagaagc atttcgacaa gatggaacag    720
ttaaatccag tctagtgttg agcggtgatg cagtagaaca aattggatca attatgaggt    780
cccaacagag cttggtaaca ctcatggttg aaacactgat aacaatgaac acaggcagga    840
atgatctgac aacaatagaa aagaatatac agattgtagg aaactacatc agagatgcag    900
gtcttgcttc atttttcaac acaatcagat atggcattga gactagaatg gcagctctaa    960
ctctgtctac ccttagaccg gatatcaaca gactcaaggc actgatcgag ttatatctat   1020
caaaggggcc acgtgctcct tttatatgca ttttgagaga tcccgtgcat ggtgagtttg   1080
caccaggcaa ctatcctgcc ctctggagtt atgcgatggg tgtagcagtt gtacaaaaca   1140
aggccatgca acagtatgta acaggaaggt cttatctgga tattgaaatg ttccaacttg   1200
gtcaagcagt ggcacgtgat gccgagtcgc agatgagttc aatattagag gatgaactgg   1260
gggtcacaca agaagccaag caaagcttga agaaacacat gaagaacatc agcagttcag   1320
atacaacctt tcataagcct acagggggat cagccataga aatggcgata gatgaagaag   1380
cagggcagcc tgaatccaga ggagatcagg atcaaggaga tgagcctcgg tcatccatag   1440
ttccttatgc atgggcagac gaaaccggga atgacaatca aactgaatca actacagaaa   1500
ttgacagcat caaaactgaa caaagaaaca tcagagacag gctgaacaaa agactcaacg   1560
agaaaaggaa acagagtgac ccgagatcaa ctgacatcac aaacaacaca aatcaaactg   1620
aaatagatga tttgttcagt gcattcggaa gcaactagtc acaaagagat gaccaggcgc   1680
gccaagtaag aaaaacttag gattaatgga cctgcaggat ggaactgctg atcctgaaag   1740
ccaacgctat tactactatc ctgaccgccg tgacattttg cttcgcatct ggacagaaca   1800
ttactgagga attctaccag tcaacatgca gcgccgtgtc caaaggatac ctgagcgccc   1860
tgcggaccgg ctggtataca tcagtgatta ctatcgagct gtccaacatc aaggaaaaca   1920
aatgtaatgg gaccgacgca aaggtgaaac tgatcaagca ggagctggat aagtacaaaa   1980
atgccgtgac agaactgcag ctgctgatgc agtccacacc agcaactaac aatcgcgccc   2040
ggagagagct gccccggttc atgaactata ccctgaacaa tgctaagaaa accaatgtga   2100
cactgtccaa gaaacgcaag aggcgcttcc tgggatttct gctgggcgtg gggtctgcca   2160
tcgctagtgg agtggccgtc tgcaaagtcc tgcacctgga gggcgaagtg aacaagatca   2220
aaagcgccct gctgtccact aacaaggcag tggtcagtct gtcaaatggc gtgtccgtcc   2280
tgaccttcaa ggtgctggac ctgaaaaatt atattgataa gcagctgctg cctatcctga   2340
acaaacagag ctgctccatt tctaatatcg agacagtgat cgaattccag cagaagaaca   2400
atagactgct ggagattacc agagagttca gcgtgaacgc cggcgtcacc acacccgtgt   2460
ccacctacat gctgacaaat agtgagctgc tgtcactgat taacgacatg cctatcacca   2520
```

```
atgatcagaa gaaactgatg tccaacaatg tgcagatcgt cagacagcag agttactcaa   2580
tcatgtgcat cattaaggag gaagtcctgg cctacgtggt ccagctgcca ctgtatggcg   2640
tgatcgacac cccctgctgg aaactgcata catctcctct gtgcactacc aacacaaagg   2700
aaggaagtaa tatctgcctg actcgaaccg accggggatg gtactgtgat aacgcaggca   2760
gcgtgtcctt ctttccacag gccgagacct gcaaggtcca gagcaacagg gtgttctgtg   2820
acactatgaa tagcctgacc ctgccttccg aagtcaacct gtgcaatgtg gacatcttta   2880
atccaaagta cgattgtaag atcatgacta gcaagaccga tgtcagctcc tctgtgatta   2940
cttctctggg ggccatcgtg agttgctacg gaaagacaaa atgtactgcc agcaacaaaa   3000
atcgcggcat cattaagacc ttctccaacg ggtgcgacta tgtctctaac aagggcgtgg   3060
atacagtgag tgtcgggaac actctgtact atgtcaataa gcaggaggga aaaagcctgt   3120
acgtgaaggg cgaacccatc attaacttct atgacccccct ggtgttccct tccgacgagt   3180
ttgatgcatc tattagtcag gtgaacgaaa aaatcaatca gagtctggcc tttattcgga   3240
agtcagatga gctgctgcac aacgtgaatg ctggcaaatc tacaactaac atcatgatca   3300
ccacaatcat catcgtgatt atcgtcattc tgctgtcact gatcgctgtg ggctgctgc    3360
tgtactgtaa ggcaagaagc accccagtca ctctgtcaaa agaccagctg tcagggatta   3420
acaacattgc cttcagtaac tgatagctag cggcgcgcca gcaacaagta agaaaaactt   3480
aggattaatg gaaattatcc aatccagaga cggaaggaca aatccagaat ccaaccacaa   3540
ctcaatcaac caaagattca tggaagacaa tgttcaaaac aatcaaatca tggattcttg   3600
ggaagaggga tcaggagata aatcatctga catctcatcg gccctcgaca tcattgaatt   3660
catactcagc accgactccc aagagaacac ggcagacagc aatgaaatca acacaggaac   3720
cacaagactt agcacgacaa tctaccaacc tgaatccaaa acaacagaaa caagcaagga   3780
aaatagtgga ccagctaaca aaaatcgaca gtttggggca tcacacgaac gtgccacaga   3840
gacaaaagat agaaatgtta atcaggagac tgtacaggga ggatatagga gaggaagcag   3900
cccagatagt agaactgaga ctatggtcac tcgaagaatc tccagaagca gcccagatcc   3960
taacaatgga acccaaatcc aggaagatat tgattacaat gaagttggag agatggataa   4020
ggactctact aagagggaaa tgcgacaatt taaagatgtt ccagtcaagg tatcaggaag   4080
tgatgccatt cctccaacaa aacaagatgg agacggtgat gatggaagag gcctggaatc   4140
tatcagtaca tttgattcag gatataccag tatagtgact gccgcaacac tagatgacga   4200
agaagaactc cttatgaaga acaacaggcc aagaaagtat caatcaacac cccagaacag   4260
tgacaaggga attaaaaaag ggttggaag gccaaaagac acagacaaac aatcatcaat    4320
attggactac gaactcaact tcaaaggatc gaagaagagc cagaaaatcc tcaaagccag   4380
cacgaataca ggagaaccaa caagaccaca gaatggatcc caggggaaga gaatcacatc   4440
ctggaacatc ctcaacagcg agagcggcaa tcgaacagaa tcaacaaacc aaacccatca   4500
gacatcaacc tcgggacaga accacacaat gggaccaagc agaacaacct ccgaaccaag   4560
gatcaagaca caaaagacgg atggaaagga aagagaggac acagaagaga gcactcgatt   4620
tacagaaagg gcgattacat tattacagaa tcttggtgta atccaatctg cagcaaaatt   4680
agacctatac caagacaaga gagttgtgtg tgtggcgaat gtcctaaaca atgcagatac   4740
tgcatcaaag atagacttcc tagcaggttt gatgatagga gtgtcaatgg atcatgatac   4800
caaattaaat cagattcaga acgagatatt aagtttgaaa actgatctta aaaagatgga   4860
```

tgaatcacat agaagactaa ttgagaatca aaaagaacaa ttatcactga tcacatcatt 4920
aatctcaaat cttaaaatta tgacagagag aggagggaag aaggaccaac cagaacctag 4980
cgggaggaca tccatgatca agacaaaagc aaaagaagag aaaataaaga aagtcaggtt 5040
tgaccctctt atggaaacac agggcatcga gaaaaacatc cctgacctct atagatcaat 5100
agagaaaaca ccagaaaacg acacacagat caaatcagaa ataaacagat tgaatgatga 5160
atccaatgcc actagattag tacctagaag aataagcagt acaatgagat cattaataat 5220
aatcattaac aacagcaatt tatcatcaaa agcaaagcaa tcatacatca acgaactcaa 5280
gctctgcaag agtgacgagg aagtgtctga gttgatggac atgttcaatg aggatgtcag 5340
ctcccagtaa accgccaacc aagggtcaac accaagaaaa ccaatagcac aaaacagcca 5400
atcagagacc accccaatac accaaaccaa tcaacacata acaaagatcg cggccgcata 5460
gatgattaag aaaaacttag gatgaaagga ctaatcaatc ctccgaaaca atgagcatca 5520
ccaactccac aatctacaca ttcccagaat cctctttctc cgagaatggc aacatagagc 5580
cgttaccact caaggtcaat gaacagagaa aggccatacc tcatattagg gttgtcaaga 5640
taggagatcc gcccaaacat ggatccagat atctggatgt ctttttactg ggcttctttg 5700
agatggaaag gtcaaaagac aggtatggga gcataagtga tctagatgat gatccaagtt 5760
acaaggtttg tggctctgga tcattgccac ttgggttggc tagatacacc ggaaatgatc 5820
aggaactcct acaggctgca accaagctcg atatagaagt aagaagaact gtaaaggcta 5880
cggagatgat agtttacact gtacaaaaca tcaaacctga actatatcca tggtccagta 5940
gattaagaaa agggatgtta tttgacgcta ataaggttgc acttgctcct caatgtcttc 6000
cactagatag agggataaaa ttcagggtga tatttgtgaa ctgcacagca attggatcaa 6060
taactctatt caaaatccct aagtccatgg cattgttatc attgcctaat acaatatcaa 6120
taaatctaca agtacatatc aaaacaggag ttcagacaga ttccaaagga gtagttcaga 6180
ttctagatga aaaaggtgaa aaatcactaa atttcatggt tcatctcggg ttgatcaaaa 6240
ggaagatggg cagaatgtac tcagttgaat attgtaagca gaagatcgag aagatgagat 6300
tattattctc attgggatta gttggaggga tcagcttcca cgtcaacgca actggctcta 6360
tatcaaagac attagcaagt caattagcat tcaaaagaga aatctgctat cccctaatgg 6420
atctgaatcc acacttaaat tcagttatat gggcatcatc agttgaaatt acaagggtag 6480
atgcagttct ccagccttca ttacctggcg aattcagata ctacccaaac atcatagcaa 6540
aaggggtcgg gaaaatcaga cagtaaaatc aacaaccctg atatccaccg gtgtattaag 6600
ccgaagcaaa taaaggataa tcaaaaactt aggacaaaag aggtcaatac caacaactat 6660
tagcagtcac actcgcaaga ataagagaga agggaccaaa aaagtcaaat aggagaaatc 6720
aaaacaaaag gtacagaaca ccagaacaac aaaatcaaaa catccaactc actcaaaaca 6780
aaaattccaa aagagaccgg caacacaaca agcactgaac acaatgccaa cttcaatact 6840
gctaattatt acaaccatga tcatggcatc tttctgccaa atagatatca caaaactaca 6900
gcacgtaggt gtattggtca acagtcccaa agggatgaag atatcacaaa actttgaaac 6960
aagatatcta attttgagcc tcataccaaa aatagaagac tctaactctt gtggtgacca 7020
acagatcaag caatacaaga agttattgga tagactgatc atccctttat atgatggatt 7080
aagattacag aaagatgtga tagtaaccaa tcaagaatcc aatgaaaaca ctgatcccag 7140
aacaaaacga ttctttggag gggtaattgg aaccattgct ctgggagtag caacctcagc 7200
acaaattaca gcggcagttg ctctggttga agccaagcag gcaagatcag acatcgaaaa 7260
actcaaagaa gcaattaggg acacaaacaa agcagtgcag tcagttcaga gctccatagg 7320
aaatttaata gtagcaatta aatcagtcca ggattatgtt aacaaagaaa tcgtgccatc 7380
gattgcgagg ctaggttgtg aagcagcagg acttcaatta ggaattgcat taacacagca 7440
ttactcagaa ttaacaaaca tatttggtga taacatagga tcgttacaag aaaaaggaat 7500
aaaattacaa ggtatagcat cattataccg cacaaatatc acagaaatat tcacaacatc 7560
aacagttgat aaatatgata tctatgatct gttatttaca gaatcaataa aggtgagagt 7620
tatagatgtt gacttgaatg attactcaat caccctccaa gtcagactcc ctttattaac 7680
taggctgctg aacactcaga tctacaaagt agattccata tcatataaca tccaaaacag 7740
agaatggtat atccctcttc ccagccatat catgacgaaa ggggcatttc taggtggagc 7800
agacgtcaaa gaatgtatag aagcattcag cagctatata tgcccttctg atccaggatt 7860
tgtattaaac catgaaatag agagctgctt atcaggaaac atatcccaat gtccaagaac 7920
aacggtcaca tcagacattg ttccaagata tgcatttgtc aatggaggag tggttgcaaa 7980
ctgtataaca accacctgta catgcaacgg aattggtaat agaatcaatc aaccacctga 8040
tcaaggagta aaaattataa cacataaaga atgtagtaca ataggtatca acggaatgct 8100
gttcaataca aataaagaag gaactcttgc attctataca ccaaatgata taacactaaa 8160
caattctgtt gcacttgatc caattgacat atcaatcgag ctcaacaagg ccaaatcaga 8220
tctagaagaa tcaaaagaat ggataagaag gtcaaatcaa aaactagatt ctattggaaa 8280
ttggcatcaa tctagcacta caatcataat tattttgata atgatcatta tattgtttat 8340
aattaatata acgataatta caattgcaat taagtattac agaattcaaa agagaaatcg 8400
agtggatcaa aatgacaagc catatgtact aacaaacaaa taacatatct acagatcatt 8460
agatattaaa attataaaaa acttaggagt aaagttacgc aatccaactc tactcatata 8520
attgaggaag gacccaatag acaaatccaa attcgagatg gaatactgga agcataccaa 8580
tcacggaaag gatgctggta atgagctgga gacgtctatg gctactcatg gcaacaagct 8640
cactaataag ataatataca tattatggac aataatcctg gtgttattat caatagtctt 8700
catcatagtg ctaattaatt ccatcaaaag tgaaaaggcc cacgaatcat tgctgcaaga 8760
cataaataat gagtttatgg aaattacaga aaagatccaa atggcatcgg ataataccaa 8820
tgatctaata cagtcaggag tgaatacaag gcttcttaca attcagagtc atgtccagaa 8880
ttacatacca atatcattga cacaacagat gtcagatctt aggaaattca ttagtgaaat 8940
tacaattaga aatgataatc aagaagtgct gccacaaaga ataacacatg atgtaggtat 9000
aaaaccttta aatccagatg atttttggag atgcacgtct ggtcttccat ctttaatgaa 9060
aactccaaaa ataaggttaa tgccagggcc gggattatta gctatgccaa cgactgttga 9120
tggctgtgtt agaactccgt ctttagttat aaatgatctg atttatgctt atacctcaaa 9180
tctaattact cgaggttgtc aggatatagg aaaatcatat caagtcttac agatagggat 9240
aataactgta aactcagact tggtacctga cttaaatcct aggatctctc ataccttttaa 9300
cataaatgac aataggaagt catgttctct agcactccta aatacagatg tatatcaact 9360
gtgttcaact cccaaagttg atgaaagatc agattatgca tcatcaggca tagaagatat 9420
tgtacttgat attgtcaatt atgatggttc aatctcaaca acaagattta agaataataa 9480
cataagcttt gatcaaccat atgctgcact atacccatct gttggaccag ggatatacta 9540
caaaggcaaa ataatatttc tcgggtatgg aggtcttgaa catccaataa atgagaatgt 9600

```
aatctgcaac acaactgggt gccccgggaa aacacagaga gactgtaatc aagcatctca   9660
tagtccatgg ttttcagata ggaggatggt caactccatc attgttgttg acaaaggctt   9720
aaactcaatt ccaaaattga aagtatggac gatatctatg cgacaaaatt actgggggtc   9780
agaaggaagg ttacttctac taggtaacaa gatctatata tatacaagat ctacaagttg   9840
gcatagcaag ttacaattag gaataattga tattactgat tacagtgata taaggataaa   9900
atggacatgg cataatgtgc tatcaagacc aggaaacaat gaatgtccat ggggacattc   9960
atgtccagat ggatgtataa caggagtata tactgatgca tatccactca atcccacagg  10020
gagcattgtg tcatctgtca tattagactc acaaaaatcg agagtgaacc cagtcataac  10080
ttactcaaca gcaaccgaaa gagtaaacga gctggccatc ctaaacagaa cactctcagc  10140
tggatataca acaacaagct gcattacaca ctataacaaa ggatattgtt ttcatatagt  10200
agaaataaat cataaaagct taaacacatt tcaacccatg ttgttcaaaa cagagattcc  10260
aaaaagctgc agttaatcat aattaaccat aatatgcatc aatctatcta taatacaagt  10320
atatgataag taatcagcaa tcagacaata gacgtacgga aataataaaa aacttaggag  10380
aaaagtgtgc aagaaaaatg gacaccgagt cccacagcgg cacaacatct gacattctgt  10440
accctgaatg tcacctcaat tctcctatag ttaaaggaaa gatagcacaa ctgcatacaa  10500
taatgagttt gcctcagccc tacgatatgg atgatgattc aatactgatt attactagac  10560
aaaaaattaa actcaataaa ttagataaaa gacaacggtc aattaggaaa ttaagatcag  10620
tcttaatgga aagagtaagt gatctaggta aatatacctt tatcagatat ccagagatgt  10680
ctagtgaaat gttccaatta tgtatacccg gaattaataa taaaataaat gaattgctaa  10740
gtaaagcaag taaaacatat aatcaaatga ctgatggatt aagagatcta tgggttacta  10800
tactatcgaa gttagcatcg aaaaatgatg gaagtaatta tgatatcaat gaagatatta  10860
gcaatatatc aaatgttcac atgacttatc aatcagacaa atggtataat ccattcaaga  10920
catggtttac tattaagtat gacatgagaa gattacaaaa agccaaaaat gagattacat  10980
tcaataggca taaagattat aatctattag aagaccaaaa gaatatattg ctgatacatc  11040
cagaactcgt cttaatatta gataaacaaa attacaatgg gtatataatg actcctgaat  11100
tggtactaat gtattgtgat gtagttgaag ggaggtggaa tataagttca tgtgcaaaat  11160
tggatcctaa gttacaatca atgtattata agggtaacaa tttatgggaa ataatagatg  11220
gactattctc gaccttagga gaaagaacat ttgacataat atcactatta gaaccacttg  11280
cattatcgct cattcaaact tatgacccgg ttaaacagct caggggggct tttttaaatc  11340
acgtgttatc agaaatggaa ttaatatttg cagctgagtg tacaacagag gaaataccta  11400
atgtggatta tatagataaa attttagatg tgttcaaaga atcaacaata gatgaaatag  11460
cagaaatttt ctctttcttc cgaacttttg gacaccctcc attagaggcg agtatagcag  11520
cagagaaagt tagaaagtat atgtatactg agaaatgctt gaaatttgat actatcaata  11580
aatgtcatgc tattttttgt acaataatta taaatggata tagagaaaga catggtggtc  11640
aatggcctcc agttacatta cctgtccatg cacatgaatt tatcataaat gcatacggat  11700
caaattctgc catatcatat gagaatgctg tagattatta taagagcttc ataggaataa  11760
aatttgacaa gtttatagag cctcaattgg atgaagactt aactatttat atgaaagata  11820
aagcattatc cccaaagaaa tcaaactggg acacagtcta tccagcttca aacctgttat  11880
accgcactaa tgtgtctcat gattcacgaa gattggttga agtatttata gcagatagta  11940
aatttgatcc ccaccaagta ttagattacg tagaatcagg atattggctg gatgatcctg  12000
```

aatttaatat ctcatatagt ttaaaagaga aagaaataaa acaagaaggt agactttttg 12060
caaaaatgac atacaagatg agggctacac aagtattatc agaaacatta ttggcgaata 12120
atatagggaa attcttccaa gagaatggga tggttaaagg agaaattgaa ttactcaaga 12180
gactaacaac aatatctatg tctggagttc cgcggtataa tgaggtatac aataattcaa 12240
aaagtcacac agaagaactt caagcttata atgcaattag cagttccaat ttatcttcta 12300
atcagaagtc aaagaagttt gaatttaaat ctacagatat atacaatgat ggatacgaaa 12360
ccgtaagctg cttcttaacg acagatctta aaaaatattg tttaaattgg aggtatgaat 12420
caacagcttt attcggtgat acttgtaatc agatatttgg gttaaaggaa ttatttaatt 12480
ggctgcaccc tcgccttgaa aagagtacaa tatatgttgg agatccttat tgcccgccat 12540
cagatattga acatttacca cttgatgacc atcctgattc aggattttat gttcataatc 12600
ctaaaggagg aatagaaggg ttttgccaaa agttatggac actcatatct atcagtgcaa 12660
tacatttagc agctgtcaaa atcggtgtaa gagttactgc aatggttcaa ggggataatc 12720
aagccatagc tgttaccaca agagtaccta ataattatga ttataaagtt aagaaagaga 12780
ttgtttataa agatgtggta agattttttg attccttgag agaggtgatg gatgatctgg 12840
gtcatgagct caaactaaat gaaactataa taagtagtaa aatgtttata tatagcaaaa 12900
ggatatacta tgacggaaga atccttcctc aggcattaaa agcattgtct agatgtgttt 12960
tttggtctga aacaatcata gatgagacaa gatcagcatc ctcaaatctg gctacatcgt 13020
ttgcaaaggc cattgagaat ggctactcac ctgtattggg atatgtatgc tcaatcttca 13080
aaaatatcca acagttgtat atagcgcttg gaatgaatat aaacccaact ataacccaaa 13140
atattaaaga tcaatatttc aggaatattc attggatgca atatgcctcc ttaatccctg 13200
ctagtgtcgg aggatttaat tatatggcca tgtcaaggtg ttttgtcaga aacattggag 13260
atcctacagt cgctgcgtta gccgatatta aaagatttat aaaagcaaat ttgttagatc 13320
gaggtgtcct ttacagaatt atgaatcaag aaccaggcga gtcttctttt ttagactggg 13380
cctcagatcc ctattcatgt aacttaccac aatctcaaaa tataaccacc atgataaaga 13440
atataactgc aagaaatgta ctacaggact caccaaaccc attactatct ggattattta 13500
caagtacaat gatagaagag gatgaggaat tagctgagtt cctaatggac aggagaataa 13560
tcctcccaag agttgcacat gacattttag ataattctct tactggaatt aggaatgcta 13620
tagctggtat gttggataca acaaaatcac taattcgagt agggataagc agaggaggat 13680
taacctataa cttattaaga aagataagca actatgatct tgtacaatat gagacactta 13740
gtaaaacttt aagactaata gtcagtgaca agattaagta tgaagatatg tgctcagtag 13800
acctagccat atcattaaga caaaaaatgt ggatgcattt atcaggagga agaatgataa 13860
atggacttga aactccagat cctttagagt tactgtctgg agtaataata acaggatctg 13920
aacattgtag gatatgttat tcaactgaag gtgaaagccc atatacatgg atgtatttac 13980
caggcaatct taatatagga tcagctgaga caggaatagc atcattaagg gtcccttact 14040
ttggatcagt tacagatgag agatctgaag cacaattagg gtatatcaaa aatctaagca 14100
aaccagctaa ggctgctata agaatagcaa tgatatatac ttgggcattt gggaatgacg 14160
aaatatcttg gatggaagca tcacagattg cacaaacacg tgcaaacttt acattggata 14220
gcttaaagat tttgacacca gtgacaacat caacaaatct atcacacagg ttaaaagata 14280
ctgctactca gatgaaattt tctagtacat cacttattag agtaagcagg ttcatcacaa 14340

```
tatctaatga taatatgtct attaaagaag caaatgaaac taaagataca aatcttattt  14400
atcaacaggt aatgttaaca ggattaagtg tatttgaata tctatttagg ttagaggaga  14460
gtacaggaca taaccctatg gtcatgcatc tacatataga ggatggatgt tgtataaaag  14520
agagttacaa tgatgagcat atcaatccgg agtctacatt agagttaatc aaataccctg  14580
agagtaatga atttatatat gataaggacc ctttaaagga tatagatcta tcaaaattaa  14640
tggttataag agatcattct tatacaattg acatgaatta ctgggatgac acagatattg  14700
tacatgcaat atcaatatgt actgcagtta caatagcaga tacaatgtcg cagctagatc  14760
gggataatct taaggagctg gttgtgattg caaatgatga tgatattaac agtctgataa  14820
ctgaatttct gaccctagat atactagtgt ttctcaaaac atttggaggg ttactcgtga  14880
atcaatttgc atataccctt tatggattga aaatagaagg aagggatccc atttgggatt  14940
atataatgag aacattaaaa gacacctcac attcagtact taaagtatta tctaatgcac  15000
tatctcatcc aaaagtgttt aagagatttt gggattgtgg agttttgaat cctatttatg  15060
gtcctaatac tgctagtcaa gatcaagtta agcttgctct ctcgatttgc gagtactcct  15120
tggatctatt tatgagagaa tggttgaatg gagcatcact tgagatctat atctgtgata  15180
gtgacatgga aatagcaaat gacagaagac aagcatttct ctcaagacat cttgcctttg  15240
tgtgttgttt agcagagata gcatcttttg gaccaaattt attaaatcta acatatctag  15300
agagacttga tgaattaaaa caatacttag atctgaacat caaagaagat cctactctta  15360
aatatgtgca agtatcagga ctgttaatta aatcattccc ctcaactgtt acgtatgtaa  15420
ggaaaactgc gattaagtat ctgaggattc gtggtattaa tccgcctgaa acgattgaag  15480
attgggatcc catagaagat gagaatatct tagacaatat tgttaaaact gtaaatgaca  15540
attgcagtga taatcaaaag agaaataaaa gtagttattt ctggggatta gctctaaaga  15600
attatcaagt cgtgaaaata agatccataa cgagtgattc tgaagttaat gaagcttcga  15660
atgttactac acatggaatg acacttcctc agggaggaag ttatctatca catcagctga  15720
ggttatttgg agtaaacagt acaagttgtc ttaaagctct tgaattatca caaatcttaa  15780
tgagggaagt taaaaaagat aaagatagac tctttttagg agaaggagca ggagctatgt  15840
tagcatgtta tgatgctaca ctcggtcctg caataaatta ttataattct ggtttaaata  15900
ttacagatgt aattggtcaa cgggaattaa aaatcttccc atcagaagta tcattagtag  15960
gtaaaaaact aggaaatgta acacagattc ttaatcgggt gagggtgtta tttaatggga  16020
atcccaattc aacatggata ggaaatatgg aatgtgagag tttaatatgg agtgaattaa  16080
atgataagtc aattggttta gtacattgtg acatggaggg agcgataggc aaatcagaag  16140
aaactgttct acatgaacat tatagtatta ttaggattac atatttaatc ggggatgatg  16200
atgttgtcct agtatcaaaa attataccaa ctattactcc gaattggtct aaaatactct  16260
atctatacaa gttgtattgg aaggatgtaa gtgtagtgtc ccttaaaaca tccaatcctg  16320
cctcaacaga gctttattta atttcaaaag atgcttactg tactgtaatg gaacccagta  16380
atcttgtttt atcaaaactt aaaaggatat catcaataga agaaaataat ctattaaagt  16440
ggataatctt atcaaaaagg aagaataacg agtggttaca gcatgaaatc aaagaaggag  16500
aaagggatta tgggataatg aggccatatc atacagcact gcaaattttt ggattccaaa  16560
ttaacttaaa tcacttagct agagaatttt tatcaactcc tgatttaacc aacattaata  16620
atataattca aagttttaca agaacaatta aagatgttat gttcgaatgg gtcaatatca  16680
ctcatgacaa taaaagacat aaattaggag gaagatataa tctattcccg cttaaaaata  16740
```

```
aggggaaatt aagattatta tcacgaagat tagtactaag ctggatatca ttatccttat  16800

caaccagatt actgacgggc cgttttccag atgaaaaatt tgaaaatagg gcacagaccg  16860

gatatgtatc attggctgat attgatttag aatccttaaa gttattatca agaaatattg  16920

tcaaaaatta caaagaacac ataggattaa tatcatactg gtttttgacc aaagaggtca  16980

aaatactaat gaagcttata ggaggagtca aactactagg aattcctaaa cagtacaaag  17040

agttagagga tcgatcatct cagggttatg aatatgataa tgaatttgat attgattaat  17100

acataaaaac aaaaaataaa acacctattc ctcacccatt cacttccaac aaaatgaaaa  17160

gtaagaaaaa catgtaatat atatatacca aacagagttt ttctcttgtt tggt        17214
```

<210> SEQ ID NO 17
<211> LENGTH: 17220
<212> TYPE: DNA
<213> ORGANISM: Artificial Sequence
<220> FEATURE:
<223> OTHER INFORMATION: Recombinant RSV sequence

<400> SEQUENCE: 17

```
accaaacaag agaagagact ggtttgggaa tattaattca aataaaaatt aacttaggat     60

taaagaactt taccgaaagg taaggggaaa gaaatcctaa gagcttagcc atgttgagtc    120

tattcgacac attcagtgcg cgtaggcagg agaacataac gaaatcagct ggtggggctg    180

ttattcccgg gcaaaaaaac actgtgtcta tatttgctct tggaccatca ataacagatg    240

acaatgataa aatgacattg gctcttctct tttgtctca ttctttagac aatgaaaagc    300

agcatgcgca aagagctgga tttttagttt ctctgttatc aatggcttat gccaacccag    360

aattatattt aacatcaaat ggtagtaatg cagatgttaa atatgttatc tacatgatag    420

agaaagaccc aggaagacag aaatatggtg ggtttgtcgt caagactaga gagatggttt    480

atgaaaagac aactgattgg atgttcggga gtgatcttga gtatgatcaa gacaatatgt    540

tgcaaaatgg tagaagcact tctacaatcg aggatcttgt tcatactttt ggatatccat    600

cgtgtcttgg agcccttata atccaagttt ggataatact tgttaaggct ataaccagta    660

tatcaggatt gaggaaagga ttctttactc ggttagaagc atttcgacaa gatggaacag    720

ttaaatccag tctagtgttg agcggtgatg cagtagaaca aattggatca attatgaggt    780

cccaacagag cttggtaaca ctcatggttg aaacactgat aacaatgaac acaggcagga    840

atgatctgac aacaatagaa aagaatatac agattgtagg aaactacatc agagatgcag    900

gtcttgcttc atttttcaac acaatcagat atggcattga gactagaatg gcagctctaa    960

ctctgtctac ccttagaccg gatatcaaca gactcaaggc actgatcgag ttatatctat   1020

caaaggggcc acgtgctcct tttatatgca ttttgagaga tcccgtgcat ggtgagtttg   1080

caccaggcaa ctatcctgcc ctctggagtt atgcgatggg tgtagcagtt gtacaaaaca   1140

aggccatgca acagtatgta acaggaaggt cttatctgga tattgaaatg ttccaacttg   1200

gtcaagcagt ggcacgtgat gccgagtcgc agatgagttc aatattagag gatgaactgg   1260

gggtcacaca agaagccaag caaagcttga agaaacacat gaagaacatc agcagttcag   1320

atacaacctt tcataagcct acagggggat cagccataga aatggcgata gatgaagaag   1380

cagggcagcc tgaatccaga ggagatcagg atcaaggaga tgagcctcgg tcatccatag   1440

ttccttatgc atgggcagac gaaaccggga atgacaatca aactgaatca actacagaaa   1500

ttgacagcat caaaactgaa caaagaaaca tcagagacag gctgaacaaa agactcaacg   1560
```

```
agaaaaggaa acagagtgac ccgagatcaa ctgacatcac aaacaacaca aatcaaactg   1620
aaatagatga tttgttcagt gcattcggaa gcaactagtc acaaagagat gaccaggcgc   1680
gccaagtaag aaaaacttag gattaatgga cctgcaggat ggaactgctg atcctgaaag   1740
ccaacgctat tactactatc ctgaccgccg tgacattttg cttcgcatct ggacagaaca   1800
ttactgagga attctaccag tcaacatgca gcgccgtgtc caaaggatac ctgagcgccc   1860
tgcggaccgg ctggtataca tcagtgatta ctatcgagct gtccaacatc aaggaaaaca   1920
aatgtaatgg gaccgacgca aaggtgaaac tgatcaagca ggagctggat aagtacaaaa   1980
atgccgtgac agaactgcag ctgctgatgc agtccacacc agcaactaac aatcgcgccc   2040
ggagagagct gccccggttc atgaactata ccctgaacaa tgctaagaaa accaatgtga   2100
cactgtccaa gaaacgcaag aggcgcttcc tgggatttct gctgggcgtg ggtctgcca   2160
tcgctagtgg agtggccgtc tgcaaagtcc tgcacctgga gggcgaagtg aacaagatca   2220
aaagcgccct gctgtccact aacaaggcag tggtcagtct gtcaaatggc gtgtccgtcc   2280
tgaccttcaa ggtgctggac ctgaaaaatt atattgataa gcagctgctg cctatcctga   2340
acaaacagag ctgctccatt tctaatatcg agacagtgat cgaattccag cagaagaaca   2400
atagactgct ggagattacc agagagttca gcgtgaacgc cggcgtcacc acacccgtgt   2460
ccacctacat gctgacaaat agtgagctgc tgtcactgat taacgacatg cctatcacca   2520
atgatcagaa gaaactgatg tccaacaatg tgcagatcgt cagacagcag agttactcaa   2580
tcatgtgcat cattaaggag gaagtcctgg cctacgtggt ccagctgcca ctgtatggcg   2640
tgatcgacac cccctgctgg aaactgcata catctcctct gtgcactacc aacacaaagg   2700
aaggaagtaa tatctgcctg actcgaaccg accggggatg gtactgtgat aacgcaggca   2760
gcgtgtcctt ctttccacag gccgagacct gcaaggtcca gagcaacagg gtgttctgtg   2820
acactatgaa tagcctgacc ctgccttccg aagtcaacct gtgcaatgtg gacatcttta   2880
atccaaagta cgattgtaag atcatgacta gcaagaccga tgtcagctcc tctgtgatta   2940
cttctctggg ggccatcgtg agttgctacg gaaagacaaa atgtactgcc agcaacaaaa   3000
atcgcggcat cattaagacc ttctccaacg ggtgcgacta tgtctctaac aagggcgtgg   3060
atacagtgag tgtcgggaac actctgtact atgtcaataa gcaggaggga aaaagcctgt   3120
acgtgaaggg cgaacccatc attaacttct atgacccccct ggtgttccct tccgacgagt   3180
ttgatgcatc tattagtcag gtgaacgaaa aaatcaatca gagtctggcc tttattcgga   3240
agtcagatga gctgctgcac aacgtgaatg ctggcaaatc tacaactaac atcatgatca   3300
ccacaatcac catcattatc gtgatgatta tcattctggt catcattaac atcacaatca   3360
ttgtggtcat cattaagttc caccggattc agggcaagga ccagaacgat aaaaatagcg   3420
agccctacat cctgaccaat agacagtgat agctagcggc gcgccagcaa caagtaagaa   3480
aaacttagga ttaatggaaa ttatccaatc cagagacgga aggacaaatc cagaatccaa   3540
ccacaactca atcaaccaaa gattcatgga agacaatgtt caaaacaatc aaatcatgga   3600
ttcttgggaa gagggatcag gagataaatc atctgacatc tcatcggccc tcgacatcat   3660
tgaattcata ctcagcaccg actcccaaga gaacacggca gacagcaatg aaatcaacac   3720
aggaaccaca agacttagca cgacaatcta ccaacctgaa tccaaaacaa cagaaacaag   3780
caaggaaaat agtggaccag ctaacaaaaa tcgacagttt ggggcatcac acgaacgtgc   3840
cacagagaca aaagatagaa atgttaatca ggagactgta cagggaggat ataggagagg   3900
aagcagccca gatagtagaa ctgagactat ggtcactcga agaatctcca gaagcagccc   3960
```

agatcctaac aatggaaccc aaatccagga agatattgat tacaatgaag ttggagagat 4020
ggataaggac tctactaaga gggaaatgcg acaatttaaa gatgttccag tcaaggtatc 4080
aggaagtgat gccattcctc caacaaaaca agatggagac ggtgatgatg gaagaggcct 4140
ggaatctatc agtacatttg attcaggata taccagtata gtgactgccg caacactaga 4200
tgacgaagaa gaactcctta tgaagaacaa caggccaaga aagtatcaat caacacccca 4260
gaacagtgac aagggaatta aaaaaggggt tggaaggcca aaagacacag acaaacaatc 4320
atcaatattg gactacgaac tcaacttcaa aggatcgaag aagagccaga aaatcctcaa 4380
agccagcacg aatacaggag aaccaacaag accacagaat ggatcccagg ggaagagaat 4440
cacatcctgg aacatcctca acagcgagag cggcaatcga acagaatcaa caaaccaaac 4500
ccatcagaca tcaacctcgg gacagaacca cacaatggga ccaagcagaa caacctccga 4560
accaaggatc aagacacaaa agacggatgg aaaggaaaga gaggacacag aagagagcac 4620
tcgatttaca gaaagggcga ttacattatt acagaatctt ggtgtaatcc aatctgcagc 4680
aaaattagac ctataccaag acaagagagt tgtgtgtgtg gcgaatgtcc taaacaatgc 4740
agatactgca tcaaagatag acttcctagc aggtttgatg ataggagtgt caatggatca 4800
tgataccaaa ttaaatcaga ttcagaacga gatattaagt ttgaaaactg atcttaaaaa 4860
gatggatgaa tcacatagaa gactaattga gaatcaaaaa gaacaattat cactgatcac 4920
atcattaatc tcaaatctta aaattatgac agagagagga gggaagaagg accaaccaga 4980
acctagcggg aggacatcca tgatcaagac aaaagcaaaa gaagagaaaa taaagaaagt 5040
caggtttgac cctcttatgg aaacacaggg catcgagaaa aacatccctg acctctatag 5100
atcaatagag aaaacaccag aaaacgacac acagatcaaa tcagaaataa acagattgaa 5160
tgatgaatcc aatgccacta gattagtacc tagaagaata agcagtacaa tgagatcatt 5220
aataataatc attaacaaca gcaatttatc atcaaaagca aagcaatcat acatcaacga 5280
actcaagctc tgcaagagtg acgaggaagt gtctgagttg atggacatgt tcaatgagga 5340
tgtcagctcc cagtaaaccg ccaaccaagg gtcaacacca agaaaaccaa tagcacaaaa 5400
cagccaatca gagaccaccc caatacacca aaccaatcaa cacataacaa agatcgcggc 5460
cgcatagatg attaagaaaa acttaggatg aaaggactaa tcaatcctcc gaaacaatga 5520
gcatcaccaa ctccacaatc tacacattcc cagaatcctc tttctccgag aatggcaaca 5580
tagagccgtt accactcaag gtcaatgaac agagaaaggc catacctcat attagggttg 5640
tcaagatagg agatccgccc aaacatggat ccagatatct ggatgtcttt ttactgggct 5700
tctttgagat ggaaaggtca aaagacaggt atgggagcat aagtgatcta gatgatgatc 5760
caagttacaa ggtttgtggc tctggatcat tgccacttgg gttggctaga tacaccggaa 5820
atgatcagga actcctacag gctgcaacca agctcgatat agaagtaaga agaactgtaa 5880
aggctacgga gatgatagtt tacactgtac aaaacatcaa acctgaacta tatccatggt 5940
ccagtagatt aagaaaaggg atgttatttg acgctaataa ggttgcactt gctcctcaat 6000
gtcttccact agatagaggg ataaaattca gggtgatatt tgtgaactgc acagcaattg 6060
gatcaataac tctattcaaa atccctaagt ccatggcatt gttatcattg cctaatacaa 6120
tatcaataaa tctacaagta catatcaaaa caggagttca gacagattcc aaaggagtag 6180
ttcagattct agatgaaaaa ggtgaaaaat cactaaattt catggttcat ctcgggttga 6240
tcaaaaggaa gatgggcaga atgtactcag ttgaatattg taagcagaag atcgagaaga 6300

```
tgagattatt attctcattg ggattagttg gagggatcag cttccacgtc aacgcaactg   6360
gctctatatc aaagacatta gcaagtcaat tagcattcaa aagagaaatc tgctatcccc   6420
taatggatct gaatccacac ttaaattcag ttatatgggc atcatcagtt gaaattacaa   6480
gggtagatgc agttctccag ccttcattac ctggcgaatt cagatactac ccaaacatca   6540
tagcaaaagg ggtcgggaaa atcagacagt aaaatcaaca accctgatat ccaccggtgt   6600
attaagccga agcaaataaa ggataatcaa aaacttagga caaaagaggt caataccaac   6660
aactattagc agtcacactc gcaagaataa gagagaaggg accaaaaaag tcaaatagga   6720
gaaatcaaaa caaaaggtac agaacaccag aacaacaaaa tcaaaacatc caactcactc   6780
aaaacaaaaa ttccaaaaga gaccggcaac acaacaagca ctgaacacaa tgccaacttc   6840
aatactgcta attattacaa ccatgatcat ggcatctttc tgccaaatag atatcacaaa   6900
actacagcac gtaggtgtat tggtcaacag tcccaaaggg atgaagatat cacaaaactt   6960
tgaaacaaga tatctaattt tgagcctcat accaaaaata gaagactcta actcttgtgg   7020
tgaccaacag atcaagcaat acaagaagtt attggataga ctgatcatcc ctttatatga   7080
tggattaaga ttacagaaag atgtgatagt aaccaatcaa gaatccaatg aaaacactga   7140
tcccagaaca aaacgattct ttggaggggt aattggaacc attgctctgg gagtagcaac   7200
ctcagcacaa attacagcgg cagttgctct ggttgaagcc aagcaggcaa gatcagacat   7260
cgaaaaactc aaagaagcaa ttagggacac aaacaaagca gtgcagtcag ttcagagctc   7320
cataggaaat ttaatagtag caattaaatc agtccaggat tatgttaaca aagaaatcgt   7380
gccatcgatt gcgaggctag gttgtgaagc agcaggactt caattaggaa ttgcattaac   7440
acagcattac tcagaattaa caaacatatt tggtgataac ataggatcgt tacaagaaaa   7500
aggaataaaa ttacaaggta tagcatcatt ataccgcaca aatatcacag aaatattcac   7560
aacatcaaca gttgataaat atgatatcta tgatctgtta tttacagaat caataaaggt   7620
gagagttata gatgttgact tgaatgatta ctcaatcacc ctccaagtca gactcccttt   7680
attaactagg ctgctgaaca ctcagatcta caaagtagat tccatatcat ataacatcca   7740
aaacagagaa tggtatatcc ctcttcccag ccatatcatg acgaaagggg catttctagg   7800
tggagcagac gtcaaagaat gtatagaagc attcagcagc tatatatgcc cttctgatcc   7860
aggatttgta ttaaaccatg aaatagagag ctgcttatca ggaaacatat cccaatgtcc   7920
aagaacaacg gtcacatcag acattgttcc aagatatgca tttgtcaatg gaggagtggt   7980
tgcaaactgt ataacaacca cctgtacatg caacggaatt ggtaatagaa tcaatcaacc   8040
acctgatcaa ggagtaaaaa ttataacaca taaagaatgt agtacaatag gtatcaacgg   8100
aatgctgttc aatacaaata aagaaggaac tcttgcattc tatacaccaa atgatataac   8160
actaaacaat tctgttgcac ttgatccaat tgacatatca atcgagctca acaaggccaa   8220
atcagatcta gaagaatcaa aagaatggat aagaaggtca aatcaaaaac tagattctat   8280
tggaaattgg catcaatcta gcactacaat cataattatt ttgataatga tcattatatt   8340
gtttataatt aatataacga taattacaat tgcaattaag tattacagaa ttcaaaagag   8400
aaatcgagtg gatcaaaatg acaagccata tgtactaaca aacaaataac atatctacag   8460
atcattagat attaaaatta taaaaaactt aggagtaaag ttacgcaatc caactctact   8520
catataattg aggaaggacc caatagacaa atccaaattc gagatggaat actggaagca   8580
taccaatcac ggaaaggatg ctggtaatga gctggagacg tctatggcta ctcatggcaa   8640
caagctcact aataagataa tatacatatt atggacaata atcctggtgt tattatcaat   8700
```

```
agtcttcatc atagtgctaa ttaattccat caaaagtgaa aaggcccacg aatcattgct   8760
gcaagacata aataatgagt ttatggaaat tacagaaaag atccaaatgg catcggataa   8820
taccaatgat ctaatacagt caggagtgaa tacaaggctt cttacaattc agagtcatgt   8880
ccagaattac ataccaatat cattgacaca acagatgtca gatcttagga aattcattag   8940
tgaaattaca attagaaatg ataatcaaga agtgctgcca caaagaataa cacatgatgt   9000
aggtataaaa cctttaaatc cagatgattt ttggagatgc acgtctggtc ttccatcttt   9060
aatgaaaact ccaaaaataa ggttaatgcc agggccggga ttattagcta tgccaacgac   9120
tgttgatggc tgtgttagaa ctccgtcttt agttataaat gatctgattt atgcttatac   9180
ctcaaatcta attactcgag gttgtcagga tataggaaaa tcatatcaag tcttacagat   9240
agggataata actgtaaact cagacttggt acctgactta aatcctagga tctctcatac   9300
ctttaacata aatgacaata ggaagtcatg ttctctagca ctcctaaata cagatgtata   9360
tcaactgtgt tcaactccca aagttgatga aagatcagat tatgcatcat caggcataga   9420
agatattgta cttgatattg tcaattatga tggttcaatc tcaacaacaa gatttaagaa   9480
taataacata agctttgatc aaccatatgc tgcactatac ccatctgttg gaccagggat   9540
atactacaaa ggcaaaataa tatttctcgg gtatggaggt cttgaacatc caataaatga   9600
gaatgtaatc tgcaacacaa ctgggtgccc cgggaaaaca cagagagact gtaatcaagc   9660
atctcatagt ccatggtttt cagataggag gatggtcaac tccatcattg ttgttgacaa   9720
aggcttaaac tcaattccaa aattgaaagt atggacgata tctatgcgac aaaattactg   9780
ggggtcagaa ggaaggttac ttctactagg taacaagatc tatatatata caagatctac   9840
aagttggcat agcaagttac aattaggaat aattgatatt actgattaca gtgatataag   9900
gataaaatgg acatggcata atgtgctatc aagaccagga aacaatgaat gtccatgggg   9960
acattcatgt ccagatggat gtataacagg agtatatact gatgcatatc cactcaatcc  10020
cacagggagc attgtgtcat ctgtcatatt agactcacaa aaatcgagag tgaacccagt  10080
cataacttac tcaacagcaa ccgaaagagt aaacgagctg gccatcctaa acagaacact  10140
ctcagctgga tatacaacaa caagctgcat tacacactat aacaaaggat attgttttca  10200
tatagtagaa ataaatcata aaagcttaaa cacatttcaa cccatgttgt tcaaaacaga  10260
gattccaaaa agctgcagtt aatcataatt aaccataata tgcatcaatc tatctataat  10320
acaagtatat gataagtaat cagcaatcag acaatagacg tacggaaata ataaaaaact  10380
taggagaaaa gtgtgcaaga aaaatggaca ccgagtccca cagcggcaca acatctgaca  10440
ttctgtaccc tgaatgtcac ctcaattctc ctatagttaa aggaaagata gcacaactgc  10500
atacaataat gagtttgcct cagccctacg atatggatga tgattcaata ctgattatta  10560
ctagacaaaa aattaaactc aataaattag ataaaagaca acggtcaatt aggaaattaa  10620
gatcagtctt aatggaaaga gtaagtgatc taggtaaata tacctttatc agatatccag  10680
agatgtctag tgaaatgttc caattatgta tacccggaat taataataaa ataaatgaat  10740
tgctaagtaa agcaagtaaa acatataatc aaatgactga tggattaaga gatctatggg  10800
ttactatact atcgaagtta gcatcgaaaa atgatggaag taattatgat atcaatgaag  10860
atattagcaa tatatcaaat gttcacatga cttatcaatc agacaaatgg tataatccat  10920
tcaagacatg gtttactatt aagtatgaca tgagaagatt acaaaaagcc aaaaatgaga  10980
ttacattcaa taggcataaa gattataatc tattagaaga ccaaaagaat atattgctga  11040
```

```
tacatccaga actcgtctta atattagata aacaaaatta caatgggtat ataatgactc  11100
ctgaattggt actaatgtat tgtgatgtag ttgaagggag gtggaatata agttcatgtg  11160
caaaattgga tcctaagtta caatcaatgt attataaggg taacaattta tgggaaataa  11220
tagatggact attctcgacc ttaggagaaa gaacatttga cataatatca ctattagaac  11280
cacttgcatt atcgctcatt caaacttatg acccggttaa acagctcagg ggggcttttt  11340
taaatcacgt gttatcagaa atggaattaa tatttgcagc tgagtgtaca acagaggaaa  11400
tacctaatgt ggattatata gataaaattt tagatgtgtt caaagaatca acaatagatg  11460
aaatagcaga aattttctct ttcttccgaa cttttggaca ccctccatta gaggcgagta  11520
tagcagcaga gaaagttaga aagtatatgt atactgagaa atgcttgaaa tttgatacta  11580
tcaataaatg tcatgctatt ttttgtacaa taattataaa tggatataga gaaagacatg  11640
gtggtcaatg gcctccagtt acattacctg tccatgcaca tgaatttatc ataaatgcat  11700
acggatcaaa ttctgccata tcatatgaga atgctgtaga ttattataag agcttcatag  11760
gaataaaatt tgacaagttt atagagcctc aattggatga agacttaact atttatatga  11820
aagataaagc attatcccca aagaaatcaa actgggacac agtctatcca gcttcaaacc  11880
tgttataccg cactaatgtg tctcatgatt cacgaagatt ggttgaagta tttatagcag  11940
atagtaaatt tgatccccac caagtattag attacgtaga atcaggatat tggctggatg  12000
atcctgaatt taatatctca tatagtttaa aagagaaaga aataaaacaa gaaggtagac  12060
tttttgcaaa aatgacatac aagatgaggg ctacacaagt attatcagaa acattattgg  12120
cgaataatat agggaaattc ttccaagaga atgggatggt taaaggagaa attgaattac  12180
tcaagagact aacaacaata tctatgtctg gagttccgcg gtataatgag gtatacaata  12240
attcaaaaag tcacacagaa gaacttcaag cttataatgc aattagcagt tccaatttat  12300
cttctaatca gaagtcaaag aagtttgaat ttaaatctac agatatatac aatgatggat  12360
acgaaaccgt aagctgcttc ttaacgacag atcttaaaaa atattgttta aattggaggt  12420
atgaatcaac agctttattc ggtgatactt gtaatcagat atttgggtta aaggaattat  12480
ttaattggct gcaccctcgc cttgaaaaga gtacaatata tgttggagat ccttattgcc  12540
cgccatcaga tattgaacat ttaccacttg atgaccatcc tgattcagga ttttatgttc  12600
ataatcctaa aggaggaata gaagggtttt gccaaaagtt atggacactc atatctatca  12660
gtgcaataca tttagcagct gtcaaaatcg gtgtaagagt tactgcaatg gttcaagggg  12720
ataatcaagc catagctgtt accacaagag tacctaataa ttatgattat aaagttaaga  12780
aagagattgt ttataaagat gtggtaagat tttttgattc cttgagagag gtgatggatg  12840
atctgggtca tgagctcaaa ctaaatgaaa ctataataag tagtaaaatg tttatatata  12900
gcaaaaggat atactatgac ggaagaatcc ttcctcaggc attaaaagca ttgtctagat  12960
gtgtttttttg gtctgaaaca atcatagatg agacaagatc agcatcctca aatctggcta  13020
catcgtttgc aaaggccatt gagaatggct actcacctgt attgggatat gtatgctcaa  13080
tcttcaaaaa tatccaacag ttgtatatag cgcttggaat gaatataaac ccaactataa  13140
cccaaaatat taaagatcaa tatttcagga atattcattg gatgcaatat gcctccttaa  13200
tccctgctag tgtcggagga tttaattata tggccatgtc aaggtgtttt gtcagaaaca  13260
ttggagatcc tacagtcgct gcgttagccg atattaaaag atttataaaa gcaaatttgt  13320
tagatcgagg tgtcctttac agaattatga atcaagaacc aggcgagtct tctttttttag  13380
actgggcctc agatccctat tcatgtaact taccacaatc tcaaaatata accaccatga  13440
```

taaagaatat aactgcaaga aatgtactac aggactcacc aaacccatta ctatctggat 13500
tatttacaag tacaatgata gaagaggatg aggaattagc tgagttccta atggacagga 13560
gaataatcct cccaagagtt gcacatgaca ttttagataa ttctcttact ggaattagga 13620
atgctatagc tggtatgttg gatacaacaa aatcactaat tcgagtaggg ataagcagag 13680
gaggattaac ctataactta ttaagaaaga taagcaacta tgatcttgta caatatgaga 13740
cacttagtaa aactttaaga ctaatagtca gtgacaagat taagtatgaa gatatgtgct 13800
cagtagacct agccatatca ttaagacaaa aaatgtggat gcatttatca ggaggaagaa 13860
tgataaatgg acttgaaact ccagatcctt tagagttact gtctggagta ataataacag 13920
gatctgaaca ttgtaggata tgttattcaa ctgaaggtga aagcccatat acatggatgt 13980
atttaccagg caatcttaat ataggatcag ctgagacagg aatagcatca ttaagggtcc 14040
cttactttgg atcagttaca gatgagagat ctgaagcaca attagggtat atcaaaaatc 14100
taagcaaacc agctaaggct gctataagaa tagcaatgat atatacttgg gcatttggga 14160
atgacgaaat atcttggatg gaagcatcac agattgcaca aacacgtgca aactttacat 14220
tggatagctt aaagattttg acaccagtga caacatcaac aaatctatca cacaggttaa 14280
aagatactgc tactcagatg aaattttcta gtacatcact tattagagta agcaggttca 14340
tcacaatatc taatgataat atgtctatta aagaagcaaa tgaaactaaa gatacaaatc 14400
ttatttatca acaggtaatg ttaacaggat taagtgtatt tgaatatcta tttaggttag 14460
aggagagtac aggacataac cctatggtca tgcatctaca tatagaggat ggatgttgta 14520
taaaagagag ttacaatgat gagcatatca atccggagtc tacattagag ttaatcaaat 14580
accctgagag taatgaattt atatatgata aggacccttt aaaggatata gatctatcaa 14640
aattaatggt tataagagat cattcttata caattgacat gaattactgg gatgacacag 14700
atattgtaca tgcaatatca atatgtactg cagttacaat agcagataca atgtcgcagc 14760
tagatcggga taatcttaag gagctggttg tgattgcaaa tgatgatgat attaacagtc 14820
tgataactga atttctgacc ctagatatac tagtgtttct caaaacattt ggagggttac 14880
tcgtgaatca atttgcatat accctttatg gattgaaaat agaaggaagg gatcccattt 14940
gggattatat aatgagaaca ttaaaagaca cctcacattc agtacttaaa gtattatcta 15000
atgcactatc tcatccaaaa gtgtttaaga gattttggga ttgtggagtt ttgaatccta 15060
tttatggtcc taatactgct agtcaagatc aagttaagct tgctctctcg atttgcgagt 15120
actccttgga tctatttatg agagaatggt tgaatggagc atcacttgag atctatatct 15180
gtgatagtga catggaaata gcaaatgaca gaagacaagc atttctctca agacatcttg 15240
cctttgtgtg ttgtttagca gagatagcat cttttggacc aaatttatta aatctaacat 15300
atctagagag acttgatgaa ttaaaacaat acttagatct gaacatcaaa gaagatccta 15360
ctcttaaata tgtgcaagta tcaggactgt taattaaatc attcccctca actgttacgt 15420
atgtaaggaa aactgcgatt aagtatctga ggattcgtgg tattaatccg cctgaaacga 15480
ttgaagattg ggatcccata gaagatgaga atatcttaga caatattgtt aaaactgtaa 15540
atgacaattg cagtgataat caaaagagaa ataaaagtag ttatttctgg ggattagctc 15600
taaagaatta tcaagtcgtg aaaataagat ccataacgag tgattctgaa gttaatgaag 15660
cttcgaatgt tactacacat ggaatgacac ttcctcaggg aggaagttat ctatcacatc 15720
agctgaggtt atttggagta aacagtacaa gttgtcttaa agctcttgaa ttatcacaaa 15780

```
tcttaatgag ggaagttaaa aaagataaag atagactctt tttaggagaa ggagcaggag  15840
ctatgttagc atgttatgat gctacactcg gtcctgcaat aaattattat aattctggtt  15900
taaatattac agatgtaatt ggtcaacggg aattaaaaat cttcccatca gaagtatcat  15960
tagtaggtaa aaaactagga aatgtaacac agattcttaa tcgggtgagg gtgttattta  16020
atgggaatcc caattcaaca tggataggaa atatggaatg tgagagttta atatggagtg  16080
aattaaatga taagtcaatt ggtttagtac attgtgacat ggagggagcg ataggcaaat  16140
cagaagaaac tgttctacat gaacattata gtattattag gattacatat ttaatcgggg  16200
atgatgatgt tgtcctagta tcaaaaaatta taccaactat tactccgaat tggtctaaaa  16260
tactctatct atacaagttg tattggaagg atgtaagtgt agtgtccctt aaaacatcca  16320
atcctgcctc aacagagctt tatttaattt caaaagatgc ttactgtact gtaatggaac  16380
ccagtaatct tgttttatca aaacttaaaa ggatatcatc aatagaagaa aataatctat  16440
taaagtggat aatcttatca aaaaggaaga ataacgagtg gttacagcat gaaatcaaag  16500
aaggagaaag ggattatggg ataatgaggc catatcatac agcactgcaa atttttggat  16560
tccaaattaa cttaaatcac ttagctagag aatttttatc aactcctgat ttaaccaaca  16620
ttaataatat aattcaaagt tttacaagaa caattaaaga tgttatgttc gaatgggtca  16680
atatcactca tgacaataaa agacataaat taggaggaag atataatcta ttcccgctta  16740
aaaataaggg gaaattaaga ttattatcac gaagattagt actaagctgg atatcattat  16800
ccttatcaac cagattactg acgggccgtt ttccagatga aaaatttgaa aatagggcac  16860
agaccggata tgtatcattg gctgatattg atttagaatc cttaaagtta ttatcaagaa  16920
atattgtcaa aaattacaaa gaacacatag gattaatatc atactggttt ttgaccaaag  16980
aggtcaaaat actaatgaag cttataggag gagtcaaact actaggaatt cctaaacagt  17040
acaaagagtt agaggatcga tcatctcagg gttatgaata tgataatgaa tttgatattg  17100
attaatacat aaaaacaaaa aataaaacac ctattcctca cccattcact tccaacaaaa  17160
tgaaaagtaa gaaaaacatg taatatatat ataccaaaca gagtttttct cttgtttggt  17220
```

<210> SEQ ID NO 18
<211> LENGTH: 14589
<212> TYPE: DNA
<213> ORGANISM: Artificial Sequence
<220> FEATURE:
<223> OTHER INFORMATION: Recombinant RSV sequence

<400> SEQUENCE: 18

```
acgggaaaaa atgcgtacaa caaacttgca taaaccaaaa aaatggggca aataagaatt     60
tgataagtac cacttaaatt taactccctt ggttagagat gggcagcaat tcattgagta    120
tgataaaagt tagattacaa aatttgtttg acaatgatga agtagcattg ttaaaaataa    180
catgctatac tgataaatta atacatttaa ctaatgcttt ggctaaggca gtgatacata    240
caatcaaatt gaatggcatt gtgtttgtgc atgttattac aagtagtgat atttgcccta    300
ataataatat tgtagtaaaa tccaatttca caacaatgcc agtactacaa aatggaggtt    360
atatatggga aatgatggaa ttaacacatt gctctcaacc taatggtcta ctagatgaca    420
attgtgaaat taaattctcc aaaaaactaa gtgattcaac aatgaccaat tatatgaatc    480
aattatctga attacttgga tttgatctta atccataaat tataattaat atcaactagc    540
aaatcaatgt cactaacacc attagttaat ataaaactta aggagagata taagatagaa    600
gatggggcaa atacaaccat ggctcttagc aaagtcaagt tgaatgatac actcaacaaa    660
```

```
gatcaacttc tgtcatccag caaatacacc atccaacgga gcacaggaga tagtattgat    720
actcctaatt atgatgtgca gaaacacatc aataagttat gtggcatgtt attaatcaca    780
gaagatgcta atcataaatt cactgggtta ataggtatgt tatatgcgat gtctaggtta    840
ggaagagaag acaccataaa aatactcaga gatgcgggat atcatgtaaa agcaaatgga    900
gtagatgtaa caacacatcg tcaagacatt aatggaaaag aaatgaaatt tgaagtgtta    960
acattggcaa gcttaacaac tgaaattcaa atcaacattg agatagaatc tagaaaatcc   1020
tacaaaaaaa tgctaaaaga aatgggagag gtagctccag aatacaggca tgactctcct   1080
gattgtggga tgataatatt atgtatagca gcattagtaa taactaaatt agcagcaggg   1140
gacagatctg gtcttacagc cgtgattagg agagctaata atgtcctaaa aaatgaaatg   1200
aaacgttaca aaggcttact acccaaggac atagccaaca gcttctatga agtgtttgaa   1260
aaacatcccc actttataga tgtttttgtt cattttggta tagcacaatc ttctaccaga   1320
ggtggcagta gagttgaagg gatttttgca ggattgttta tgaatgccta tggtgcaggg   1380
caagtgatgt tacggtgggg agtcttagca aaatcggtta aaaatattat gttaggacat   1440
gctagtgtgc aagcagaaat ggaacaagtt gttgaggttt atgaatatgc ccaaaaattg   1500
ggtggtgaag caggattcta ccatatattg aacaacccaa aagcatcatt attatctttg   1560
actcaatttc ctcacttctc cagtgtagta ttaggcaatg ctgctggcct aggcataatg   1620
ggagagtaca gaggtacacc gaggaatcaa gatctatatg atgcagcaaa ggcatatgct   1680
gaacaactca aagaaaatgg tgtgattaac tacagtgtac tagacttgac agcagaagaa   1740
ctagaggcta tcaaacatca gcttaatcca aaagataatg atgtagagct ttgagttaat   1800
aaaaaatggg gcaaataaat catcatggaa aagtttgctc ctgaattcca tggagaagat   1860
gcaaacaaca gggctactaa attcctagaa tcaataaagg gcaaattcac atcacccaaa   1920
gatcccaaga aaaaagatag tatcatatct gtcaactcaa tagatataga agtaaccaaa   1980
gaaagcccta taacatcaaa ttcaactatt atcaacccaa caaatgagac agatgatact   2040
gcagggaaca agcccaatta tcaaagaaaa cctctagtaa gtttcaaaga agaccctaca   2100
ccaagtgata atcccttttc taaactatac aaagaaacca tagaaacatt tgataacaat   2160
gaagaagaat ccagctattc atacgaagaa ataaatgatc agacaaacga taatataaca   2220
gcaagattag ataggattga tgaaaaatta agtgaaatac taggaatgct tcacacatta   2280
gtagtggcaa gtgcaggacc tacatctgct cgggatggta taagagatgc catggttggt   2340
ttaagagaag aaatgataga aaaaatcaga actgaagcat taatgaccaa tgacagatta   2400
gaagctatgg caagactcag gaatgaggaa agtgaaaaga tggcaaaaga cacatcagat   2460
gaagtgtctc tcaatccaac atcagagaaa ttgaacaacc tattggaagg gaatgatagt   2520
gacaatgatc tatcacttga agatttctga ttagttacca atcttcacat caacacacaa   2580
taccaacaga agaccaacaa actaaccaac ccaatcatcc aaccaaacat ccatccgcca   2640
atcagccaaa cagccaacaa aacaaccagc caatccaaaa ctaaccaccc ggaaaaaatc   2700
tataatatag ttacaaaaaa aggaaagggt ggggcaaata tggaaacata cgtgaacaag   2760
cttcacgaag gctccacata cacagctgct gttcaataca atgtcttaga aaaagacgat   2820
gaccctgcat cacttacaat atgggtgccc atgttccaat catctatgcc agcagattta   2880
cttataaaag aactagctaa tgtcaacata ctagtgaaac aaatatccac acccaaggga   2940
ccttcactaa gagtcatgat aaactcaaga agtgcagtgc tagcacaaat gcccagcaaa   3000
```

```
tttaccatat gcgctaatgt gtccttggat gaaagaagca aactagcata tgatgtaacc   3060
acaccctgtg aaatcaaggc atgtagtcta acatgcctaa aatcaaaaaa tatgttgact   3120
acagttaaag atctcactat gaagacactc aaccctacac atgatattat tgctttatgt   3180
gaatttgaaa acatagtaac atcaaaaaaa gtcataatac caacatacct aagatccatc   3240
agtgtcagaa ataaagatct gaacacactt gaaaatataa caaccactga attcaaaaat   3300
gctatcacaa atgcaaaaat catcccttac tcaggattac tattagtcat cacagtgact   3360
gacaacaaag gagcattcaa atacataaag ccacaaagtc aattcatagt agatcttgga   3420
gcttacctag aaaaagaaag tatatattat gttaccacaa attggaagca cacagctaca   3480
cgatttgcaa tcaaacccat ggaagattaa cctttttcct ctacatcagt gtgttaattc   3540
atacaaactt tctacctaca ttcttcactt caccatcaca atcacaaaca ctctgtggtt   3600
caaccaatca aacaaaactt atctgaagtc ccagatcatc ccaagtcatt gtttatcaga   3660
tctagtactc aaataagtta ataaaaaata tacacatggg gcaaataatc attggaggaa   3720
atccaactaa tcacaatatc tgttaacata gacaagtcca cacaccatac agaatcaacc   3780
aatggaaaat acatccataa caatagaatt ctcaagcaaa ttctggcctt actttacact   3840
aatacacatg atcacaacaa taatctcttt gctaatcata atctccatca tgattgcaat   3900
actaaacaaa ctttgtgaat ataacgtatt ccataacaaa acctttgagt taccaagagc   3960
tcgagttaat acttgataaa gtagttaatt aaaaatagtc ataacaatga actaggatat   4020
caagactaac aataacattg gggcaaatgc aaacatgtcc aaaaacaagg accaacgcac   4080
cgctaagaca ttagaaagga cctgggacac tctcaatcat ttattattca tatcatcgtg   4140
cttatataag ttaaatctta aatctgtagc acaaatcaca ttatccattc tggcaatgat   4200
aatctcaact tcacttataa ttgcagccat catattcata gcctcggcaa accacaaagt   4260
cacaccaaca actgcaatca tacaagatgc aacaagccag atcaagaaca caaccccaac   4320
atacctcacc cagaatcctc agcttggaat cagtccctct aatccgtctg aaattacatc   4380
acaaatcacc accatactag cttcaacaac accaggagtc aagtcaaccc tgcaatccac   4440
aacagtcaag accaaaaaca caacaacaac tcaaacacaa cccagcaagc ccaccacaaa   4500
acaacgccaa aacaaaccac caagcaaacc caataatgat tttcactttg aagtgttcaa   4560
ctttgtaccc tgcagcatat gcagcaacaa tccaacctgc tgggctatct gcaaaagaat   4620
accaaacaaa aaaccaggaa agaaaaccac taccaagccc acaaaaaaac caaccctcaa   4680
gacaaccaaa aaagatccca aacctcaaac cactaaatca aaggaagtac ccaccaccaa   4740
gcccacagaa gagccaacca tcaacaccac caaaacaaac atcataacta cactactcac   4800
ctccaacacc acaggaaatc cagaactcac aagtcaaatg gaaaccttcc actcaacttc   4860
ctccgaaggc aatccaagcc cttctcaagt ctctacaaca tccgagtacc catcacaacc   4920
ttcatctcca cccaacacac cacgccagta gttacttaaa aacatattat cacaaaaggc   4980
cttgaccaac ttaaacagaa tcaaaataaa ctctggggca aataacaatg gagttgctaa   5040
tcctcaaagc aaatgcaatt accacaatcc tcactgcagt cacattttgt tttgcttctg   5100
gtcaaaacat cactgaagaa ttttatcaat caacatgcag tgcagttagc aaaggctatc   5160
ttagtgctct gagaactggt tggtatacca gtgttataac tatagaatta agtaatatca   5220
agaaaaataa gtgtaatgga acagatgcta aggtaaaatt gataaaacaa gaattagata   5280
aatataaaaa tgctgtaaca gaattgcagt tgctcatgca aagcacacaa gcaacaaaca   5340
atcgagccag aagagaacta ccaaggttta tgaattatac actcaacaat gccaaaaaaa   5400
```

ccaatgtaac attaagcaag aaaaggaaaa gaagatttct tggtttttttg ttaggtgttg 5460
gatctgcaat cgccagtggc gttgctgtat ctaaggtcct gcacctagaa ggggaagtga 5520
acaagatcaa aagtgctcta ctatccacaa acaaggctgt agtcagctta tcaaatggag 5580
ttagtgtttt aaccagcaaa gtgttagacc tcaaaaacta tatagataaa caattgttac 5640
ctattgtgaa caagcaaagc tgcagcatat caaatataga aactgtgata gagttccaac 5700
aaaagaacaa cagactacta gagattacca gggaatttag tgttaatgca ggcgtaacta 5760
cacctgtaag cacttacatg ttaactaata gtgaattatt gtcattaatc aatgatatgc 5820
ctataacaaa tgatcagaaa aagttaatgt ccaacaatgt tcaaatagtt agacagcaaa 5880
gttactctat catgtccata ataaaagagg aagtcttagc atatgtagta caattaccac 5940
tatatggtgt tatagataca ccctgttgga aactacacac atcccctcta tgtacaacca 6000
acacaaaaga agggtccaac atctgtttaa caagaactga cagaggatgg tactgtgaca 6060
atgcaggatc agtatctttc ttcccacaag ctgaaacatg taaagttcaa tcaaatcgag 6120
tattttgtga cacaatgaac agtttaacat taccaagtga agtaaatctc tgcaatgttg 6180
acatattcaa ccccaaatat gattgtaaaa ttatgacttc aaaaacagat gtaagcagct 6240
ccgttatcac atctctagga gccattgtgt catgctatgg caaaactaaa tgtacagcat 6300
ccaataaaaa tcgtggaatc ataaagacat tttctaacgg gtgcgattat gtatcaaata 6360
aaggggtgga cactgtgtct gtaggtaaca cattatatta tgtaaataag caagaaggta 6420
aaagtctcta tgtaaaaggt gaaccaataa taaatttcta tgacccatta gtattcccct 6480
ctgatgaatt tgatgcatca atatctcaag tcaacgagaa gattaaccag agcctagcat 6540
ttattcgtaa atccgatgaa ttattacata atgtaaatgc tggtaaatcc accacaaata 6600
tcatgataac tactataatt atagtgatta tagtaatatt gttatcatta attgctgttg 6660
gactgctctt atactgtaag gccagaagca caccagtcac actaagcaaa gatcaactga 6720
gtggtataaa taatattgca tttagtaact aaataaaaat agcacctaat catgttctta 6780
caatggttta ctatctgctc atagacaacc catctgtcat tggattttct taaaatctga 6840
acttcatcga aactctcatc tataaaccat ctcacttaca ctatttaagt agattcctag 6900
tttatagtta tataaaacac aattgcatgc cagattaact taccatctgt aaaaatgaaa 6960
actggggcaa atatgtcacg aaggaatcct tgcaaatttg aaattcgagg tcattgctta 7020
aatggtaaga ggtgtcattt tagtcataat tattttgaat ggccaccccca tgcactgctt 7080
gtaagacaaa actttatgtt aaacagaata cttaagtcta tggataaaag tatagatacc 7140
ttatcagaaa taagtggagc tgcagagttg gacagaacag aagagtatgc tcttggtgta 7200
gttggagtgc tagagagtta tataggatca ataaacaata taactaaaca atcagcatgt 7260
gttgccatga gcaaactcct cactgaactc aatagtgatg atatcaaaaa gctgagggac 7320
aatgaagagc taaattcacc caagataaga gtgtacaata ctgtcatatc atatattgaa 7380
agcaacagga aaaacaataa acaaactatc catctgttaa aaagattgcc agcagacgta 7440
ttgaagaaaa ccatcaaaaa cacattggat atccataaga gcataaccat caacaaccca 7500
aaagaatcaa ctgttagtga tacaaatgac catgccaaaa ataatgatac tacctgacaa 7560
atatccttgt agtataactt ccatactaat aacaagtaga tgtagagtta ctatgtataa 7620
tcaaaagaac acactatatt tcaatcaaaa caacccaaat aaccatatgt actcaccgaa 7680
tcaaacattc aatgaaatcc attggacctc tcaagaattg attgacacaa ttcaaaattt 7740

```
tctacaacat ctaggtatta ttgaggatat atatacaata tatatattag tgtcataaca   7800
ctcaattcta acactcacca catcgttaca ttattaattc aaacaattca agttgtggga   7860
caaaatggat cccattatta atggaaattc tgctaatgtt tatctaaccg atagttattt   7920
aaaaggtgtt atctctttct cagagtgtaa tgctttagga agttacatat tcaatggtcc   7980
ttatctcaaa aatgattata ccaacttaat tagtagacaa aatccattaa tagaacacat   8040
gaatctaaag aaactaaata taacacagtc cttaatatct aagtatcata aaggtgaaat   8100
aaaattagaa gaacctactt attttcagtc attacttatg acatacaaga gtatgacctc   8160
gtcagaacag attgctacca ctaatttact taaaaagata ataagaagag ctatagaaat   8220
aagtgatgtc aaagtctatg ctatattgaa taaactaggg cttaaagaaa aggacaagat   8280
taaatccaac aatggacaag atgaagacaa ctcagttatt acgaccataa tcaaagatga   8340
tatactttca gctgttaaag ataatcaatc tcatcttaaa gcagacaaaa atcactctac   8400
aaaacaaaaa gacacaatca aaacaacact cttgaagaaa ttgatgtgtt caatgcaaca   8460
tcctccatca tggttaatac attggtttaa cttatacaca aaattaaaca acatattaac   8520
acagtatcga tcaaatgagg taaaaaacca tgggtttaca ttgatagata atcaaactct   8580
tagtggattt caatttattt tgaaccaata tggttgtata gtttatcata aggaactcaa   8640
aagaattact gtgacaacct ataatcaatt cttgacatgg aaagatatta gccttagtag   8700
attaaatgtt tgtttaatta catggattag taactgcttg aacacattaa ataaaagctt   8760
aggcttaaga tgcggattca ataatgttat cttgacacaa ctattccttt atggagattg   8820
tatactaaag ctatttcaca atgaggggtt ctacataata aaagaggtag agggatttat   8880
tatgtctcta attttaaata taacagaaga agatcaattc agaaaacgat tttataatag   8940
tatgctcaac aacatcacag atgctgctaa taaagctcag aaaaatctgc tatcaagagt   9000
atgtcataca ttattagata agacagtgtc cgataatata ataaatggca gatggataat   9060
tctattaagt aagttcctta aattaattaa gcttgcaggt gacaataacc ttaacaatct   9120
gagtgaacta tattttttgt tcagaatatt tggacaccca atggtagatg aaagacaagc   9180
catggatgct gttaaaatta attgcaatga gaccaaattt tacttgttaa gcagtctgag   9240
tatgttaaga ggtgccttta tatatagaat tataaaaggg tttgtaaata attacaacag   9300
atggcctact ttaagaaatg ctattgtttt acccttaaga tggttaactt actataaact   9360
aaacacttat ccttctttgt tggaacttac agaaagagat ttgattgtgt tatcaggact   9420
acgtttctat cgtgagtttc ggttgcctaa aaaagtggat cttgaaatga ttataaatga   9480
taaagctata tcacctccta aaaatttgat atggactagt ttccctagaa attacatgcc   9540
atcacacata caaaactata tagaacatga aaaattaaaa ttttccgaga gtgataaatc   9600
aagaagagta ttagagtatt atttaagaga taacaaattc aatgaatgtg atttatacaa   9660
ctgtgtagtt aatcaaagtt atctcaacaa ccctaatcat gtggtatcat tgacaggcaa   9720
agaaagagaa ctcagtgtag gtagaatgtt tgcaatgcaa ccgggaatgt tcagacaggt   9780
tcaaatattg gcagagaaaa tgatagctga aaacatttta caattctttc ctgaaagtct   9840
tacaagatat ggtgatctag aactacaaaa aatattagaa ctgaaagcag gaataagtaa   9900
caaatcaaat cgctacaatg ataattacaa caattacatt agtaagtgct ctatcatcac   9960
agatctcagc aaattcaatc aagcatttcg atatgaaacg tcatgtattt gtagtgatgt  10020
gctggatgaa ctgcatggtg tacaatctct attttcctgg ttacatttaa ctattcctca  10080
tgtcacaata atatgcacat ataggcatgc acccccctat ataggagatc atattgtaga  10140
```

tcttaacaat gtagatgaac aaagtggatt atatagatat cacatgggtg gcatcgaagg 10200
gtggtgtcaa aaactatgga ccatagaagc tatatcacta ttggatctaa tatctctcaa 10260
agggaaattc tcaattactg ctttaattaa tggtgacaat caatcaatag atataagcaa 10320
accaatcaga ctcatggaag gtcaaactca tgctcaagca gattatttgc tagcattaaa 10380
tagccttaaa ttactgtata aagagtatgc aggcataggc cacaaattaa aaggaactga 10440
gacttatata tcacgagata tgcaatttat gagtaaaaca attcaacata acggtgtata 10500
ttacccagct agtataaaga aagtcctaag agtgggaccg tggataaaca ctatacttga 10560
tgatttcaaa gtgagtctag aatctatagg tagtttgaca caagaattag aatatagagg 10620
tgaaagtcta ttatgcagtt taatatttag aaatgtatgg ttatataatc agattgctct 10680
acaattaaaa aatcatgcat tatgtaacaa taaactatat ttggacatat taaaggttct 10740
gaaacactta aaaacctttt ttaatcttga taatattgat acagcattaa cattgtatat 10800
gaatttaccc atgttatttg gtggtggtga tcccaacttg ttatatcgaa gtttctatag 10860
aagaactcct gacttcctca cagaggctat agttcactct gtgttcatac ttagttatta 10920
tacaaaccat gacttaaaag ataaacttca agatctgtca gatgatagat tgaataagtt 10980
cttaacatgc ataatcacgt ttgacaaaaa ccctaatgct gaattcgtaa cattgatgag 11040
agatcctcaa gctttagggt ctgagagaca agctaaaatt actagcgaaa tcaatagact 11100
ggcagttaca gaggttttga gtacagctcc aaacaaaata ttctccaaaa gtgcacaaca 11160
ttatactact acagagatag atctaaatga tattatgcaa aatatagaac ctacatatcc 11220
tcatgggcta agagttgttt atgaaagttt acccttttat aaagcagaga aaatagtaaa 11280
tcttatatca ggtacaaaat ctataactaa catactggaa aaaacttctg ccatagactt 11340
aacagatatt gatagagcca ctgagatgat gaggaaaaac ataactttgc ttataaggat 11400
acttccattg gattgtaaca gagataaaag agagatattg agtatggaaa acctaagtat 11460
tactgaatta agcaaatatg ttagggaaag atcttggtct ttatccaata tagttggtgt 11520
tacatcaccc agtatcatgt atacaatgga catcaaatat actacaagca ctatatctag 11580
tggcataatt atagagaaat ataatgttaa cagtttaaca cgtggtgaga gaggacccac 11640
taaaccatgg gttggttcat ctacacaaga gaaaaaaaca atgccagttt ataatagaca 11700
agtcttaacc aaaaaacaga gagatcaaat agatctatta gcaaaattgg attgggtgta 11760
tgcatctata gataacaagg atgaattcat ggaagaactc tcaataggaa cccttgggtt 11820
aacaaaagaa aaggccaaga aattatttcc acaatattta agtgtcaatt atttgcatcg 11880
ccttacagtc agtagtagac catgtgaatt ccctgcatca ataccagctt atagaacaac 11940
aaattatcac tttgacacta gccctattaa tcgcatatta acagaaaagt atggtgatga 12000
agatattgac atagtattcc aaaactgtat aagctttggc cttagtttaa tgtcagtagt 12060
agaacaattt actaatgtat gtcctaacag aattattctc atacctaagc ttaatgagat 12120
acatttgatg aaacctccca tattcacagg tgatgttgat attcacaagt taaaacaagt 12180
gatacaaaaa cagcatatgt ttttaccaga caaaaataagt ttgactcaat atgtggaatt 12240
attcttaagt aataaaacac tcaaatctgg atctcatgtt aattctaatt taatattggc 12300
acataaaata tctgactatt ttcataatac ttacatttta agtactaatt tagctggaca 12360
ttggattctg attatacaac ttatgaaaga ttctaaaggt atttttgaaa aagattgggg 12420
agagggatat ataactgatc atatgtttat taatttgaaa gttttcttca atgcttataa 12480

```
gacctatctc ttgtgttttc ataaaggtta tggcaaagca aagctggagt gtgatatgaa  12540
cacttcagat cttctatgtg tattggaatt aatagacagt agttattgga agtctatgtc  12600
taaggtattt ttagaacaaa aagttatcaa atacattctt agccaagatg caagtttaca  12660
tagagtaaaa ggatgtcata gcttcaaatt atggtttctt aaacgtctta atgtagcaga  12720
attcacagtt tgcccttggg ttgttaacat agattatcat ccaacacata tgaaagcaat  12780
attaacttat atagatcttg ttagaatggg attgataaat atagatagaa tacacattaa  12840
aaataaacac aaattcaatg atgaatttta tacttctaat ctcttctaca ttaattataa  12900
cttctcagat aatactcatc tattaactaa acatataagg attgctaatt ctgaattaga  12960
aaataattac aacaaattat atcatcctac accagaaacc ctagagaata tactagccaa  13020
tccgattaaa agtaatgaca aaaagacact gaatgactat tgtataggta aaaatgttga  13080
ctcaataatg ttaccattgt tatctaataa gaagcttatt aaatcgtctg caatgattag  13140
aaccaattac agcaaacaag atttgtataa tttattccct atggttgtga ttgatagaat  13200
tatagatcat tcaggcaata cagccaaatc caaccaactt tacactacta cttcccacca  13260
aatatcctta gtgcacaata gcacatcact ttactgcatg cttccttggc atcatattaa  13320
tagattcaat tttgtattta gttctacagg ttgtaaaatt agtatagagt atattttaaa  13380
agatcttaaa attaaagatc ccaattgtat agcattcata ggtgaaggag cagggaattt  13440
attattgcgt acagtagtgg aacttcatcc tgacataaga tatatttaca gaagtctgaa  13500
agattgcaat gatcatagtt tacctattga gtttttaagg ctgtacaatg gacatatcaa  13560
cattgattat ggtgaaaatt tgaccattcc tgctacagat gcaaccaaca acattcattg  13620
gtcttattta catataaagt ttgctgaacc tatcagtctt tttgtctgtg atgccgaatt  13680
gtctgtaaca gtcaactgga gtaaaattat aatagaatgg agcaagcatg taagaaagtg  13740
caagtactgt tcctcagtta ataaatgtat gttaatagta aaatatcatg ctcaagatga  13800
tattgatttc aaattagaca atataactat attaaaaact tatgtatgct taggcagtaa  13860
gttaaaggga tcggaggttt acttagtcct tacaataggt cctgcgaata tattcccagt  13920
atttaatgta gtacaaaatg ctaaattgat actatcaaga accaaaaatt tcatcatgcc  13980
taagaaagct gataaagagt ctattgatgc aaatattaaa agtttgatac cctttctttg  14040
ttaccctata acaaaaaaag gaattaatac tgcattgtca aaactaaaga gtgttgttag  14100
tggagatata ctatcatatt ctatagctgg acgtaatgaa gttttcagca ataaacttat  14160
aaatcataag catatgaaca tcttaaaatg gttcaatcat gttttaaatt tcagatcaac  14220
agaactaaac tataaccatt tatatatggt agaatctaca tatccttacc taagtgaatt  14280
gttaaacagc ttgacaacca atgaacttaa aaaactgatt aaaatcacag gtagtctgtt  14340
atacaacttt cataatgaat aatgaataaa gatcttataa taaaaattcc catagctata  14400
cactaacact gtattcaatt atagttatta aaaattaaaa atcatataat tttttaaata  14460
acttttagtg aactaatcct aaagttatca ttttaatctt ggaggaataa atttaaaccc  14520
taatctaatt ggtttatatg tgtattaact aaattacgag atattagttt ttgacacttt  14580
ttttctcgt                                                          14589
```

<210> SEQ ID NO 19
<211> LENGTH: 14586
<212> TYPE: DNA
<213> ORGANISM: Artificial Sequence
<220> FEATURE:
<223> OTHER INFORMATION: Recombinant RSV sequence

<400> SEQUENCE: 19
acgggaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta aggagagata taagatagaa 600
gatggggcaa atacaaccat ggctcttagc aaagtcaagt tgaatgatac actcaacaaa 660
gatcaacttc tgtcatccag caaatacacc atccaacgga gcacaggaga tagtattgat 720
actcctaatt atgatgtgca gaaacacatc aataagttat gtggcatgtt attaatcaca 780
gaagatgcta atcataaatt cactgggtta ataggtatgt tatatgcgat gtctaggtta 840
ggaagagaag acaccataaa aatactcaga gatgcgggat atcatgtaaa agcaaatgga 900
gtagatgtaa caacacatcg tcaagacatt aatggaaaag aaatgaaatt tgaagtgtta 960
acattggcaa gcttaacaac tgaaattcaa atcaacattg agatagaatc tagaaaatcc 1020
tacaaaaaaa tgctaaaaga aatgggagag gtagctccag aatacaggca tgactctcct 1080
gattgtggga tgataatatt atgtatagca gcattagtaa taactaaatt agcagcaggg 1140
gacagatctg gtcttacagc cgtgattagg agagctaata atgtcctaaa aaatgaaatg 1200
aaacgttaca aaggcttact acccaaggac atagccaaca gcttctatga agtgtttgaa 1260
aaacatcccc actttataga tgtttttgtt cattttggta tagcacaatc ttctaccaga 1320
ggtggcagta gagttgaagg gatttttgca ggattgttta tgaatgccta tggtgcaggg 1380
caagtgatgt tacggtgggg agtcttagca aaatcggtta aaaatattat gttaggacat 1440
gctagtgtgc aagcagaaat ggaacaagtt gttgaggttt atgaatatgc ccaaaaattg 1500
ggtggtgaag caggattcta ccatatattg aacaacccaa aagcatcatt attatctttg 1560
actcaatttc ctcacttctc cagtgtagta ttaggcaatg ctgctggcct aggcataatg 1620
ggagagtaca gaggtacacc gaggaatcaa gatctatatg atgcagcaaa ggcatatgct 1680
gaacaactca aagaaaatgg tgtgattaac tacagtgtac tagacttgac agcagaagaa 1740
ctagaggcta tcaaacatca gcttaatcca aaagataatg atgtagagct ttgagttaat 1800
aaaaaatggg gcaaataaat catcatggaa aagtttgctc ctgaattcca tggagaagat 1860
gcaaacaaca gggctactaa attcctagaa tcaataaagg gcaaattcac atcacccaaa 1920
gatcccaaga aaaaagatag tatcatatct gtcaactcaa tagatataga agtaaccaaa 1980
gaaagcccta taacatcaaa ttcaactatt atcaacccaa caaatgagac agatgatact 2040
gcagggaaca agcccaatta tcaaagaaaa cctctagtaa gtttcaaaga agaccctaca 2100
ccaagtgata atcccttttc taaactatac aaagaaacca tagaaacatt tgataacaat 2160
gaagaagaat ccagctattc atacgaagaa ataaatgatc agacaaacga taatataaca 2220
gcaagattag ataggattga tgaaaaatta agtgaaatac taggaatgct tcacacatta 2280
gtagtggcaa gtgcaggacc tacatctgct cgggatggta taagagatgc catggttggt 2340
ttaagagaag aaatgataga aaaaatcaga actgaagcat taatgaccaa tgacagatta 2400
gaagctatgg caagactcag gaatgaggaa agtgaaaaga tggcaaaaga cacatcagat 2460
gaagtgtctc tcaatccaac atcagagaaa ttgaacaacc tattggaagg gaatgatagt 2520
gacaatgatc tatcacttga agatttctga ttagttacca atcttcacat caacacacaa 2580
taccaacaga agaccaacaa actaaccaac ccaatcatcc aaccaaacat ccatccgcca 2640
atcagccaaa cagccaacaa aacaaccagc caatccaaaa ctaaccaccc ggaaaaaatc 2700
tataatatag ttacaaaaaa aggaaagggt ggggcaaata tggaaacata cgtgaacaag 2760
cttcacgaag gctccacata cacagctgct gttcaataca atgtcttaga aaaagacgat 2820
gaccctgcat cacttacaat atgggtgccc atgttccaat catctatgcc agcagattta 2880
cttataaaag aactagctaa tgtcaacata ctagtgaaac aaatatccac acccaaggga 2940
ccttcactaa gagtcatgat aaactcaaga agtgcagtgc tagcacaaat gcccagcaaa 3000
tttaccatat gcgctaatgt gtccttggat gaaagaagca aactagcata tgatgtaacc 3060
acaccctgtg aaatcaaggc atgtagtcta acatgcctaa aatcaaaaaa tatgttgact 3120
acagttaaag atctcactat gaagacactc aaccctacac atgatattat tgctttatgt 3180
gaatttgaaa acatagtaac atcaaaaaaa gtcataatac caacatacct aagatccatc 3240
agtgtcagaa ataaagatct gaacacactt gaaaatataa caaccactga attcaaaaat 3300
gctatcacaa atgcaaaaat catcccttac tcaggattac tattagtcat cacagtgact 3360
gacaacaaag gagcattcaa atacataaag ccacaaagtc aattcatagt agatcttgga 3420
gcttacctag aaaaagaaag tatatattat gttaccacaa attggaagca cacagctaca 3480
cgatttgcaa tcaaacccat ggaagattaa cctttttcct ctacatcagt gtgttaattc 3540
atacaaactt tctacctaca ttcttcactt caccatcaca atcacaaaca ctctgtggtt 3600
caaccaatca aacaaaactt atctgaagtc ccagatcatc ccaagtcatt gtttatcaga 3660
tctagtactc aaataagtta ataaaaaata tacacatggg gcaaataatc attggaggaa 3720
atccaactaa tcacaatatc tgttaacata gacaagtcca cacaccatac agaatcaacc 3780
aatggaaaat acatccataa caatagaatt ctcaagcaaa ttctggcctt actttacact 3840
aatacacatg atcacaacaa taatctcttt gctaatcata atctccatca tgattgcaat 3900
actaaacaaa ctttgtgaat ataacgtatt ccataacaaa acctttgagt taccaagagc 3960
tcgagttaat acttgataaa gtagttaatt aaaaatagtc ataacaatga actaggatat 4020
caagactaac aataacattg gggcaaatgc aaacatgtcc aaaaacaagg accaacgcac 4080
cgctaagaca ttagaaagga cctgggacac tctcaatcat ttattattca tatcatcgtg 4140
cttatataag ttaaatctta aatctgtagc acaaatcaca ttatccattc tggcaatgat 4200
aatctcaact tcacttataa ttgcagccat catattcata gcctcggcaa accacaaagt 4260
cacaccaaca actgcaatca tacaagatgc aacaagccag atcaagaaca caaccccaac 4320
atacctcacc cagaatcctc agcttggaat cagtccctct aatccgtctg aaattacatc 4380
acaaatcacc accatactag cttcaacaac accaggagtc aagtcaaccc tgcaatccac 4440
aacagtcaag accaaaaaca caacaacaac tcaaacacaa cccagcaagc ccaccacaaa 4500
acaacgccaa aacaaaccac caagcaaacc caataatgat tttcactttg aagtgttcaa 4560
ctttgtaccc tgcagcatat gcagcaacaa tccaacctgc tgggctatct gcaaaagaat 4620
accaaacaaa aaaccaggaa agaaaaccac taccaagccc acaaaaaaac caaccctcaa 4680
gacaaccaaa aaagatccca aacctcaaac cactaaatca aaggaagtac ccaccaccaa 4740
gcccacagaa gagccaacca tcaacaccac caaaacaaac atcataacta cactactcac 4800
ctccaacacc acaggaaatc cagaactcac aagtcaaatg gaaaccttcc actcaacttc 4860
ctccgaaggc aatccaagcc cttctcaagt ctctacaaca tccgagtacc catcacaacc 4920
ttcatctcca cccaacacac cacgccagta gttacttaaa aacatattat cacaaaaggc 4980
cttgaccaac ttaaacagaa tcaaaataaa ctctggggca aataacaatg gagttgctaa 5040
tcctcaaagc aaatgcaatt accacaatcc tcactgcagt cacattttgt tttgcttctg 5100
gtcaaaacat cactgaagaa ttttatcaat caacatgcag tgcagttagc aaaggctatc 5160
ttagtgctct gagaactggt tggtatacca gtgttataac tatagaatta agtaatatca 5220
agaaaaataa gtgtaatgga acagatgcta aggtaaaatt gataaaacaa gaattagata 5280
aatataaaaa tgctgtaaca gaattgcagt tgctcatgca aagcacacaa gcaacaaaca 5340
atcgagccag aagagaacta ccaaggttta tgaattatac actcaacaat gccaaaaaaa 5400
ccaatgtaac attaagcaag aaaaggaaaa gaagatttct tggtttttg ttaggtgttg 5460 gatctgcaat cgccagtggc gttgctgtat ctaaggtcct gcacctagaa ggggaagtga 5520
acaagatcaa aagtgctcta ctatccacaa acaaggctgt agtcagctta tcaaatggag 5580
ttagtgtttt aaccagcaaa gtgttagacc tcaaaaacta tatagataaa caattgttac 5640
ctattgtgaa caagcaaagc tgcagcatat caaatataga aactgtgata gagttccaac 5700
aaaagaacaa cagactacta gagattacca gggaatttag tgttaatgca ggcgtaacta 5760
cacctgtaag cacttacatg ttaactaata gtgaattatt gtcattaatc aatgatatgc 5820
ctataacaaa tgatcagaaa aagttaatgt ccaacaatgt tcaaatagtt agacagcaaa 5880
gttactctat catgtccata ataaaagagg aagtcttagc atatgtagta caattaccac 5940
tatatggtgt tatagataca ccctgttgga aactacacac atcccctcta tgtacaacca 6000
acacaaaaga agggtccaac atctgtttaa caagaactga cagaggatgg tactgtgaca 6060
atgcaggatc agtatctttc ttcccacaag ctgaaacatg taaagttcaa tcaaatcgag 6120
tattttgtga cacaatgaac agtttaacat taccaagtga agtaaatctc tgcaatgttg 6180
acatattcaa ccccaaatat gattgtaaaa ttatgacttc aaaaacagat gtaagcagct 6240
ccgttatcac atctctagga gccattgtgt catgctatgg caaaactaaa tgtacagcat 6300
ccaataaaaa tcgtggaatc ataaagacat tttctaacgg gtgcgattat gtatcaaata 6360
aaggggtgga cactgtgtct gtaggtaaca cattatatta tgtaaataag caagaaggta 6420
aaagtctcta tgtaaaaggt gaaccaataa taaatttcta tgacccatta gtattcccct 6480
ctgatgaatt tgatgcatca atatctcaag tcaacgagaa gattaaccag agcctagcat 6540
ttattcgtaa atccgatgaa ttattacata atgtaaatgc tggtaaatcc accacaaata 6600
tcatgataac tactataatt atagtgatta tagtaatatt gttatcatta attgctgttg 6660
gactgctctt atactgtaag gccagaagca caccagtcac actaagcaaa gatcaactga 6720
gtggtataaa taatattgca tttagtaact aaataaaaat agcacctaat catgttctta 6780
caatggttta ctatctgctc atagacaacc catctgtcat tggattttct taaaatctga 6840
acttcatcga aactctcatc tataaaccat ctcacttaca ctatttaagt agattcctag 6900
tttatagtta tataaaacac aattgcatgc cagattaact taccatctgt aaaaatgaaa 6960
actggggcaa atatgtcacg aaggaatcct tgcaaatttg aaattcgagg tcattgctta 7020
aatggtaaga ggtgtcattt tagtcataat tattttgaat ggccacccca tgcactgctt 7080
gtaagacaaa actttatgtt aaacagaata cttaagtcta tggataaaag tatagatacc 7140
ttatcagaaa taagtggagc tgcagagttg gacagaacag aagagtatgc tcttggtgta 7200
gttggagtgc tagagagtta tataggatca ataaacaata taactaaaca atcagcatgt 7260
gttgccatga gcaaactcct cactgaactc aatagtgatg atatcaaaaa gctgagggac 7320
aatgaagagc taaattcacc caagataaga gtgtacaata ctgtcatatc atatattgaa 7380
agcaacagga aaaacaataa acaaactatc catctgttaa aaagattgcc agcagacgta 7440
ttgaagaaaa ccatcaaaaa cacattggat atccataaga gcataaccat caacaaccca 7500
aaagaatcaa ctgttagtga tacaaatgac catgccaaaa ataatgatac tacctgacaa 7560
atatccttgt agtataactt ccatactaat aacaagtaga tgtagagtta ctatgtataa 7620
tcaaaagaac acactatatt tcaatcaaaa caacccaaat aaccatatgt actcaccgaa 7680
tcaaacattc aatgaaatcc attggacctc tcaagaattg attgacacaa ttcaaaattt 7740
tctacaacat ctaggtatta ttgaggatat atatacaata tatatattag tgtcataaca 7800
ctcaattcta acactcacca catcgttaca ttattaattc aaacaattca agttgtggga 7860
caaaatggat cccattatta atggaaattc tgctaatgtt tatctaaccg atagttattt 7920
aaaaggtgtt atctctttct cagagtgtaa tgctttagga agttacatat tcaatggtcc 7980
ttatctcaaa aatgattata ccaacttaat tagtagacaa aatccattaa tagaacacat 8040
gaatctaaag aaactaaata taacacagtc cttaatatct aagtatcata aaggtgaaat 8100
aaaattagaa gaacctactt attttcagtc attacttatg acatacaaga gtatgacctc 8160
gtcagaacag attgctacca ctaatttact taaaaagata ataagaagag ctatagaaat 8220
aagtgatgtc aaagtctatg ctatattgaa taaactaggg cttaaagaaa aggacaagat 8280
taaatccaac aatggacaag atgaagacaa ctcagttatt acgaccataa tcaaagatga 8340
tatactttca gctgttaaag ataatcaatc tcatcttaaa gcagacaaaa atcactctac 8400
aaaacaaaaa gacacaatca aaacaacact cttgaagaaa ttgatgtgtt caatgcaaca 8460
tcctccatca tggttaatac attggtttaa cttatacaca aaattaaaca acatattaac 8520
acagtatcga tcaaatgagg taaaaaacca tgggtttaca ttgatagata atcaaactct 8580
tagtggattt caatttattt tgaaccaata tggttgtata gtttatcata aggaactcaa 8640
aagaattact gtgacaacct ataatcaatt cttgacatgg aaagatatta gccttagtag 8700
attaaatgtt tgtttaatta catggattag taactgcttg aacacattaa ataaaagctt 8760
aggcttaaga tgcggattca ataatgttat cttgacacaa ctattccttt atggagattg 8820
tatactaaag ctatttcaca atgaggggtt ctacataata aaagaggtag agggatttat 8880
tatgtctcta attttaaata taacagaaga agatcaattc agaaaacgat tttataatag 8940
tatgctcaac aacatcacag atgctgctaa taaagctcag aaaaatctgc tatcaagagt 9000
atgtcataca ttattagata agacagtgtc cgataatata ataaatggca gatggataat 9060
tctattaagt aagttcctta aattaattaa gcttgcaggt gacaataacc ttaacaatct 9120
gagtgaacta tattttttgt tcagaatatt tggacaccca atggtagatg aaagacaagc 9180
catggatgct gttaaaatta attgcaatga gaccaaattt tacttgttaa gcagtctgag 9240
tatgttaaga ggtgccttta tatatagaat tataaaaggg tttgtaaata attacaacag 9300
atggcctact ttaagaaatg ctattgtttt acccttaaga tggttaactt actataaact 9360
aaacacttat ccttctttgt tggaacttac agaaagagat ttgattgtgt tatcaggact 9420

```
acgtttctat cgtgagtttc ggttgcctaa aaaagtggat cttgaaatga ttataaatga   9480
taaagctata tcacctccta aaaatttgat atggactagt ttccctagaa attacatgcc   9540
atcacacata caaaactata tagaacatga aaaattaaaa ttttccgaga gtgataaatc   9600
aagaagagta ttagagtatt atttaagaga taacaaattc aatgaatgtg atttatacaa   9660
ctgtgtagtt aatcaaagtt atctcaacaa ccctaatcat gtggtatcat tgacaggcaa   9720
agaaagagaa ctcagtgtag gtagaatgtt tgcaatgcaa ccgggaatgt tcagacaggt   9780
tcaaatattg gcagagaaaa tgatagctga aaacatttta caattctttc ctgaaagtct   9840
tacaagatat ggtgatctag aactacaaaa aatattagaa ctgaaagcag gaataagtaa   9900
caaatcaaat cgctacaatg ataattacaa caattacatt agtaagtgct ctatcatcac   9960
agatctcagc aaattcaatc aagcatttcg atatgaaacg tcatgtattt gtagtgatgt  10020
gctggatgaa ctgcatggtg tacaatctct attttcctgg ttacatttaa ctattcctca  10080
tgtcacaata atatgcacat ataggcatgc acccccctat ataggagatc atattgtaga  10140
tcttaacaat gtagatgaac aaagtggatt atatagatat cacatgggtg gcatcgaagg  10200
gtggtgtcaa aaactatgga ccatagaagc tatatcacta ttggatctaa tatctctcaa  10260
agggaaattc tcaattactg ctttaattaa tggtgacaat caatcaatag atataagcaa  10320
accaatcaga ctcatggaag gtcaaactca tgctcaagca gattatttgc tagcattaaa  10380
tagccttaaa ttactgtata aagagtatgc aggcataggc cacaaattaa aaggaactga  10440
gacttatata tcacgagata tgcaatttat gagtaaaaca attcaacata acggtgtata  10500
ttacccagct agtataaaga aagtcctaag agtgggaccg tggataaaca ctatacttga  10560
tgatttcaaa gtgagtctag aatctatagg tagtttgaca caagaattag aatatagagg  10620
tgaaagtcta ttatgcagtt taatatttag aaatgtatgg ttatataatc agattgctct  10680
acaattaaaa aatcatgcat tatgtaacaa taaactatat ttggacatat taaaggttct  10740
gaaacactta aaaacctttt ttaatcttga taatattgat acagcattaa cattgtatat  10800
gaatttaccc atgttatttg gtggtggtga tcccaacttg ttatatcgaa gtttctatag  10860
aagaactcct gacttcctca cagaggctat agttcactct gtgttcatac ttagttatta  10920
tacaaaccat gacttaaaag ataaacttca agatctgtca gatgatagat tgaataagtt  10980
cttaacatgc ataatcacgt ttgacaaaaa ccctaatgct gaattcgtaa cattgatgag  11040
agatcctcaa gctttagggt ctgagagaca agctaaaatt actagcgaaa tcaatagact  11100
ggcagttaca gaggttttga gtacagctcc aaacaaaata ttctccaaaa gtgcacaaca  11160
ttatactact acagagatag atctaaatga tattatgcaa aatatagaac ctacatatcc  11220
tcatgggcta agagttgttt atgaaagttt acccttttat aaagcagaga aaatagtaaa  11280
tcttatatca ggtacaaaat ctataactaa catactggaa aaaacttctg ccatagactt  11340
aacagatatt gatagagcca ctgagatgat gaggaaaaac ataactttgc ttataaggat  11400
acttccattg gattgtaaca gagataaaag agagatattg agtatggaaa acctaagtat  11460
tactgaatta agcaaatatg ttagggaaag atcttggtct ttatccaata tagttggtgt  11520
tacatcaccc agtatcatgt atacaatgga catcaaatat actacaagca ctatatctag  11580
tggcataatt atagagaaat ataatgttaa cagtttaaca cgtggtgaga gaggacccac  11640
taaaccatgg gttggttcat ctacacaaga gaaaaaaaca atgccagttt ataatagaca  11700
agtcttaacc aaaaaacaga gagatcaaat agatctatta gcaaaattgg attgggtgta  11760
```

```
tgcatctata gataacaagg atgaattcat ggaagaactc ctgggaaccc ttgggttaac  11820
atatgaaaag gccaagaaat tatttccaca atatttaagt gtcaattatt tgcatcgcct  11880
tacagtcagt agtagaccat gtgaattccc tgcatcaata ccagcttata gaacaacaaa  11940
ttatcacttt gacactagcc ctattaatcg catattaaca gaaaagtatg gtgatgaaga  12000
tattgacata gtattccaaa actgtataag ctttggcctt agtttaatgt cagtagtaga  12060
acaatttact aatgtatgtc ctaacagaat tattctcata cctaagctta atgagataca  12120
tttgatgaaa cctcccatat tcacaggtga tgttgatatt cacaagttaa aacaagtgat  12180
acaaaaacag catatgtttt taccagacaa aataagtttg actcaatatg tggaattatt  12240
cttaagtaat aaaacactca aatctggatc tcatgttaat tctaatttaa tattggcaca  12300
taaaatatct gactattttc ataatactta cattttaagt actaatttag ctggacattg  12360
gattctgatt atacaactta tgaaagattc taaaggtatt tttgaaaaag attggggaga  12420
gggatatata actgatcata tgtttattaa tttgaaagtt ttcttcaatg cttataagac  12480
ctatctcttg tgttttcata aaggttatgg caaagcaaag ctggagtgtg atatgaacac  12540
ttcagatctt ctatgtgtat tggaattaat agacagtagt tattggaagt ctatgtctaa  12600
ggtattttta gaacaaaaag ttatcaaata cattcttagc caagatgcaa gtttacatag  12660
agtaaaagga tgtcatagct tcaaattatg gtttcttaaa cgtcttaatg tagcagaatt  12720
cacagtttgc ccttgggttg ttaacataga ttatcatcca acacatatga aagcaatatt  12780
aacttatata gatcttgtta gaatgggatt gataaatata gatagaatac acattaaaaa  12840
taaacacaaa ttcaatgatg aattttatac ttctaatctc ttctacatta attataactt  12900
ctcagataat actcatctat taactaaaca tataaggatt gctaattctg aattagaaaa  12960
taattacaac aaattatatc atcctacacc agaaacccta gagaatatac tagccaatcc  13020
gattaaaagt aatgacaaaa agacactgaa tgactattgt ataggtaaaa atgttgactc  13080
aataatgtta ccattgttat ctaataagaa gcttattaaa tcgtctgcaa tgattagaac  13140
caattacagc aaacaagatt tgtataattt attccctatg gttgtgattg atagaattat  13200
agatcattca ggcaatacag ccaaatccaa ccaactttac actactactt cccaccaaat  13260
atccttagtg cacaatagca catcacttta ctgcatgctt ccttggcatc atattaatag  13320
attcaatttt gtatttagtt ctacaggttg taaaattagt atagagtata ttttaaaaga  13380
tcttaaaatt aaagatccca attgtatagc attcataggt gaaggagcag ggaatttatt  13440
attgcgtaca gtagtggaac ttcatcctga cataagatat atttacagaa gtctgaaaga  13500
ttgcaatgat catagtttac ctattgagtt tttaaggctg tacaatggac atatcaacat  13560
tgattatggt gaaaatttga ccattcctgc tacagatgca accaacaaca ttcattggtc  13620
ttatttacat ataaagtttg ctgaacctat cagtcttttt gtctgtgatg ccgaattgtc  13680
tgtaacagtc aactggagta aaattataat agaatggagc aagcatgtaa gaaagtgcaa  13740
gtactgttcc tcagttaata aatgtatgtt aatagtaaaa tatcatgctc aagatgatat  13800
tgatttcaaa ttagacaata taactatatt aaaaacttat gtatgcttag gcagtaagtt  13860
aaagggatcg gaggtttact tagtccttac aataggtcct gcgaatatat tcccagtatt  13920
taatgtagta caaaatgcta aattgatact atcaagaacc aaaaatttca tcatgcctaa  13980
gaaagctgat aaagagtcta ttgatgcaaa tattaaaagt ttgataccct ttctttgtta  14040
ccctataaca aaaaaaggaa ttaatactgc attgtcaaaa ctaaagagtg ttgttagtgg  14100
agatatacta tcatattcta tagctggacg taatgaagtt ttcagcaata aacttataaa  14160
```

tcataagcat atgaacatct taaaatggtt caatcatgtt ttaaatttca gatcaacaga 14220
actaaactat aaccatttat atatggtaga atctacatat ccttacctaa gtgaattgtt 14280
aaacagcttg acaaccaatg aacttaaaaa actgattaaa atcacaggta gtctgttata 14340
caactttcat aatgaataat gaataaagat cttataataa aaattcccat agctatacac 14400
taacactgta ttcaattata gttattaaaa attaaaaatc atataatttt ttaaataact 14460
tttagtgaac taatcctaaa gttatcattt taatcttgga ggaataaatt taaaccctaa 14520
tctaattggt ttatatgtgt attaactaaa ttacgagata ttagtttttg acactttttt 14580
tctcgt 14586

<210> SEQ ID NO 20
<211> LENGTH: 78
<212> TYPE: DNA
<213> ORGANISM: Artificial Sequence
<220> FEATURE:
<223> OTHER INFORMATION: Recombinant RSV sequence

<400> SEQUENCE: 20
ggggcaaata agaatttgat aagtaccact taaatttaac tcccttggtt agagatggct 60
cttagcaaag tcaagttg 78

<210> SEQ ID NO 21
<211> LENGTH: 8
<212> TYPE: PRT
<213> ORGANISM: Artificial Sequence
<220> FEATURE:
<223> OTHER INFORMATION: Recombinant RSV sequence

<400> SEQUENCE: 21

Met Asp Thr Thr His Asn Asp Asn
1 5

<210> SEQ ID NO 22
<211> LENGTH: 8
<212> TYPE: PRT
<213> ORGANISM: Artificial Sequence
<220> FEATURE:
<223> OTHER INFORMATION: Recombinant RSV sequence

<400> SEQUENCE: 22

Met Ala Leu Ser Lys Val Lys Leu
1 5

<210> SEQ ID NO 23
<211> LENGTH: 5
<212> TYPE: PRT
<213> ORGANISM: Artificial Sequence
<220> FEATURE:
<223> OTHER INFORMATION: Recombinant RSV sequence

<400> SEQUENCE: 23

Ala Arg Val Asn Thr
1 5

<210> SEQ ID NO 24
<211> LENGTH: 7
<212> TYPE: PRT
<213> ORGANISM: Artificial Sequence
<220> FEATURE:
<223> OTHER INFORMATION: Recombinant RSV sequence

<400> SEQUENCE: 24

Met Glu Leu Leu Ile Leu Lys
1               5

<210> SEQ ID NO 25
<211> LENGTH: 4
<212> TYPE: PRT
<213> ORGANISM: Artificial Sequence
<220> FEATURE:
<223> OTHER INFORMATION: Recombinant RSV sequence

<400> SEQUENCE: 25

Met Ser Lys Asn
1

<210> SEQ ID NO 26
<211> LENGTH: 4
<212> TYPE: PRT
<213> ORGANISM: Artificial Sequence
<220> FEATURE:
<223> OTHER INFORMATION: Recombinant RSV sequence

<400> SEQUENCE: 26

Thr Pro Arg Gln
1

<210> SEQ ID NO 27
<211> LENGTH: 4
<212> TYPE: PRT
<213> ORGANISM: Artificial Sequence
<220> FEATURE:
<223> OTHER INFORMATION: Recombinant RSV sequence

<400> SEQUENCE: 27

Met Asp Thr Thr
1

<210> SEQ ID NO 28
<211> LENGTH: 12
<212> TYPE: DNA
<213> ORGANISM: Artificial Sequence
<220> FEATURE:
<223> OTHER INFORMATION: Recombinant RSV sequence

<400> SEQUENCE: 28
ctcgagttca cc 12

<210> SEQ ID NO 29
<211> LENGTH: 30
<212> TYPE: DNA
<213> ORGANISM: Artificial Sequence
<220> FEATURE:
<223> OTHER INFORMATION: Recombinant RSV sequence

<400> SEQUENCE: 29
agttaataaa aaatggggca aatactcgag 30